(12) United States Patent
Alitalo et al.

(10) Patent No.: US 6,965,010 B2
(45) Date of Patent: Nov. 15, 2005

(54) MATERIALS AND METHODS INVOLVING HYBRID VASCULAR ENDOTHELIAL GROWTH FACTOR DNAS AND PROTEINS

(75) Inventors: Kari Alitalo, Helsinki (FI); Markku Michael Jeltsch, Helsinki (FI)

(73) Assignees: Licentia, Ltd., Helsinki (FI); Ludwig Institute for Cancer Research, New York, NY (US)

( * ) Notice: Subject to any disclaimer, the term of this patent is extended or adjusted under 35 U.S.C. 154(b) by 360 days.

(21) Appl. No.: 09/795,006

(22) Filed: Feb. 26, 2001

(65) Prior Publication Data

US 2002/0151680 A1 Oct. 17, 2002

Related U.S. Application Data

(60) Provisional application No. 60/205,331, filed on May 18, 2000, and provisional application No. 60/185,205, filed on Feb. 25, 2000.

(51) Int. Cl.⁷ .......................... C07K 14/00; C12P 21/04
(52) U.S. Cl. ..................... 530/350; 530/324; 435/69.7
(58) Field of Search ............................. 435/69.7, 372; 550/350, 324

(56) References Cited

U.S. PATENT DOCUMENTS

| | | | |
|---|---|---|---|
| 5,607,918 A | 3/1997 | Eriksson et al. ............... 514/12 |
| 5,776,755 A | 7/1998 | Alitalo et al. ............... 435/194 |
| 5,785,965 A | 7/1998 | Pratt et al. ............... 424/93.21 |
| 5,792,453 A | 8/1998 | Hammond et al. ....... 424/93.21 |
| 5,840,693 A | 11/1998 | Eriksson et al. ............... 514/12 |
| 5,851,521 A | 12/1998 | Branellec et al. ........... 424/93.2 |
| 5,928,939 A | 7/1999 | Eriksson et al. ............. 435/325 |
| 5,932,540 A | 8/1999 | Hu et al. ........................ 514/2 |
| 5,935,820 A | 8/1999 | Hu et al. .................... 435/69.4 |
| 5,955,291 A | 9/1999 | Alitalo et al. .............. 435/7.23 |
| 6,040,157 A | 3/2000 | Hu et al. .................... 435/69.4 |
| 6,107,046 A | 8/2000 | Alitalo et al. ................. 435/7.1 |
| 6,130,071 A | 10/2000 | Alitalo et al. .............. 435/69.4 |
| 6,221,839 B1 | 4/2001 | Alitalo et al. ................. 514/12 |
| 6,235,713 B1 | 5/2001 | Achen et al. ................. 514/12 |
| 6,245,530 B1 | 6/2001 | Alitalo et al. .............. 435/69.4 |
| 6,331,301 B1 | 12/2001 | Eriksson et al. .......... 424/145.1 |
| 6,361,946 B1 | 3/2002 | Alitalo et al. ................... 435/6 |
| 6,383,484 B1 | 5/2002 | Achen et al. ............. 424/133.1 |
| 6,403,088 B1 | 6/2002 | Alitalo et al. ............. 424/139.1 |
| 6,451,764 B1 | 9/2002 | Lee et al. ...................... 514/12 |
| 6,576,608 B1 | 6/2003 | Lee et al. ........................ 514/2 |
| 6,608,182 B1 | 8/2003 | Rosen et al. ................. 530/399 |
| 6,645,933 B1 | 11/2003 | Alitalo et al. ................... 514/2 |
| 6,689,580 B1 | 2/2004 | Achen et al. .............. 435/69.1 |
| 6,730,658 B1 | 5/2004 | Alitalo et al. ................. 514/12 |
| 2002/0120123 A1 | 8/2002 | Rosen et al. |
| 2002/0123481 A1 | 9/2002 | Oliviero |
| 2002/0127222 A1 | 9/2002 | Achen et al. |
| 2002/0182683 A1 | 12/2002 | Hu et al. |
| 2003/0008357 A1 | 1/2003 | Hu et al. |
| 2003/0028007 A1 | 2/2003 | Hu et al. |
| 2003/0125537 A1 | 7/2003 | Achen et al. |
| 2003/0166523 A1 | 9/2003 | Achen et al. |
| 2003/0166547 A1 | 9/2003 | Oliviero |
| 2003/0166873 A1 | 9/2003 | Lee et al. |
| 2003/0211101 A1 | 11/2003 | Wise et al. |
| 2003/0211988 A1 | 11/2003 | Epstein |

FOREIGN PATENT DOCUMENTS

| | | |
|---|---|---|
| EP | 0935001 | 8/1999 |
| WO | WO 91 02058 | 2/1991 |
| WO | WO 96 26736 | 9/1996 |
| WO | WO 97 09427 | 3/1997 |
| WO | WO 97/12972 | 4/1997 |
| WO | WO 97 44453 | 11/1997 |
| WO | WO 98/02543 | 1/1998 |
| WO | WO 98/07832 | 2/1998 |
| WO | WO 98 20027 | 5/1998 |
| WO | WO 98 33917 | 8/1998 |
| WO | WO 99 30157 | 6/1999 |
| WO | WO 00 21560 | 4/2000 |
| WO | WO 00 24412 | 5/2000 |
| WO | WO 00 25805 | 5/2000 |
| WO | WO 00/45835 | 8/2000 |

OTHER PUBLICATIONS

Achen et al., *Proc. Nat'l. Acad. Sci. USA*, 95:548–553 (1998).
Ataliotis et al., *Int Rev Cytology*, 172:95–127 (1997).
Barleon et al., *Blood*, 87:3336–3343 (1996).
Bellomo et al., *Circ Res.*, 2000: E29–E35.
Betscholtz et al., *Cell*, 39:447–57 (1984).
Birkenhager et al., *Biochemical Journal*, 316:703–707 (1996).
Breier et al., *Dev.*, 114:521–532 (1992).
Cao et al., *J. Biol. Chem.*, 271:3154–62 (1996).
Chang et al , *Nature Biotechnology*, 17:793–797 (1999).
Claesson–Welsh et al., *Proc. Nat'l. Acad. Sci. (USA)*, 86(13):4917–4921 (1989).
Claesson–Welsh et al., *Mol. Cell. Biol.*, 8:3476–3486 (1988).
Collins et al., *Nature*, 316:748–750 (1985).
Cowling and Dexter, *TIBTECH*, 10(10):349–357 (1992).
DeVries et al., *Science*, 255:989–991 (1992).
Dumont et al., *Science*, 282:946–949 (1998).
EMBL database Account No. AF091434.
Fairbrother et al., *Biochemistry*, 37(51):17754–17764 (1998).

(Continued)

*Primary Examiner*—Janet Andres
(74) *Attorney, Agent, or Firm*—Marshall, Gerstein & Borun LLP

(57) ABSTRACT

The present invention provides polypeptides that bind cellular receptors for vascular endothelial growth factor polypeptides; polynucleotides encoding such polypeptides; compositions comprising the polypeptides and polynucleotides; and methods and uses involving the foregoing. Some polypeptides of the invention exhibit unique receptor binding profiles compared to known, naturally occurring vascular endothelial growth factors.

50 Claims, 7 Drawing Sheets

OTHER PUBLICATIONS

Figure 1:
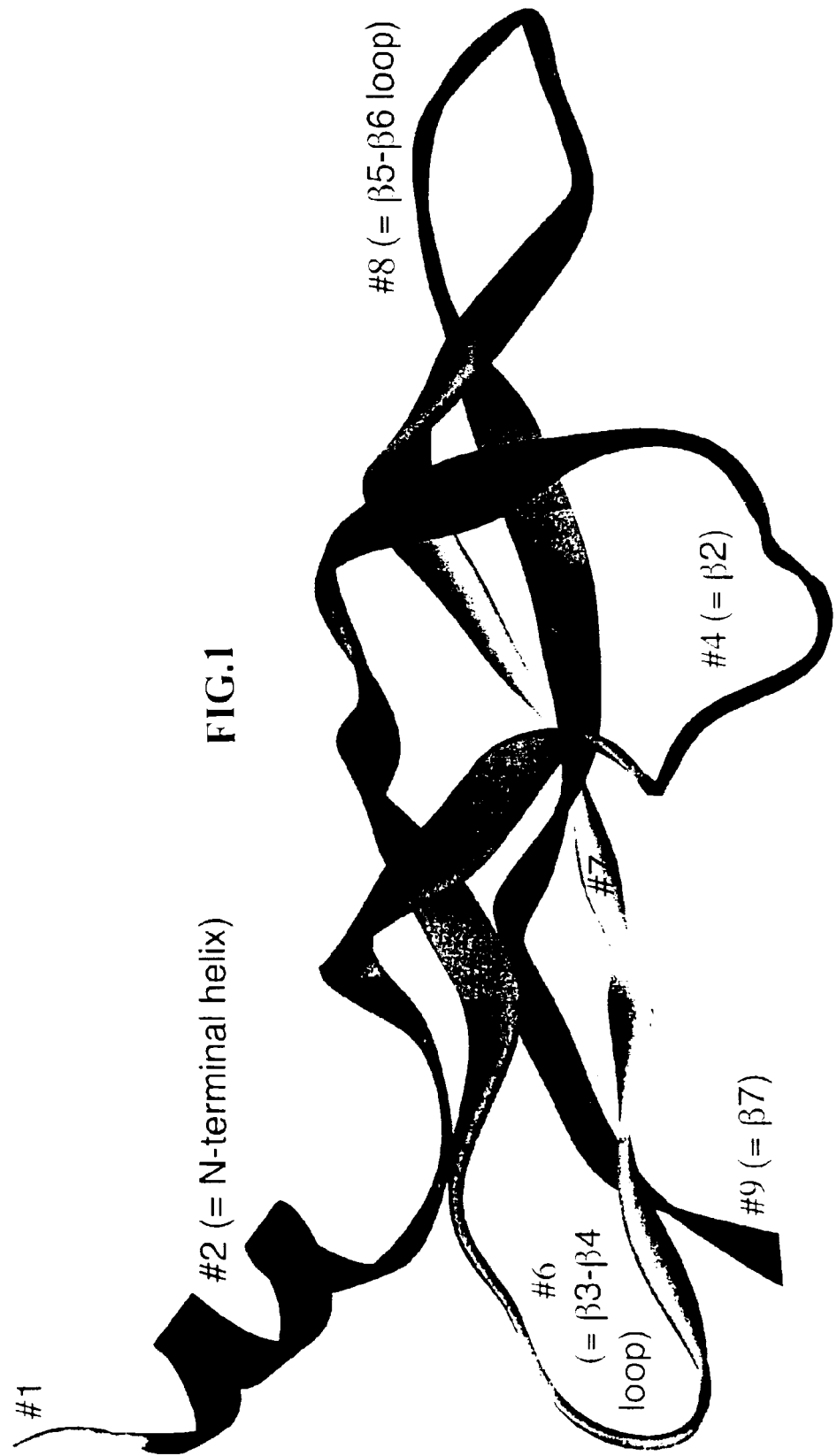

Ferrara, *J. Mol. Med.*, 77:527–543 (1999).
Ferrara and Alitalo, *Nature Med.*, 5:1359–1364 (1999).
Ferrell et al., *Hum. Mol. Genetics*, 7:2073–78 (1998).
Folkman et al., *Proc. Nat'l Acad. Sci. (USA)*, 76:5217–5221 (1979).
Folkman, *Nature Med.*, 1:27–31 (1995).
Friesel et al., *FASEB J.*, 9:919–25 (1995).
Fuh et al., *J Biol. Chem.*, 273:11197–11204 (1998).
Gnatenko et al., *J. Investig. Med.*, 45:87–98 (1997).
Harayama et al., *TIBTECH*, 16:76–82 (1998).
Hauser et al., *Growth Factors*, 9:259–268 (1993).
Hein, *Methods Enzymol.*, 183:626–645 (1990).
Heldin et al., *Growth Factors*, 8:245–252 (1993).
Heldin et al., *Biochemica et Biophysica Acta*, 1378:F79–113 (1998).
Henikoff et al., *Proc. Nat'l Acad. Sci. USA*, 89:10915–10919 (1992).
Isner et al., *Circulation*, 91:2687–2692 (1995).
Isner et al., *Human Gene Therapy*, 7:989–1011 (1996).
Jeltsch et al., *Science*, 276:1423–1425 (1997).
Joukov et al., *The EMBO Journal*, 16(13):3898–3911 (1997).
Joukov et al., *J. Cell Physiol.*, 173:211–215 (1997).
Joukov et al, *The EMBO Journal*, 15(2):290–8 (1996).
Kaipainen et al., *Proc. Nat'l. Acad. Sci. USA*, 92 3566–3570 (1995).
Keating et al., *Science*, 239:914–916 (1988).
Keyt et al., *Journal of Biological Chemistry*, 271(10):5638–5648 (1996).
Kikuchi et al., *Gene*, 236:159–167 (1999).
Korhonen et al., *Blood*, 86(5):1828–1835 (1995).
Lambert et al., *Coron. Artery Dis.*, 4 469–475 (1993).
Lehner et al., *J. Clin. Microbiol.*, 29:2494–2502 (1991).
Lincoff et al., *Circulation*, 90:2070–2084 (1994).
Maglione et al., *Proc. Nat'l. Acad. Sci. (USA)*, 88(20):9267–9271 (1996).
Maglione et al., *Oncogene*, 8:925–931 (1993).
Makinen et al., *J. Biol. Chem.*, 274:21217–22 (1999).
Matthews et al., *Proc. Nat'l. Acad. Sci. USA*, 88:9026–9030 (1991).
Mazur et al., *Texas Heart Institute Journal*, 21:104–111 (1994).
Meyer et al., *The EMBO Journal*, 18:363–374 (1999).
Miles and Miles, *J. Physiol.*, 118:228–257 (1952).
Muller et al., *Structure*, 5:1325–1338 (1997).
Muragaki et al., *Proc. Nat'l. Acad. Sci. (USA)*, 92:8763–8776 (1995).
Mustonen et al., *J. Cell. Biol*, 129:895–98 (1995).
Nachman et al., *Regal. Pept.*, 57:359–370 (1995).
Needleman et al., *J. Mol. Biol.*, 48:443–453 (1970).
Nelson et al., *J. Cell Biol.*, 97:244–251 (1983).
Neufeld et al., *FASEB J.*, 13:9–22 (1999).
Oh et al., *Dev. Biol.*, 188:96–109 (1997).
Oliyai and Stella, *Ann. Rev. Pharmacol. Toxicol.*, 32:521–544 (1993).
Olofsson et al., *Proc. Nat'l. Acad. Sci. (USA)*, 93:2576–2581 (1996).
Orlandini, S., *Proc. Nat'l. Acad. Sci. (USA)*, 93(21):11675–11680 (1996).
Ortega et al., *Fron. Biosci.*, 4:141–152 (1999).
Ostermeier et al., *Nature Biotechnology*, 17:1205–1209 (1999).
Pajusola et al., *Oncogene*, 9:3545–3555 (1994).
Pertovaara et al., *J. Biol. Chem.*, 269:6271–74 (1994).
Petrova et al., *Exp. Cell Res.*, 253:117–130 (1999).
Risau et al., *Dev. Biol.*, 125:441–450 (1988).
Rosenfeld et al., *Cell*, 68:143–155 (1992).
Rosenkranz et al., *Growth Factors*, 16:201–16 (1999).
Schmelz et al., *Differentiation*, 57 97–117 (1994).
Shih et al., *Proc. Nat'l. Acad. Sci. USA*, 87:1436–1440 (1990).
Soker et al., *J. Biol. Chem.*, 271:5761–7 (1996).
Stacker and Achen, *Growth Factors*, 17:1–11 (1999).
Steg et al., *Circulation*, 96:408–411 (1997).
Steg et al., *Circulation*, 90:1648–1656 (1994).
Taipale et al., *Curr Top Microbiol Immunol.*, 237:85–96 (1999).
Terman et al., *Biochem Biophys Res Comm*, 187:1579–1586 (1992).
Thompson et al., *Nucl Acids Res.*, 22:4673–80 (1994).
Valtola et al., *Am. J. Path*, 154:1381–90 (1999).
Vassar et al., *Proc. Nat'l. Acad. Sci. (USA)*, 86:1563–1567 (1989).
Vassar et al., *Genes Dev.*, 5:714–727 (1991).
Waltenberger et al., *J. Biol. Chem.*, 269:26988–26995 (1994).
Wilensky et al., *Trends Cardiovasc. Med.*, 3:163–170 (1993).
Wolinsky et al., *J. Am. Coll. Cardiol.*, 15:475–481 (1990).
Zachary, *Intl J. Biochem Cell Bio.* 30:1169–1174 (1998).
Zhang et al., *Proc. Nat'l. Acad. Sci. USA*, 94:4504–09 (1997).

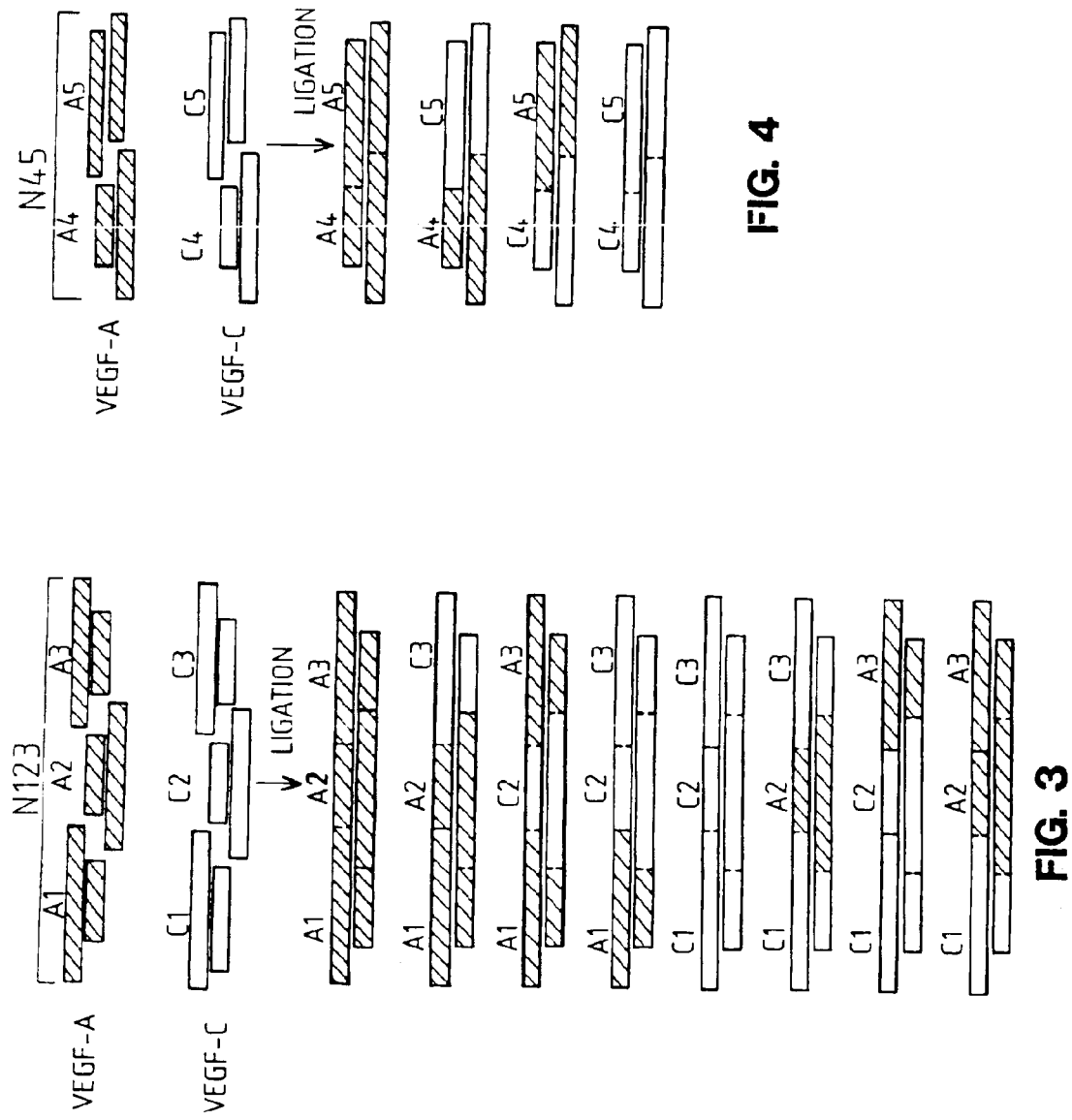

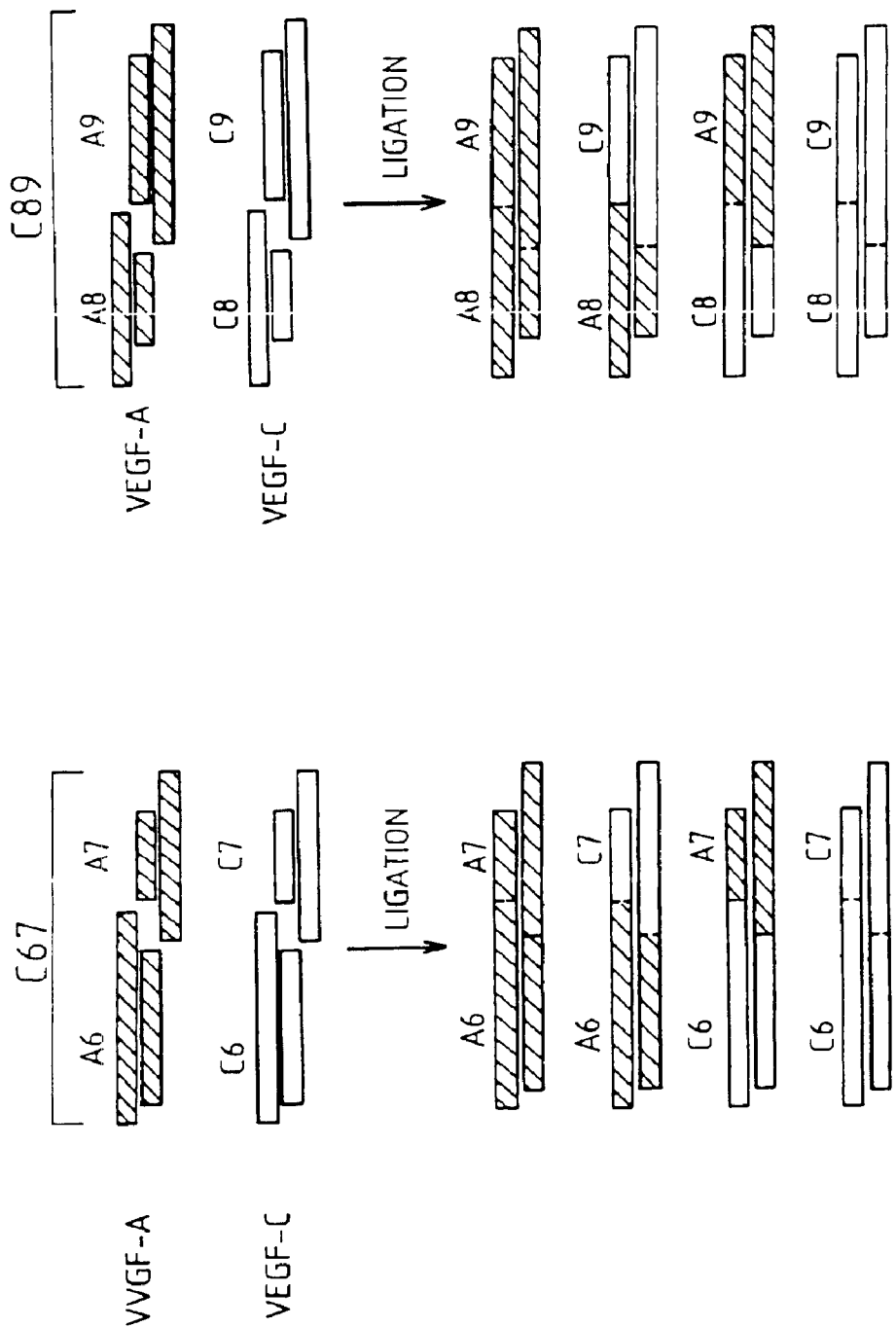

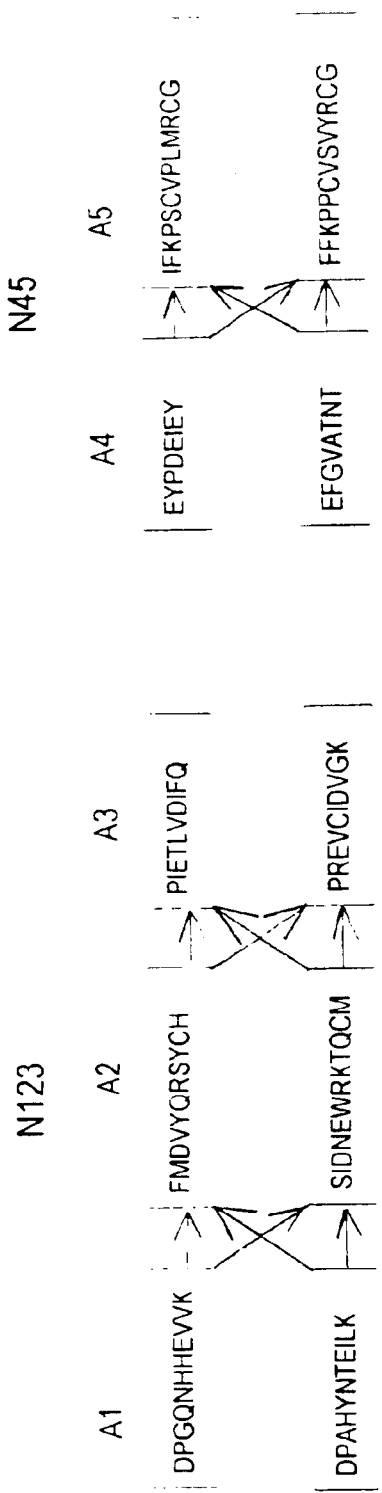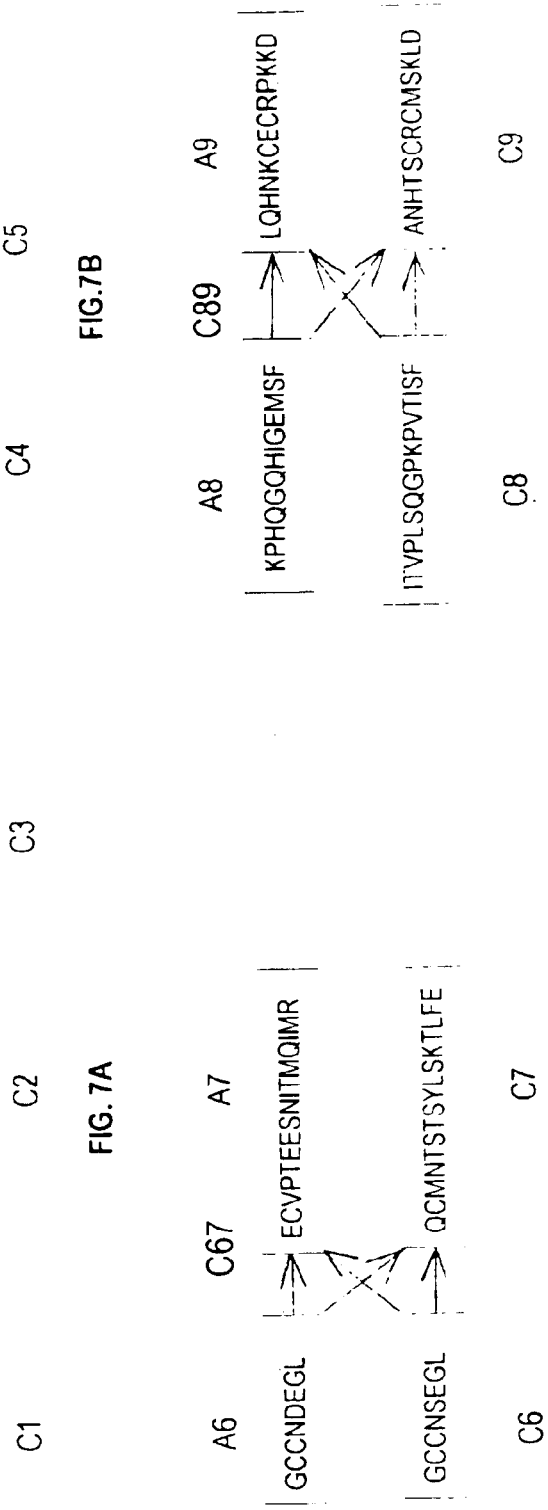
FIG. 7A
FIG. 7B
FIG. 7C
FIG. 7D

MATERIALS AND METHODS INVOLVING HYBRID VASCULAR ENDOTHELIAL GROWTH FACTOR DNAS AND PROTEINS

The present application claims benefit of priority to U.S. Provisional Patent Application No. 60/205,331 filed May 18, 2000 and U.S. Provisional Patent Application No. 60/185, 205 filed Feb. 25, 2000. The entire text and drawing of each of the priority applications is specifically incorporated herein by reference, without prejudice or disclaimer.

BACKGROUND OF THE INVENTION

The PDGF proteins and their receptors (PDGFRs) are involved in regulation of cell proliferation, survival and migration of several cell types. The VEGF proteins and their receptors (VEGFRs) play important roles in both vasculogenesis, the development of the embryonic vasculature from early differentiating endothelial cells, and angiogenesis, the process of forming new blood vessels from pre-existing ones [Risau et al., Dev Biol 125:441–450 (1988); Zachary, Intl J Biochem Cell Bio 30:1169–1174 (1998); Neufeld et al., FASEB J 13:9–22 (1999); Ferrara, J Mol Med 77:527–543 (1999)]. Both processes depend on the tightly controlled endothelial cell proliferation, migration, differentiation, and survival. Dysfunction of the endothelial cell regulatory system is a key feature of cancer and several diseases associated with abnormal angiogenesis, such as proliferative retinopathies, age-related muscular degeneration, rheumatoid arthritis, and psoriasis. Understanding of the specific biological function of the key players involved in regulating endothelial cells will lead to more effective therapeutic applications to treat such diseases [Zachary, Intl J Biochem Cell Bio 30:1169–1174 (1998); Neufeld et al., FASEB J 13:9–22 (1999); Ferrara, J Mol Med 77:527–543 (1999)].

The PDGF/VEGF Family

The PDGF/VEGF family of growth factors includes at least the following members: PDGF-A (see e.g., GenBank Acc. No. X06374), PDGF-B (see e.g., GenBank Acc. No. M12783), VEGF (see e.g., GenBank Acc. No. Q16889 referred to herein for clarity as VEGF-A or by particular isoform), PlGF (see e.g., GenBank Acc. No. X54936 placental growth factor), VEGF-B (see e.g., GenBank Acc. No. U48801; also known as VEGF-related factor (VRF)), VEGF-C (see e.g., GenBank Acc. No. X94216; also known as VEGF related protein (VRP)), VEGF-D (also known as c-fos-induced growth factor (FIGF); see e.g., Genbank Acc. No. AJ000185), VEGF-E (also known as NZ7 VEGF or OV NZ7; see e.g., GenBank Acc. No. S67522), NZ2 VEGF (also known as OV NZ2; see e.g., GenBank Acc. No. S67520), D1701 VEGF-like protein (see e.g., GenBank Acc. No. AF106020; Meyer et al., EMBO J 18:363–374), and NZ10 VEGF-like protein (described in International Patent Application PCT/US99/25869) [Stacker and Achen, Growth Factors 17:1–11 (1999); Neufeld et al., FASEB J 13:9–22 (1999); Ferrara, J Mol Med 77:527–543 (1999)].

Members of the PDGF/VEGF family are characterized by a number of structural motifs including a conserved PDGF motif defined by the sequence: P-[PS]-C-V-X(3)-R-C-[GSTA]-G-C-C (SEQ ID NO: 1200). The brackets indicate that this position within the polypeptide can be any one of the amino acids contained within the brackets. The number contained within the parentheses indicates the number of amino acids that separate the "V" and "R" residues. This conserved motif falls within a large domain of 70–150 amino acids defined in part by eight highly conserved cysteine residues that form inter- and intramolecular disulfide bonds. This domain forms a cysteine knot motif composed of two disulfide bonds which form a covalently linked ring structure between two adjacent β strands, and a third disulfide bond that penetrates the ring [see for example, FIG. 1 in Muller et al., Structure 5:1325–1338 (1997)], similar to that found in other cysteine knot growth factors, e.g., transforming growth factor-β, (TGF-β). The amino acid sequence of all known PDGF/VEGF proteins, with the exception of VEGF-E, contains the PDGF domain. The PDGF/VEGF family proteins are predominantly secreted glycoproteins that form either disulfide-linked or non-covalently bound homo- or heterodimers whose subunits are arranged in an anti-parallel manner [Stacker and Achen, Growth Factors 17:1–11 (1999); Muller et al., Structure 5:1325–1338 (1997)].

The PDGF Subfamily

The PDGFs regulate cell proliferation, cell survival and chemotaxis of many cell types in vitro (reviewed in [Heldin et al., Biochimica et Biophysica Acta 1378:F79–113 (1998)]. The two chains that make up PDGF, PDGF-A and PDGF-B, can home- or heterodimerize producing three different isoforms: PDGF-AA, PDGF-AB, or PDGF-BB. PDGF-A is only able to bind the PDGF α-receptor (PDGFR-α), whereas PDGF-B can bind both the PDGF-α and a second PDGF receptor (PDGF-β). In vivo, the PDGF proteins exert their effects in a paracrine manner since they often are expressed in epithelial (PDGF-A) or endothelial (PDGF-B) cells in close apposition to the PDGF receptor-expressing mesenchyme (reviewed in Ataliotis et al., Int Rev Cytology 172:95–127 (1997)]. Overexpression of the PDGFs has been observed in several pathological conditions, including malignancies, atherosclerosis, and fibroproliferative diseases. In tumor cells and cell lines grown in vitro, coexpression of the PDGFs and PDGF receptors generates autocrine loops, which are important for cellular transformation [Betsholtz et al., Cell 39:447–57 (1984); Keating et al., Science 239:914–6 (1988)].

The importance of the PDGFs as regulators of cell proliferation and cell survival is well illustrated by recent gene targeting studies in mice. Homozygous null mutations for either PDGF-A or PDGF-B are lethal in mice. Approximately 50% of the homozygous PDGF-A deficient mice have an early lethal phenotype, while the surviving animals have a complex postnatal phenotype with lung emphysema due to improper alveolar septum formation, and a dermal phenotype characterized by thin dermis, misshapen hair follicles, and thin hair. PDGF-A is also required for normal development of oligodendrocytes and subsequent myelination of the central nervous system. The PDGF-B deficient mice develop renal, hematological and cardiovascular abnormalities; where the renal and cardiovascular defects, at least in part, are due to the lack of proper recruitment of mural cells (vascular smooth muscle cells, pericytes or mesangial cells) to blood vessels.

The VEGF Subfamily

The VEGF subfamily is composed of PDGF/VEGF members which share a VEGF homology domain (VHD) characterized by the sequence: C-X(22–24)-P-[PSR]-C-V-X(3)-R-C-[GSTA]-G-C-C-X(6)-C-X(32–41)-C (SEQ ID NO: 1201). The VHD domain, determined through analysis of the VEGF subfamily members, comprises the PDGF motif but is more specific.

VEGF-A was originally purified from several sources on the basis of its mitogenic activity toward endothelial cells, and also by its ability to induce microvascular permeability, hence it is also called vascular permeability factor (VPF). VEGF-A has subsequently been shown to induce a number of biological processes including the mobilization of intracellular calcium, the induction of plasminogen activator and plasminogen activator inhibitor-1 synthesis, promotion of monocyte migration in vitro, induction of antiapoptotic protein expression in human endothelial cells, induction of fenestrations in endothelial cells, promotion of cell adhesion molecule expression in endothelial cells and induction of nitric oxide mediated vasodilation and hypotension [Ferrara, *J Mol Med* 77:527–543 (1999); Neufeld et al., *FASEB J* 13:9–22 (1999); Zachary, *Intl J Biochem Cell Bio* 30:1169–1174 (1998)].

VEGF-A is a secreted, disulfide-linked homodimeric glycoprotein composed of 23 kD subunits. Five human VEGF-A isoforms of 121, 145, 165, 189 or 206 amino acids in length ($VEGF_{121-206}$), encoded by distinct mRNA splice variants, have been described, all of which are capable of stimulating mitogenesis in endothelial cells. However, each isoform differs in biological activity, receptor specificity, and affinity for cell surface- and extracellular matrix-associated heparan-sulfate proteoglycans, which behave as low affinity receptors for VEGF-A. $VEGF_{121}$, does not bind to either heparin or heparan-sulfate; $VEGF_{145}$ and $VEGF_{165}$ (GenBank Acc. No. M32977) are both capable of binding to heparin; and $VEGF_{189}$ and $VEGF_{206}$ show the strongest affinity for heparin and heparan-sulfates. $VEGF_{121}$, $VEGF_{145}$, and $VEGF_{165}$ are secreted in a soluble form, although most of $VEGF_{165}$ is confined to cell surface and extracellular matrix proteoglycans, whereas $VEGF_{189}$ and $VEGF_{206}$ remain associated with extracellular matrix. Both $VEGF_{189}$ and $VEGF_{206}$ can be released by treatment with heparin or heparinase, indicating that these isoforms are bound to extracellular matrix via proteoglycans. Cell-bound $VEGF_{189}$ can also be cleaved by proteases such as plasmin, resulting in release of an active soluble $VEGF_{110}$. Most tissues that express VEGF are observed to express several VEGF isoforms simultaneously, although $VEGF_{121}$ and $VEGF_{165}$ are the predominant forms, whereas $VEGF_{206}$ is rarely detected [Ferrara, *J Mol Med* 77:527–543 (1999)]. $VEGF_{145}$ differs in that it is primarily expressed in cells derived from reproductive organs [Neufeld et al., *FASEB J* 13:9–22 (1999)].

The pattern of VEGF-A expression suggests its involvement in the development and maintenance of the normal vascular system, and in angiogenesis associated with tumor growth and other pathological conditions such as rheumatoid arthritis. VEGF-A is expressed in embryonic tissues associated with the developing vascular system, and is secreted by numerous tumor cell lines. Analysis of mice in which VEGF-A was knocked out by targeted gene disruption indicate that VEGF-A is critical for survival, and that the development of the cardiovascular system is highly sensitive to VEGF-A concentration gradients. Mice lacking a single copy of VEGF-A die between day 11 and 12 of gestation. These embryos show impaired growth and several developmental abnormalities including defects in the developing cardiovasculature. VEGF-A is also required post-naturally for growth, organ development, regulation of growth plate morphogenesis and endochondral bone formation. The requirement for VEGF-A decreases with age, especially after the fourth postnatal week. In mature animals, VEGF-A is required primarily for active angiogenesis in processes such as wound healing and the development of the corpus luteum. [Neufeld et al., *FASEB J* 13:9–22 (1999); Ferrara, *J Mol Med* 77:527–543 (1999)]. VEGF-A expression is influenced primarily by hypoxia and a number of hormones and cytokines including epidermal growth factor (EGF), TGF-β, and various interleukins. Regulation occurs transcriptionally and also post-transcriptionally such as by increased mRNA stability [Ferrara, *J Mol Med* 77:527–543 (1999)].

PlGF, a second member of the VEGF subfamily, is generally a poor stimulator of angiogenesis and endothelial cell proliferation in comparison to VEGF-A, and the in vivo role of PlGF is not well understood. Three isoforms of PlGF produced by alternative mRNA splicing have been described [Hauser et al., *Growth Factors* 9:259–268 (1993); Maglione et al., *Oncogene* 8:925–931 (1993)]. PlGF forms both disulfide-liked homodimers and heterodimers with VEGF-A. The PlGF-VEGF-A heterodimers are more effective at inducing endothelial cell proliferation and angiogenesis than PlGF homodimers. PlGF is primarily expressed in the placenta, and is also co-expressed with VEGF-A during early embryogenesis in the trophoblastic giant cells of the parietal yolk sac [Stacker and Achen, *Growth Factors* 17:1–11 (1999)].

VEGF-B, described in detail in International Patent Publication No. WO 96/26736 and U.S. Pat. Nos. 5,840,693 and 5,607,918, shares approximately 44% amino acid identity with VEGF-A. Although the biological functions of VEGF-B in vivo remain incompletely understood, it has been shown to have angiogenic properties, and may also be involved in cell adhesion and migration, and in regulating the degradation of extracellular matrix. It is expressed as two isoforms of 167 and 186 amino acid residues generated by alternative splicing. $VEGF-B_{167}$ is associated with the cell surface or extracellular matrix via a heparin-binding domain, whereas $VEGF-B_{186}$ is secreted. Both $VEGF-B_{167}$ and $VEGF-B_{186}$ can form disulfide-linked homodimers or heterodimers with VEGF-A. The association to the cell surface of $VEGF-B_{186}$–$VEGF-B_{167}$ heterodimers appears to be determined by the VEGF-B component, suggesting that heterodimerization may be important for sequestering VEGF-A. VEGF-B is expressed primarily in embryonic and adult cardiac and skeletal muscle tissues [Joukov et al., *J Cell Physiol* 73:211–215 (1997); Stacker and Achen, *Growth Factors* 17:1–11 (1999)]. Mice lacking VEGF-B survive but have smaller hearts, dysfunctional coronary vasculature, and exhibit impaired recovery from cardiac ischemia [Bellomo et al., *Circ Res* 2000;E29–E35].

A fourth member of the VEGF subfamily, VEGF-C, comprises a VHD that is approximately 30% identical at the amino acid level to VEGF-A. VEGF-C is originally expressed as a larger precursor protein, prepro-VEGF-C, having extensive amino- and carboxy-terminal peptide sequences flanking the VHD, with the C-terminal peptide containing tandemly repeated cysteine residues in a motif typical of Balbiani ring 3 protein. Prepro-VEGF-C undergoes extensive proteolytic maturation involving the successive cleavage of a signal peptide, the C-terminal pro-peptide, and the N-terminal pro-peptide. Secreted VEGF-C protein consists of a non-covalently-linked homodimer, in which each monomer contains the VHD. The intermediate forms of VEGF-C produced by partial proteolytic processing show increasing affinity for the VEGFR-3 receptor, and the mature protein is also able to bind to the VEGFR-2 receptor. [Joikov et al., *EMBO J.*, 16:(13):3898–3911 (1997).] It has also been demonstrated that a mutant VEGF-C, in which a single cysteine at position 156 is either substituted by another amino acid or deleted, loses the ability to bind VEGFR-2 but remains capable of binding and activating VEGFR-3 [International Patent Publication No. WO 98/33917]. In mouse embryos, VEGF-C mRNA is expressed primarily in the allantois, jugular area, and the metanephros. [Joukov et al., *J Cell Physiol* 173:211–215 (1997)]. VEGF-C is involved in the regulation of lymphatic angiogenesis: when VEGF-C was overexpressed in the skin of transgenic mice, a hyperplastic lymphatic vessel network was observed, suggesting that VEGF-C induces lymphatic growth [Jeltsch et al., Science, 276:1423–1425 (1997)]. Continued expression of VEGF-C in the adult also indicates a role in maintenance of differentiated lymphatic endothelium [Ferrara, J Mol Med 77:527–543 (1999)]. VEGF-C also shows angiogenic properties: it can stimulate migration of bovine capillary endothelial (BCE) cells in collagen and promote growth of human endothelial cells [see, e.g., International Patent Publication No. WO 98/33917, incorporated herein by reference].

VEGF-D is structurally and functionally most closely related to VEGF-C [see International Patent Publ. No. WO 98/07832, incorporated herein by reference]. Like VEGF-C, VEGF-D is initially expressed as a prepro-peptide that undergoes N-terminal and C-terminal proteolytic processing, and forms non-covalently linked dimers. VEGF-D stimulates mitogenic responses in endothelial cells in vitro. During embryogenesis, VEGF-D is expressed in a complex temporal and spatial pattern, and its expression persists in the heart, lung, and skeletal muscles in adults. Isolation of a biologically active fragment of VEGF-D designated VEGF-DΔNΔC, is described in International Patent Publication No. WO 98/07832, incorporated herein by reference. VEGF-DΔNΔC consists of amino acid residues 93 to 201 of VEGF-D linked to the affinity tag peptide FLAG®.

Four additional members of the VEGF subfamily have been identified in poxviruses, which infect humans, sheep and goats. The orf virus-encoded VEGF-E and NZ2 VEGF are potent mitogens and permeability enhancing factors. Both show approximately 25% amino acid identity to mammalian VEGF-A, and are expressed as disulfide-liked homodimers. Infection by these viruses is characterized by pustular dermititis which may involve endothelial cell proliferation and vascular permeability induced by these viral VEGF proteins. [Ferrara, J Mol Med 77:527–543 (1999); Stacker and Achen, Growth Factors 17:1–11 (1999)]. VEGF-like proteins have also been identified from two additional strains of the orf virus, D1701 [GenBank Acc. No. AF106020; described in Meyer et al., EMBO J 18:363–374 (1999)] and NZ10 [described in International Patent Application PCT/US99/25869, incorporated herein by reference]. These viral VEGF-like proteins have been shown to bind VEGFR-2 present on host endothelium, and this binding is important for development of infection and viral induction of angiogenesis [Meyer et al., EMBO J 18:363–374 (1999); International Patent Application PCT/US99/25869].

PDGF/VEGF Receptors

Seven cell surface receptors that interact with PDGF/VEGF family members have been identified. These include PDGFR-α (see e.g., GenBank Acc. No. NM006206), PDGFR-β (see e.g., GenBank Acc. No. NM002609), VEGFR-1/Flt-1 ( fms-like tyrosine kinase-1; GenBank Acc. No. X51602; De Vries et al., Science 255:989–991 (1992)); VEGFR-2/KDR/Flk-1 (kinase insert domain containing receptor/fetal liver kinase-1; GenBank Acc. Nos. X59397 (Flk-1) and L04947 (KDR); Terman et al., Biochem Biophys Res Comm 187:1579–1586 (1992); Matthews et al., Proc Natl Acad Sci USA 88:9026–9030 (1991)); VEGFR-3/Flt4 (fms-like tyrosine kinase 4; U.S. Pat. No. 5,776,755 and GenBank Acc. No. X68203 and S66407; Pajusola et al., Oncogene 9:3545–3555 (1994)), neuropilin-1 (Gen Bank Acc. No. NM003873), and neuropilin-2 (Gen Bank Acc. No. NM003872). The two PDGF receptors mediate signaling of PDGFs as described above. $VEGF_{121}$, $VEGF_{165}$, VEGF-B, PlGF-1 and PlGF-2 bind VEGF-R1; $VEGF_{121}$, $VEGF_{145}$, $VEGF_{165}$, VEGF-C, VEGF-D, VEGF-E, and NZ2 VEGF bind VEGF-R2; VEGF-C and VEGF-D bind VEGFR-3; $VEGF_{165}$, PlGF-2, and NZ2 VEGF bind neuropilin-1; and $VEGF_{165}$ binds neuropilin-2.[Neufeld et al., FASEB J 13:9–22 (1999); Stacker and Achen, Growth Factors 17:1–11 (1999); Ortega et al., Fron Biosci 4:141–152 (1999); Zachary, Intl J Biochem Cell Bio 30:1169–1174 (1998); Petrova et al., Exp Cell Res 253:117–130 (1999)].

The PDGF receptors are protein tyrosine kinase receptors (PTKs) that contain five immunoglobulin-like loops in their extracellular domains. VEGFR-1, VEGFR-2, and VEGFR-3 comprise a subgroup of the PDGF subfamily of PTKs, distinguished by the presence of seven Ig domains in their extracellular domain and a split kinase domain in the cytoplasmic region. Both neuropilin-1 and neuropilin-2 are non-PTK VEGF receptors. NP-1 has an extracellular portion includes a MAM domain; regions of homology to coagulation factors V and VIII, MFGPs and the DDR tyrosine kinase; and two CUB-like domains.

Several of the VEGF receptors are expressed as more than one isoform. A soluble isoform of VEGFR-1 lacking the seventh Ig-like loop, transmembrane domain, and the cytoplasmic region is expressed in human umbilical vein endothelial cells. This VEGFR-1 isoform binds VEGF-A with high affinity and is capable of preventing VEGF-A-induced mitogenic responses [Ferrara, J Mol Med 77:527–543 (1999); Zachary, Intl J Biochem Cell Bio 30:1169–1174 (1998)]. A C-terminal truncated from of VEGFR-2 has also been reported [Zachary, Intl J Biochem Cell Bio 30:1169–1174 (1998)]. In humans, there are two isoforms of the VEGFR-3 protein which differ in the length of their C-terminal ends. Studies suggest that the longer isoform is responsible for most of the biological properties of VEGFR-3.

The receptors for the PDGFs, PDGF α-receptor (PDGFR-α) and the β-receptor (PDGFR-β), are expressed by many in vitro grown cell lines, and they are mainly expressed by mesenchymal cells in vivo (reviewed in [Raines et al., Peptide growth factors and their receptors, Heidelberg, Springer-Verlag (1990)]. As mentioned above, PDGF-B binds both PDGFRs, while PDGF-A selectively binds PDGFR-α.

Gene targeting studies in mice have revealed distinct physiological roles for the PDGF receptors despite the overlapping ligand specificities of the PDGFRs [Rosenkranz et al., Growth Factors 16:201–16 (1999)]. Homozygous null mutations for either of the two PDGF receptors are lethal. PDGFR-α deficient mice die during embryogenesis at e10, and show incomplete cephalic closure, impaired neural crest development, cardiovascular defects, skeletal defects, and odemas. The PDGFR-β deficient mice develop similar phenotypes to animals deficient in PDGF-B, that are characterized by renal, hematological and cardiovascular abnormalities; where the renal and cardiovascular defects, at least in part, are due to the lack of proper recruitment of mural cells (vascular smooth muscle cells, pericytes or mesangial cells) to blood vessels.

The expression of VEGFR-1 occurs mainly in vascular endothelial cells, although some may be present on monocytes, trophoblast cells, and renal mesangial cells [Neufeld et al., FASEB J 13:9–22 (1999)]. High levels of VEGFR-1 mRNA are also detected in adult organs, suggesting that VEGFR-1 has a function in quiescent endothelium of mature vessels not related to cell growth. VEGFR-1-/- mice die in utero between day 8.5 and 9.5. Although endothelial cells developed in these animals, the formation of functional blood vessels was severely impaired, suggesting that VEGFR-1 may be involved in cell-cell or cell-matrix interactions associated with cell migration. Recently, it has been demonstrated that mice expressing a mutated VEGFR-1 in which only the tyrosine kinase domain was missing show normal angiogenesis and survival, suggesting that the signaling capability of VEGFR-1 is not essential. [Neufeld et al., *FASEB J* 13:9–22 (1999); *Ferrara, J Mol Med* 77:527–543 (1999)].

VEGFR-2 expression is similar to that of VEGFR-1 in that it is broadly expressed in the vascular endothelium, but it is also present in hematopoietic stem cells, megakaryocytes, and retinal progenitor cells [Neufeld et al., *FASEB J* 13:9–22 (1999)]. Although the expression pattern of VEGFR-1 and VEGFR-2 overlap extensively, evidence suggests that, in most cell types, VEGFR-2 is the major receptor through which most of the VEGFs exert their biological activities. Examination of mouse embryos deficient in VEGFR-2 further indicate that this receptor is required for both endothelial cell differentiation and the development of hematopoietic cells [Joukov et al., *J Cell Physiol* 173:211–215 (1997)].

VEGFR-3 is expressed broadly in endothelial cells during early embryogenesis. During later stages of development, the expression of VEGFR-3 becomes restricted to developing lymphatic vessels [Kaipainen, A., et al., *Proc. Natl. Acad. Sci. USA*, 92:3566–3570 (1995)]. In adults, the lymphatic endothelia and some high endothelial venules express VEGFR-3, and increased expression occurs in lymphatic sinuses in metastatic lymph nodes and in lymphangioma. VEGFR-3 is also expressed in a subset of $CD34^+$ hematopoietic cells which may mediate the myelopoietic activity of VEGF-C demonstrated by overexpression studies [WO 98/33917]. Targeted disruption of the VEGFR-3 gene in mouse embryos leads to failure of the remodeling of the primary vascular network, and death after embryonic day 9.5 [Dumont et al., Science, 282:946–949 (1998)]. These studies suggest an essential role for VEGFR-3 in the development of the embryonic vasculature, and also during lymphangiogenesis.

Structural analyses of the VEGF receptors indicate that the VEGF-A binding site on VEGFR-1 and VEGFR-2 is located in the second and third Ig-like loops. Similarly, the VEGF-C and VEGF-D binding sites on VEGFR-2 and VEGFR-3 are also contained within the second Ig-loop [Taipale et al., *Curr Top Microbiol Immunol* 237:85–96 (1999)]. The second Ig-like loop also confers ligand specificity as shown by domain swapping experiments [Ferrara, *J Mol Med* 77:527–543 (1999)]. Receptor-ligand studies indicate that dimers formed by the VEGF family proteins are capable of binding two VEGF receptor molecules, thereby dimerizing VEGF receptors. The fourth Ig-like loop on VEGFR-1, and also possibly on VEGFR-2, acts as the receptor dimerization domain that links two receptor molecules upon binding of the receptors to a ligand dimer [Ferrara, *J Mol Med* 77:527–543 (1999)]. Although the regions of VEGF-A that bind VEGFR-1 and VEGFR-2 overlap to a large extent, studies have revealed two separate domains within VEGF-A that interact with either VEGFR-1 or VEGFR-2, as well as specific amino acid residues within these domains that are critical for ligand-receptor interactions. Mutations within either VEGF receptor-specific domain that specifically prevent binding to one particular VEGF receptor have also been recovered [Neufeld et al., *FASEB J* 13:9–22 (1999)].

VEGFR-1 and VEGFR-2 are structurally similar, share common ligands ($VEGF_{121}$ and $VEGF_{165}$), and exhibit similar expression patterns during development. However, the signals mediated through VEGFR-1 and VEGFR-2 by the same ligand appear to be slightly different. VEGFR-2 has been shown to undergo autophosphorylation in response to VEGF-A, but phosphorylation of VEGFR-1 under identical conditions was barely detectable. VEGFR-2 mediated signals cause striking changes in the morphology, actin reorganization, and membrane ruffling of porcine aortic endothelial cells recombinantly overexpressing this receptor. In these cells, VEGFR-2 also mediated ligand-induced chemotaxis and mitogenicity; whereas VEGFR-1-transfected cells lacked mitogenic responses to VEGF-A. Mutations in VEGF-A that disrupt binding to VEGFR-2 fail to induce proliferation of endothelial cells, whereas VEGF-A mutants that are deficient in binding VEGFR-1 are still capable of promoting endothelial proliferation. Similarly, VEGF stimulation of cells expressing only VEGFR-2 leads to a mitogenic response whereas comparable stimulation of cells expressing only VEGFR-1 also results in cell migration, but does not induce cell proliferation. In addition, phosphoproteins co-precipitating with VEGFR-1 and VEGFR-2 are distinct, suggesting that different signaling molecules interact with receptor-specific intracellular sequences.

The emerging hypothesis is that the primary function of VEGFR-1 in angiogenesis may be to negatively regulate the activity of VEGF-A by binding it and thus preventing its interaction with VEGFR-2, whereas VEGFR-2 is thought to be the main transducer of VEGF-A signals in endothelial cells. In support of this hypothesis, mice deficient in VEGFR-1 die as embryos while mice expressing a VEGFR-1 receptor capable of binding VEGF-A but lacking the tyrosine kinase domain survive and do not exhibit abnormal embryonic development or angiogenesis. In addition, analyses of VEGF-A mutants that bind only VEGFR-2 show that they retain the ability to induce mitogenic responses in endothelial cells. However, VEGF-mediated migration of monocytes is dependent on VEGFR-1, indicating that signaling through this receptor is important for at least one biological function. In addition, the ability of VEGF-A to prevent the maturation of dendritic cells is also associated with VEGFR-1 signaling, suggesting that VEGFR-1 may function in cell types other than endothelial cells. [Ferrara, *J Mol Med* 77:527–543 (1999); Zachary, *Intl J Biochem Cell Bio* 30:1169–1174 (1998)].

Neuropilin-1 was originally cloned as a receptor for the collapsin/semaphorin family of proteins involved in axon guidance [Stacker and Achen, *Growth Factors* 17:1–11 (1999)]. It is expressed in both endothelia and specific subsets of neurons during embryogenesis, and it thought to be involved in coordinating the developing neuronal and vascular system. Although activation of neuropilin-1 does not appear to elicit biological responses in the absence of the VEGF family tyrosine-kinase receptors, their presence on cells leads to more efficient binding of $VEGF_{165}$ and VEGFR-2 mediated responses. [Neufeld et al., *FASEB J* 13:9–22 (1999).] Mice lacking neuropilin-1 show abnormalities in the developing embryonic cardiovascular system. [Neufeld et al., *FASEB J* 13:9–22 (1999)].

Neuropilin-2 was identified by expression cloning and is a collapsin/semaphorin receptor closely related to neuropilin-1. Neuropilin-2 is an isoform-specific VEGF receptor in that it only binds $VEGF_{165}$. Like neuropilin-1, neuropilin-2 is expressed in both endothelia and specific neurons, and is not predicted to function independently due to its relatively short intracellular domain. The function of neuropilin-2 in vascular development is unknown [Neufeld et al., *FASEB J* 13:9–22 (1999); WO 99/30157].

Therapeutic Applications for VEGF Polypeptides and Antagonists

The discovery of VEGF-A as a key regulator of vascular development has spurred active research using VEGF-based therapeutic angiogenesis in cardiovascular medicine, as well as for treating diseases characterized by pathological angiogenesis with VEGF antagonists. Subsequent identification of additional VEGF family proteins and their roles in vascularization have also led to the development of therapies based on these growth factors [Ferrara and Alitalo, *Nature Med* 5:1359–1364 (1999)]. Animal studies of hindlimb ischemia, and myocardial ischemia using VEGF-A or VEGF-C, delivered by administration of recombinant protein or gene transfer using naked DNA or adenoviral vectors, implicate these molecules in promoting vascularization and increasing coronary blood flow. These promising results have led to clinical trials in which patients with limb ischemia were treated by arterial or intramuscular gene transfer of naked DNA encoding $VEGF_{165}$. Patients with myocardial ischemia or Burger's disease (thromboangiitis obliterans) were also injected locally with $VEGF_{165}$ plasmid DNA. Although these trials were not placebo-controlled, the patients showed clinical improvement and evidence of angiogenesis in ischemic tissues. Trials using gene transfer of VEGF-C naked DNA or gene therapy with $VEGF_{121}$ using adenoviral vectors to treat patients with myocardial ischemia are currently in Phase I [Ferrara, *J Mol Med* 77:527–543 (1999); Neufeld et al., *FASEB J* 13:9–22 (1999); Ferrara and Alitalo, *Nature Med* 5:1359–1364 (1999)]. The therapeutic effects of administering recombinant VEGF-A protein are also being tested in ongoing clinical trials. Results from a Phase I study of patients with coronary ischemia treated with intracoronary infusion of recombinant $VEGF_{165}$ show evidence of improved perfusion and collateralization. However, in the subsequent Phase II study, the patients did not show significant improvement over the placebo-controlled group. Other potential therapeutic uses for VEGF growth factors include using VEGF-C to promote lymphangiogenesis in patients whose axillary lymph nodes were removed during breast carcinoma surgery. Therapies using combinations of growth factors to promote vascularization in tissues may also prove to be preferable in treating certain diseases [Ferrara and Alitalo, *Nature Med* 5:1359–1364 (1999)].

Therapies based on inhibiting the activity of VEGF growth factors are being tested to treat disease states characterized by pathological angiogenesis. VEGF expression is upregulated in most human tumors including primary breast cancer and gastric carcinoma. Studies in mice indicate that tumor-associated angiogenesis and growth of the tumor cells can be inhibited by treating the animals with monoclonal antibodies against VEGF-A. Further animal studies showed that expression of a dominant negative VEGFR-2 mutant that prevents signaling through this receptor, or administration of recombinant VEGFR-1 or VEGFR-2 mutants, which only contain the extracellular portion of these receptors, suppresses growth of several tumor cell lines. These encouraging results led to clinical trials using humanized high affinity monoclonal antibodies against VEGF-A (rhuMAb VEGF) as VEGF-A inhibitors. Phase II studies using rhuMAb VEGF to treat non-small cell lung carcinoma, colorectal carcinoma, breast, and renal cell carcinoma are currently ongoing. Compounds targeting inhibition of VEGF-C activity are also being tested for therapeutic uses in cancer patients: small molecule inhibitors of VEGF-C are in Phase II trials, and monoclonal antibodies against VEGF-C are entering clinical trials.

Retinopathy associated with diabetes mellitus, occlusion of central retinal vein or prematurity has been correlated with increased levels of VEGF-A. Animal studies using monoclonal antibodies against VEGF-A or soluble VEGFR-1 or VEGFR-2 mutants containing only the extracellular domain fused to immunoglobulin γFc domain show suppression of retinal angiogenesis. VEGF-A is also detected in age-related macular degeneration (AMD), and its expression is thought to be the cause of neovascularization in this disease. Intravitreal delivery of recombinant humanized anti-VEGF-A Fab antibody fragment or injection of 2'-fluoropyrimidine RNA oligonucleotide ligands (aptamers) to treat AMD are currently in clinical trials. Compounds that inhibit the activity of VEGF growth factors may also be used to treat other disease states involving abnormal angiogenesis. These include ischemic-reperfusion related brain edema and injury, conditions associated with ovarian hyperplasia and hypervascularity such as the polycystic ovary syndrome, endometriosis, and ovarian hyperstimulation syndrome [Ferrara and Alitalo, *Nature Med* 5:1359–1364 (1999)].

From the foregoing discussion, it will be apparent that the VEGF family of growth factors, and inhibitors thereof, have tremendous potential as therapeutics. For example, such growth factors and inhibitors are useful to promote or inhibit angiogenesis where needed, such as in the treatment of ischemic disorders, the promotion of wound healing, or the inhibition or elimination of neoplastic disorders that are angiogenesis-dependent. However, the various naturally-occurring members of this growth factor family often bind multiple receptors, and the various known receptors are expressed on multiple cell types and have expression patterns that may vary depending on stage of development and the presence or absence of pathological conditions. The biological effects of any particular growth factor may be receptor-dependent, isoform dependent, and cell-type dependent. A desirable therapeutic effect mediated through one receptor may be accompanied by undesirable side-effects mediated through another receptor. Alternatively, a desirable therapeutic effect might be enhanced through stimulation of multiple receptors that cannot be stimulated with any single known growth factor that occurs in nature. Therefore, a need exists for novel peptide growth factors with their own unique profile of receptor binding and receptor-stimulating or receptor-inhibiting activities.

SUMMARY OF THE INVENTION

The present invention satisfies needs identified above by providing novel polypeptide binding molecules for naturally occurring vascular endothelial growth factor receptors, and polynucleotides that encode the novel polypeptides and are useful for recombinant expression of the polypeptides. For the purpose of describing the invention, the term "vascular endothelial growth factor" and the abbreviation "VEGF" (without modifier) are used herein in a generic sense, to describe any of a family of growth factor polypeptides including but not limited to Vascular Endothelial Growth Factor-A (VEGF-A), Vascular Endothelial Growth Factor-B (VEGF-B), Vascular Endothelial Growth Factor-C (VEGF-C), Vascular Endothelial Growth Factor-D (VEGF-D), Platelet Derived Growth Factor-A (PDGF-A), Platelet Derived Growth Factor-B (PDGF-B), Placenta Growth Factor (PlGF), and virally encoded VEGF-like molecules. VEGF-A is commonly referred to in the art as "Vascular Endothelial Growth Factor" or as "VEGF," but for clarity shall be referred to herein as VEGF-A or referred to as specific isoforms (e.g., $VEGF_{165}$) of VEGF-A.

For example, in one aspect, the invention provides a chimeric polypeptide comprising a plurality of peptide subunits derived from two or more naturally-occurring vertebrate vascular endothelial growth factor polypeptides that have different vascular endothelial growth factor receptor binding profiles, wherein the chimeric polypeptide binds at least one receptor of one of the naturally-occurring vascular endothelial growth factor polypeptides, and wherein the chimeric polypeptide has a different receptor binding profile than the naturally-occurring growth factor polypeptides. Isolated and purified chimeric polypeptides are preferred.

In this context, the term "naturally-occurring vertebrate vascular endothelial growth factor polypeptides" means polypeptides having the following characteristics:

(1) the polypeptide is encoded by genomic DNA of a vertebrate (e.g., a reptile, amphibian, bird, or mammal, preferably a bird or mammal, most preferably a mammal; especially a primate mammal such as a monkey, ape, or human) or is encoded by the genome of a vertebrate pathogen such as mammalian pox viruses;

(2) the polypeptide comprises all or a portion of an amino acid sequence that is expressed by a vertebrate (i.e., from transcription/translation of the vertebrate's genomic DNA or from virally-induced transcription/translation, in the case of polypeptides encoded by viral nucleic acids);

(3) the polypeptide or portion comprises a VEGF/PDGF homology domain (V/PHD) of about 70–150 amino acids that binds to naturally-occurring receptors and that is characterized in part by the amino acid motif: C-X(18–28)-P-X-C-X(4)-R-C-X-G-C(1–2)-X(6–12)-C-X(30–46)-C (SEQ ID NO: 1202), where X represents any amino acid and numbers in parentheses represent a permissible range of amino acids (e.g., X(18–28) represents a stretch of any 18–28 amino acids; C(1–2) represents one or two cysteine residues). The V/PHD usually includes eight conserved cysteines which form a cysteine knot motif similar to that found in human Vascular Endothelial Growth Factors A, B, C, and D (VEGF-A, -B, -C, and -D), and human platelet-derived growth factors (PDGFs). Preferred polypeptides or portions comprise a V/PHD that is characterized by the more particular amino acid motif C-X(22–24)-P-[PSR]-C-V-X(3)-R-C-X-G-C-C-X(6)-C-X(32–41)-C (SEQ ID NO: 1203), where amino acids in brackets (e.g., [PSR]) represent alternatives for a single position in the amino acid sequence; and (4) the polypeptide binds to at least one cell surface receptor that is expressed on endothelial cells that line vertebrate blood or lymphatic vessels or pericytes/smooth muscle cells that line and support blood vessels. Preferred polypeptides bind to a least one cell surface receptor that is expressed on endothelial cells.

Thus, the term "naturally-occurring vertebrate VEGF polypeptides" means polypeptides that have certain specified structural and functional properties. The term is not intended in this context to imply a source of origin. Thus, recombinantly produced polypeptides that satisfy the above criteria because they have an amino acid sequences and receptor binding properties of VEGF polypeptides that exist in nature are considered "naturally-occurring". Numerous exemplary naturally occurring vascular endothelial growth factor polypeptides are already known in the art, including but not limited to human Vascular Endothelial Growth Factor-A (VEGF-A), Vascular Endothelial Growth Factor-B (VEGF-B), Vascular Endothelial Growth Factor-C (VEGF-C), Vascular Endothelial Growth Factor-D (VEGF-D), Platelet Derived Growth Factor-A (PDGF-A), Platelet Derived Growth Factor-B (PDGF-B), Placenta Growth Factor (PlGF); mammalian and avian orthologs thereof (where the term "ortholog" means species homolog); and Vascular Endothelial Growth Factor E (VEGF-E), NZ2 VEGF, and the two VEGF-like proteins identified in strains D1701 and NZ10, which have been identified in poxviruses. The use of naturally occurring human VEGF's is preferred for the purposes of developing chimeric molecules that are useful as human therapeutics, in order to minimize the likelihood of developing chimerics that generate an immune response in humans. However, in many cases there is very high homology between VEGF species orthologs, especially in receptor binding domains, and it is contemplated that non-human naturally occurring VEGFs also can be used to generate chimeric molecules for use in treating humans. Although the invention is described herein in part with reference to particular VEGF-A/VEGF-C chimeric polypeptides, chimeric polypeptides derived from any pair, or three, or four, or more of the VEGFs described herein or their species orthologs is particularly contemplated.

As used to describe this aspect of the invention, the term "chimeric requires that the amino acid sequence of the chimeric molecule include at least one stretch of one or more amino acids (preferably stretches of 1, 2, 3, 4, 5, 6, 7, 8, 9, 10, 11, 12, 13, 14, 15, 16, 17, 18, 19, 20, or more amino acids) from each of the naturally-occurring VEGF's from which it was derived. Thus, the chimeric polypeptide is a "hybrid" or "mosaic" of two or more polypeptides. By "chimeric" is meant that the polypeptide of the invention is not identical to any naturally occurring VEGF sequence (or fragment of a natural VEGF sequence).

As used to describe this aspect of the invention, the term "derived from" "(as in "derived from two or more naturally occurring VEGF polypeptides") means that, when the amino acid sequences of the chimeric polypeptide and the two or more naturally occurring VEGF's are aligned using a standard algorithm, substantially all of the amino acids in the chimeric polypeptide are aligned with an identical residue in one or more of the naturally occurring VEGF's from which the chimeric was derived. Standard protein alignment algorithms, for example, the clustral method [*Nucl Acids Res* 22:4673–80 (1994)], the Jotun-Hein method [Methds Enzymol 183:626–645 (1990)], or the Feng-Doolittle method [*J Mol Evol* 25:351–360 (1987)], can be used to align naturally-occurring vertebrate vascular endothelial growth factor polypeptides, such alignments being greatly facilitated by the presence of the eight highly conserved cysteines dispersed through the V/PHD. Thus, it is readily established that a chimeric polypeptide is "derived from" two or more naturally occurring VEGF's by performing an alignment using any generally accepted protein alignment algorithm. If, after aligning the amino acid sequences of a chimeric polypeptide and two or more naturally occurring VEGF's using any standard algorithm, substantially all of the amino acids in the chimeric polypeptide are aligned with an identical residue in one or more of the naturally occurring VEGF's, then the chimeric polypeptide was derived from the naturally occurring VEGFs. In one embodiment, all of the amino acids of the chimeric molecule will align in this manner. However, the use of the term "substantially all" reflects the fact that techniques described herein for making chimeric polypeptides will sometimes introduce mutations such as insertions, deletions, or substitutions, preventing 100% correlation to parent sequences. In such cases, at least about 90%, 92%, 94%, 95%. 96%, 97%, 98%, or 99% of the residues of the chimeric polypeptide will align with identical residues from at least one of the natural VEGF's.

When presented with a chimeric polypeptide of the invention that aligns perfectly or substantially with the natural VEGF polypeptides from which it was derived, it is within the skill of the art to intentionally introduce mutations (especially conserved mutations) into the chimeric polypeptide and test such a modified chimeric polypeptide for its receptor binding profile. Modifications of chimeric polypeptides (especially conserved amino acid substitutions) that do not introduce substantial changes in receptor binding profile are intended as equivalents within the scope of the present invention.

In the context of such chimeric polypeptides, the term "plurality of peptide subunits" means two or more peptide subunits. Exemplified herein are chimeric polypeptides obtained by fragmenting two naturally occurring VEGF cDNA's (human VEGF-A and human VEGF-C) into nine subunits of about 8–16 codons each, recombining these fragments into all 512 permutations of the nine subunits (maintaining subunit order), and expressing the resultant chimeric cDNAs. The number and the size of fragments is not intended as a critical feature. In preferred embodiments, plurality comprises 2, 3, 4, 5, 6, 7, 8, 9, 10, 11, 12, 13, 14, 15, 16, 17, 18, 19, 20, 21, 22, 23, 24, or 25 or more subunits. As exemplified herein, the "subunits" are joined by peptide bonds to form a polypeptide chain.

In the context of chimeric polypeptides of the invention or naturally occurring VEGF polypeptides, determination of "vascular endothelial growth factor receptor binding profile" means the determination of the receptors to which a polypeptide will bind and the receptors to which it will not. Known VEGF receptors, including VEGFR-1, VEGFR-2, and VEGFR-3, are described in greater detail elsewhere herein. Known PDGF receptors are also described in greater detail elsewhere herein. Where a chimeric polypeptide has been derived in part from a naturally occurring PDGF sequence, screening the chimeric polypeptide for binding to PDGF receptors is contemplated as part of the receptor binding profile determination.) By way of example, if a chimeric polypeptide was derived from a VEGF-A that binds to VEGFR-1 and VEGFR-2 and from a VEGF-C that binds to VEGFR-2 and VEGFR-3, the chimeric polypeptide has a different receptor binding profile than either of its parent molecules if it binds to only one of the three receptors, or if it binds to all three receptors, or if it binds to VEGFR-1 and VEGFR-3 but not VEGFR-2. In one preferred embodiment, the invention provides chimeric polypeptides wherein the chimeric polypeptide binds to at least two VEGF receptors bound by the two or more naturally occurring vertebrate VEGF polypeptides, and wherein each of the naturally-occurring VEGF polypeptides from which the chimeric polypeptide was derived fail to bind to one or more of the at least two VEGF polypeptides.

Screening polypeptides of the invention for binding to the neuropilins NP-1 and NP-2 are not contemplated as part of the receptor binding profile determination, because the portions of VEGF (and other family members) responsible for NP-1 and NP-2 binding are portions outside of the V/PHD core region. NP-1 binding is mediated by amino acid residues 142 to 185 of SEQ ID NO: 2 for VEGF-A, and amino acid residues 138 to 182 for VEGF-B [Soker et al., *J Biol Chem* 271:5761–7 (1996); Makinen et al., *J Biol Chem* 274:21217–22 (1999)]. As explained below, addition of upstream or downstream sequences to chimeric polypeptides of the invention is contemplated, and some added sequences are contemplated to result in NP-1 or NP-2 binding.

The present invention is believed to provide the first disclosure of a polypeptide that is capable of binding to all of VEGFR-1, VEGFR-2, and VEGFR-3. All polypeptides having this receptor binding profile are intended as within the scope of the invention.

Naturally occurring VEGF polypeptides generally bind their respective receptors with high affinity, which is generally understood in this context to mean binding with a sub-nanomolar dissociation constant. For example, VEGF-A binds VEGFR-1 and VEGFR-2 with Kd of approximately 16 pM and 760 pM, respectively; and VEGF-C binds VEGFR-2 and VEGFR-3 with Kd of approximately 410 pM and 135 pM, respectively. Because it is possible to administer a therapeutic growth factor protein to achieve concentrations exceeding normal serum concentrations, and to formulate such polypeptides to increase biological half-life, it is contemplated that chimeric polypeptides having less receptor affinity (i.e., higher dissociation constants) nonetheless will be useful as receptor agonists and antagonists. For the purposes of scoring receptor binding of chimeric polypeptides, a 50 nanomolar dissociation constant cutoff is selected. Chimeric polypeptides that bind a receptor with a dissociation constant of less than 50 nanomolar as determined by any conventional and recognized method, such as those described in Coligan et al., *Current Protocols in Protein Science*, Vol. 2, New York, John Wiley & Sons, Inc., p. A.5A.1–A.5A.40 (1998), incorporated herein by reference, is scored as binding to a receptor, and polypeptides with lower affinities are scored as non-binding.

It is well known in the literature that naturally occurring VEGF's are expressed as splice variants and/or as pre-protein molecules and/or as prepro-protein molecules that undergo proteolytic processing. Chimeric polypeptides of the invention include chimeric (hybrid) receptor binding domains as explained in the preceding paragraphs, and optionally may include additional upstream or downstream sequences from naturally occurring VEGF's, including upstream and downstream sequences that are present in mature isoforms of naturally occurring circulating VEGF's; and/or upstream or downstream pro-peptide sequences that are removed during normal intracellular or extracellular processing. By way of illustration, the chimeric polypeptides described in Example 1 were prepared using residues 34–135 (SEQ ID NO: 2) of VEGF-A and using 112–216 of human prepro-VEGF-C (SEQ ID NO: 22). Chimeric polypeptides of the invention include the peptides actually exemplified, and also include such peptides modified by the addition of upstream or downstream VEGF-A or VEGF-C sequences from SEQ ID NOs: 2 or 22. With respect to VEGF-A/VEGF-C chimeric polypeptides as exemplified herein, the addition of upstream and downstream sequences that correspond with amino- and/or carboxyl-terminal sequences characteristic of natural VEGF-A or VEGF-C isoforms is particularly contemplated.

It is also well known in the literature to recombinantly express proteins with an initiator methionine, with a heterologous signal peptide, with one or more tag sequences to facilitate purification, as fusions with other polypeptides, and the like. It is also well known to modify polypeptides with glycosylation, pegylation, or other modifications, some of which improve stability, circulating half-life, or (in the case of glycosylation) may make the polypeptide more similar to endogenous vascular endothelial growth factors. Chimeric polypeptides according to the invention may comprise any such modifications and additions to the amino acid sequence derived from two or more naturally-occurring vertebrate vascular endothelial growth factor polypeptides.

In addition to chimeric molecules having different receptor binding profiles, an additional aspect of the invention includes chimeric molecules having increased receptor binding affinity. For example, the invention provides a chimeric polypeptide comprising a plurality of peptide subunits derived from two or more naturally-occurring vertebrate vascular endothelial growth factor polypeptides, wherein the chimeric polypeptide binds at least one naturally-occurring vascular endothelial growth factor receptor with an increased binding affinity compared to the binding affinity of the two or more naturally-occurring vascular endothelial growth factors for the receptor. Chimeric molecules that bind a receptor with greater affinity than naturally occurring VEGF's are among the preferred chimeric molecules of the invention, even if the receptor binding profile for the chimeric molecules is identical to that of a naturally occurring VEGF. Increased receptor binding affinity is expected to correlate with great potency as receptor activators or inhibitors. Generally, dissociation constants ($K_d$) determined by any accepted procedure are indicative of receptor affinity, with lower $K_d$ indicative of greater binding affinity. Particularly contemplated are chimeric molecules that display any reduction in $K_d$ that is statistically significant at a level of p<0.05 in side-by-side tests [see, e.g., Coligan et al., *Current Protocols in Protein Science*, Vol. 2, New York, John Wiley & Sons, Inc., p. A.5A.1–A.5A.40 (1998)] compared to naturally-occurring molecules from which the chimera was derived. Chimeras that show a twenty percent reduction in $K_d$ (i.e., increased binding affinity) with respect to a VEGF receptor are preferred. Reductions of 33% or 50% are highly preferred. A 3-fold reduction (e.g., a $K_d$ of 33.3 pM for a chimeric polypeptide compared to a 100 pM $K_d$ of a naturally occurring VEGF), 5-fold reduction, 10-fold reduction, or 20-fold reduction in dissociation constants or is very highly preferred.

Another related preferred class of chimeric molecules are those molecules that display any reduction in $EC_{50}$ concentration that is statistically significant at a level of $p<0.05$ in side-by-side tests compared to naturally-occurring molecules from which the chimera was derived. Chimeras that show a twenty percent reduction in $EC_{50}$ (i.e., increased binding affinity) with respect to a VEGF receptor are preferred. Reductions of 33% or 50% are highly preferred. $EC_{50}$, or the half effective concentration, is the concentration that produces 50% of a maximal effect. An exemplary assay for determining the $EC_{50}$ of a putative ligand for a specific receptor is set forth in Example 6, below.

The Examples set forth below provide a description of the synthesis and assaying of numerous specific hybrid polypeptides of the invention, every one of which is itself intended as an aspect of the invention. A preferred group of hybrid polypeptides from among the exemplified polypeptides are polypeptides that comprise an amino acid sequence of the formula:

$$NH_2\text{-}X_1\text{-}X_2\text{-}X_3\text{-}X_4\text{-}X_5\text{-}X_6\text{-}X_7\text{-}X_8\text{-}X_9\text{-}COOH$$

wherein $X_1$ comprises an amino acid sequence selected from the group consisting of amino acids 3–11 of SEQ ID NO: 128 and amino acids 3–11 of SEQ ID NO:137; wherein $X_2$ comprises an amino acid sequence selected from the group consisting of SEQ ID NOs: 129 and 138; wherein $X_3$ comprises an amino acid sequence selected from the group consisting of SEQ ID NOs: 130 and 139; wherein $X_4$ comprises an amino acid sequence selected from the group consisting of SEQ ID NOs: 131 and 140; wherein $X_5$ comprises an amino acid sequence selected from the group consisting of SEQ ID NOs: 132 and 141; wherein $X_6$ comprises an amino acid sequence selected from the group consisting of SEQ ID NOs: 133 and 142; wherein $X_7$ comprises an amino acid sequence selected from the group consisting of SEQ ID NOs: 134 and 143; wherein $X_8$ comprises an amino acid sequence selected from the group consisting of SEQ ID NOs: 135 and 144; wherein $X_9$ comprises an amino acid sequence selected from the group consisting of SEQ ID NOs: 136 and 145; wherein $NH_2\text{-}X_1\text{-}X_2\text{-}X_3\text{-}X_4\text{-}X_5\text{-}X_6\text{-}X_7\text{-}X_8\text{-}X_9\text{-}COOH$ is not identical to amino acids 34 to 135 of SEQ ID NO: 2 or amino acids 112 to 216 of SEQ ID NO: 22; and wherein the polypeptide binds to at least one receptor selected from the group consisting of human VEGFR-1, human VEGFR-2, and human VEGFR-3. As described below in greater detail, each of the specified amino acid sequence pairs (e.g., SEQ ID NO: 128 and 137) are encoded by a VEGF-A cDNA fragment or a VEGF-C cDNA fragment that align with each other when the receptor binding domains of VEGF-A and VEGF-C are aligned to maximize sequence homology, using standard alignment algorithms.

With respect to the foregoing genus of hybrid of polypeptides, one preferred subgenus comprises those polypeptides which bind to exactly one receptor selected from the group consisting of human VEGFR-1, human VEGFR-2, and human VEGFR-3. Initial screens suggest that the following specific constructs (described below in detail) satisfy this criteria: 82-14, 82-16, 22-3, 72-6, 12-14, 12-16, 32-9, 32-11, 32-14, 32-15, 32-16, 52-9, 52-11, 52-14, 52-15, 14-7, 23-10, 23-12, 23-14, 33-1, 33-3, 33-6, 33-9, 53-1, 53-3, 53-7, 62-8, 62-10, 62-13, 63-3, 63-6, 73-7, 73-15, -8, 74-10, 74-12, 11-9, 11-13, 12-1, 12-5, 81-9, 81-13, 13-9, 13-11, 13-13, 13-15, 14-1, 14-5, 41-1, 43-1, 83-9, 83-13, 83-15, 61-1, 61-3, 62-1, 82-5, 84-1, 84-5.

Another preferred subgenus comprises those hybrid polypeptides that bind to VEGFR-1 and VEGFR-3, but not to VEGFR-2. Initial screens suggest that the following specific constructs satisfy this criteria: 12-9, 12-13, 14-9, 82-9, 82-13, 84-9.

A highly preferred subgenus comprises hybrid polypeptides of the invention that bind VEGFR-1, VEGFR-2, and VEGFR-3. Initial screens suggest that the following specific constructs satisfy this criteria: 12-7, 12-11, 82-11, 84-11.

Other subgenuses include hybrid polypeptides that bind VEGFR-1 and VEGFR-2 (both of which are bound by VEGF-A) but not VEGFR-3; and hybrid polypeptides that bind VEGFR-2 and VEGFR-3 (both of which are bound by fully processed VEGF-C) but not VEGFR-1.

As taught in greater detail below, the fourth fragment ($X_4$) appears to include residues that are important for conferring VEGFR-3 binding affinity. For this reason, another preferred genus of the hybrid polypeptides are those wherein $X_4$ comprises SEQ ID NO: 140, and wherein the polypeptide binds to VEGFR-3. Fragments 5 and 8 of VEGF-C also appear to contribute to VEGFR-3 binding. Thus, highly preferred are polypeptides further characterized by $X_5$ comprising SEQ ID NO: 141, and/or $X_8$ comprising SEQ ID NO: 144.

Similarly, the data below suggests that fragments 2 and 7 of VEGF-A contribute to VEGF-R1 binding. Thus, another preferred gene of the hybrid polypeptides are those wherein $X_2$ comprises SEQ ID NO: 129, and wherein the polypeptide binds to VEGFR-1. In a highly preferred embodiment, $X_7$ comprises SEQ ID NO: 134. In an embodiment where it is desirous for this polypeptide also to bind to VEGFR-3, a preferred construct is one wherein $X_4$ comprises SEQ ID NO: 140. To confer VEGFR-3 binding, it is still more preferable for $X_5$ to comprise SEQ ID NO: 141, and/or for $X_8$ to comprise SEQ ID NO: 144.

The recombination experiments described below to generate hybrid molecules were performed only with receptor binding domains of human VEGF-A and VEGF-C, rather than with sequences corresponding to natural secreted forms of VEGF-A and VEGF-C or pre-protein or prepro-protein sequences. However, routine recombinant DNA techniques, such as those described in Ausubel, et al. (Eds.), *Protocols in Molecular Biology*, John Wiley & Sons (1994–1999) or Sambrook et al., (Eds.), *Molecular Cloning: A Laboratory Manual*, Cold Spring Harbor Laboratory Press: Cold Spring Harbor, N.Y. (1989), can be used to join polynucleotides encoding the hybrid proteins with polynucleotides encoding VEGF-A or VEGF-C sequences that are found upstream or downstream of the receptor binding domain in naturally-occurring proteins, especially sequences found in naturally-occurring secreted and circulating forms of VEGF-A or VEGF-C.

Thus, the invention provides a polypeptide comprising an amino acid sequence of the formula $X_N$-V/PHD-$X_C$, wherein $X_N$ is selected from the group consisting of amino acids 1–34 of SEQ ID NO: 2, amino acids 1–111 of SEQ ID NO: 22, amino acids 1–34 of SEQ ID NO: 147, or fragments thereof;

wherein V/PHD is a chimeric polypeptide as described elsewhere herein;

wherein $X_C$ is selected from the group consisting of amino acids 136–191 of SEQ ID NO: 2, amino acids 217–419 of SEQ ID NO: 22, amino acids 136–232 of SEQ ID NO: 147, or fragments thereof; and wherein $X_N$ and $X_C$ are each identical to amino acid sequence in a naturally occurring human VEGF-A or VEGF-C precursor protein or a naturally occurring human VEGF-A or VEGF-C isoform.

In one specific variation, the invention provides hybrid polypeptides as described above, wherein the polypeptide further includes one or more amino acid sequences selected from the group consisting of a prepro-VEGF-C signal peptide, a prepro-VEGF-C amino-terminal propeptide, and a prepro-VEGF-C carboxy-terminal pro-peptide.

Expression of hybrid polypeptides of the invention is not restricted to expression only with naturally-occurring flanking VEGF-A or VEGF-C sequences, however. Expression of polypeptides of the invention in bacteria may be accomplished by including an initiator methionine or methionine-lysine upstream of the hybrid VEGF sequences, whereas expression and secretion in mammalian cells is most conveniently accomplished by including at least a signal peptide. Thus, in one embodiment, the invention provides a polypeptide as described above, wherein the polypeptide further includes an amino terminal methionine residue or an amino-terminal Met-Lys sequence. In another embodiment, the polypeptide further includes a signal peptide amino acid sequence connected to the amino acid sequence of the formula $NH_2$-$X_1$-$X_2$-$X_3$-$X_4$-$X_5$-$X_6$-$X_7$-$X_8$-$X_9$-COOH.

Expression of polypeptides of the invention as fusions with other heterologous sequences, such as tag sequences to facilitate purification or expression as part of larger fusion peptides also is contemplated. An exemplary tag of this type is a poly-histine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention. Exemplary fusions include use of commercially available vectors that express a desired polypeptide as part of glutathione-S-transferase (GST) fusion product. After cleavage of the GST component from the desired polypeptide, an additional glycine residue at position -1 may remain. Variants which result from expression in other vector systems are also contemplated.

By virtue of the receptor binding and activity assays described herein, the present application also provides variants (analogs) of the hybrid polypeptides of the invention, wherein one or more amino acids of the hybrid peptide amino acid sequence has been added, deleted, or substituted by another amino acid, and wherein the hybrid retains the receptor binding and/or a biological activity characteristic of the hybrid polypeptide.

Substitution variants wherein merely conservative substitutions have been introduced (e.g., by modification of polynucleotides encoding polypeptides of the invention) are intended as equivalents of hybrid polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions based on amino acid side chain properties are set out in the table immediately below, using standard one letter abbreviations.

| SIDE CHAIN CHARACTERISTIC | AMINO ACID |
|---|---|
| Aliphatic | |
| Non-polar | G, A, P, I, L, V |
| Polar-uncharged | C, S, T, M, N, Q |
| Polar-charged | D, E, K, R |
| Aromatic | F, W, Y |
| Other | N, Q, D, E |

Alternatively, conservative amino acids can be grouped as described in Lehninger, [*Biochemistry*, Second Edition; Worth Publishers, Inc. NY:N.Y. (1975), pp. 71–77] as set out in the table immediately below.

| | |
|---|---|
| Non-polar (hydrophobic) side chain | |
| Aliphatic: | A, L, I, V, P |
| Aromatic: | F, W |
| Sulfur-containing: | M |
| Borderline: | G |
| Uncharged-polar side chain | |
| Hydroxyl: | S, T, Y |
| Amides: | N, Q |
| Sulfhydryl: | C |
| Borderline: | G |
| Positively Charged (Basic): | K, R, H |
| Negatively Charged (Acidic): | D, E |

The following table provides still an another alternative, exemplary set of conservative amino acid substitutions. Both one letter and three letter abbreviations are shown:

| Original Residue | Conservative Substitutions |
|---|---|
| Ala (A) | Val, Leu, Ile |
| Arg (R) | Lys, Gln, Asn |
| Asn (N) | Gln, His, Lys, Arg |
| Asp (D) | Glu |

-continued

| Original Residue | Conservative Substitutions |
|---|---|
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Vat, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

For many proteins, the effects of any individual or small group of amino acid changes is unlikely to significantly alter biological properties, especially if the changes are conservative substitutions, provided the changes are not introduced at critical residues. Preferred variants of the hybrid polypeptides of the invention share at least about 70%, 80%, 90%, 95%, 96%, 97%, 98%, or 99% amino acid identity with hybrids that consist entirely of amino acid sequences derived from naturally occurring VEGF's.

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403–410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Preferred parameters for a polypeptide sequence comparison include the following:
Algorithm: Needleman et al., J. Mol. Biol., 48, 443–453 (1970);
Comparison matrix: BLOSUM 62 from Henikoff et al., Proc. Natl. Acad. Sci. USA, 89:10915–10919 (1992);
Gap Penalty: 12
Gap Length Penalty: 4
Threshold of Similarity: 0
Preferred parameters for nucleic acid molecule sequence comparisons include the following:

Algorithm: Needleman et al., J. Mol Biol., 48:443–453 (1970);
Comparison matrix: matches=+10, mismatch=0
Gap Penalty: 50
Gap Length Penalty: 3

Thus, in still another embodiment, the invention provides a polypeptide comprising a non-naturally occurring vascular endothelial growth factor amino acid sequence, wherein said non-naturally occurring vascular endothelial growth factor amino acid sequence consists of an amino acid sequence that is at least 95% identical to an amino acid sequence of the formula:

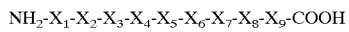

$$NH_2\text{-}X_1\text{-}X_2\text{-}X_3\text{-}X_4\text{-}X_5\text{-}X_6\text{-}X_7\text{-}X_8\text{-}X_9\text{-}COOH$$

wherein $X_1$ comprises an amino acid sequence selected from the group consisting of amino acids 3–11 of SEQ ID NO: 128 and amino acids 3–11 of SEQ ID NO: 137; wherein $X_2$ comprises an amino acid sequence selected from the group consisting of SEQ ID NOs: 129 and 138; wherein $X_3$ comprises an amino acid sequence selected from the group consisting of SEQ ID NOs: 130 and 139; wherein $X_4$ comprises an amino acid sequence selected from the group consisting of SEQ ID NOs: 131 and 140; wherein $X_5$ comprises an amino acid sequence selected from the group consisting of SEQ ID NOs: 132 and 141; wherein $X_6$ comprises an amino acid sequence selected from the group consisting of SEQ ID NOs: 133 and 142; wherein $X_7$ comprises an amino acid sequence selected from the group consisting of SEQ ID NOs: 134 and 143; wherein $X_8$ comprises an amino acid sequence selected from the group consisting of SEQ ID NOs: 135 and 144; wherein $X_9$ comprises an amino acid sequence selected from the group consisting of SEQ ID NOs: 136 and 145; and wherein the polypeptide binds to at least one receptor selected from the group consisting of human VEGFR-1, human VEGFR-2, and human VEGFR-3. In a preferred embodiment, $NH_2\text{-}X_1\text{-}X_2\text{-}X_3\text{-}X_4\text{-}X_5\text{-}X_6\text{-}X_7\text{-}X_8\text{-}X_9\text{-}COOH$ is not identical to amino acids 34 to 135 of SEQ ID NO: 2 or amino acids 112 to 216 of SEQ ID NO: 22.

By "non-naturally occurring vascular endothelial growth factor amino acid sequence" is meant a sequence that is not identical to any known, naturally occurring amino acid sequence, such as, in this case, receptor binding domains from known VEGF-A or VEGF-C sequences.

Stated more generally, the invention provides a polypeptide that comprises an amino acid sequence that is at least about 70%, 80%, 90%, 95%, 96%, 97%, 98%, or 99% identical to any specific amino acid sequence of the invention, and that binds at least one of the naturally-occurring vascular endothelial growth factor or platelet derived growth factor receptors, and that has a different receptor binding profile or an improved receptor binding affinity than a naturally-occurring growth factor polypeptide. Polypeptides that satisfy the percent identity criteria and that display the same receptor binding profile as the referent polypeptide are especially contemplated. For example, the invention provides a polypeptide that comprises an amino acid sequence that is at least about 70%, 80%, 90%, 95%, 96%, 97%, 98%, or 99% identical to the amino acid sequences encoded by constructs 12-7 (SEQ ID NO: 63), 12-11 (SEQ ID NO: 71), 82-11, or 84-11, wherein the polypeptide binds VEGFR-1, VEGFR-2, and VEGFR-3.

In yet another aspect, the invention provides a dimeric protein molecule comprising a first polypeptide associated with a second polypeptide, wherein at least one of the polypeptides is a polypeptide according to the present invention. The association between the polypeptides may be by way of covalent bonding (e.g., disulfide bonding) or non-covalent bonding of polypeptide chains (e.g., hydrogen bonding, bonding due to stable or induced dipole-dipole interactions, bonding due to hydrophobic or hydrophilic interactions, combinations of these bonding mechanisms, and the like).

In another embodiment, the invention provides polynucleotides (e.g., cDNA, cDNA with introns introduced to facilitate expression in eukaryotic systems, synthetic DNA, RNA, or combinations thereof, single or double stranded) that comprise a nucleotide sequence encoding the amino acid sequence of the polypeptides of the invention. Purified and isolated polynucleotides are preferred. Due to the well-known degeneracy of the genetic code, several polynucleotides sequences exist that encode each polypeptide amino acid sequence of the invention. Such polynucleotides are useful for recombinantly expressing the polypeptides of the invention.

The invention also embraces polynucleotides that encode VEGF receptor binding polypeptides and that hybridize under moderately stringent or high stringency conditions to the complete non-coding strand, or complement, of the polynucleotides specifically described herein that encode VEGF receptor binding polypeptides. This genus of polynucleotides embraces polynucleotides that encode polypeptides with one or a few amino acid differences (additions, insertions, or deletions) relative to amino acid sequences specifically taught herein. Such changes are easily introduced by performing site directed mutagenesis, for example, or by substituting a fragment from a non-human ortholog VEGF-A or VEGF-C polypeptide for a fragment of a human VEGF-A or VEGF-C polypeptide used to construct the hybrid polypeptides of the invention.

Exemplary highly stringent hybridization conditions are as follows: hybridization at 65° C. for at least 12 hours in a hybridization solution comprising 5×SSPE, 5×Denhardt's, 0.5% SDS, and 2 mg sonicated non-homologous DNA per 100 ml of hybridization solution; washing twice for 10 minutes at room temperature in a wash solution comprising 2×SSPE and 0.1% SDS; followed by washing once for 15 minutes at 65° C. with 2×SSPE and 0.1% SDS; followed by a final wash for 10 minutes at 65° C. with 0.1×SSPE and 0.1% SDS. Moderate stringency washes can be achieved by washing with 0.5×SSPE instead of 0.1×SSPE in the final 10 minute wash at 65° C. Low stringency washes can be achieved by using 1×SSPE for the 15 minute wash at 65° C., and omitting the final 10 minute wash. It is understood in the art that conditions of equivalent stringency can be achieved through variation of temperature and buffer, or salt concentration as described Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook et al., (Eds.), *Molecular Cloning: A Laboratory Manual*, Cold Spring Harbor Laboratory Press: Cold Spring Harbor, N.Y. (1989), pp. 9.47 to 9.51. For example, the invention provides a polynucleotide that comprises a nucleotide sequence that hybridizes under moderately stringent or high stringency hybridization conditions to any specific nucleotide sequence of the invention, and that encodes a polypeptide that binds at least one of the naturally-occurring vascular endothelial growth factor or platelet derived growth factor receptors, and that has a different receptor binding profile or an improved receptor binding affinity than a naturally-occurring growth factor polypeptide. Polynucleotides that satisfy the hybridization criteria and that display the same receptor binding profile as the referent polynucleotide are especially contemplated. For example, the invention provides a polynucleotide that comprises a nucleotide sequence that hybridizes under moderately stringent or high stringency hybridization conditions to the nucleotide sequences taught herein for constructs 12-7 (SEQ ID NO: 62), 12-11 (SEQ ID NO: 70), 82-11, or 84-11, wherein the polynucleotide encodes a polypeptide that binds VEGFR-1, VEGFR-2, and VEGFR-3.

In a related embodiment, the invention provides a polynucleotide that comprises a nucleotide sequence that is at least 80%, 85%, 90%, 95%, 97%, 98%, or 99% identical to any specific nucleotide sequence of the invention, and that encodes a polypeptide that binds at least one of the naturally-occurring vascular endothelial growth factor or platelet derived growth factor receptors, and that has a different receptor binding profile or an improved receptor binding affinity than a naturally-occurring growth factor polypeptide. Polynucleotides that satisfy the percent identity criteria and that display the same receptor binding profile as the referent polynucleotide are especially contemplated. For example, the invention provides a polynucleotide that comprises a nucleotide sequence that is at least 95% identical to the nucleotide sequences taught herein for constructs 12-7 (SEQ ID NO: 62), 12-11 (SEQ ID NO: 70), 82-11, or 84-11, wherein the polynucleotide encodes a polypeptide that binds VEGFR-1, VEGFR-2, and VEGFR-3.

In a related embodiment, the invention provides vectors comprising a polynucleotide of the invention. Such vectors are useful, e.g., for amplifying the polynucleotides in host cells to create useful quantities thereof. In preferred embodiments, the vector is an expression vector wherein the polynucleotide of the invention is operatively linked to a polynucleotide comprising an expression control sequence. Autonomously replicating recombinant expression constructs such as plasmid and viral DNA vectors incorporating polynucleotides of the invention are specifically contemplated. Expression control DNA sequences include promoters, enhancers, and operators, and are generally selected based on the expression systems in which the expression construct is to be utilized. Preferred promoter and enhancer sequences are generally selected for the ability to increase gene expression, while operator sequences are generally selected for the ability to regulate gene expression. Expression vectors are useful for recombinant production of polypeptides of the invention. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Vectors also are useful for "gene therapy" treatment regimens, wherein a polynucleotide that encodes a polypeptide of the invention is introduced into a subject in need of treatment involving the modulation (stimulation or blockage) of vascular endothelial growth factor receptors, in a form that causes cells in the subject to express the polypeptide of the invention in vivo.

In another related embodiment, the invention provides host cells, including prokaryotic and eukaryotic cells, that are transformed or transfected (stably or transiently) with polynucleotides of the invention or vectors of the invention. Polynucleotides of the invention may be introduced into the host cell as part of a circular plasmid, or as linear DNA comprising an isolated protein coding region or a viral vector. Methods for introducing DNA into the host cell well known and routinely practiced in the art include transformation, transfection, electroporation, nuclear injection, or fusion with carriers such as liposomes, micelles, ghost cells, and protoplasts. As stated above, such host cells are useful for amplifying the polynucleotides and also for expressing the polypeptides of the invention encoded by the polynucleotide. Such host cells are useful in assays as described herein. For expression of polypeptides of the invention, any host cell is acceptable, including but not limited to bacterial, yeast, plant, invertebrate (e.g., insect), vertebrate, and mammalian host cells. For developing therapeutic preparations, expression in mammalian cell lines, especially human cell lines, is preferred. Use of mammalian host cells is expected to provide for such post-translational modifications (e.g., glycosylation, truncation, lipidation, and phosphorylation) as may be desirable to confer optimal biological activity on recombinant expression products of the invention. Glycosylated and non-glycosylated forms of polypeptides are embraced by the present invention. Similarly, the invention further embraces polypeptides described above that have been covalently modified to include one or more water soluble polymer attachments such as polyethylene glycol, polyoxyethylene glycol, or polypropylene glycol.

Polypeptides of the invention also may be chemically synthesized.

In still another related embodiment, the invention provides a method for producing a vascular endothelial growth factor receptor binding protein, comprising the steps of growing a host cell of the invention in a nutrient medium and isolating the polypeptide or variant thereof from the cell or the medium. Isolation of the polypeptide from the cells or from the medium in which the cells are grown is accomplished by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein. Cleavage of the fusion component may produce a form of the desired protein having additional amino acid residues as a result of the cleavage process.

Also within the scope of the invention are compositions comprising polypeptides or polynucleotides of the invention. In a preferred embodiment, such compositions comprise one or more polynucleotides or polypeptides of the invention that have been formulated with a pharmaceutically acceptable (e.g., sterile and non-toxic) diluent or carrier. Liquid, semisolid, or solid diluents that serve as pharmaceutical vehicles, excipients, or media are preferred. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter. Such formulations are useful, e.g., for administration of polypeptides or polynucleotides of the invention to mammalian (including human) subjects in therapeutic regimens.

Similarly, the invention provides for the use of polypeptides or polynucleotides of the invention in the manufacture of a medicament for the treatment of disorders described herein, including but not limited to disorders characterized by undesirable endothelial cell proliferation and/or disorders characterized by ischemia and/or vessel occlusion, wherein neovascularization is desirable.

In a related embodiment, the invention provides a kit comprising a polynucleotide, polypeptide, or composition of the invention packaged in a container, such as a vial or bottle, and further comprising a label attached to or packaged with the container, the label describing the contents of the container and providing indications and/or instructions regarding use of the contents of the container to treat one or more disease states as described herein.

In yet another aspect, the present invention provides methods of producing polypeptides having novel VEGF receptor binding and stimulation properties, and methods for producing polynucleotides that encodes such polypeptides. For example, the invention provides a method for making a polynucleotide that encodes a polypeptide that modulates the growth of mammalian endothelial cells or mammalian pericytes/smooth muscle cells; comprising the steps of: preparing polynucleotides that encode amino acid fragments of at least two vertebrate vascular endothelial growth factor polypeptides; commingling the polynucleotides under conditions wherein the polynucleotides recombine to form hybrid polynucleotides; expressing the hybrid polynucleotides to make hybrid polypeptides encoded by the hybrid polynucleotides; screening the hybrid polypeptides to identify a hybrid polypeptide that binds to a receptor for a vertebrate vascular endothelial growth factor; and selecting the polynucleotide that encodes the hybrid polypeptide that binds to the receptor in the screening step. Expression of the selected polynucleotide (to produce the desired polypeptide) also is contemplated.

In this context, "modulate the growth of mammalian endothelial cells" means stimulate such growth by inducing a mitogenic signal through binding cell surface receptors expressed on vascular endothelial cells, or inhibiting such growth. As explained elsewhere herein, inhibition may be due to blockage of vascular endothelial growth factor receptors, or the formation of heterodimers with endogenous growth factors that prevent stimulation of endogenous receptors by the endogenous growth factors. Inhibition also may be achieved by conjugating cytotoxic agents to polypeptides of the invention that bind VEGF receptors. Exemplary toxins are known in the art and described elsewhere herein. Polypeptides of the invention conjugated to cytotoxic agents or other agents that modulate cell growth are contemplated as another aspect of the invention.

In this context, "vertebrate vascular endothelial growth factor polypeptides" again means polypeptides having the following characteristics:

(1) the polypeptide is encoded by genomic DNA of a vertebrate (e.g., a reptile, amphibian, bird, or mammal, preferably a bird or mammal, most preferably a mammal; especially a primate mammal such as a monkey, ape, or human) or is encoded by the genome of a vertebrate pathogen such as mammalian pox viruses;

(2) the polypeptide comprises all or a portion of a coding sequence that is expressed by a vertebrate (i.e., from transcription/translation of the vertebrate's genomic DNA or from virally-induced transcription/translation, in the case of polypeptides encoded by viral nucleic acids);

(3) the polypeptide or portion comprises a VEGF homology domain (V/PHD) of about 70–150 amino acids that binds to naturally occurring receptors and that is characterized in part by the amino acid motif: C-X(18–28)-P-X-C-X(4)-R-C-X-G-C(1–2)-X(6–12)-C-X(30–46)-C, where X represents any amino acid and numbers in parentheses represent a permissible range of amino acids (e.g., X(18–28) represents a stretch of any 18–28 amino acids; C(1–2) represents one or two cysteine residues). The V/PHD includes eight conserved cysteines which form a cysteine knot motif similar to that found in human vascular endothelial growth factors A, B, C, and D (VEGF-A, -B, -C, and -D, and human platelet-derived growth factor (PDGF). Preferred polypeptides or portions comprise a VPHD that is characterized by the more particular amino acid motif C-X(22–24)-P-[PSR]-C-V-X(3)-R-C-X-G-C-C-X(6)-C-X(32–41)-C, where amino acids in brackets (e.g., [PSR]) represent alternatives for a single position in the amino acid sequence; and (4) the polypeptide binds to at least one cell surface receptor that is expressed on endothelial cells that line vertebrate blood or lymphatic vessels or pericytes/smooth muscle cells that line and support blood vessels. Preferred polypeptides bind to a least one cell surface receptor that is expressed on endothelial cells.

Several methods exist for practicing the preparing step. In one variation, single-stranded oligonucleotides are prepared based on knowledge of mammalian VEGF polypeptide sequences and the universal genetic code and using conventional chemical synthesis techniques. Example 1 below demonstrates such a technique, wherein synthetic oligonucleotide pairs were prepared and annealed to prepare double-stranded polynucleotides having single-stranded cohesive ends that encoded fragments of human VEGF-A and human VEGF-C. In another variation, cDNAs or genomic DNAs (preferably cDNAs) encoding natural VEGF's are fragmented using one or more restriction endonucleases, using DNaseI, or using Exonuclease III. [See, e.g., Chang et al., Nature Biotechnology, 17:793–797 (1999) (DNaseI procedure); Kikuchi et al., Gene, 236:159–167 (1999) (restriction endonuclease procedure); Harayama et al., TIBTECH, 16:76–82 (1998) (review); Patten et al., Curr. Opin. Biotechnology, 8:724–733 (1997) (review, DNase I); Zhang et al., Proc. Natl. Acad. Sci. USA, 94:4504–09 (1997) (DNase I procedure); Stemmer, Proc. Natl. Acad. Sci. USA, 91:10747–1074 (1997) (DNase I procedure); Stemmer, Nature, 370:389–391 (1994) (DNase I procedure); and Ostermeier et al, Nature Biotechnology, 17:1205–1209 (1999) (ExoIII procedure), all incorporated herein by reference in their entirety]. In still another variation, a cDNA (coding or non-coding strand) is used as a template to synthesize complementary fragments, using DNA polymerase and chain-termination reagents. [See, e.g., Lehtovaara et al., Protein Engineering, 2:63–68 (1988), incorporated by reference.]

Several methods also exist for practicing the comingling step. In one variation, the polynucleotides are prepared with complementary cohesive single-stranded ends, to facilitate annealing of fragments in a desired order under conventional annealing and ligation conditions for polynucleotides. Example 1 below provides a demonstration of this technique to generate 510 human VEGF-A/VEGF-C hybrids. Such a technique also may be suitable for annealing fragment mixtures of two or more VEGF cDNAs that have been digested with restriction endonucleases. Alternatively, the commingling step is accomplished by mixing the polynucleotides and subjecting them to a self-priming PCR reaction that involves successive steps of denaturation, annealing, and extension. [See, e.g., Chang et al (1999); Kikuchi et al. (1999); Patten et al. (1997); Zhang et al. (1997); Stemmer Proc. Natl. Acad. Sci. USA, 91:10747–1074 (1994); and Stemmer, Nature, 370:389–391 (1994).]. Optionally, the PCR is performed under conditions that introduce errors (mutations) in the PCR products. Such mutations introduce additional molecular variation, and are expected to reduce the overall percentage of biologically active molecules, but also may produce molecules with unexpectedly superior activities.

After synthesizing the hybrid DNA molecules, the molecules are expressed by any means known in the art. In one variation the molecules are cloned into expression vectors, which are in turn used to transform or transfect cells to express the polypeptides. In another variation, the polynucleotides are cloned into a phage display vector system for screening. [See, e.g., Chang et al (1999).] The screening assay may entail a direct receptor binding assay as described below in Example 3. Alternatively, receptor binding may be assayed indirectly by assaying for a biological activity induced by receptor binding. Thus, in one variation, the screening step comprises contacting the hybrid polypeptide to a cell that expresses the receptor, wherein changes in cell growth or cell survival induced by the hybrid polypeptide is indicative of binding between the hybrid polypeptide and the receptor.

Figure 10:
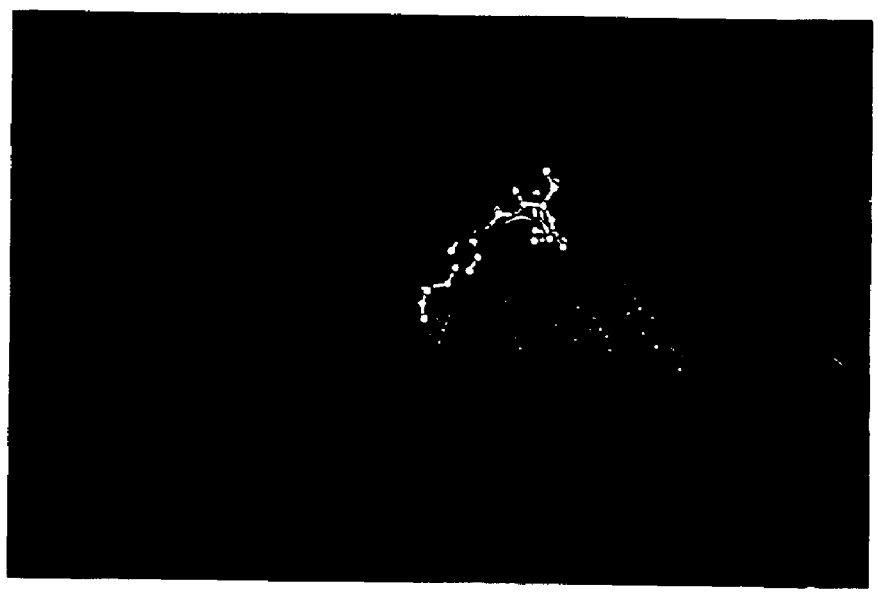

In a preferred variation of the method, the screening and selecting steps are designed to select polynucleotides that encode polypeptides that have novel receptor binding profiles not possessed by the naturally occurring VEGFs from which the polypeptide was derived. For example, the method is practiced wherein the screening step comprises screening to identify a hybrid polypeptide that binds human VEGFR-b 1and human VEGFR-3, and the selecting step comprises selecting a hybrid polypeptide that binds human VEGFR-1 and human VEGFR-3, but fails to bind human VEGFR-2. Alternatively, the method is practiced whereby the screening step comprises screening to identify a hybrid polypeptide that binds human VEGFR-1, VEGFR-2, and human VEGFR-3, and the selecting step comprises selecting a hybrid polypeptide that binds human VEGFR-1, VEGFR-2, and human VEGFR-3.

In a related embodiment, the invention provides a method for making a polynucleotide that encodes a polypeptide that modulates the growth of mammalian endothelial cells, comprising the steps of: (a) preparing a set of polynucleotide fragments having the following characteristics: (i) the set includes a first subset of coding polynucleotide fragments, wherein each coding polynucleotide fragment of the first subset encodes at least four amino acids of the amino acid sequence of a first mammalian vascular endothelial growth factor; (ii) the set includes a second subset of coding polynucleotide fragments, wherein each coding polynucleotide fragment of the second subset encodes at least four amino acids of the amino acid sequence of a second mammalian vascular endothelial growth factor; (b) commingling the polynucleotide fragments which comprise the set under conditions wherein the coding polynucleotide fragments from the first and second subsets recombine to form hybrid polynucleotides; (c) expressing the hybrid polynucleotides to make hybrid polypeptides encoded by the hybrid polynucleotides; (d) screening the hybrid polypeptides to identify a hybrid polypeptide that modulates the growth of mammalian endothelial cells; and (e) selecting the polynucleotide that encodes the hybrid polypeptide that modulates the growth of mammalian endothelial cells in the screening step.

Practice of these methods of generating hybrid polynucleotides using mammalian vascular endothelial growth factors that comprise a receptor binding domain characterized by eight cysteines that are conserved in human Vascular Endothelial Growth Factor A (VEGF-A), human Vascular Endothelial Growth Factor B (VEGF-B), human Vascular Endothelial Growth Factor C (VEGF-C), and human Vascular Endothelial Growth Factor D (VEGF-D) is preferred. Exemplary starting molecules include VEGF-A VEGF-B, VEGF-C, VEGF-D, VEGF-E, PlGF, PDGF-A, and PDGF-B polypeptides of human and other mammals. Also included is the recently described protein, fallotein, disclosed in the EMBL database (Acc. No. AF091434) (SEQ ID NO: 149), which has structural characteristics of the PDGF/VEGF family of growth factors. Thus, it is also contemplated to use fallotein in generating hybrid proteins together with other mammalian VEGFs.

The polynucleotide and encoded polypeptide products of the foregoing methods are themselves considered to be additional aspects of the present invention.

Antibodies that may be generated against polypeptides of the invention, and that bind polypeptides of the invention with an affinity greater than for any natural occurring VEGF, also are contemplated as aspects of the invention. Polypeptides comprising the antigen-binding fragments of such antibodies also are contemplated as an aspect of the invention. Antibodies that bind to the polypeptides of the invention but not to vertebrate VEGF's are contemplated.

In yet another embodiment, the invention provides numerous in vitro and in vivo methods of using polypeptides and polynucleotides of the invention. Such methods are described in greater detail below in the Detailed Description. Generally speaking, polypeptides of the invention are useful for modulating (stimulating or inhibiting) cellular processes that are mediated through any of the PDGF/VEGF family of receptors, such as PDGFR-α, PDGFR-β, VEGFR-1, VEGFR-2, and/or VEGFR-3. These receptors may be involved singularly in certain processes and in combination, to varying extents, in other processes. Polypeptides of the invention possess many different receptor binding profiles, and one of the advantages of the invention is the ability to select a polypeptide with a receptor binding profile that matches the receptor expression profile of the biological process to be modulated.

Thus, in one variation, the invention provides a method of modulating the signaling of one or more of PDGFR-α, PDGFR-β, VEGFR-1, VEGFR-2, and/or VEGFR-3 in a cell, comprising the step of contacting a cell that expresses one or more of PDGFR-α, PDGFR-β, VEGFR-1, VEGFR-2, and/or VEGFR-3 with a composition comprising a polypeptide of the invention. In one variation, modulation to activate signaling is contemplated, and the cell is contacted with a polypeptide of the invention that stimulates receptor signaling in an amount sufficient to bind to the one or more receptors and induce receptor signaling. In another variation, modulation to inhibit signaling is contemplated. The cell is contacted with a polypeptide that inhibits ligand-induced receptor activation (or a polypeptide conjugated to a cytotoxin), in an amount sufficient to inhibit signaling that is induced by receptor ligand growth factor polypeptides that exist endogenously in the cell's environment. Dose-response studies permit accurate determination of a proper quantity of polypeptide to employ. Effective quantities can be estimated from measurements of the binding affinity of a polypeptide for a target receptor, of the quantity of receptor present on target cells, of the expected dilution volume (e.g., patient weight and blood volume for in vivo embodiments), and of polypeptide clearance rates.

In another variation, the invention provides a method of modulating the signaling of one or more of PDGFR-α, PDGFR-β, VEGFR-1, VEGFR-2, and/or VEGFR-3, comprising the step or administering to a patient in need of modulation of the signaling of one or more of these receptors a composition comprising a polynucleotide of the invention, under conditions in which cells of the patient are transformed or transfected by the polynucleotide and express the polypeptide of the invention encoded thereby, wherein the expressed polypeptide modulates signaling of the one or more receptors.

As discussed below, analysis of the chimeras receptor binding properties and the sequences of VEGFR-3 ligands in relation to the sequence of VEGF-A suggests that Fragments 4 and 5 from the VEGF-C molecule are important for conferring VEGFR-3 binding affinity, and in particular the sequence of residues TNTFxxxP (SEQ ID NO: 1204) found within Fragments 4 and 5. Thus, in another variation, the invention provides molecules designed using these core residues and other substituents to modulate VEGFR-3 biological activity. For example, in one embodiment, the invention provides a molecule comprising the peptide sequence TNTF$X_n$P (SEQ ID NO: 1212), wherein $X_n$ comprises from one to seven amino acids, and wherein the molecule inhibits VEGF-C-mediated activation of VEGFR-3. The molecule may include additional residues or organic moieties. In one variation, it is contemplated that this epitope will be linked by a non-VEGF-C amino acid sequence to other epitopes involved in receptor binding, thereby creating a molecule capable of interacting with receptor loci involved in ligand binding and blocking ligand-mediated activation of the receptor. In a preferred embodiment, $X_n$ comprises three amino acids, which represents the same amino acid spacing as native VEGF-C.

In a related embodiment, the invention provides a molecule comprising the human VEGF-C peptide sequence EFGVATNTFFKPPCVSVYRCG (SEQ ID NO: 1205) or a fragment or variant thereof, wherein the molecule inhibits VEGF-C-mediated activation of VEGFR-3. In one variation, the fragment is such that the molecule comprises the amino acid sequence EFGVATNTFFKPPCVSVYRCG (SEQ ID NO: 1205). In another variation, the fragment is such that the molecule comprises the amino acid sequence TNTFFKPP (SEQ ID NO: 1206). In still another variation, the fragment or variant comprises the amino acid sequence TNTFFKPPCVxxxR (SEQ ID NO: 1207), or the amino acid sequence TNTFFKPPCVxxxRCGGCC (SEQ ID NO: 1208).

In a related embodiment, the invention provides a method for identifying a modulator of VEGFR-1 binding to VEGF-A comprising the steps of (i) measuring binding between VEGFR-1 and VEGF-A in the presence and absence of a test compound under conditions that allow binding of VEGFR-1 to VEGF-A, and (ii) identifying as a modulator a test compound which alters VEGFR-1 binding to VEGF-A and which binds VEGF-A at a site defined by $Lys^{42}$, $Phe^{43}$, $Met^{44}$, $Tyr^{47}$, $Gln^{48}$, $Tyr^{51}$, $Ile^{72}$, $Lys^{74}$, $Asp^{89}$, $Gly^{91}$, $Leu^{92}$, $Gln^{105}$, $Met^{107}$, $Ile^{109}$, $Phe^{111}$, $His^{112}$, $Gln^{115}$, $Ile^{117}$, $Glu^{129}$, $Arg^{131}$, and $Pro^{132}$ of SEQ ID NO: 2, or which binds VEGFR-1 at VEGFR-1 residues which interface with said residues of SEQ ID NO: 2.

Similarly, the invention provides a method for identifying a modulator of VEGFR-3 binding to VEGF-C comprising the steps of (i) measuring binding between VEGFR-3 and VEGF-C in the presence and absence of a test compound under conditions that allow binding of VEGFR-3 to VEGF-C, and (ii) identifying as a modulator a test compound which alters VEGFR-3 binding to VEGF-C and which binds VEGF-C at a site defined by Lys$^{120}$, Ser$^{121}$, Ile$^{122}$, Trp$^{126}$, Arg$^{127}$, Gln$^{130}$, Phe$^{151}$, Lys$^{153}$, Ser$^{168}$, Gly$^{170}$, Leu$^{171}$, Tyr184, Phe$^{186}$, Ile$^{190}$, Pro$^{191}$, Pro$^{196}$, Pro$^{198}$, Arg$^{210}$, Met$^{212}$, and Ser$^{213}$ of SEQ ID NO: 22, or which binds VEGFR-3 at VEGFR-3 residues which interface with said residues of SEQ ID NO: 22. The invention also provides a method for identifying a modulator of VEGFR-3 binding to VEGF-C comprising the steps of (i) measuring binding between VEGFR-3 and VEGF-C in the presence and absence of a test compound under conditions that allow binding of VEGFR-3 to VEGF-C, and (ii) identifying as a modulator a test compound which alters VEGFR-3 binding to VEGF-C and which binds VEGF-C at a site defined by $Thr^{148}$, $Asn^{149}$, $Thr^{150}$, $Phe^{151}$, and $Pro^{155}$ of SEQ ID NO: 22, or which binds VEGFR-3 at VEGFR-3 residues which interface with said residues of SEQ ID NO: 22.

Also contemplated as aspects of the invention are compositions that comprise modulators identified by the foregoing methods, especially compositions comprising substantially purified modulators in a pharmaceutically acceptable carrier. Similarly, use of such modulators in the manufacture of a medicament for the treatment of disease states characterized by abnormal vascular endothelial growth factor receptor activity is contemplated.

In still another variation, any of the foregoing methods optionally include the additional step of administering the identified modulator to a patient in need of treatment for a disease state characterized by undesirable levels of receptor activity; or a step of contacting cells that express the receptor to modulate the level of receptor activity in the cells.

Additional embodiments, features, and variations of the invention will be apparent to those skilled in the art from the entirety of this application, including the Drawing and the Detailed Description, and all such features are intended as aspects of the invention.

Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

With respect to aspects of the invention that have been described as a set or genus, every individual member of the set or genus is intended, individually, as an aspect of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWING

The patent or application file contains at least one drawing executed in color. Copies of this patent or patent application publication with color drawings will be provided by the Patent and Trademark Office upon request and payment of the necessary fee.

FIG. 1 depicts a perspective view of a three-dimensional model of a VEGF-A monomer, in which selected secondary structure elements are identified. A VEGF-A-encoding polynucleotide was divided into nine segments for construction of VEGF-A/VEGF-C chimeras, and labels 1–9 identify the location of the peptides encoded by each of the nine segments.

FIG. 2 is a schematic diagram of the 9 VEGF-A and 9 VEGF-C DNA fragments used to construct the VEGF-A/VEGF-C hybrid molecules. These fragments are numbered 1 through 9 on top. The N123, N45, C67 and C89 groups of fragments are also indicated. N123 consists of 3 VEGF-A fragments and 3 VEGF-C fragments (fragments 1–3), whereas N45 (fragments 4–5), C67 (fragments 6–7), and C89 (fragments 8–9) each consist of 2 VEGF-A fragments and 2 VEGF-C fragments. Selected restriction endonuclease sites also are depicted.

FIG. 3 schematically depicts all 8 possible DNA molecules corresponding to the N123 region, resulting from ligating different combinations of fragments 1, 2, and 3 from VEGF-A (A1, A2, and A3) and VEGF-C (C1, C2, and C3).

FIG. 4 schematically depicts all 4 possible DNA molecules corresponding to the N45 region resulting from ligating different combinations of fragments 4 and 5 from VEGF-A and VEGF-C.

FIG. 5 schematically depicts all 4 possible DNA molecules corresponding to the C67 region resulting from ligating different combinations of fragments 6 and 7 from VEGF-A and VEGF-C.

FIG. 6 schematically depicts all 4 possible DNA molecules corresponding to the C89 region resulting from ligating different combinations of fragments 8 and 9 from VEGF-A and VEGF-C.

FIGS. 7A–7D depict in boxes the amino acid sequences encoded by DNA fragments A1–A9 (SEQ ID NOs: 128–136) and C1–C9 (SEQ ID NOs: 137–145), and depict the manner in which longer encoded amino acid sequences were formed through the joining of fragments A1–A3 and C1–C3 in the N123 ligation (FIG. 7A); of fragments A4–A5 and C4–C5 in the N45 ligation (FIG. 7B); of fragments A6–A7 and C6–C7 in the C67 ligation; and of fragments A8–A9 and C8–C9 in the C89 ligation. In each figure, arrows represent peptide bonds between encoded amino acid sequences that result from proper ligation of compatible DNA fragments and translation of the resultant ligated DNA.

FIG. 8 is a three-dimensional model showing the interaction of a VEGF-A dimer with two VEGFR-1 molecules. The two VEGF-A monomers are colored in green and blue, respectively. The two VEGFR-1 receptors are depicted in gray. Red represents the location of residues within the VEGF-A monomers important for interfacing with VEGFR-1. These residues are clustered at the two ends of the VEGF-A dimer and include the N-terminal helix and part of the β5 strand.

FIG. 9 is a three-dimensional model depicting the groove formed by a VEGF-C dimer. The entry and the sides of this groove are formed by the fragments, described in Example 4, that appear to be important for conferring VEGFR-3 specificity. The green and blue indicate the two VEGF-C monomers and the gray indicates a VEGFR-3 receptor molecule. The VEGF-C residues that participate in binding VEGFR-3 are indicated in yellow.

FIG. 10 is a three-dimensional model of a the interaction between a VEGF-C dimer and a single VEGFR-3 molecule, extrapolated from the VEGF-A/VEGFR-A model. Blue and green represent the two VEGF-C monomers and grey represents VEGFR-3. Fragment 5 of the green VEGF-C monomer is shown in orange and fragment 4 of the same monomer is shown in white. Residues in red are those located within fragment 4 or 5 that are probably in contact with the receptor.

DETAILED DESCRIPTION

The present invention provides novel polypeptides that bind cellular receptors for vascular endothelial growth factor polypeptides; polynucleotides encoding such polypeptides; compositions comprising the polypeptides and polynucleotides; and methods and uses involving the foregoing. These materials and methods are described in detail in the preceding Summary of Invention section, which is hereby incorporated into the Detailed Description in its entirety. Some polypeptides of the invention exhibit unique receptor binding profiles compared to known, naturally occurring vascular endothelial growth factors.

Methods of Making Peptides

The peptides of the present invention may be synthesized using a variety of methods, including those described in the summary of invention and the examples. The peptides of the present invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co., (1984); Tam et al., *J. Am. Chem. Soc.*, 105:6442, (1983); Merrifield, *Science*, 232:341–347, (1986); and Barany and Merrifield, *The Peptides*, Gross and Meienhofer, eds, Academic Press, New York, 1–284; Barany et al., *Int. J. Peptide Protein Res.*, 30, 705–739 (1987); and U.S. Pat. No. 5,424,398), each incorporated herein by reference.

Solid phase peptide synthesis methods use a copoly (styrene-divinylbenzene) containing 0.1–1.0 mMol amines/g polymer. These methods for peptide synthesis use butyloxycarbonyl (t-BOC) or 9-fluorenylmethyloxycarbonyl (FMOC) protection of alpha-amino groups. Both methods involve stepwise syntheses whereby a single amino acid is added at each step starting from the C-terminus of the peptide (See, Coligan, et al., Current Protocols in Immunology, Wiley Interscience, 1991, Unit 9) On completion of chemical synthesis, the peptides can be deprotected to remove the t-t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Other methods, such as selecting peptides from a phage display library, are available for improving upon peptide specifically described herein. Libraries can be prepared from sets of amino acids as described herein. Phage display can be particularly effective in identifying binding peptides useful according to the invention. Briefly, one prepares a phage library (using e.g. m113, fd, or lambda phage), displaying inserts from 4 to about 80 amino acid residues. The inserts may represent, for example, a completely degenerate or biased array. One then can select phage-bearing inserts which bind to the target VEGF receptor(s). This process can be repeated through several cycles of reselection of phage that bind to the target receptor(s). Repeated rounds lead to enrichment of phage bearing particular sequences. DNA sequence analysis can be conducted to identify the sequences of the expressed polypeptides. The minimal linear portion of the sequence that binds to the target receptor(s) can be determined. One can repeat the procedure using a biased library containing inserts containing part or all of the minimal linear portion plus one or more additional degenerate residues upstream or downstream thereof. These techniques may identify peptides of the invention with still greater receptor binding affinity than peptides already identified herein. Screening resultant peptide against multiple receptors will identify peptides with multiple receptor binding affinities. Yeast two-hybrid screening methods also may be used to identify polypeptides that bind to the target receptor(s).

Alternatively, a variety of expression vector/host systems may be utilized to contain and express the chimeric peptides of the present invention. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the protein are described herein below.

For example, the chimeric peptide may be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted peptide is purified from the yeast growth medium by, e.g., the methods used to purify the chimeric peptide from bacterial and mammalian cell supernatants.

Alternatively, the cDNA encoding the peptide may be cloned into the baculovirus expression vector pVL1393 (PharMingen, San Diego, Calif.). This vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Porton 2090 Peptide Sequencer confirms its N-terminal sequence.

Alternatively, the peptide may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. The peptide coding sequence is cloned into a nonessential region of the virus, such as the polyhedrin gene, and placed under control of the polyhedrin promoter. Successful insertion of the peptide will render the polyhedrin gene inactive and produce recombinant virus lacking coat protein coat. The recombinant viruses are then used to infect *S. frugiperda* cells or *Trichoplusia* larvae in which peptide is expressed (Smith et al., *J Virol* 46:584, 1983; Engelhard E K et al., *Proc Nat Acad Sci* 91:3224–7, 1994).

In another example, the DNA sequence encoding the peptide is amplified by PCR and cloned into an appropriate vector for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include for example, an appropriate cleavage site.

Where the fusion partner was used solely to facilitate expression or is otherwise not desirable as an attachment to the peptide of interest, the recombinant fusion protein may then be cleaved from the GST portion of the fusion protein. The pGEX-3X/chimeric peptide construct is transformed into *E. coli* XL-1 Blue cells (Stratagene, La Jolla Calif.), and individual transformants were isolated and grown. Plasmid DNA from individual transformants is purified and partially sequenced using an automated sequencer to confirm the presence of the desired chimeric peptide encoding nucleic acid insert in the proper orientation.

Particularly preferred peptide compositions of the present invention are those which are conjugated to any anti-tumor peptide such as a tumor necrosis factor (TNF). In a particularly preferred method, the TNF-peptides chimeras are generated as recombinant fusions with peptide-encoding sequences fused in frame to TNF (Novagen) encoding sequences. Peptide-TNF cDNA is cloned into pET-11b vector (Novagen) and the expression of TNF-peptides in BL21 *E. coli* is induced according to the pET11b manufacturer's instruction. Soluble TNF-peptides are purified from bacterial lysates by ammonium sulfate preparation, hydrophobic interaction chromatography on Phenyl-Sepharose 6 Fast Flow, ion exchange chromatography on DEAE-Sepharose Fast Flow and gel filtration chromatography on Sephacryl-S-300 HR.

It is contemplated that recombinant protein production also may be used to produce the chimeric peptide compositions. For example, induction of the GST/chimeric peptide is achieved by growing the transformed XL-1 Blue culture at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis Mo.).

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate is cleared by sonication, and cell debris is pelleted by centrifugation for 10 minutes at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/chimeric peptide fusion protein is produced in bacteria as a soluble protein, it may be purified using the GST Purification Module (Pharmacia Biotech).

The fusion protein maybe subjected to digestion to cleave the GST from the chimeric peptide of the invention. The digestion reaction (20–40 µg fusion protein, 20–30 units human thrombin (4000 U/mg (Sigma) in 0.5 ml PBS) is incubated 16–48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of chimeric peptide may be confirmed by amino acid sequence analysis using an automated sequencer (Applied Biosystems Model 473A, Foster City, Calif.). Alternatively, the identity may be confirmed by performing HPLC and/or mass spectometry of the peptides.

Alternatively, the DNA sequence encoding the chimeric peptide may be cloned into a plasmid containing a desired promoter and, optionally, a leader sequence (see, e.g., Better et al., *Science*, 240:1041–43, 1988). The sequence of this construct may be confirmed by automated sequencing. The plasmid is then transformed into *E. coli* strain MC1061 using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the chimeric peptide and be cleaved during secretion.

The secreted recombinant protein is purified from the bacterial culture media by the method described herein below.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, W138, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the desired expression cassette, the cells may be allowed to grow for 1–2 days in an enriched media before they are switched to selective media. The selectable marker is designed to confer resistance to selection and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; also that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

For certain applications, it may be desirable to produce peptides or polypeptides of the present invention which are resistant to proteolytic digestion. Such peptides may include non-hydrolyzable peptide bonds, and peptides having end modifications such as an amide (e.g., $CONH_2$) at the C-terminus or a acetyl group at the N-terminus. It is contemplated that the peptides of the invention are modified such that their in vivo half life is increased, their physical stability is increased, rate of in vivo release and rate of in vivo clearance also may be affected.

To prepare non-hydrolyzable peptides, one may select peptides from a library non-hydrolyzable peptides, or introduce modifications to select peptides, such as one or more D-amino acids or one or more non-hydrolyzable peptide bonds linking amino acids. For example, one can select peptides having a desired receptor binding profile and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of the peptides of the present invention with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include —[$CH_2NH$]— reduced amide peptide bonds, —[$COCH_2$]— ketomethylene peptide bonds, —[$CH(CN)NH$]— (cyanomethylene)amino peptide bonds, —[$CH_2CH(OH)$]— hydroxyethylene peptide bonds, —[$CH_2O$]— peptide bonds, and —[$CH_2S$]— thiomethylene peptide bonds (see e.g., U.S. Pat. No. 6,172,043).

Peptides useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (Int. J Pep. Protein Res. 36:392–399, 1990) and Rivera-Baeza et al. (Neuropeptides 30:327–333, 1996) are also known in the art.

Furthermore, nonpeptide analogs of peptides which provide a stabilized structure or lessened biodegradation, are also contemplated. Peptide mimetic analogs can be prepared based on a selected peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., *Regul. Pept.* 57:359–370 (1995). Peptide as used herein embraces all of the foregoing.

The polypeptides of the invention include polypeptides that are modified, for instance, by glycosylation, amidation, carboxylation, or phosphorylation, or by the creation of acid addition salts, amides, esters, in particular C-terminal esters, and N-acyl derivatives.

Also, as described above, the invention embraces polypeptides modified by forming covalent or noncovalent complexes with other moieties. Covalently-bound complexes can be prepared by linking the chemical moieties to functional groups on the side chains of amino acids comprising the peptides, or at the N- or C-terminus.

In particular, it is anticipated that the aforementioned peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising a chimeric polypeptide comprising a plurality of peptide subunits derived from two or more vascular endothelial growth factor polypeptides, wherein the chimeric polypeptide preferably further comprises a reporter group selected from the group consisting of a radiolabel, a fluorescent label, an enzyme, a substrate, a solid matrix, and a carrier. The use of such labels is well known and is described in, e.g., U.S. Pat. Nos. 3,817,837; 3,850,752; 3,996,345 and 4,277,437. Other labels that will be useful include but are not limited to radioactive labels, fluorescent labels and chemiluminescent labels. U.S. Patents concerning use of such labels include for example U.S. Pat. Nos. 3,817,837; 3,850,752; 3,939,350 and 3,996,345. Any of the peptides of the present invention may comprise one, two, or more of any of these labels.

Methods of Using the Polypeptides of the Invention

The many biological activities mediated through the PDGF/VEGF receptor family (including but not limited to affecting growth and migration of vascular endothelial cells and blood vessels; promoting growth of lymphatic endothelial cells and lymphatic vessels; increasing vascular permeability; and affecting myelopoiesis) support numerous diagnostic and in vitro and in vivo clinical utilities for polypeptides of the invention that are capable of binding one of more members of the VEGF receptor family, for modulating (stimulating or inhibiting) these biological activities.

Multiple mechanisms exist through which polypeptides of the invention will act as growth factors (i.e., agonists or receptor stimulants). For example, polypeptides of the invention that form homodimers that bind and activate one or more members of the VEGF receptor family will be useful as vascular endothelial growth factors. Alternatively, polypeptides of the invention that form heterodimers with endogenous growth factor polypeptides (VEGF-A or VEGF-C or other family members) will also be effective agonists, provided that the heterodimers so formed are capable of binding and activating receptors to induce signal transduction.

Multiple mechanisms exist through which polypeptides of the invention will act as inhibitors (antagonists) of growth factors of the VEGF family. Polypeptides of the invention that bind but fail to stimulate one or more receptors will inhibit stimulation of the receptor by endogenous growth factor, thereby acting as an inhibitor of endogenous growth factor. Such failure to stimulate may be due, in whole or in part, to an inability to dimerize the receptor, perhaps due to an inability of the hybrid polypeptide of the invention to form growth factor homodimers. Polypeptides of the invention that form heterodimers with endogenous growth factor polypeptides will inhibit stimulation of VEGF receptors if the heterodimer fails to bind receptors, or if the heterodimer binds only to an individual receptor or a heterologous receptor pair in a manner that prevents receptor activation and signal transduction. Whichever the mechanism, polypeptides of the invention that form activity-destroying heterodimers with endogenous VEGF polypeptides (and that do not form active homodimers) are useful as antagonists of natural endogenous VEGF activity. Also, any polypeptide that binds a receptor can be conjugated to a cytotoxic or cytostotic agent in order to deliver such agents to target cells. The attachment of such agent is another means for inhibiting growth of cells in which VEGF polypeptides exhibit a mitogenic response. Exemplary toxins include chemotherapeutic, radionuclide, ricin A chain, cholera toxin, pertussis toxin, etc.

It also will be apparent that two or more hybrid polypeptides of the invention can be mixed, and that heterodimers so formed will be useful as modulators depending upon their receptor binding and stimulating properties. Because polypeptides of the invention are hybrids derived from naturally-occurring vascular endothelial growth factors that may have different receptor binding profiles, it is contemplated that some of the hybrids will act as activators of one or more receptors, and some will act as inhibitors of one or more receptors. Procedures described herein and other procedures known in the art can be used to determine receptor binding, receptor activation, and receptor inhibition properties of polypeptides of the invention.

The polypeptides of the invention that bind and activate one or more VEGF receptors may be useful for promoting angiogenesis and/or lymphangiogenesis, for example, to promote wound healing, to facilitate tissue transplantation, and to promote the formation of collateral vessels around arterial stenoses, and into injured tissues after infarction, to treat ischemia. On the other hand, polypeptides of the invention that behave as antagonists of endogenous VEGF proteins can be used in therapeutic applications to treat diseases such as neoplasias, retinopathy, rheumatoid arthritis, and psoriasis, in which suppression of angiogenesis is desirable.

Polypeptides of the present invention differ from natural VEGF receptor ligands in that some of them selectively bind one of the VEGF receptors and can thus be used to specifically induce signaling through one particular VEGF receptor. For example, polypeptides that solely induce VEGFR-3 signaling can be used therapeutically to target the lymphatic endothelia of individuals affected with lymphatic disorders, to improve the structure and function of the lymphatic vasculature of such individuals. Such polypeptides also can be used to target neoplasia characterized by cells expressing VEGFR-3 on their surfaces. Chemotaxis of monocytes/macrophages [Barleon et al., Blood 87:3336–3343 (1996)] due to VEGFs is mediated by VEGFR-1. Thus, molecules that specifically target the VEGFR-1 receptor can be used to direct therapeutic effects on this particular VEGF receptor. For example, inhibitors of VEGFR-1 may be used to prevent virally induced angiogenesis, and molecules that specifically activate VEGFR-1 can be used to enhance monocyte/macrophage migration. VEGFR-2 is essential for angiogenesis and sufficient for virally-induced angiogenesis. Thus, inhibitors of VEGFR-2 may be used for inhibiting angiogenesis, including that induced by viral VEGFs., whereas molecules that stimulate VEGFR-2 can be useful for promoting angiogenesis.

A subset of the polypeptides of the present invention can bind combinations of VEGF receptors not demonstrated for known natural VEGF ligands, or are able to bind all three known VEGF receptors VEGFR-1, R-2, and R-3. These polypeptides may be useful for therapies in which the activation or inhibition of different combinations of VEGF receptors is desired.

Polypeptides of the invention that can activate VEGFR-3 can be used to promote the endothelial functions of lymphatic vessels and tissues such as to treat loss of lymphatic vessels, occlusions of lymphatic vessels, lymphangiomas, and primary idiopathic lymphedemas, including Milroy's disease and lymphedema praecox, as well as secondary lymphedemas, including those resulting from removal of lymph nodes and vessels, radiotherapy and surgery in treatment of cancer, trauma and infection. Polynucleotides or polypeptides of the invention could be administered purely as a prophylactic treatment to prevent lymphedema in subjects at risk for developing lymphedema, or as a therapeutic treatment to subjects afflicted with lymphedema, for the purpose of ameliorating its symptoms (e.g., swelling due to the accumulation of lymph).

The polynucleotides and polypeptides of the invention that activate VEGFR-3 can also be used to promote re-growth or permeability of lymphatic vessels in patients whose axillary lymphatic vessels were removed during surgical interventions in the treatment of cancer (e.g., breast cancer). Polynucleotides and polypeptides of the invention can be used to treat vascularization in, for example, organ transplant patients. A composition containing the polypeptide(s) of the invention may be directly applied to the isolated vessel segment prior to its being grafted in vivo to minimize rejection of the transplanted material and to stimulate vascularization of the transplanted materials.

Polypeptides of the invention that activate VEGF receptor activity may be used to treat wounds, surgical incisions, sores, and other indications where healing is reasonably expected to be promoted if the process of neovascularization can be induced and/or accelerated.

As explained in greater detail above and reported in the literature, the expression of receptors for vascular endothelial growth factors have been observed in certain progenitor cells, such as hematopoietic progenitor cells, and VEGF-C has been observed to have myelopoietic activity. These observations provide an indication that polynucleotides or polypeptides according to the invention may be used to treat or prevent inflammation, infection, or immune disorders by modulating the proliferation, differentiation and maturation, or migration of immune cells or hematopoietic cells. Polynucleotides or polypeptides according to the invention may also be useful to promote or inhibit trafficking of leukocytes between tissues and lymphatic vessels and migration in and out of the thymus.

Polynucleotides and polypeptides of the invention can be used for stimulating myelopoiesis (especially growth of neutrophilic granuloctyes) or inhibiting it. Thus, the invention includes a method for modulating myelopoiesis in a mammalian subject comprising administering to a mammalian subject in need of modulation of myelopoiesis an amount of a polypeptide of the invention that is effective to modulate myelopoiesis. In one embodiment, a mammalian subject suffering from granulocytopenia is selected, and the method comprises administering to the subject an amount of a polypeptide effective to stimulate myelopoiesis. In particular, a polypeptide of the invention is administered in an amount effective to increase the neutrophil count in blood of the subject.

In a related embodiment, the invention includes a method of increasing the number of neutrophils in the blood of a mammalian subject comprising the step of expressing in a cell in a subject in need of an increased number of blood neutrophils a DNA encoding a polynucleotide of the invention that is able to activate signaling through VEGF receptors, the DNA operatively linked to a promoter or other control sequence that promotes expression of the DNA in the cell. Similarly, the invention includes a method of modulating the growth of neutrophilic granulocytes in vitro or in vivo comprising the step of contacting mammalian stem cells with a polypeptide of the invention in an amount effective to modulate the growth of mammalian endothelial cells.

The invention also includes a method for modulating the growth of CD34+ progenitor cells (especially hematopoietic progenitor cells and endothelial progenitor cells) in vitro or in vivo comprising the step of contacting mammalian CD34+ progenitor cells with a polypeptide of the invention in an amount effective to modulate the growth of mammalian endothelial cells. For in vitro methods, CD34+ progenitor cells isolated from cord blood or bone marrow are specifically contemplated. In vitro and in vivo methods of the invention for stimulating the growth of CD34+ precursor cells also include methods wherein polypeptides of the invention are employed together (simultaneously or sequentially) with other polypeptide factors for the purpose of modulating hematopoiesis/myelopoiesis or endothelial cell proliferation. Such other factors include, but are not limited to colony stimulating factors ("CSFs," e.g., granulocyte-CSF (G-CSF), macrophage-CSF (M-CSF), and granulocyte-macrophage-CSF (GM-CSF)), interleukin-3 (IL-3, also called multi-colony stimulating factor), other interleukins, stem cell factor (SCF), other polypeptide factors, and their analogs that have been described and are known in the art. See generally *The Cytokine Handbook, Second Ed.*, Angus Thomson (editor), Academic Press (1996); Callard and Gearing, *The Cytokine FactsBook*, Academic Press Inc. (1994); and Cowling and Dexter, *TIBTECH*, 10(10):349–357 (1992). The use of a polypeptide of the invention as a progenitor cell or myelopoietic cell growth factor or co-factor with one or more of the foregoing factors may potentiate previously unattainable myelopoietic effects and/or potentiate previously attainable myelopoietic effects while using less of the foregoing factors than would be necessary in the absence of a polypeptide of the invention.

Polynucleotides and polypeptides of the invention may also be used in the treatment of lung disorders to improve blood circulation in the lung and/or gaseous exchange between the lungs and the blood stream; to improve blood circulation to the heart and $O_2$ gas permeability in cases of cardiac insufficiency; to improve blood flow and gaseous exchange in chronic obstructive airway disease; and to treat conditions such as congestive heart failure, involving accumulations of fluid in, for example, the lung resulting from increases in vascular permeability, by exerting an offsetting effect on vascular permeability in order to counteract the fluid accumulation.

Polynucleotides and polypeptides of the invention could be used to treat malabsorptive syndromes in the intestinal tract as a result of its blood circulation increasing and vascular permeability increasing activities.

Polypeptides of the invention that bind but do not stimulate signaling through one or more of the VEGF receptors may be used to treat chronic inflammation caused by increased vascular permeability, retinopathy associated with diabetes, rheumatoid arthritis and psoriasis.

Polynucelotides or polypeptides according to the invention that are able to inhibit the function of one or more VEGF receptors can also be used to treat edema, peripheral arterial disease, Kaposi's sarcoma, or abnormal retinal development in premature newborns.

In another embodiment, the invention provides a method for modulating the growth of endothelial cells in a mammalian subject comprising the steps of exposing mammalian endothelial cells to a polypeptide according to the invention in an amount effective to modulate the growth of the mammalian endothelial cells. In one embodiment, the modulation of growth is affected by using a polypeptide capable of stimulating tyrosine phosphorylation of VEGF receptors in a host cell expressing the VEGF receptors. In modulating the growth of endothelial cells, the invention contemplates the modulation of endothelial cell-related disorders. In a preferred embodiment, the subject, and endothelial cells, are human. The endothelial cells may be provided in vitro or in vivo, and they may be contained in a tissue graft. An effective amount of a polypeptide is an amount necessary to achieve a reproducible change in cell growth rate (as determined by microscopic or macroscopic visualization and estimation of cell doubling time, or nucleic acid synthesis assays).

Since angiogenesis and neovascularization are essential for tumor growth, inhibition of angiogenic activity can prevent further growth and even lead to regression of solid tumors. Likewise inhibition of lymphangrogenesis may be instrumental in preventing metastases. Polynucleotides and polypeptides of the invention may be useful to treat neoplasias including sarcomas, melanomas, carcinomas, and gliomas by inhibiting tumor angiogenesis.

Thus, it is contemplated that a wide variety of cancers may be treated using the peptides of the present invention including cancers of the brain (glioblastoma, astrocytoma, oligodendroglioma, ependymomas), lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree or localized to a specific area and inhibited from spread to disparate sites. It may be that the tumor growth is completely blocked, however, or that some tumor regression is achieved. Clinical terminology such as "remission" and "reduction of tumor" burden also are contemplated given their normal usage. In the context of the present invention, the therapeutic effect may result from an inhibition of angiogenesis and/or an inhibition of lymphangiogenesis.

Thus, the invention includes a method of treating a mammalian organism suffering from a neoplastic disease characterized by expression of one or more VEGF receptor (s) in cells, comprising the steps of: identifying a mammalian organism suffering from a neoplastic disease state characterized by expression of VEGF receptor(s), and administering to the mammalian organism in need of such treatment a composition, the composition comprising one or more polynucleotide(s) or polypeptide(s) of the invention effective to inhibit VEGF receptor-mediated proliferation of the cells. Such treatment methodologies are particularly indicated for neoplastic disease states that are characterized by neovascularization involving vessels lined with endothelial cells that express increased levels of one or more VEGF receptors, relative to endothelial cells lining quiescent vessels; and disease states characterized by a cancer cells that express VEGF receptors. Targeting VEGFR-3 in tumor imaging and anti-tumor therapy is described in PCT/US99/23525 (WO 00/21560), published Apr. 20, 2000, incorporated herein by reference. Other VEGF receptors (e.g., VEGFR-1) also have been implicated in tumor angiogenesis or metastasis.

Evidence exists that at least VEGF-C and VEGF-D of the VEGF family of growth factors have utility for preventing stenosis or restenosis of blood vessels. See International Patent Application No. PCT/US99/24054 (WO 00/24412), "Use of VEGF-C or VEGF-D Gene or Protein to Prevent Restenosis," filed Oct. 26, 1999, incorporated herein by reference in its entirety. Polypeptides and polynucleotides of the invention also will have utility for these indications. Thus, in another aspect, the invention provides a method of treating a mammalian subject to prevent stenosis or restenosis of a blood vessel, comprising the step of administering to a mammalian subject in need of treatment to prevent stenosis or restenosis of a blood vessel a composition comprising one or more polypeptide(s) of the invention, in an amount effective to prevent stenosis or restenosis of the blood vessel. In a preferred embodiment, the administering comprises implanting an intravascular stent in the mammalian subject, where the stent is coated or impregnated with the composition. Exemplary materials for constructing a drug-coated or drug-impregnated stent are described in literature cited above and reviewed in Lincoff et al., Circulation, 90:2071–2084 (1994). In another preferred embodiment, the composition comprises microparticles composed of biodegradable polymers such as PGLA, non-degradable polymers, or biological polymers (e.g., starch) which particles encapsulate or are impregnated by a polypeptide(s) of the invention. Such particles are delivered to the intravascular wall using, e.g., an infusion angioplasty catheter. Other techniques for achieving locally sustained drug delivery are reviewed in Wilensky et al., Trends Caridovasc. Med., 3:163–170 (1993), incorporated herein by reference.

Administration via one or more intravenous injections subsequent to the angioplasty or bypass procedure also is contemplated. Localization of the polypeptides of the invention to the site of the procedure occurs due to expression of VEGF receptors on proliferating endothelial cells. Localization is further facilitated by recombinantly expressing the polypeptides of the invention as a fusion polypeptide (e.g., fused to an apolipoprotein B-100 oligopeptide as described in Shih et al., Proc. Nat'l. Acad. Sci. USA, 87:1436–1440 (1990). Co-administration of polynucleotides and polypeptides of the invention is also contemplated.

Likewise, the invention also provides surgical devices that are used to treat circulatory disorders, such as intravascular or endovascular stents, balloon catheters, infusion-perfusion catheters, extravascular collars, elastomeric membranes, and the like, which have been improved by coating with, impregnating with, adhering to, or encapsulating within the device a composition comprising a polynucleotide or polypeptide of the invention.

Polynucleotides or polypeptides of the invention could be administered purely as a prophylactic treatment to prevent stenosis, or shortly before, and/or concurrently with, and/or shortly after a percutaneous transluminal coronary angioplasty procedure, for the purpose of preventing restenosis of the subject vessel. In another preferred embodiment, the polynucleotide or polypeptide is administered before, during, and/or shortly after a bypass procedure (e.g., a coronary bypass procedure), to prevent stenosis or restenosis in or near the transplanted (grafted) vessel, especially stenosis at the location of the graft itself. In yet another embodiment, the polynucleotide or polypeptide is administered before, during, or after a vascular transplantation in the vascular periphery that has been performed to treat peripheral ischemia or intermittent claudication. By prevention of stenosis or restenosis is meant prophylactic treatment to reduce the amount/severity of, and/or substantially eliminate, the stenosis or restenosis that frequently occurs in such surgical procedures. The polynucleotide or polypeptide is included in the composition in an amount and in a form effective to promote stimulation of VEGF receptors in a blood vessel of the mammalian subject, thereby preventing stenosis or restenosis of the blood vessel.

In a preferred embodiment, the mammalian subject is a human subject. For example, the subject is a person suffering from coronary artery disease that has been identified by a cardiologist as a candidate who could benefit from a therapeutic balloon angioplasty (with or without insertion of an intravascular stent) procedure or from a coronary bypass procedure. Practice of methods of the invention in other mammalian subjects, especially mammals that are conventionally used as models for demonstrating therapeutic efficacy in humans (e.g., primate, porcine, canine, or rabbit animals), also is contemplated.

Polypeptides according to the invention may be administered in any suitable manner using an appropriate pharmaceutically-acceptable vehicle, e.g., a pharmaceutically-acceptable diluent, adjuvant, excipient or carrier. The composition to be administered according to methods of the invention preferably comprises (in addition to the polynucleotide or vector) a pharmaceutically-acceptable carrier solution such as water, saline, phosphate-buffered saline, glucose, or other carriers conventionally used to deliver therapeutics intravascularly. Multi-gene therapy is also contemplated, in which case the composition optionally comprises both the polynucleotide of the invention/vector and another polynucleotide/vector selected to prevent restenosis. Exemplary candidate genes/vectors for co-transfection with transgenes encoding polypeptides of the invention are described in the literature cited above, including genes encoding cytotoxic factors, cytostatic factors, endothelial growth factors, and smooth muscle cell growth/migration inhibitors.

The "administering" that is performed according to the present method may be performed using any medically-accepted means for introducing a therapeutic directly or indirectly into the vasculature of a mammalian subject, including but not limited to injections (e.g., intravenous, intramuscular, subcutaneous, or catheter); oral ingestion; intranasal or topical administration; and the like. In a preferred embodiment, administration of the composition comprising a polynucleotide of the invention is performed intravascularly, such as by intravenous, intra-arterial, or intracoronary arterial injection. The therapeutic composition may be delivered to the patient at multiple sites. The multiple administrations may be rendered simultaneously or may be administered over a period of several hours. In certain cases it may be beneficial to provide a continuous flow of the therapeutic composition. Additional therapy may be administered on a period basis, for example, daily, weekly or monthly.

In general, peroral dosage forms for the therapeutic delivery of peptides is ineffective because in order for such a formulation to the efficacious, the peptide must be protected from the enzymatic environment of the gastrointestinal tract. Additionally, the peptide must be formulated such that it is readily absorbed by the epithelial cell barrier in sufficient concentrations to effect a therapeutic outcome. The peptides of the present invention may be formulated with uptake or absorption enhancers to increase their efficacy. Such enhancer include for example, salicylate, glycocholate/ linoleate, glycholate, aprotinin, bacitracin, SDS caprate and the like. For an additional discussion of oral formulations of peptides for therapeutic delivery, those of skill in the art are referred to Fix (*J. Pharm. Sci.*, 85(12) 1282–1285, 1996) and Oliyai and Stella (*Ann. Rev. Pharmacol. Toxicol.*, 32:521–544, 1993).

The amounts of peptides in a given dosage will vary according to the size of the individual to whom the therapy is being administered as well as the characteristics of the disorder being treated. In exemplary treatments, it may be necessary to administer about 50 mg/day, 75 mg/day, 100 mg/day, 150 mg/day, 200 mg/day, 250 mg/day. These concentrations may be administered as a single dosage form or as multiple doses.

The polypeptides may also be employed in accordance with the present invention by expression of such polypeptide in vivo, which is often referred to as gene therapy. The present invention provides a recombinant DNA vector containing a heterologous segment encoding a polypeptide of the invention that is capable of being inserted into a microorganism or eukaryotic cell and that is capable of expressing the encoded protein.

In a highly preferred embodiment, the composition is administered locally. Thus, in the context of treating restenosis or stenosis, administration directly to the site of angioplasty or bypass is preferred. For example, the administering comprises a catheter-mediated transfer of the transgene-containing composition into a blood vessel of the mammalian subject, especially into a coronary artery of the mammalian subject. Exemplary materials and methods for local delivery are reviewed in Lincoff et al., Circulation, 90:2070–2084 (1994); and Wilensky et al., Trends Cardiovasc. Med., 3:163–170 (1993), both incorporated herein by reference. For example, the composition is administered using infusion-perfusion balloon catheters (preferably mircroporous balloon catheters) such as those that have been described in the literature for intracoronary drug infusions. See, e.g., U.S. Pat. No. 5,713,860 (Intravascular Catheter with Infusion Array); U.S. Pat. Nos. 5,087,244; 5,653,689; and Wolinsky et al., J. Am. Coll. Cardiol., 15:475–481 (1990) (Wolinsky Infusion Catheter); and Lambert et al., Coron. Artery Dis., 4:469–475 (1993), all of which are incorporated herein by reference in their entirety. Use of such catheters for site-directed somatic cell gene therapy is described, e.g., in Mazur et al., Texas Heart Institute Journal, 21; 104–111 (1994), incorporated herein by reference. In an embodiment where the transgene encoding a polypeptide of the invention is administered in an adenovirus vector, the vector is preferably administered in a pharmaceutically acceptable carrier at a titer of $10^7$–$10^{13}$ viral particles, and more preferably at a titer of $10^9$–$10^{11}$ viral particles. The adenoviral vector composition preferably is infused over a period of 15 seconds to 30 minutes, more preferably 1 to 10 minutes.

For example, in patients with angina pectoris due to a single or multiple lesions in coronary arteries and for whom PTCA is prescribed on the basis of primary coronary angiogram findings, an exemplary protocol involves performing PTCA through a 7F guiding catheter according to standard clinical practice using the femoral approach. If an optimal result is not achieved with PTCA alone, then an endovascular stent also is implanted. (A nonoptimal result is defined as residual stenosis of >30% of the luminal diameter according to a visual estimate, and B or C type dissection.) Arterial gene transfer at the site of balloon dilatation is performed with a replication-deficient adenoviral vector expressing a polypeptide of the invention immediately after the angioplasty, but before stent implantation, using an infusion-perfusion balloon catheter. The size of the catheter will be selected to match the diameter of the artery as measured from the angiogram, varying, e.g., from 3.0 to 3.5 F in diameter. The balloon is inflated to the optimal pressure and gene transfer is performed during a 10 minute infusion at the rate of 0.5 ml/min with virus titer of $1.15 \times 10^{10}$.

In another embodiment, intravascular administration with a gel-coated catheter is contemplated, as has been described in the literature to introduce other transgenes. See, e.g., U.S. Pat. No. 5,674,192 (Catheter coated with tenaciously-adhered swellable hydrogel polymer); Riessen et al., Human Gene Therapy, 4:749–758 (1993); and Steg et al., Circulation, 96:408–411 (1997) and 90:1648–1656 (1994); all incorporated herein by reference. Briefly, DNA in solution (e.g., a polynucleotide of the invention) is applied one or more times ex vivo to the surface of an inflated angioplasty catheter balloon coated with a hydrogel polymer (e.g., Slider with Hydroplus, Mansfield Boston Scientific Corp., Watertown, Mass.). The Hydroplus coating is a hydrophilic polyacrylic acid polymer that is cross-linked to the balloon to form a high molecular weight hydrogel tightly adhered to the balloon. The DNA covered hydrogel is permitted to dry before deflating the balloon. Re-inflation of the balloon intravascularly, during an angioplasty procedure, causes the transfer of the DNA to the vessel wall.

In yet another embodiment, an expandable elastic membrane or similar structure mounted to or integral with a balloon angioplasty catheter or stent is employed to deliver the transgene encoding a polypeptide of the invention. See, e.g., U.S. Pat. Nos. 5,707,385, 5,697,967, 5,700,286, 5,800, 507, and 5,776,184, all incorporated by reference herein.

In another variation, the composition containing the transgene encoding a polypeptide of the invention is administered extravascularly, e.g., using a device to surround or encapsulate a portion of vessel. See, e.g., International Patent Publication WO 98/20027, incorporated herein by reference, describing a collar that is placed around the outside of an artery (e.g., during a bypass procedure) to deliver a transgene to the arterial wall via a plasmid or liposome vector.

In still another variation, endothelial cells or endothelial progenitor cells are transfected ex vivo with the transgene encoding a polypeptide of the invention, and the transfected cells as administered to the mammalian subject. Exemplary procedures for seeding a vascular graft with genetically modified endothelial cells are described in U.S. Pat. No. 5,785,965, incorporated herein by reference.

In preferred embodiments, polynucleotides of the invention further comprises additional sequences to facilitate the gene therapy. In one embodiment, a "naked" transgene encoding a polypeptide of the invention (i.e., a transgene without a viral, liposomal, or other vector to facilitate transfection) is employed for gene therapy. In this embodiment, the polynucleotide of the invention preferably comprises a suitable promoter and/or enhancer sequence (e.g., cytomegalovirus promoter/enhancer [Lehner et al., J. Clin. Microbiol., 29:2494–2502 (1991); Boshart et al., Cell, 41:521–530 (1985)]; Rous sarcoma virus promoter [Davis et al., Hum. Gene Ther., 4:151 (1993)]; Tie promoter

[Korhonen et al., Blood, 86(5): 1828–1835 (1995)]; or simian virus 40 promoter) for expression in the target mammalian cells, the promoter being operatively linked upstream (i.e., 5') of the polypeptide-coding sequence. The polynucleotides of the invention also preferably further includes a suitable polyadenylation sequence (e.g., the SV40 or human growth hormone gene polyadenylation sequence) operably linked downstream (i.e., 3') of the polypeptide-coding sequence. The polynucleotides of the invention also preferably comprise a nucleotide sequence encoding a secretory signal peptide fused in-frame with the polypeptide sequence. The secretory signal peptide directs secretion of the polypeptide of the invention by the cells that express the polynucleotide, and is cleaved by the cell from the secreted polypeptide. The signal peptide sequence can be that of another secreted protein, or can be a completely synthetic signal sequence effective to direct secretion in cells of the mammalian subject.

The polynucleotide may further optionally comprise sequences whose only intended function is to facilitate large-scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention. One can manufacture and administer such polynucleotides to achieve successful gene therapy using procedures that have been described in the literature for other transgenes. See, e.g., Isner et al., Circulation, 91:2687–2692 (1995); and Isner et al., Human Gene Therapy, 7:989–1011 (1996); incorporated herein by reference in the entirety.

Any suitable vector may be used to introduce the transgene encoding one of the polypeptides of the invention, into the host. Exemplary vectors that have been described in the literature include replication-deficient retroviral vectors, including but not limited to lentivirus vectors [Kim et al., J. Virol., 72(1): 811–816 (1998); Kingsman & Johnson, Scrip Magazine, October, 1998, pp. 43–46.]; adeno-associated viral vectors [U.S. Pat. Nos. 5,474,935; 5,139,941; 5,622,856; 5,658,776; 5,773,289; 5,789,390; 5,834,441; 5,863,541; 5,851,521; 5,252,479; Gnatenko et al., J. Investig. Med., 45:87–98 (1997)]; adenoviral vectors [See, e.g., U.S. Pat. Nos. 5,792,453; 5,824,544; 5,707,618; 5,693,509; 5,670,488; 5,585,362; Quantin et al., Proc. Natl. Acad. Sci. USA, 89:2581–2584 (1992); Stratford-Perricadet et al., J. Clin. Invest., 90:626–630 (1992); and Rosenfeld et al., Cell, 68: 143–155 (1992)]; an adenoviral-adenoassociated viral hybrid (see for example, U.S. Pat. No. 5,856,152) or a vaccinia viral or a herpesviral (see for example, U.S. Pat. Nos. 5,879,934; 5,849,571; 5,830,727; 5,661,033; 5,328,688; Lipofectin-mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in their entirety. Replication-deficient adenoviral vectors constitute a preferred embodiment.

Other non-viral delivery mechanisms contemplated include calcium phosphate precipitation (Graham and Van Der Eb, *Virology*, 52:456–467, 1973; Chen and Okayama, *Mol. Cell Biol.*, 7:2745–2752, 1987; Rippe et al., *Mol. Cell Biol.*, 10:689–695, 1990) DEAE-dextran (Gopal, *Mol. Cell Biol.*, 5:1188–1190, 1985), electroporation (Tur-Kaspa et al., *Mol. Cell Biol.*, 6:716–718, 1986; Potter et al., *Proc. Nat. Acad. Sci. USA*, 81:7161–7165, 1984), direct microinjection (Harland and Weintraub, *J. Cell Biol.*, 101:1094–1099, 1985.), DNA-loaded liposomes (Nicolau and Sene, *Biochim. Biophys. Acta*, 721:185–190, 1982; Fraley et al., *Proc. Natl. Acad. Sci. USA*, 76:3348–3352, 1979; Felgner, *Sci Am.* 276(6):102–6, 1997; Felgner, *Hum Gene Ther.* 7(15):1791–3, 1996), cell sonication (Fechheimer et al., *Proc. Natl. Acad. Sci. USA*, 84:8463–8467, 1987), gene bombardment using high velocity microprojectiles (Yang et al., *Proc. Natl. Acad. Sci USA*, 87:9568–9572, 1990), and receptor-mediated transfection (Wu and Wu, *J. Biol. Chem.*, 262:4429–4432, 1987; Wu and Wu, *Biochemistry*, 27:887–892, 1988; Wu and Wu, *Adv. Drug Delivery Rev.*, 12:159–167, 1993).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: *Liver diseases, targeted diagnosis and therapy using specific receptors and ligands*, Wu G, Wu C ed., New York: Marcel Dekker, pp. 87–104, 1991). The addition of DNA to cationic liposomes causes a topological transition from liposomes to optically birefringent liquid-crystalline condensed globules (Radler et al., *Science*, 275(5301):810–4, 1997). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda et al., *Science*, 243:375–378, 1989). In other embodiments, the liposome may be complexed or employed in conjunction with nuclear nonhistone chromosomal proteins (HMG-1) (Kato et al., *J. Biol. Chem.*, 266:3361–3364, 1991). In yet further embodiments, the liposome maybe complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987, supra) and transferrin (Wagner et al., *Proc. Nat'l. Acad Sci. USA*, 87(9):3410–3414, 1990). Recently, a synthetic neoglycoprotein, which recognizes the same receptor as ASOR, has been used as a gene delivery vehicle (Ferkol et al., *FASEB J.*, 7:1081–1091, 1993; Perales et al., *Proc. Natl. Acad. Sci., USA* 91:4086–4090, 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (*Methods Enzymol.*, 149:157–176, 1987) employed lactosylceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky et al. (*Proc. Nat. Acad. Sci. USA*, 81:7529–7533, 1984) successfully injected polyomavirus DNA in the form of $CaPO_4$ precipitates into liver and spleen of adult and newborn mice demonstrating active viral replication and acute infection. Benvenisty and Neshif (*Proc. Nat. Acad. Sci. USA*, 83:9551–9555, 1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., *Nature*, 327:70–73, 1987). Several devices for accelerating small particles have been developed. One such device relies on a high voltage discharge to generate an electrical current, which in turn provides the motive force (Yang et al., *Proc. Natl. Acad. Sci USA*, 87:9568–9572, 1990). The microprojectiles used have consisted of biologically inert substances such as tungsten or gold beads.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the invention.

Thus, in one embodiment the composition to be administered comprises a vector, wherein the vector comprises a polynucleotide of the invention. In a preferred embodiment, the vector is an adenovirus vector. In a highly preferred embodiment, the adenovirus vector is replication-deficient, i.e., it cannot replicate in the mammalian subject due to deletion of essential viral-replication sequences from the adenoviral genome. For example, the inventors contemplate a method wherein the vector comprises a replication-deficient adenovirus, the adenovirus comprising the polynucleotide of the invention operably connected to a promoter and flanked on either end by adenoviral polynucleotide sequences.

Similarly, the invention includes kits which comprise compounds or compositions of the invention packaged in a manner which facilitates their use to practice methods of the invention. In a simplest embodiment, such a kit includes a compound or composition described herein as useful for practice of the invention (e.g., polynucleotides or polypeptides of the invention), packaged in a container such as a sealed bottle or vessel, with a label affixed to the container or included in the package that describes use of the compound or composition to practice the method of the invention. Preferably, the compound or composition is packaged in a unit dosage form. In another embodiment, a kit of the invention includes a composition of both a polynucleotide or polypeptide packaged together with a physical device useful for implementing methods of the invention, such as a stent, a catheter, an extravascular collar, a polymer film, or the like. In another embodiment, a kit of the invention includes compositions of both a polynucleotide or polypeptide of the invention packaged together with a hydrogel polymer, or microparticle polymers, or other carriers described herein as useful for delivery of the polynucleotides or polypeptides to the patient.

The polypeptides of the present invention are useful in diagnostic or prognostic assays for detecting VEGF receptor protein expression. Polypeptides of the invention that bind to one or more VEGF receptors may be used for detecting and measuring the presence of specific receptor proteins in samples for purposes such as e.g., medical imaging, detection, screening, or targeted therapy. Detectable labels such as radioactive or non-radioactive labels, including enzyme labels or labels of the biotin/avidin system, may be used to tag the polypeptide of the invention. The polypeptide may also be covalently or non-covalently coupled to a suitable supermagnetic, paramagnetic, electron dense, ecogenic or radioactive agent for imaging.

The present invention also relates to a diagnostic assay for detecting altered levels of VEGF receptor proteins in various tissues since over-expression of the proteins compared to normal control tissue samples may detect the presence of a disease or susceptibility to a disease, for example, abnormal cell growth or differentiation. Polypeptides of the invention can be used to quantify future metastatic risk by assaying biopsy material for the presence of active receptors or ligands in a binding assay or kit using detectably-labeled polypeptides of the invention.

A related aspect of the invention is a method for the detection of specific cells, e.g., endothelial cells. These cells may be found in vivo, or in ex vivo biological tissue samples. The method of detection comprises the steps of contacting a biological tissue comprising, e.g., endothelial cells, with a hybrid polypeptide according to the invention which is capable of binding to VEGFR(s), under conditions wherein the hybrid polypeptide binds to the cells, optionally washing the biological tissue, and detecting the hybrid polypeptide bound to the cells in the biological tissue, thereby detecting the cells. It will be apparent that certain polypeptides of the invention are useful for detecting and/or imaging cells that express more than one VEGFR, whereas other polypeptides are useful for imaging cells which specifically express a particular VEGFR.

The invention also is directed to a method for imaging vertebrate tissue suspected of containing cells that express a specific VEGFR comprising the steps of: (a) contacting vertebrate tissue with a composition comprising polypeptide(s) of the invention that specifically bind the particular VEGFR; and (b) imaging the tissue by detecting the VEGFR-binding polypeptide bound to the tissue. Preferably, the tissue is human tissue, and the method further comprises the step of washing the tissue, after the contacting step and before the imaging step, under conditions that remove from the tissue polypeptides that are not bound to the VEGFR in the tissue.

In a related variation, the invention provides a method for imaging tumors in tissue from a vertebrate organism, comprising the steps of: (a) contacting vertebrate tissue suspected of containing a tumor with a composition comprising a VEGFR binding compound; (b) detecting the VEGFR binding compound bound to cells in said tissue; and (c) imaging solid tumors by identifying blood vessel endothelial cells bound by the VEGFR binding compound, wherein blood vessels expressing VEGFR are correlated with the presence and location of a tumor in the tissue.

The present invention also is directed to the use of hybrid polypeptides of the invention that bind VEGF receptors as specific markers for particular tissues and cell types. For example, those polypeptides of the invention that specifically bind VEGFR-3 can serve as markers for lymphatic endothelial cells.

Similarly, polypeptides of the invention may be screened for an ability to modulate the growth of isolated cells or cell lines. For example, certain neoplastic disease states are characterized by the appearance of VEGF receptors on cell surfaces [Valtola et al., *Am J Path* 154:1381–90 (1999)]. Polypeptides of the invention may be screened to determine the ability of the polypeptide to modulate the growth of the neoplastic cells. Other disease states are likely characterized by mutations in VEGF receptors [Ferrell et al., *Hum Mol Genetics* 7:2073–78 (1998)]. Polypeptides of the invention that modulate the activity of the mutant forms of the VEGF receptor in a manner different than naturally-occurring vascular endothelial growth factors will be useful at modulating the symptoms and severity of the such disease states.

In vivo imaging or tissue biopsy may reveal that certain neoplastic cells are expressing a particular combination of receptors, thereby providing an indication for polypeptides of the invention that bind the expressed set of receptors and inhibit ligand mediated growth.

The use of such diagnostic imaging is particularly suitable in obtaining an image of, for example, a tumor mass or the neovascularizarion near a tumor mass. It is contemplated that the peptides of the present invention may be employed for imaging in a manner analogous to the antibody-based methods disclosed in U.S. Pat. No. 6,107,046, incorporated herein by reference.

Many appropriate imaging agents are known in the art, as are methods of attaching the labeling agents to the peptides of the invention (see, e.g., U.S. Pat. Nos. 4,965,392, 4,472,509, 5,021,236 and U.S. Pat. No. 5,037,630, incorporated herein by reference). The labeled peptides are administered to a subject in a pharmaceutically acceptable carrier, and allowed to accumulate at a target site having the VEGFR-3 receptor. This peptide imaging agent then serves as a contrast reagent for X-ray, magnetic resonance, sonographic or scintigraphic imaging of the target site. The peptides of the present invention are a convenient and important addition to the available arsenal of medical imaging tools for the diagnostic investigation of cancer and other VEGFR-3 related disorders.

Paramagnetic ions useful in the imaging agents of the present invention include for example chromium(III), manganese(II), iron(III), iron(II), cobalt(II), nickel(II) copper(II), neodymium(III), samarium(III), ytterbium(III), gadolinium(III), vanadium(II), terbium(III), dysprosium (III), holmium(III) and erbium(III). Ions useful for X-ray imaging include but are not limited to lantanum(III), gold (III), lead(II) and particularly bismuth(III). Radioisotopes for diagnostic applications include for example, $^{211}$astatine, $^{14}$carbon, $^{51}$chromium, $^{36}$chlorine, $^{57}$cobalt, $^{67}$copper, $^{152}$Eu, $^{67}$gallium, $^{3}$hydrogen, $^{123}$iodine, $^{125}$iodine, $^{111}$indium, $^{59}$iron, $^{32}$phosphorus, $^{186}$rhenium, $^{75}$selenium, $^{35}$sulphur, $^{99m}$technicium and $^{90}$yttrium.

The peptides of the present invention may be labeled according to techniques well known to those of skill in the art. For example, the peptides can be iodinated by contacting the peptide with sodium or potassium iodide and a chemical oxidizing agent such as sodium hypochlorite or an enzymatic oxidant such as lactoperoxidase. Peptides may be labeled with technetium-99m by ligand exchange, for example, by reducing pertechnate with stannous solution, chelating the reduced technetium onto a Sephadex column and applying the peptide to the column. These and other techniques for labeling proteins and peptides are well known to those of skill in the art.

Using Polypeptides of the Invention in Combined Therapy for Neoplastic Disorders Tumor cell resistance to DNA damaging agents represents a major problem in clinical oncology. One goal of current cancer research is to find ways to improve the efficacy of chemo- and radiotherapy. As described above, the peptides of the present invention may be administered in conjunction with chemo- or radiotherapeutic intervention, immunotherapy, or with other anti-angiogenic/anti-lymphangiogenic therapy.

To kill cells, inhibit cell growth, inhibit metastasis, inhibit angiogenesis or otherwise reverse or reduce the malignant phenotype of tumor cells via combination therapy, using the methods and compositions of the present invention, one would generally contact a "target" cell or tissue, (e.g., a tumor and/or its vasculature) with the therapeutic peptides of the present invention (either as a peptide composition or as an expression construct that will express the peptide) and at least one other agent, which optionally is conjugated to the peptide of the invention. These compositions would be provided in a combined amount effective to kill or inhibit proliferation of the cancer by killing and/or inhibiting the proliferation of the cancer cells and/or the endothelia of blood and lymphatic vessels supplying and serving the cancer cells. This process may involve contacting the cells with the peptide or expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the peptide or expression construct and the other includes the second agent.

Alternatively, the therapeutic treatment employing the peptides of the present invention may precede or follow the other agent treatment by intervals ranging from minutes to weeks. In embodiments where the other agent and expression construct are administered separately, one would generally ensure that a significant period of time did not expire between the time of each delivery, such that the agent and the peptide-based therapeutic would still be able to exert an advantageously combined effect. In such instances, it is contemplated that one would administer both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated. In specific embodiments, an anti-cancer therapy may be delivered which directly attacks the cancer cells in a manner to kill, inhibit or necrotize the cancer cell, in addition a therapeutic composition based on the peptides of the present invention also is administered to the individual in amount effective to have an antiangiogenic and/or anti-lymphangiogenic effect. The peptide compositions may be administered following the other anti-cancer agent, before the other anti-cancer agent or indeed at the same time as the other anti-cancer agent, optionally conjugated to the other agent.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells and/or the endothelia of the tumor vessels with an agent in addition to the therapeutic agent comprising one or more peptide of the present invention. This may be achieved by irradiating the localized tumor site with radiation such as X-rays, UV-light, gamma-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or cisplatin. Kinase inhibitors also contemplated to be useful in combination therapies with the peptides of the present invention. The agent may be prepared and used as a combined therapeutic composition, or kit, by combining it with a chimeric peptide of the invention, as described above.

Agents that directly cross-link nucleic acids, specifically DNA, are envisaged to facilitate DNA damage leading to a synergistic, antineoplastic combination with chimeric peptide-based therapy. Agents such as cisplatin, and other DNA alkylating agents may be used. Cisplatin has been widely used to treat cancer, with efficacious doses used in clinical applications of 20 mg/$M^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/$m^2$ at 21 day intervals for adriamycin, to 35–50 mg/$m^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

By way of example the following is a list of chemotherapeutic agents and the cancers which have been shown to be managed by administration of such agents. Combinations of these chemotherapeutics with the peptides of the present invention may prove to be useful in amelioration of various neoplastic disorders. Examples of these compounds include adriamycin (also known as doxorubicin), VP-16 (also known as etoposide), and the like, daunorubicin (intercalates into DNA, blocks DNA-directed RNA polymerase and inhibits DNA synthesis); mitomycin (also known as mutamycin and/or mitomycin-C) is an antibiotic isolated from the broth of *Streptomyces caespitosus* which has been shown to have antitumor activity; Actinomycin D also may be a useful drug to employ in combination with the peptides of the present invention because tumors which fail to respond to systemic treatment sometimes respond to local perfusion with dactinomycin which also is known to potentiate radiotherapy. It also is used in combination with primary surgery, radiotherapy, and other drugs, particularly vincristine and cyclophosphamide and has been found to be effective against Ewing's tumor, Kaposi's sarcoma, and soft-tissue sarcomas, choriocarcinoma, metastatic testicular carcinomas, Hodgkin's disease and non-Hodgkin's lymphomas.

Bleomycin is a mixture of cytotoxic glycopeptide antibiotics isolated from a strain of *Streptomyces verticillus*, is effective in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Cisplatin has been widely used to treat cancers such as metastatic testicular or ovarian carcinoma, advanced bladder cancer, head or neck cancer, cervical cancer, lung cancer or other tumors and may be a useful combination with the peptides of the present invention. VP16 (etoposide) and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS). Tumor Necrosis Factor [TNF; Cachectin] glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. TNF can be quite toxic when used alone in effective doses, so that the optimal regimens probably will use it in lower doses in combination with other drugs. Its immunosuppressive actions are potentiated by γ-interferon, so that the combination potentially is dangerous. A hybrid of TNF and interferon-α also has been found to possess anti-cancer activity.

Taxol an antimitotic agent original isolated from the bark of the ash tree, *Taxus brevifolia*, and its derivative paclitaxol have proven useful against breats cancer and may be used in the combination therapies of the present invention. Beneficial responses to vincristine have been reported in patients with a variety of other neoplasms, particularly Wilms' tumor, neuroblastoma, brain tumors, rhabdomyosarcoma, and carcinomas of the breast, bladder, and the male and female reproductive systems. Vinblastine also is indicated as a useful therapeutic in the same cancers as vincristine. The most frequent clinical use of vinblastine is with bleomycin and cisplatin in the curative therapy of metastatic testicular tumors. It is also active in Kaposi's sarcoma, neuroblastoma, and Letterer-Siwe disease (histiocytosis X), as well as in carcinoma of the breast and choriocarcinoma in women.

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. Melphalan is the active L-isomer of the D-isomer, known as medphalan, which is less active against certain animal tumors, and the dose needed to produce effects on chromosomes is larger than that required with the L-isomer. Melphalan is available in form suitable for oral administration and has been used to treat multiple myeloma. Available evidence suggests that about one third to one half of the patients with multiple myeloma show a favorable response to oral administration of the drug. Melphalan has been used in the treatment of epithelial ovarian carcinoma.

Cyclophosphamide is stable in the gastrointestinal tract, tolerated well and effective by the oral and parental routes and does not cause local vesication, necrosis, phlebitis or even pain. Chlorambucil, a bifunctional alkylating agent of the nitrogen mustard type that has been found active against selected human neoplastic diseases. Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Other factors that cause DNA damage and have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. (See, e.g., Remington's Pharmaceutical Sciences" 15th Edition, chapter 33, in particular pages 624–652.) Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining chimeric peptide-based therapies with chemo- and radiotherapies, it also is contemplated that combination with gene therapies will be advantageous. For example, targeting of chimeric peptide-based therapies and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

In addition to the anticancer therapeutics discussed above, it is contemplated that the peptides of the invention may be combined with other angiogenesis inhibitors. The peptides of the present invention are expected to have both anti-lymphangiogenic and anti-angiogenic properties. Many anti-angiogenic drugs also may have anti-lymphangiogenic properties. http://cancertrials.nci.nih.gov/news/angio is a website maintained by the National Institutes of Health which provides current information on the trials presently being conducted with anti-angiogenic agents. These agents include, for example, Marimastat (British Biotech, Annapolis, Md.; indicated for non-small cell lung, small cell lung and breast cancers); AG3340 (Agouron, LaJolla, Calif.; for glioblastoma multiforme); COL-3 (Collagenex, Newtown Pa.; for brain tumors); Neovastat (Aetema, Quebec, Canada; for kidney and non-small cell lung cancer) BMS-275291 (Bristol-Myers Squibb, Wallingford Conn.; for metastatic non-small cell ling cancer); Thalidomide (Celgen; for melanoma, head and neck cancer, ovarian, metastatic prostate, and Kaposi's sarcoma; recurrent or metastatic colorectal cancer (with adjuvants); gynecologic sarcomas, liver cancer; multiple myeloma; CLL, recurrent or progressive brain cancer, multiple myeloma, non-small cell lung, nonmetastatic prostate, refractory multiple myeloma, and renal cancer); Squalamine (Magainin Pharmaceuticals Plymouth Meeting, Pa.; non-small cell cancer and ovarian cancer); Endostatin (EntreMEd, Rockville, Md.; for solid tumors); SU5416 (Sugen, San Francisco, Calif.; recurrent head and neck, advanced solid tumors, stage IIIB or IV breast cancer, recurrent or progressive brain (pediatric); Ovarian, AML; glioma, advanced malignancies, advanced colorectal, von-Hippel Lindau disease, advanced soft tissue; prostate cancer, colorectal cancer, metastatic melanoma, multiple myeloma, malignant mesothelioma: metastatic renal, advanced or recurrent head and neck, metastatic colorectal cancer); SU6668 (Sugen San Francisco, Calif.; advanced tumors); interferon-α; Anti-VEGF antibody (NAtional Cancer Institute, Bethesda Md.; Genentech San Franscisco, Calif.; refractory solid tumors; metastatic renal cell cancer, in untreated advanced colorectal); EMD121974 (Merck KCgaA, Darmstadt, Germany; HIV related Kaposi's Sarcoma, progressive or recurrent Anaplastic Glioma); Interleukin 12 (Genetics Institute, Cambridge, Mass.; Kaposi's sarcoma) and IM862 (Cytran, Kirkland, Wash.; ovarian cancer, untreated metastatic cancers of colon and rectal origin and Kaposi's sarcoma). The parenthetical information following the agents indicates the cancers against which the agents are being used in these trials. It is contemplated that any of these disorders may be treated with the peptides of the present invention either alone or in combination with the agents listed.

Additional features of the invention will be apparent from the following Examples.

EXAMPLE 1

Construction of VEGF-A/VEGF-C Hybrid Molecules

Although the amino acid residues of the receptor binding domain of VEGF family members are share conserved motifs, these proteins exhibit different receptor specificities. In the following experiment, DNA molecules encoding polypeptides containing different portions of the receptor binding domains of either VEGF-A or VEGF-C were constructed using a combinatorial approach to create novel hybrid molecules with unique structural and functional characteristics.

To generate the novel molecules, the nucleotide sequences of VEGF-A and mature VEGF-C were analyzed to determine localized regions of nucleotide identity which would be suitable for designing short DNA fragments which could be synthesized and readily recombined. Eight corresponding regions of identity were selected in each molecule as sites for fragmentization (into nine fragments) and recombination into chimeric (hybrid) molecules. These fragmentation sites were chosen based on nucleotide sequence and also because the resultant fragments would correspond to structural elements (e.g., alpha helix, loop, etc.) based on the crystal structure of VEGF-A (see FIG. 1).

Fragmentation of VEGF-A

Nine pairs of synthetic oligonucleotides were designed based on the coding sequence for $VEGF_{121}$, for the purpose of forming nine DNA fragments that encompass the receptor binding domain encoding region of VEGF-A (corresponding to nucleotides 156 to 461 of SEQ ID NO: 1, which encode amino acid residues 34 to 135 of SEQ ID NO: 2). Each oligonucleotide pair comprised a forward primer containing coding sequence and a reverse primer with nucleotide sequence complementary to a portion of the forward primer, to permit annealing of the primers to each other into a double-stranded DNA fragment. Either the forward or reverse primer of each pair also included a short 5' and 3' nucleotide sequence that was not complementary to any sequence of its paired primer. These short additional sequences correspond to the localized regions of nucleotide identity set forth above. Following annealing of primer pairs, this additional sequence formed single-stranded overhangs compatible with annealing with other double-stranded annealed primer pairs, as described in greater detail below. The nucleotide sequences from the VEGF-A forward and reverse primers are set forth below in Tables 1A and 1B, respectively.

The nucleotide sequences of forward primers A1-F to A9-F are set forth in SEQ ID NOs: 3–11, respectively. For each of the primers listed, the top strand shows the DNA sequence and the bottom strand indicates the amino acids encoded by that particular primer, SEQ ID NOs: 128–136, respectively. In some instances, only two nucleotides of a given codon is contained in one primer, and the remaining nucleotide of the codon is contained in the preceding or following primer. In these cases, the amino acid is listed under the primer that contains 2 out of the 3 nucleotides of that particular codon. Boldface type indicate nucleotides coding for amino acids that constitute a protein linker region and are not part of the parent VEGF-A or VEGF-C molecule; underlined nucleotides are those that are removed during assembly of the fragments into hybrid constructs; and the lowercase letters are those nucleotides that produce an overhang when the oligonucleotide pairs are annealed to each other to produce the 9 fragments.

TABLE 1A

Forward (Coding) Primers for VEGF-A

```
A1-F  gat cCT GGG CAG AAT CAT CAC GAA GTG Gtg aaa t
          D   P   G   Q   N   H   H   E   V   V   K A2-F  TC ATG GAT GTC TAT CAG CGC AGC TAC TGC CAT
       F   M   D   V   Y   Q   R   S   Y   C   H A3-F  ccg aTC GAG ACA CTG GTG GAC ATC TTC CAG GAATAGAAGAGC
          P   I   E   T   L   V   D   I   F   Q A4-F  CGCTCTTCGAA TAC CCT GAT GAG ATC GAG TAC A
                    E   Y   P   D   E   I   E   Y A5-F  tc ttc aag cca TCC TGC GTG CCC CTG ATG AGA TGT GGC
        I   F   K   P   S   C   V   P   L   M   R   C   G

A6-F  CCG GGT TGC TGC AAT GAC GAA GGG CTG G
       G   C   C   N   D   E   G   L

A7-F  ag tgC GTT CCC ACC GAG GAG TCC AAC ATC ACC ATG CAG ATT ATG AG
         E   C   V   P   T   E   E   S   N   I   T   M   Q   I   M   R

A8-F  a att AAA CCT CAC CAA GGG CAG CAC ATC GGA GAG ATG agc ttt
          I   K   P   H   Q   G   Q   H   I   G   E   M   S   F A9-F  CTC CAG CAT AAC AAA TGT GAA TGT AGA CCA AAG AAA GATTGAGTCTTCGC
       L   Q   H   N   K   C   E   C   R   P   K   K   D
```

TABLE 1B

Reverse (Non-Coding) Primers for VEGF-A

```
A1-R  CCACTTCGTGATGATTCTGCCCAG

A2-R  tcggATGGCAGTAGCTGCGCTGATAGACATCCATGAatttca

A3-R  tcgaGCTCTTCTATTCCTGGAAGATGTCCACCAGTGTCTCGA

A4-R  tggcttgaagatGTACTCGATCTCATCAGGGTATTCGAAGAGCGgtac

A5-R  catgGCCACATCTCATCAGGGGCACGCAGGA

A6-R  gcactCCAGCCCTTCGTCATTGCAGCAACCCGGGTAC

A7-R  aattCTCATAATCTGCATGGTGATGTTGGACTCCTCGGTGGGAAC
```

TABLE 1B-continued

Reverse (Non-Coding) Primers for VEGF-A

A8-R CATCTCTCCGATGTGCTGCCCTTGGTGAGGTTT

A9-R <u>GGCCGCGAAGACTCA</u>ATCTTTCTTTGGTCTACATTCACATTTGTTATGCTGGAGaaagct

The nucleotide sequences of reverse primers A1-R to A9-R are set forth in SEQ ID NOs: 12–20, respectively. Boldface, underlined and lowercase letters are used as described in Table 1A.

Nine VEGF-A polynucleotide fragments were assembled by annealing a matched pair of synthetic oligonucleotide primers. For example, fragment A1 was created by annealing primer A1-F with primer A1-R, fragment A2 was created by annealing A2-F with A2-R, and so on. Annealing was accomplished by incubating 2 pmol/μl of each appropriate primer, 20 mM Tris/HCl, 2 mM $MgCl_2$, and 50 mM NaCl, pH 7.4 at 95° C. for 5 minutes, followed by cooling of the solution to 37° C. at a rate of 1° C./minute. As shown in Table 1A, fragment A1 encodes amino acid residues 34 to 42, and part of amino acid 43 of SEQ ID NO: 2; fragment A2 encodes part of amino acid 43, and amino acids 44–53 of SEQ ID NO: 2; fragment A3 encodes amino acids 54 to 63, and part of amino acid 64 of SEQ ID NO: 2; fragment A4 encodes part of amino acid 64, amino acids 65 to 71, and part of amino acid 72 of SEQ ID NO: 2; fragment A5 encodes part of amino acid 72, amino acids 73 to 83, and part of amino acid 84 of SEQ ID NO: 2; fragment A6 encodes part of amino acid 84, amino acids 85 to 92, and part of amino acid 93 of SEQ ID NO: 2; fragment A7 encodes part of amino acid 93, amino acids 94 to 107, and part of amino acid 108 of SEQ ID NO: 2; fragment A8 encodes part of amino acid 108, and amino acids 109 to 122 of SEQ ID NO: 2; and fragment A9 encodes amino acids 123 to 135 of SEQ ID NO: 2.

Fragmentation of VEGF-C

In a similar manner, nine pairs of oligonucleotides were designed and synthesized based upon the amino acid sequence of the receptor binding domain of VEGF-C (corresponding to nucleotides 658 to 999 of SEQ ID NO: 21, which encode amino acid residues 112 to 216 of SEQ ID NO: 22). The nucleotide sequences of the nine forward primers and nine reverse primers are set forth in Table 2A (SEQ ID NOs: 23–31) and Table 2B (SEQ ID NOs: 32–40), respectively. The amino acid sequence encoded by the nine forward primers are set forth in SEQ ID NOs: 137–145, respectively.

TABLE 2A

Forward (Coding) Primers for VEGF-C

```
C1-F  gat cCT GCA CAT TAT AAT ACC GAG ATC Ctg aaa t
          D   P   A   H   Y   N   T   E   I   L   K C2-F  CT ATT GAT AAT GAG TGG AGA AAG ACT CAG TGC ATG
       S   I   D   N   E   W   R   K   T   Q   C   M C3-F  ccg aGA GAG GTG TGT ATC GAC GTG GGG AAG GAATAGAAGAGC
          P   R   E   V   C   I   D   V   G   K C4-F  CGCTCTTCGAA TTT GGA GTC GCG ACA AAC ACC T
                   E   F   G   V   A   T   N   T C5-F  tc ttc aag cca CCA TGT GTG TCC GTG TAC AGA TGT GGC
         F   F   K   P   P   C   V   S   V   Y   R   C   G

C6-F  CCG GGT TGC TGC AAT AGT GAG GGG CTG C
       G   C   C   N   S   E   G   L

C7-F  ag tgc ATG AAC ACG TCC ACG AGC TAC CTC AGC AAG ACG CTG TTT GA
          Q   C   M   N   T   S   T   S   Y   L   S   K   T   L   F   E C8-F  a att ACA GTG CCT CTC TCT CAA GGG CCC AAA CCA GTG ACA ATC agcttt
           I   T   V   P   L   S   Q   G   P   K   P   V   T   I   S   F C9-F  GCC AAT CAC ACT TCC TGC CGA TGC ATG TCT AAG CTG GATTGAGTCTTCGC
       A   N   H   T   S   C   R   C   M   S   K   L   D
```

TABLE 2B

Forward (Coding) Primers for VEGF-C

C1-R GGATCTCGGTATTATAATGTGCAG

C2-R tcggCATGCACTGAGTCTTTCTCCACTCATTATCAATAGatttca

C3-R <u>tcga</u>GCTCTTCTATTCCTTCCCCACGTCGATACACACCTCTC

TABLE 2B-continued

Forward (Coding) Primers for VEGF-C

C4-R tggcttgaagaAGGTGTTTGTCGCGACTCCAAATTCGAAGAGCGgtac

C5-R catgGCCACATCTGTACACGGACACACATGG

C6-R gcactGCAGCCCCTCACTATTGCAGCAACCCGGgctac

C7-R aattTCAAACAGCGTCTTGCTGAGGTAGCTCGTGGACGTGTTCAT

C8-R GATTGTCACTGGTTTGGGCCCTTGAGAGAGGCACTGT

C9-R ggccGCGAAGACTCAATCCAGCTTAGACATGCATCGGCAGGAAGTGTGATTGGCaaagct

Boldface, underlined and lowercase letters are used in Tables 2A and 2B as described in Table 1A.

Primer pairs were annealed to form nine double-stranded DNA fragments which together encoded the receptor binding domain of VEGF-C, and which possessed appropriate single stranded overhangs for annealing to other fragments, as described above for VEGF-A.

Fragment C1 encodes amino acid residues 112 to 120, and part of amino acid 121 of SEQ ID NO: 22; fragment C2 encodes part of amino acid 121 and amino acids 122 to 132 of SEQ ID NO: 22; fragment C3 encodes amino acids 133 to 142, and part of amino acid 143 of SEQ ID NO: 22; fragment C4 encodes part of amino acid 143, amino acids 144 to 150, and part of amino acid 151 of SEQ ID NO: 22; fragment C5 encodes part of amino acid 151, amino acids 152 to 162, and part of amino acid 163 of SEQ ID NO: 22; fragment C6 encodes part of amino acid 163, and amino acids 164 to 171, and part of amino acid 172 of SEQ ID NO: 22; fragment C7 encodes part of amino acid 172, amino acids 173 to 186, and part of amino acid 187 of SEQ ID NO: 22; fragment C8 encodes part of amino acid 187, amino acid 188 to 203 of SEQ ID NO: 22; and fragment C9 encodes amino acid 204 to 216 of SEQ ID NO: 22.

Discussion Regarding the Synthesis of the VEGF-A and VEGF-C Fragments

Figure 2:
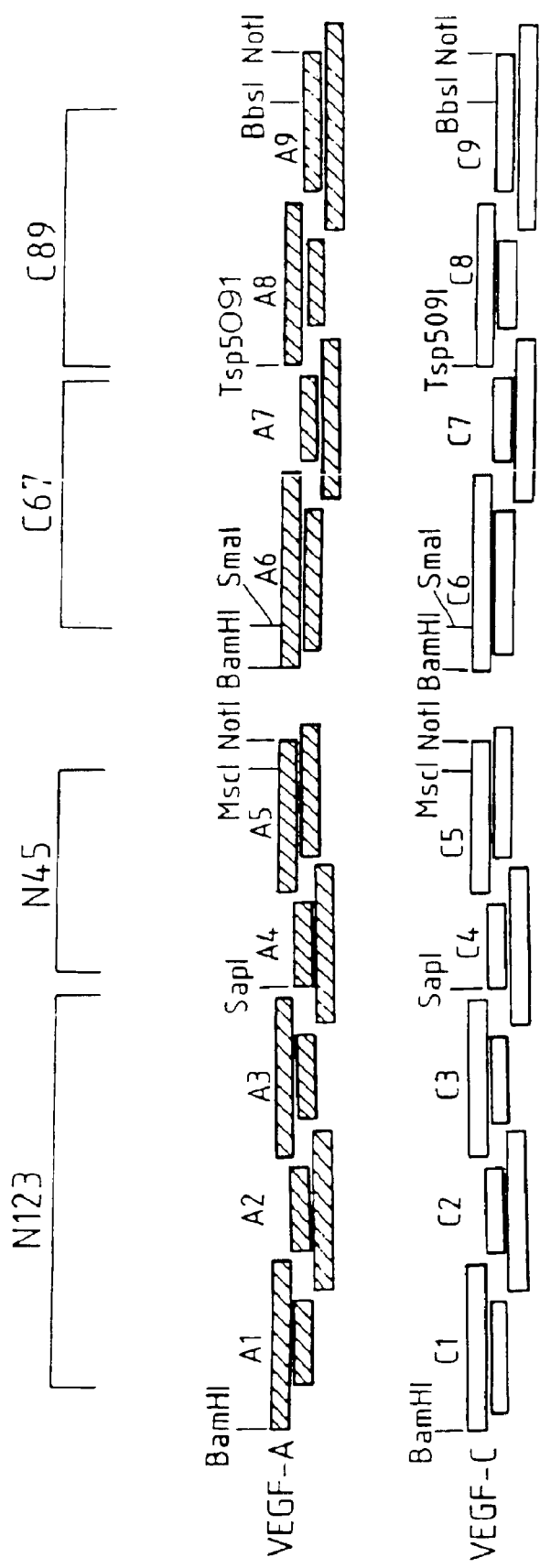
Figure 8:
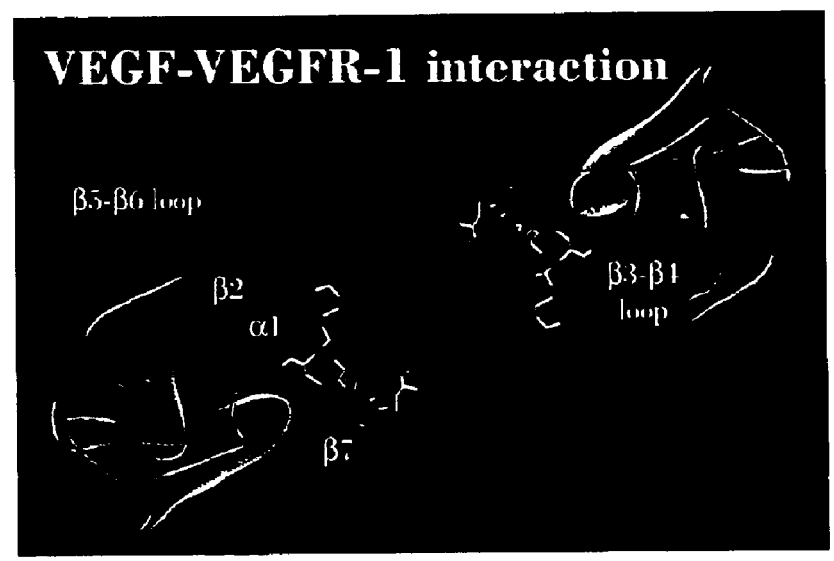

Thus, by synthesizing and annealing nine pairs of primers designed from the VEGF-A amino acid sequence and nine pairs of primers designed from the VEGF-C amino acid sequence, eighteen DNA fragments were generated. FIG. 2 is a schematic diagram illustrating the construction of the 9 VEGF-A and 9 VEGF-C DNA fragments. The oligonucleotides were designed to produce double-stranded DNA fragments containing unique cohesive ends upon annealing. Ligation of the 9 VEGF-A DNA fragments produces a single linear double-stranded DNA encoding amino acids 34–135 of VEGF-A (SEQ ID NO: 2), and ligation of the 9 VEGF-C DNA fragments results in a single DNA encoding amino acids 112–216 of VEGF-C (SEQ ID NO: 22).

While the insertion of cohesive ends greatly facilitated ligation of fragments in a desired order and orientation, it will be appreciated that ligation of fragments can also be accomplished without cohesive ends. Blunt-end fragments also can be synthesized and annealed to generate hybrid proteins using the method described above. With a blunt-end strategy, the nucleotide sequences of the parent molecules do not need to be examined for the presence of nucleotide identity to enable the creation of cohesive ends. However, additional post-ligation screening may be required to identify hybrids that contain fragments in the desired order and orientation.

Several additional details regarding the synthetic primers and the double-stranded DNA fragments deserve emphasis.

First, it is worth noting that, for VEGF-A fragment A1 and VEGF-C fragment C1, the first two encoded amino acids, Asp and Pro, constitute a protein linker (encoded by an engineered BamHI recognition site) and do not correspond to either VEGF-A or VEGF-C sequences.

Second, referring to FIGS. 1 and 2, it is noteworthy that many of the fragments were designed to correspond to discrete structural elements within the receptor binding domain of VEGF family proteins. Fragment 2 corresponds to the N-terminal helix; fragment 4 corresponds to β2; fragment 6 corresponds to the β3–β4 loop, fragment 7 corresponds to β5; fragment 8 corresponds to the β5–β6 loop; and fragment 9 corresponds to β7.

Third, it is noteworthy that the thirty-six oligonucleotides that were designed do not correspond exactly with native human VEGF-A or VEGF-C cDNA sequences (i.e., DNA counterparts of naturally-occurring human mRNA sequences), notwithstanding the fact that the oligonucleotides were designed to retain encoded amino acid sequences of the human VEGF-A and VEGF-C polypeptides. For example, the oligonucleotides were designed such that the native (endogenous) human nucleotide sequence encoding the receptor binding domain for both VEGF-A and VEGF-C were modified to generate new restriction sites, to provide longer stretches of nucleotide identity where overlaps were desired between the "A" and "C" fragments, or to improve codon usage for expression in human cell culture. All nucleotide mutations (relevant to the native sequences) were silent. Thus, the amino acid sequences of the receptor binding domain of VEGF-A (resulting from annealing fragments A1–A9) and VEGF-C (from annealing fragments C1–C9) are identical to that of the respective parent molecule.

Fourth, referring again to FIG. 2, it is noteworthy that each of the nine VEGF-A fragments aligns with the corresponding VEGF-C fragment, and has a compatible cohesive end to anneal to adjacent fragments from the other molecule. For example, fragments A1 and C1 correspond to the same relative portions of VEGF-A and VEGF-C, respectively, and have identical top strand cohesive ends. These cohesive ends are exactly complementary to bottom strand cohesive ends of both fragments A2 and C2, such that A1 could anneal to either A2 or C2, and C1 also could anneal to A2 or C2. Fragments A2 and C2 correspond to the same relative portions of VEGF-A and VEGF-C, and each possesses another bottom strand cohesive end that is exactly complementary to top strand cohesive ends of fragments A3 and C3, and so on. Thus, each set of nine fragments was designed not only to anneal to adjacent fragments of its parent VEGF-A/VEGF-C molecule, but also to anneal to adjacent fragments of the other molecule.

Assembly of Chimeric (Hybrid) VEGF Molecules

Assembly of the 9 VEGF-A and 9 VEGF-C DNA fragments into hybrid DNAs containing regions from both VEGF-A and VEGF-C was accomplished by ligating different combinations of the VEGF-A and VEGF-C DNA fragments. All DNA fragments were isolated after digestion with appropriate restriction enzymes and gel electrophoresis using Qiaex II beads (Qiagen). It will be apparent that, if the proper order (1–2–3–4–5–6–7–8–9) of fragments is preserved, the nine VEGF-A fragments and the nine VEGF-C fragments can be recombined and annealed into 512 distinct hybrids, two of which represent naturally-occurring sequences (A1–A2–A3–A4–A5–A6–A7–A8–A9 and C1–C2–C3–C4–C5–C6–C7–C8–C9) and 510 of which represent novel hybrids. All 512 sequences were reconstructed using the following three step process.

First, the receptor binding domains of VEGF-A and VEGF-C were divided into 4 subdomains designated N123, N45, C67 and C89, as shown in FIG. 2. N123 consists of the first 3 DNA fragments encoding the receptor binding domain of both VEGF-A and VEGF-C. N45, C67 and C89 each consists of 2 DNA fragments where N45 includes fragments 4 and 5, C67 consists of fragments 6 and 7, and C89 includes fragments 8 and 9.

Continuous DNA's corresponding to the N123 region were constructed by ligating fragments 1, 2, and 3 from either VEGF-A or VEGF-C, thus producing a total of eight possible different N123 DNA segments shown schematically in FIG. 3. Similarly, continuous DNAs corresponding to the N45, C67, and C89 regions were constructed by ligating the two appropriate DNA fragments from VEGF-A or VEGF-C. In these cases, all four possible different molecules were produced for each of the regions. FIG. 4 is a schematic diagram illustrating all four possible N45 DNA segments, FIG. 5 depicts all four possible C67 DNA segments, and FIG. 6 shows all four possible C89 DNA segments. All of these molecules were cloned into the multiple cloning site of the pKO-Scrambler-V912-BX vector (Lexicon Genetics Inc.) as part of the ligation reaction. All ligations were carried out by combining 8 nmol/µl of vector cut with the appropriate restriction enzyme that enables cloning of the inserts into the vector, and dephosphorylated; 80 nmol/µl each of DNA fragments that are to be inserted into the vector; and 5 Weiss Units of T4 DNA ligase in 50 mM Tris/HCl, 10 mM MgCl$_2$, 10 mM DTT, 1 mM ATP, 25 µg/ml BSA, and 5% PEG-4000, pH 7.5, followed by incubation for 12 hours at 16° C. FIGS. 7A–7D depict the amino acid sequences encoded by each of fragments A1–A9 and C1–C9; and schematically depict all the permutations of encoded peptides that result from recombinations that form the eight N123 constructs (FIG. 7A), four N45 constructs (FIG. 7B), four C67 constructs (FIG. 7C), and four C89 constructs (FIG. 7D).

In the second step, the N123 fragments were joined with N45 fragments, and the C67 fragments were joined with C89 fragments. The N123 and N45 fragments were removed from their pKO-Scrambler-V912 host vector by digestion with restriction enzymes that allowed ligation of N 123 to N45, and which also achieved removal of the non-protein coding regions of fragments 3 and 4 (see Tables 1A, 1B, 2A and 2B). By ligating each of the eight different N123 regions to all four possible N45 regions, 32 distinct N-terminal portions of the receptor binding domains were obtained. These clones were further inserted into the pSecTagI vector (SEQ ID NO: 41). The pSecTagI vector is a combined *E. coli*/mammalian expression vector which was constructed by modifying the pSecTagA vector (Invitrogen). pSecTagA was modified to eliminate specific restriction sites using site-directed mutagenesis and synthetic linkers, and the EM7 promoters from pICZα-A (Invitrogen) and pTRACER-CMV were added downstream to the CMV promoter of pSecTagA. Both pSecTagI and it's parent vector, pSecTagA, allow high level of expression in mammalian cell culture using suitable cell lines e.g., 293T cells, zeocin selection of stably transfected mammalian cells, contain a mammalian signal peptide for secretion of the expressed protein, and contain a C-terminal myc epitope and polyhistidine tag for detection, quantitation and purification of the expressed protein. The pSecTagI vector differs from the pSpecTagA vector in that expression in *E. coli* is constitutive and modification of the restriction sites facilitated cloning of the hybrid constructs.

The C67 and C89 fragments were removed from their pKO-Scrambler-V912 host vector by digestion with appropriate restriction enzymes, which also achieved removal of the non-protein coding regions of fragments 6 and 9 (see Tables 1A, 1B, 2A and 2B). Ligation of the four different C67 molecules to the four different C89 molecules produced 16 distinct C-terminal halves of the receptor binding domain. The C67–C89 fragments were cloned into the pKO-Scrambler vector during these ligations. Finally, 512 final ligations that combined the 32 different N-terminal portions and the 16 distinct C-terminal regions resulted in a total of 512 distinct molecules of which 510 are hybrids composed of both VEGF-A and VEGF-C amino acid residues. During this step the 512 constructs were cloned into the pSecTagI vector which contained the 32 different N-terminal portions. The remaining 2 molecules correspond to the original VEGF-A and VEGF-C sequences encoding the receptor binding domain. The predicted nucleotide and amino acid sequences for all 512 hybrid molecules are set forth in the sequence listing as summarized in Table 2.5.

TABLE 2.5

| VEGF-A/VEGF-C* Chimera | Predicted DNA Sequence Seq ID NO: | Predicted Protein Sequence Seq ID NO: |
| --- | --- | --- |
| AAAAAAAAA | 176 | 177 |
| CAAAAAAAA | 178 | 179 |
| ACAAAAAAA | 180 | 181 |
| CCAAAAAAA | 182 | 183 |
| AACAAAAAA | 184 | 185 |
| CACAAAAAA | 186 | 187 |
| ACCAAAAAA | 188 | 189 |
| CCCAAAAAA | 190 | 191 |
| AAACAAAAA | 192 | 193 |
| CAACAAAAA | 194 | 195 |
| ACACAAAAA | 196 | 197 |
| CCACAAAAA | 198 | 199 |
| AACCAAAAA | 200 | 201 |
| CACCAAAAA | 202 | 203 |
| ACCCAAAAA | 204 | 205 |
| CCCCAAAAA | 206 | 207 |
| AAAACAAAA | 208 | 209 |
| CAAACAAAA | 210 | 211 |
| ACAACAAAA | 212 | 213 |
| CCAACAAAA | 214 | 215 |
| AACACAAAA | 216 | 217 |
| CACACAAAA | 218 | 219 |
| ACCACAAAA | 220 | 221 |
| CCCACAAAA | 222 | 223 |
| AAACCAAAA | 224 | 225 |
| CAACCAAAA | 226 | 227 |
| ACACCAAAA | 228 | 229 |
| CCACCAAAA | 230 | 231 |
| AACCCAAAA | 232 | 233 |
| CACCCAAAA | 234 | 235 |
| ACCCCAAAA | 236 | 237 |

TABLE 2.5-continued

| VEGF-A/VEGF-C* Chimera | Predicted DNA Sequence Seq ID NO: | Predicted Protein Sequence Seq ID NO: |
|---|---|---|
| CCCCCAAAA | 238 | 239 |
| AAAAACAAA | 240 | 241 |
| CAAAACAAA | 242 | 243 |
| ACAAACAAA | 244 | 245 |
| CCAAACAAA | 246 | 247 |
| AACAACAAA | 248 | 249 |
| CACAACAAA | 250 | 251 |
| ACCAACAAA | 252 | 253 |
| CCCAACAAA | 254 | 255 |
| AAACACAAA | 256 | 257 |
| CAACACAAA | 258 | 259 |
| ACACACAAA | 260 | 261 |
| CCACACAAA | 262 | 263 |
| AACCACAAA | 264 | 265 |
| CACCACAAA | 266 | 267 |
| ACCCACAAA | 268 | 269 |
| CCCCACAAA | 270 | 271 |
| AAAACCAAA | 272 | 273 |
| CAAACCAAA | 274 | 275 |
| ACAACCAAA | 276 | 277 |
| CCAACCAAA | 278 | 279 |
| AACACCAAA | 280 | 281 |
| CACACCAAA | 282 | 283 |
| ACCACCAAA | 284 | 285 |
| CCCACCAAA | 286 | 287 |
| AAACCCAAA | 288 | 289 |
| CAACCCAAA | 290 | 291 |
| ACACCCAAA | 292 | 293 |
| CCACCCAAA | 294 | 295 |
| AACCCCAAA | 296 | 297 |
| CACCCCAAA | 298 | 299 |
| ACCCCCAAA | 300 | 301 |
| CCCCCCAAA | 302 | 303 |
| AAAAAACAA | 304 | 305 |
| CAAAAACAA | 306 | 307 |
| ACAAAACAA | 308 | 309 |
| CCAAAACAA | 310 | 311 |
| AACAAACAA | 312 | 313 |
| CACAAACAA | 314 | 315 |
| ACCAAACAA | 316 | 317 |
| CCCAAACAA | 318 | 319 |
| AAACAACAA | 320 | 321 |
| CAACAACAA | 322 | 323 |
| ACACAACAA | 324 | 325 |
| CCACAACAA | 326 | 327 |
| AACCAACAA | 328 | 329 |
| CACCAACAA | 330 | 331 |
| ACCCAACAA | 332 | 333 |
| CCCCAACAA | 334 | 335 |
| AAAACACAA | 336 | 337 |
| CAAACACAA | 338 | 339 |
| ACAACACAA | 340 | 341 |
| CCAACACAA | 342 | 343 |
| AACACACAA | 344 | 345 |
| CACACACAA | 346 | 347 |
| ACCACACAA | 348 | 349 |
| CCCACACAA | 350 | 351 |
| AAACCACAA | 352 | 353 |
| CAACCACAA | 354 | 355 |
| ACACCACAA | 356 | 357 |
| CCACCACAA | 358 | 359 |
| AACCCACAA | 360 | 361 |
| CACCCACAA | 362 | 363 |
| ACCCCACAA | 364 | 365 |
| CCCCCACAA | 366 | 367 |
| AAAAACCAA | 368 | 369 |
| CAAAACCAA | 370 | 371 |
| ACAAACCAA | 372 | 373 |
| CCAAACCAA | 374 | 375 |
| AACAACCAA | 376 | 377 |
| CACAACCAA | 378 | 379 |
| ACCAACCAA | 380 | 381 |
| CCCAACCAA | 382 | 383 |
| AAACACCAA | 384 | 385 |
| CAACACCAA | 386 | 387 |

TABLE 2.5-continued

| VEGF-A/VEGF-C* Chimera | Predicted DNA Sequence Seq ID NO: | Predicted Protein Sequence Seq ID NO: |
|---|---|---|
| ACACACCAA | 388 | 389 |
| CCACACCAA | 390 | 391 |
| AACCACCAA | 392 | 393 |
| CACCACCAA | 394 | 395 |
| ACCCACCAA | 396 | 397 |
| CCCCACCAA | 398 | 399 |
| AAAACCCAA | 400 | 401 |
| CAAACCCAA | 402 | 403 |
| ACAACCCAA | 404 | 405 |
| CCAACCCAA | 406 | 407 |
| AACACCCAA | 408 | 409 |
| CACACCCAA | 410 | 411 |
| ACCACCCAA | 412 | 413 |
| CCCACCCAA | 414 | 415 |
| AAACCCCAA | 416 | 417 |
| CAACCCCAA | 418 | 419 |
| ACACCCCAA | 420 | 421 |
| CCACCCCAA | 422 | 423 |
| AACCCCCAA | 424 | 425 |
| CACCCCCAA | 426 | 427 |
| ACCCCCCAA | 428 | 429 |
| CCCCCCCAA | 430 | 431 |
| AAAAAAACA | 432 | 433 |
| CAAAAAACA | 434 | 435 |
| ACAAAAACA | 436 | 437 |
| CCAAAAACA | 438 | 439 |
| AACAAAACA | 440 | 441 |
| CACAAAACA | 442 | 443 |
| ACCAAAACA | 444 | 445 |
| CCCAAAACA | 446 | 447 |
| AAACAAACA | 448 | 449 |
| CAACAAACA | 450 | 451 |
| ACACAAACA | 452 | 453 |
| CCACAAACA | 454 | 455 |
| AACCAAACA | 456 | 457 |
| CACCAAACA | 458 | 459 |
| ACCCAAACA | 460 | 461 |
| CCCCAAACA | 462 | 463 |
| AAAACAACA | 464 | 465 |
| CAAACAACA | 466 | 467 |
| ACAACAACA | 468 | 469 |
| CCAACAACA | 470 | 471 |
| AACACAACA | 472 | 473 |
| CACACAACA | 474 | 475 |
| ACCACAACA | 476 | 477 |
| CCCACAACA | 478 | 479 |
| AAACCAACA | 480 | 481 |
| CAACCAACA | 482 | 483 |
| ACACCAACA | 484 | 485 |
| CCACCAACA | 486 | 487 |
| AACCCAACA | 488 | 489 |
| CACCCAACA | 490 | 491 |
| ACCCCAACA | 492 | 493 |
| CCCCCAACA | 494 | 495 |
| AAAAACACA | 496 | 497 |
| CAAAACACA | 498 | 499 |
| ACAAACACA | 500 | 501 |
| CCAAACACA | 502 | 503 |
| AACAACACA | 504 | 505 |
| CACAACACA | 506 | 507 |
| ACCAACACA | 508 | 509 |
| CCCAACACA | 510 | 511 |
| AAACACACA | 512 | 513 |
| CAACACACA | 514 | 515 |
| ACACACACA | 516 | 517 |
| CCACACACA | 518 | 519 |
| AACCACACA | 520 | 521 |
| CACCACACA | 522 | 523 |
| ACCCACACA | 524 | 525 |
| CCCCACACA | 526 | 527 |
| AAAACCACA | 528 | 529 |
| CAAACCACA | 530 | 531 |
| ACAACCACA | 532 | 533 |
| CCAACCACA | 534 | 535 |
| AACACCACA | 536 | 537 |

TABLE 2.5-continued

| VEGF-A/VEGF-C* Chimera | Predicted DNA Sequence Seq ID NO: | Predicted Protein Sequence Seq ID NO: |
|---|---|---|
| CACACCACA | 538 | 539 |
| ACCACCACA | 540 | 541 |
| CCCACCACA | 542 | 543 |
| AAACCCACA | 544 | 545 |
| CAACCCACA | 546 | 547 |
| ACACCCACA | 548 | 549 |
| CCACCCACA | 550 | 551 |
| AACCCCACA | 552 | 553 |
| CACCCCACA | 554 | 555 |
| ACCCCCACA | 556 | 557 |
| CCCCCCACA | 558 | 559 |
| AAAAAACCA | 560 | 561 |
| CAAAAACCA | 562 | 563 |
| ACAAAACCA | 564 | 565 |
| CCAAAACCA | 566 | 567 |
| AACAAACCA | 568 | 569 |
| CACAAACCA | 570 | 571 |
| ACCAAACCA | 572 | 573 |
| CCCAAACCA | 574 | 575 |
| AAACAACCA | 576 | 577 |
| CAACAACCA | 578 | 579 |
| ACACAACCA | 580 | 581 |
| CCACAACCA | 582 | 583 |
| AACCAACCA | 584 | 585 |
| CACCAACCA | 586 | 587 |
| ACCCAACCA | 588 | 589 |
| CCCCAACCA | 590 | 591 |
| AAAACACCA | 592 | 593 |
| CAAACACCA | 594 | 595 |
| ACAACACCA | 596 | 597 |
| CCAACACCA | 598 | 599 |
| AACACACCA | 600 | 601 |
| CACACACCA | 602 | 603 |
| ACCACACCA | 604 | 605 |
| CCCACACCA | 606 | 607 |
| AAACCACCA | 608 | 609 |
| CAACCACCA | 610 | 611 |
| ACACCACCA | 612 | 613 |
| CCACCACCA | 614 | 615 |
| AACCCACCA | 616 | 617 |
| CACCCACCA | 618 | 619 |
| ACCCCACCA | 620 | 621 |
| CCCCCACCA | 622 | 623 |
| AAAAACCCA | 624 | 625 |
| CAAAACCCA | 626 | 627 |
| ACAAACCCA | 628 | 629 |
| CCAAACCCA | 630 | 631 |
| AACAACCCA | 632 | 633 |
| CACAACCCA | 634 | 635 |
| ACCAACCCA | 636 | 637 |
| CCCAACCCA | 638 | 639 |
| AAACACCCA | 640 | 641 |
| CAACACCCA | 642 | 643 |
| ACACACCCA | 644 | 645 |
| CCACACCCA | 646 | 647 |
| AACCACCCA | 648 | 649 |
| CACCACCCA | 650 | 651 |
| ACCCACCCA | 652 | 653 |
| CCCCACCCA | 654 | 655 |
| AAAACCCCA | 656 | 657 |
| CAAACCCCA | 658 | 659 |
| ACAACCCCA | 660 | 661 |
| CCAACCCCA | 662 | 663 |
| AACACCCCA | 664 | 665 |
| CACACCCCA | 666 | 667 |
| ACCACCCCA | 668 | 669 |
| CCCACCCCA | 670 | 671 |
| AAACCCCCA | 672 | 673 |
| CAACCCCCA | 674 | 675 |
| ACACCCCCA | 676 | 677 |
| CCACCCCCA | 678 | 679 |
| AACCCCCCA | 680 | 681 |
| CACCCCCCA | 682 | 683 |
| ACCCCCCCA | 684 | 685 |
| CCCCCCCCA | 686 | 687 |
| AAAAAAAAC | 688 | 689 |
| CAAAAAAAC | 690 | 691 |
| ACAAAAAAC | 692 | 693 |
| CCAAAAAAC | 694 | 695 |
| AACAAAAAC | 696 | 697 |
| CACAAAAAC | 698 | 699 |
| ACCAAAAAC | 700 | 701 |
| CCCAAAAAC | 702 | 703 |
| AAACAAAAC | 704 | 705 |
| CAACAAAAC | 706 | 707 |
| ACACAAAAC | 708 | 709 |
| CCACAAAAC | 710 | 711 |
| AACCAAAAC | 712 | 713 |
| CACCAAAAC | 714 | 715 |
| ACCCAAAAC | 716 | 717 |
| CCCCAAAAC | 718 | 719 |
| AAAACAAAC | 720 | 721 |
| CAAACAAAC | 722 | 723 |
| ACAACAAAC | 724 | 725 |
| CCAACAAAC | 726 | 727 |
| AACACAAAC | 728 | 729 |
| CACACAAAC | 730 | 731 |
| ACCACAAAC | 732 | 733 |
| CCCACAAAC | 734 | 735 |
| AAACCAAAC | 736 | 737 |
| CAACCAAAC | 738 | 739 |
| ACACCAAAC | 740 | 741 |
| CCACCAAAC | 742 | 743 |
| AACCCAAAC | 744 | 745 |
| CACCCAAAC | 746 | 747 |
| ACCCCAAAC | 748 | 749 |
| CCCCCAAAC | 750 | 751 |
| AAAAACAAC | 752 | 753 |
| CAAAACAAC | 754 | 755 |
| ACAAACAAC | 756 | 757 |
| CCAAACAAC | 758 | 759 |
| AACAACAAC | 760 | 761 |
| CACAACAAC | 762 | 763 |
| ACCAACAAC | 764 | 765 |
| CCCAACAAC | 766 | 767 |
| AAACACAAC | 768 | 769 |
| CAACACAAC | 770 | 771 |
| ACACACAAC | 772 | 773 |
| CCACACAAC | 774 | 775 |
| AACCACAAC | 776 | 777 |
| CACCACAAC | 778 | 779 |
| ACCCACAAC | 780 | 781 |
| CCCCACAAC | 782 | 783 |
| AAAACCAAC | 784 | 785 |
| CAAACCAAC | 786 | 787 |
| ACAACCAAC | 788 | 789 |
| CCAACCAAC | 790 | 791 |
| AACACCAAC | 792 | 793 |
| CACACCAAC | 794 | 795 |
| ACCACCAAC | 796 | 797 |
| CCCACCAAC | 798 | 799 |
| AAACCCAAC | 800 | 801 |
| CAACCCAAC | 802 | 803 |
| ACACCCAAC | 804 | 805 |
| CCACCCAAC | 806 | 807 |
| AACCCCAAC | 808 | 809 |
| CACCCCAAC | 810 | 811 |
| ACCCCCAAC | 812 | 813 |
| CCCCCCAAC | 814 | 815 |
| AAAAAACAC | 816 | 817 |
| CAAAAACAC | 818 | 819 |
| ACAAAACAC | 820 | 821 |
| CCAAAACAC | 822 | 823 |
| AACAAACAC | 824 | 825 |
| CACAAACAC | 826 | 827 |
| ACCAAACAC | 828 | 829 |
| CCCAAACAC | 830 | 831 |
| AAACAACAC | 832 | 833 |
| CAACAACAC | 834 | 835 |
| ACACAACAC | 836 | 837 |

TABLE 2.5-continued

| VEGF-A/VEGF-C* Chimera | Predicted DNA Sequence Seq ID NO: | Predicted Protein Sequence Seq ID NO: |
|---|---|---|
| CCACAACAC | 838 | 839 |
| AACCAACAC | 840 | 841 |
| CACCAACAC | 842 | 843 |
| ACCCAACAC | 844 | 845 |
| CCCCAACAC | 846 | 847 |
| AAAACACAC | 848 | 849 |
| CAAACACAC | 850 | 851 |
| ACAACACAC | 852 | 853 |
| CCAACACAC | 854 | 855 |
| AACACACAC | 856 | 857 |
| CACACACAC | 858 | 859 |
| ACCACACAC | 860 | 861 |
| CCCACACAC | 862 | 863 |
| AAACCACAC | 864 | 865 |
| CAACCACAC | 866 | 867 |
| ACACCACAC | 868 | 869 |
| CCACCACAC | 870 | 871 |
| AACCCACAC | 872 | 873 |
| CACCCACAC | 874 | 875 |
| ACCCCACAC | 876 | 877 |
| CCCCCACAC | 878 | 879 |
| AAAAACCAC | 880 | 881 |
| CAAAACCAC | 882 | 883 |
| ACAAACCAC | 884 | 885 |
| CCAAACCAC | 886 | 887 |
| AACAACCAC | 888 | 889 |
| CACAACCAC | 890 | 891 |
| ACCAACCAC | 892 | 893 |
| CCCAACCAC | 894 | 895 |
| AAACACCAC | 896 | 897 |
| CAACACCAC | 898 | 899 |
| ACACACCAC | 900 | 901 |
| CCACACCAC | 902 | 903 |
| AACCACCAC | 904 | 905 |
| CACCACCAC | 906 | 907 |
| ACCCACCAC | 908 | 909 |
| CCCCACCAC | 910 | 911 |
| AAAACCCAC | 912 | 913 |
| CAAACCCAC | 914 | 915 |
| ACAACCCAC | 916 | 917 |
| CCAACCCAC | 918 | 919 |
| AACACCCAC | 920 | 921 |
| CACACCCAC | 922 | 923 |
| ACCACCCAC | 924 | 925 |
| CCCACCCAC | 926 | 927 |
| AAACCCCAC | 928 | 929 |
| CAACCCCAC | 930 | 931 |
| ACACCCCAC | 932 | 933 |
| CCACCCCAC | 934 | 935 |
| AACCCCCAC | 936 | 937 |
| CACCCCCAC | 938 | 939 |
| ACCCCCCAC | 940 | 941 |
| CCCCCCCAC | 942 | 943 |
| AAAAAAACC | 944 | 945 |
| CAAAAAACC | 946 | 947 |
| ACAAAAACC | 948 | 949 |
| CCAAAAACC | 950 | 951 |
| AACAAAACC | 952 | 953 |
| CACAAAACC | 954 | 955 |
| ACCAAAACC | 956 | 957 |
| CCCAAAACC | 958 | 959 |
| AAACAAACC | 960 | 961 |
| CAACAAACC | 962 | 963 |
| ACACAAACC | 964 | 965 |
| CCACAAACC | 966 | 967 |
| AACCAAACC | 968 | 969 |
| CACCAAACC | 970 | 971 |
| ACCCAAACC | 972 | 973 |
| CCCCAAACC | 974 | 975 |
| AAAACAACC | 976 | 977 |
| CAAACAACC | 978 | 979 |
| ACAACAACC | 980 | 981 |
| CCAACAACC | 982 | 983 |
| AACACAACC | 984 | 985 |
| CACACAACC | 986 | 987 |

TABLE 2.5-continued

| VEGF-A/VEGF-C* Chimera | Predicted DNA Sequence Seq ID NO: | Predicted Protein Sequence Seq ID NO: |
|---|---|---|
| ACCACAACC | 988 | 989 |
| CCCACAACC | 990 | 991 |
| AAACCAACC | 992 | 993 |
| CAACCAACC | 994 | 995 |
| ACACCAACC | 996 | 997 |
| CCACCAACC | 998 | 999 |
| AACCCAACC | 1000 | 1001 |
| CACCCAACC | 1002 | 1003 |
| ACCCCAACC | 1004 | 1005 |
| CCCCCAACC | 1006 | 1007 |
| AAAAACACC | 1008 | 1009 |
| CAAAACACC | 1010 | 1011 |
| ACAAACACC | 1012 | 1013 |
| CCAAACACC | 1014 | 1015 |
| AACAACACC | 1016 | 1017 |
| CACAACACC | 1018 | 1019 |
| ACCAACACC | 1020 | 1021 |
| CCCAACACC | 1022 | 1023 |
| AAACACACC | 1024 | 1025 |
| CAACACACC | 1026 | 1027 |
| ACACACACC | 1028 | 1029 |
| CCACACACC | 1030 | 1031 |
| AACCACACC | 1032 | 1033 |
| CACCACACC | 1034 | 1035 |
| ACCCACACC | 1036 | 1037 |
| CCCCACACC | 1038 | 1039 |
| AAAACCACC | 1040 | 1041 |
| CAAACCACC | 1042 | 1043 |
| ACAACCACC | 1044 | 1045 |
| CCAACCACC | 1046 | 1047 |
| AACACCACC | 1048 | 1049 |
| CACACCACC | 1050 | 1051 |
| ACCACCACC | 1052 | 1053 |
| CCCACCACC | 1054 | 1055 |
| AAACCCACC | 1056 | 1057 |
| CAACCCACC | 1058 | 1059 |
| ACACCCACC | 1060 | 1061 |
| CCACCCACC | 1062 | 1063 |
| AACCCCACC | 1064 | 1065 |
| CACCCCACC | 1066 | 1067 |
| ACCCCCACC | 1068 | 1069 |
| CCCCCCACC | 1070 | 1071 |
| AAAAAACCC | 1072 | 1073 |
| CAAAAACCC | 1074 | 1075 |
| ACAAAACCC | 1076 | 1077 |
| CCAAAACCC | 1078 | 1079 |
| AACAAACCC | 1080 | 1081 |
| CACAAACCC | 1082 | 1083 |
| ACCAAACCC | 1084 | 1085 |
| CCCAAACCC | 1086 | 1087 |
| AAACAACCC | 1088 | 1089 |
| CAACAACCC | 1090 | 1091 |
| ACACAACCC | 1092 | 1093 |
| CCACAACCC | 1094 | 1095 |
| AACCAACCC | 1096 | 1097 |
| CACCAACCC | 1098 | 1099 |
| ACCCAACCC | 1100 | 1101 |
| CCCCAACCC | 1102 | 1103 |
| AAAACACCC | 1104 | 1105 |
| CAAACACCC | 1106 | 1107 |
| ACAACACCC | 1108 | 1109 |
| CCAACACCC | 1110 | 1111 |
| AACACACCC | 1112 | 1113 |
| CACACACCC | 1114 | 1115 |
| ACCACACCC | 1116 | 1117 |
| CCCACACCC | 1118 | 1119 |
| AAACCACCC | 1120 | 1121 |
| CAACCACCC | 1122 | 1123 |
| ACACCACCC | 1124 | 1125 |
| CCACCACCC | 1126 | 1127 |
| AACCCACCC | 1128 | 1129 |
| CACCCACCC | 1130 | 1131 |
| ACCCCACCC | 1132 | 1133 |
| CCCCCACCC | 1134 | 1135 |
| AAAAACCCC | 1136 | 1137 |

TABLE 2.5-continued

| VEGF-A/VEGF-C* Chimera | Predicted DNA Sequence Seq ID NO: | Predicted Protein Sequence Seq ID NO: |
|---|---|---|
| CAAAACCCC | 1138 | 1139 |
| ACAAACCCC | 1140 | 1141 |
| CCAAACCCC | 1142 | 1143 |
| AACAACCCC | 1144 | 1145 |
| CACAACCCC | 1146 | 1147 |
| ACCAACCCC | 1148 | 1149 |
| CCCAACCCC | 1150 | 1151 |
| AAACACCCC | 1152 | 1153 |
| CAACACCCC | 1154 | 1155 |
| ACACACCCC | 1156 | 1157 |
| CCACACCCC | 1158 | 1159 |
| AACCACCCC | 1160 | 1161 |
| CACCACCCC | 1162 | 1163 |
| ACCCACCCC | 1164 | 1165 |
| CCCCACCCC | 1166 | 1167 |
| AAAACCCCC | 1168 | 1169 |
| CAAACCCCC | 1170 | 1171 |
| ACAACCCCC | 1172 | 1173 |
| CCAACCCCC | 1174 | 1175 |
| AACACCCCC | 1176 | 1177 |
| CACACCCCC | 1178 | 1179 |
| ACCACCCCC | 1180 | 1181 |
| CCCACCCCC | 1182 | 1183 |
| AAACCCCCC | 1184 | 1185 |
| CAACCCCCC | 1186 | 1187 |
| ACACCCCCC | 1188 | 1189 |
| CCACCCCCC | 1190 | 1191 |
| AACCCCCCC | 1192 | 1193 |
| CACCCCCCC | 1194 | 1195 |
| ACCCCCCCC | 1196 | 1197 |
| CCCCCCCCC | 1198 | 1199 |

*Construct nomenclature is identical to nomenclature of Table 3.

Assembly of the hybrid molecules can also be accomplished in fewer ligation steps than outlined above. For example, ligation of N123, N45, C67 and C89 can be completed in a single ligation reaction. By designing fragments with cohesive ends that are perfect complements only with cohesive ends of adjacent fragments, it is possible to ligate multiple fragments in a correct order in a single ligation reaction.

EXAMPLE 2

Expression of the Hybrid Molecules

Each of the 512 constructs were separately transfected transiently into 293T cells to express the different hybrid constructs. 293T cells were grown according to standard protocols in medium consisting of Dulbecco's modified Eagle's medium (D-MEM), and 10% fetal bovine serum (FBS). Twenty-four hours prior to transfection, confluent dishes were diluted 1:10 with fresh media into 6 wells. Four hours prior to transfection, the medium was changed. For each construct, 3 ug of DNA was transfected using standard protocols for calcium phosphate-mediated transfection [Sambrook et al., Molecular Cloning: A Laboratory Manual pp. 16.33–16.36 (1989)]. Twenty hours post-transfection, cells were washed twice with warn PBS and 2 ml of medium was added to each well.

Initial experiments were conducted to determine if the transfected cells were expressing the hybrid VEGF polypeptides encoded by the hybrid DNA molecules. Thus, 48 hours post-transfection, metabolic labeling with $^{35}$S-methionine and $^{35}$S-cysteine was initiated using 1.3 ml/well of labeling medium composed of MEM deficient for cysteine and methionine, 0.1% BSA, 24 $\mu$Ci $^{35}$S-methionine-cysteine/ml (Redivue PRO-MIX, Amersham). The cell supernatant was harvested 72–78 hours post-transfection, cleared by centrifugation, and stored at 4° C.

The supernatant was immunoprecipitated with anti-pentahistidine antibody (Qiagen) by mixing 175 $\mu$l of sample supernatant with 100 $\mu$l IP mix (PBS with 1.5% BSA, 0.05% Tween 20, and 12 $\mu$l/ml anti-pentahistidine antibody) at 4° C. overnight, with agitation. (The pSecTag I expression vector was engineered to express each of the hybrid VEGF proteins with a polyhistidine tag.) To collect immunoprecipitated protein, 50 $\mu$l of a 30% protein A sepharose (PAS, Pharmacia) slurry in PBS was added and incubated under agitation for at least 1.5 hr at 4° C. Standard buffer was added to each immunoprecipitation sample and boiled for 5 minutes at 95° C. during which the immunopreciptated proteins become dissociated from the protein A sepharose. After centrifugation, 10 $\mu$l of each sample was analyzed on 15% SDS-PAGE under reducing conditions. The gels were dried and exposed for either 12 hours on phosphorimager plates or 4 weeks on X-ray film. Results of these experiments are shown in Table 3 below, in the column marked "EXP" for expression. As shown in the table with "Yes", initial attempts to express the vast majority of the hybrid constructs were successful. Constructs for which weak ("weak"), and no expression ("none") were observed in preliminary studies also are indicated. The failure to achieve expression in initial studies is reported for completeness, and not intended to reflect a conclusion of non-viability or other identified problems. However, it is noteworthy that of the non-expressed constructs, almost all were those chimeric molecules in which fragment 3 was derived from VEGF-A and fragment 7 was derived from VEGF-C. Analysis of the physical relationship between these two fragments shows that residues from these two fragments barely contact each other at the atomic level as judged from the VEGF-A crystal structure. The incompatibility of fragment 3 from VEGF-A and fragment 7 from VEGF-C may arise from incorrect folding of the molecule, perhaps caused in part by rapid glycosylation of the VEGF-C-derived fragment 7 when the molecule appears in the endoplasmic reticulum. The glycosylation sites within VEGF-A are located at a distance from the receptor binding domain, whereas the glycosylation sites within VEGF-C are positioned closer towards the region of the molecule formed by fragment 3 that is predicted to form contacts with the third domain of the receptor. The carbohydrate residues may also be involved in the interaction between ligand and receptor.

EXAMPLE 3

Binding Assays of Hybrid Molecules to Soluble VEGF Receptor-Fc Fusion Proteins The hybrid proteins that were expressed in 293T cells (see Example 2 and Table 1) were tested for the ability to bind soluble VEGF receptor-Fc fusion proteins. Binding of the hybrid proteins to all three VEGF receptors, VEGFR-1, VEGFR-2, and VEGFR-3, was analyzed in this manner. Exemplary binding assays have been described in Achen et al., *Proc Natl Acad Sci USA* 95:548–53 (1998), incorporated by reference in its entirety.

It will be appreciated that binding assays can be performed with any form of naturally occurring VEGF receptors that retain the ability to bind their respective ligands, including but not limited to whole cells that naturally express a receptor or that have been recombinantly modified to express the receptor; truncated, solublized extracellular ligand binding domains of receptors; fusions comprising receptor extracellular domains fused to other proteins such as alkaline phosphatase (e.g., VEGFR-2-AP described in Cao et al., *J. Biol. Chem.* 271:3154–62 (1996)) or immunoglobulin sequences; and fusions comprising receptor extracellular domains fused to tag sequences (e.g., a polyhistidine tag) useful for capturing the protein with an antibody or with a solid support; and receptor extracellular domains chemically attached to solid supports such as CNBr-activated Sepharose beads.

For the present experiments, receptor binding was assayed using constructs comprising the extracellular domain of VEGFR-1, VEGFR-2, or VEGFR-3 fused to immunoglobulin constant region chains. The first three Ig domains of VEGFR-1 were fused to the Fc fragment from the Signal-pIgPlus vector (Ingenius/Novagen/R&D Systems). This construct (VEGFR-1-Fc) was stably expressed in *Drosophila* Schneider 2 (S2) cells, and purified using Protein A sepharose. Purity was analyzed by silver staining of a PAGE gel and the functionality of the fusion protein was tested by its ability to bind $^{35}$S-labeled VEGF protein. The VEGFR-2-Fc receptor comprises the first 3 Ig domains of VEGFR-2 (encoded by nucleotides 64–972 of GenBank Acc. No. X61656) fused to the Fc fragment in the pIg vector. The VEGFR-3-Fc receptor similarly consists if the first three Ig domains of VEGFR-3 (encoded by nucleotides 20–1005 of GenBank Acc. No. X68203) fused to the Fc fragment of the pIg vector. VEGFR-2-Fc and VEGFR-3-Fc proteins were expressed in 293T cells and purified as described above for VEGFR-1-Fc.

The binding assay procedure was identical to the immunoprecipitation using pentahistidine antibody described in Example 2, apart from the composition of the immunoprecipitation (IP) mixes. The IP mixes used for the receptor binding analysis were as follows: For VEGFR-1 binding assays, the IP mix was phosphate buffered saline (PBS) containing 1.5% BSA, 0.06% Tween 20, 3 µg/ml heparin and 400 ng/ml VEGFR-1-Fc fusion protein (100 µl of this IP mix was added to 200 µl of sample supernatant); for VEGFR-2 binding assays, the IP mix was 82% conditioned cell supernatant from 293T cells transiently expressing VEGFR-2-Fc fusion protein in mixture with 18% of a PBS solution that contained 5% BSA, 0.2% Tween 20, and 10 µg/ml heparin (250 µl of IP mix was added to 200 µl of sample supernatant); and for VEGFR-3 binding assays, the IP mix was 82% conditioned cell supernatant from 293T cells transiently expressing VEGFR-3-Fc fusion protein, 18% of PBS containing 5% BSA, 0.2% Tween 20, and 10 µg/ml heparin (250 µl of IP mix was added to 200 µl of sample supernatant). A few selected constructs (clones 12-1, 12-5, 12-7, 12-9, 12-11, 12-13, 12-14, 14-9, 23-1, 32-14, 52-15, 53-3, 82-7,82-9, 82-11, 82-13, 83-15, 84-9, and 84-11) were examined more than one time.

Results from the binding assays using $^{35}$S labeled hybrid proteins are summarized in Table 3 below. The apparent molecular weights of the detected proteins were between 18 and 27 kD. Usually two bands were visible with different band intensities. Sometimes, the second band was only detectable after long exposures. The presence of two bands correlates with the origin of fragment 7 and 9 of the hybrid protein being examined. Fragment 7 contains a potential N-glycosylation site irrespective of whether it was derived from VEGF-A or VEGF-C, whereas fragment 9 only contains an N-glycosylation site if it originated from VEGF-C. Thus, the multiple bands are likely due to differential glycosylation of the hybrid protein being analyzed. The following are predicted bands for different combinations of glycosylation sites:

(1) fragment 7 derived from VEGF-A and fragment 9 from VEGF-A produces two bands of ~18 and ~22 kD (2) fragment 7 derived from VEGF-A and fragment 9 from VEGF-C produces an ~26 kD band (a second band of ~22 kD is sometimes missing, a third extremely weak band of ~18 kD is sometimes visible)

(3) fragment 7 derived from VEGF-C and fragment 9 from VEGF-A produces an ~22 kD band (a second band of ~18 kD is sometimes missing)

(4) fragment 7 derived from VEGF-C and fragment 9 from VEGF-C produces one band of ~23 kD.

Results of the binding assays indicate that if both glycosylation sites were derived from VEGF-C, less heterogeneous glycosylation is observed. Molecules containing both fragment 7 from VEGF-A and fragment 9 from VEGF-C appear to promote artificial hyperglycosylation. The VEGF-A glycosylation site contained in fragment 7 is also prone to incomplete glycosylation.

The binding assay data indicate that several of the hybrid molecules exhibit novel binding properties. Although the analysis was not quantitative, some of the hybrid molecules show different relative signal strengths. For example, clone 72-10 appears to have lost much of its affinity for VEGFR-3 while retaining most of its affinity for VEGFR-2. These results suggest that among the hybrid proteins that retained the receptor specificities of either parent protein (VEGF-A or VEGF-C), some may have undergone differential changes in their binding affinities towards the corresponding receptors.

In Table 3 below, column 1 lists the names of the constructs examined. Column 2 sequentially lists the 9 fragments of each construct, where A=fragment from VEGF-A, and C=fragment from VEGF-C. Column 3 labeled "EXP" lists the results from the experiments to express the constructs in 293T cells, as described in Example 2. In this column, "none" indicates that no detectable protein was expressed; "weak" indicates that weak expression was detectable; and "yes" indicates that the expressed protein was readily detectable. The final three columns list results from the receptor binding assays described in Example 3, where binding to VEGFR-1-Fc; VEGFR-2-Fc; and VEGFR-3-Fc were examined. For these last three columns, "yes" indicates binding, "none" indicates no detectable binding to the receptor, and "0" indicates that this construct was not expressed in 293T cells, thus, could not be used for binding assays.

TABLE 3

Results of hybrid molecule expression and receptor binding analysis

| | | EXP | VEGFR-1 | VEGFR-2 | VEGFR-3 |
|---|---|---|---|---|---|
| 31-1 | ACAAAAAAA | yes | none | none | none |
| 31-5 | ACAAAACAA | none | 0 | 0 | 0 |
| 31-13 | ACAAACCAA | none | 0 | 0 | 0 |
| 31-9 | ACAAACAAA | yes | none | none | none |
| 31-2 | ACAAAAAAC | yes | none | none | none |
| 31-10 | ACAAACAAC | yes | none | none | none |
| 31-6 | ACAAAACAC | yes | none | none | none |
| 31-14 | ACAAACCAC | none | 0 | 0 | 0 |

TABLE 3-continued

Results of hybrid molecule expression and receptor binding analysis

| | | EXP | VEGFR-1 | VEGFR-2 | VEGFR-3 |
|---|---|---|---|---|---|
| 31-12 | ACAAACACA | yes | none | none | none |
| 31-11 | ACAAACACA | yes | none | none | none |
| 31-7 | ACAAAACCA | none | 0 | 0 | 0 |
| 31-4 | ACAAAAACC | yes | none | none | none |
| 31-8 | ACAAAACCC | yes | 0 | 0 | 0 |
| 31-3 | ACAAAAACA | yes | none | none | none |
| 31-15 | ACAAACCCA | none | 0 | 0 | 0 |
| 31-16 | ACAAACCCC | none | 0 | 0 | 0 |
| 21-1 | CCCAAAAAA | yes | none | none | none |
| 21-2 | CCCAAACAA | yes | none | none | none |
| 21-3 | CCCAACAAA | yes | none | none | none |
| 21-4 | CCCAACCAA | yes | none | none | none |
| 21-5 | CCCAAAAAC | yes | none | none | none |
| 21-6 | CCCAAACAC | yes | none | none | none |
| 21-7 | CCCAACAAC | yes | none | none | none |
| 21-8 | CCCAACCAC | yes | none | none | none |
| 21-9 | CCCAAAACA | yes | none | none | none |
| 21-10 | CCCAAACCA | yes | none | none | none |
| 21-11 | CCCAACACA | yes | none | none | none |
| 21-12 | CCCAACCCA | yes | none | none | none |
| 21-13 | CCCAAAACC | yes | none | none | none |
| 21-14 | CCCAAACCC | yes | none | none | none |
| 21-15 | CCCAACACC | yes | none | none | none |
| 21-16 | CCCAACCCC | yes | none | none | none |
| 22-1 | CCCCCAAAA | yes | none | none | none |
| 22-2 | CCCCCACAA | yes | none | yes | yes |
| 22-3 | CCCCCCAAA | yes | none | none | yes |
| 22-4 | CCCCCCCAA | yes | none | yes | yes |
| 22-5 | CCCCCAAAC | yes | none | none | none |
| 22-6 | CCCCCACAC | yes | none | yes | yes |
| 22-7 | CCCCCCAAC | yes | none | none | none |
| 22-8 | CCCCCCCAC | yes | none | yes | yes |
| 22-9 | CCCCCAACA | yes | none | none | none |
| 22-10 | CCCCCACCA | yes | none | yes | yes |
| 22-11 | CCCCCCACA | yes | none | none | none |
| 22-12 | CCCCCCCCA | yes | none | yes | yes |
| 22-13 | CCCCCAACC | yes | none | none | none |
| 22-14 | CCCCCACCC | yes | none | yes | yes |
| 22-15 | CCCCCCACC | yes | none | none | none |
| 22-16 | CCCCCCCCC | yes | none | yes | yes |
| 72-1 | ACCCCAAAA | yes | none | none | none |
| 72-2 | ACCCCACAA | yes | none | yes | yes |
| 72-3 | ACCCCCAAA | yes | none | none | none |
| 72-4 | ACCCCCCAA | yes | none | yes | yes |
| 72-5 | ACCCCAAAC | yes | none | none | none |
| 72-6 | ACCCCACAC | yes | none | none | yes |
| 72-7 | ACCCCCAAC | yes | none | none | none |
| 72-8 | ACCCCCCAC | yes | none | yes | yes |
| 72-9 | ACCCCAACA | yes | none | none | none |
| 72-10 | ACCCCACCA | yes | none | yes | yes |
| 72-11 | ACCCCCACA | yes | none | none | none |
| 72-12 | ACCCCCCCA | yes | none | yes | yes |
| 72-13 | ACCCCAACC | yes | none | none | none |
| 72-14 | ACCCCACCC | yes | none | yes | yes |
| 72-15 | ACCCCCACC | yes | none | none | none |
| 72-16 | ACCCCCCCC | yes | none | yes | yes |
| 11-1 | AAAAAAAA | yes | yes | yes | none |
| 11-2 | AAAAAACAA | none | 0 | 0 | 0 |
| 11-3 | AAAAACAAA | yes | yes | yes | none |
| 11-4 | AAAAACCAA | none | 0 | 0 | 0 |
| 11-5 | AAAAAAAC | yes | yes | yes | none |
| 11-6 | AAAAAACAC | none | 0 | 0 | 0 |
| 11-7 | AAAAACAAC | yes | yes | yes | none |
| 11-8 | AAAAACCAC | none | 0 | 0 | 0 |
| 11-9 | AAAAAACA | yes | yes | none | none |
| 11-10 | AAAAAACCA | none | 0 | 0 | 0 |
| 11-11 | AAAAACACA | yes | yes | yes | none |
| 11-12 | AAAAACCCA | none | 0 | 0 | 0 |
| 11-13 | AAAAAAACC | yes | yes | none | none |
| 11-14 | AAAAAACCC | none | 0 | 0 | 0 |
| 11-15 | AAAAACACC | yes | yes | yes | none |
| 11-16 | AAAAACCCC | none | 0 | 0 | 0 |
| 12-1 | AAACCAAAA | yes | yes | yes | yes |
| 12-2 | AAACCACAA | none | 0 | 0 | 0 |

TABLE 3-continued

Results of hybrid molecule expression and receptor binding analysis

|  |  | EXP | VEGFR-1 | VEGFR-2 | VEGFR-3 |
|---|---|---|---|---|---|
| 12-3 | AAACCCAAA | yes | yes | yes | none |
| 12-4 | AAACCCCAA | none | 0 | 0 | 0 |
| 12-5 | AAACCAAAC | yes | yes | none | none |
| 12-6 | AAACCACAC | none | 0 | 0 | 0 |
| 12-7 | AAACCCAAC | yes | yes | yes | yes |
| 12-8 | AAACCCCAC | none | 0 | 0 | 0 |
| 12-9 | AAACCAACA | yes | yes | none | yes |
| 12-10 | AAACCACCA | none | 0 | 0 | 0 |
| 12-11 | AAACCCACA | yes | yes | yes | yes |
| 12-12 | AAACCCCCA | none | 0 | 0 | 0 |
| 12-13 | AAACCAACC | yes | yes | none | yes |
| 12-14 | AAACCACCC | yes | none | none | yes |
| 12-15 | AAACCCACC | yes | none | yes | yes |
| 12-16 | AAACCCCCC | yes | none | none | yes |
| 81-1 | CAAAAAAAA | yes | yes | yes | none |
| 81-2 | CAAAAACAA | none | 0 | 0 | 0 |
| 81-3 | CAAAACAAA | yes | yes | yes | none |
| 81-4 | CAAAACCAA | none | 0 | 0 | 0 |
| 81-5 | CAAAAAAAC | yes | yes | yes | none |
| 81-6 | CAAAAACAC | none | 0 | 0 | 0 |
| 81-7 | CAAAACAAC | yes | yes | yes | none |
| 81-8 | CAAAACCAC | none | 0 | 0 | 0 |
| 81-9 | CAAAAAACA | yes | yes | none | none |
| 81-10 | CAAAAACCA | none | 0 | 0 | 0 |
| 81-11 | CAAAACACA | yes | yes | yes | none |
| 81-12 | CAAAACCCA | none | 0 | 0 | 0 |
| 81-13 | CAAAAAACC | yes | yes | none | none |
| 81-14 | CAAAACCCC | none | 0 | 0 | 0 |
| 81-15 | CAAAACACC | yes | yes | yes | none |
| 81-16 | CAAAACCCC | none | 0 | 0 | 0 |
| 13-1 | AAAACAAAA | yes | yes | yes | none |
| 13-2 | AAAACACAA | none | 0 | 0 | 0 |
| 13-3 | AAAACCAAA | none | 0 | 0 | 0 |
| 13-4 | AAAACCCAA | yes | none | none | none |
| 13-5 | AAAACAAAC | yes | yes | yes | none |
| 13-6 | AAAACACAC | yes | none | none | none |
| 13-7 | AAAACCAAC | yes | yes | yes | none |
| 13-8 | AAAACCCAC | yes | none | none | none |
| 13-9 | AAAACAACA | yes | yes | none | none |
| 13-10 | AAAACACCA | none | 0 | 0 | 0 |
| 13-11 | AAAACCACA | yes | yes | none | none |
| 13-12 | AAAACCCCA | none | 0 | 0 | 0 |
| 13-13 | AAAACAACC | yes | yes | none | none |
| 13-14 | AAAACACCC | yes | none | none | none |
| 13-15 | AAAACCACC | yes | yes | none | none |
| 13-16 | AAAACCCCC | none | 0 | 0 | 0 |
| 14-1 | AAACAAAAA | yes | yes | none | none |
| 14-2 | AAACAACAA | none | 0 | 0 | 0 |
| 14-3 | AAACACAAA | yes | yes | yes | none |
| 14-4 | AAACACCAA | none | 0 | 0 | 0 |
| 14-5 | AAACAAAAC | yes | yes | none | none |
| 14-6 | AAACAACAC | none | 0 | 0 | 0 |
| 14-7 | AAACACAAC | yes | none | yes | none |
| 14-8 | AAACACCAC | none | 0 | 0 | 0 |
| 14-9 | AAACAAACA | yes | yes | yes | yes |
| 14-10 | AAACAACCA | none | 0 | 0 | 0 |
| 14-11 | AAACACACA | none | 0 | 0 | 0 |
| 14-12 | AAACACCCA | none | 0 | 0 | 0 |
| 14-13 | AAACAAACC | yes | none | none | none |
| 14-14 | AAACAACCC | none | 0 | 0 | 0 |
| 14-15 | AAACACACC | yes | none | none | none |
| 14-16 | AAACACCCC | none | 0 | 0 | 0 |
| 23-1 | CCCACAAAA | yes | none | none | none |
| 23-2 | CCCACACAA | yes | none | none | none |
| 23-3 | CCCACCAAA | yes | none | none | none |
| 23-4 | CCCACCCAA | yes | none | none | none |
| 23-5 | CCCACAAAC | yes | none | none | none |
| 23-6 | CCCACACAC | yes | none | none | none |
| 23-7 | CCCACCAAC | yes | none | none | none |
| 23-8 | CCCACCCAC | yes | none | none | none |
| 23-9 | CCCACAACA | yes | none | none | none |
| 23-10 | CCCACACCA | yes | none | yes | none |
| 23-11 | CCCACCACA | yes | none | none | none |
| 23-12 | CCCACCCCA | yes | none | yes | none |

TABLE 3-continued

Results of hybrid molecule expression and receptor binding analysis

| | | EXP | VEGFR-1 | VEGFR-2 | VEGFR-3 |
|---|---|---|---|---|---|
| 23-13 | CCCACAACC | yes | none | none | none |
| 23-14 | CCCACACCC | yes | none | yes | none |
| 23-15 | CCCACCACC | yes | none | none | none |
| 23-16 | CCCACCCCC | yes | none | none | none |
| 33-1 | ACAACAAAA | yes | none | yes | none |
| 33-2 | ACAACACAA | yes | none | none | none |
| 33-3 | ACAACCAAA | yes | none | yes | none |
| 33-4 | ACAACCCAA | yes | none | none | none |
| 33-5 | ACAACAAAC | yes | none | none | none |
| 33-6 | ACAACACAC | yes | none | none | none |
| 33-7 | ACAACCAAC | yes | none | none | none |
| 33-8 | ACAACCCAC | yes | none | none | none |
| 33-9 | ACAACAACA | yes | none | yes | none |
| 33-10 | ACAACACCA | none | 0 | 0 | 0 |
| 33-11 | ACAACCACA | yes | none | none | none |
| 33-12 | ACAACCCCA | none | 0 | 0 | 0 |
| 33-13 | ACAACAACC | yes | none | none | none |
| 33-14 | ACAACACCC | yes | none | none | none |
| 33-15 | ACAACCACC | yes | none | none | none |
| 33-16 | ACAACCCCC | yes | none | none | none |
| 34-1 | ACACAAAAA | yes | none | none | none |
| 34-2 | ACACAACAA | none | 0 | 0 | 0 |
| 34-3 | ACACACAAA | yes | none | none | none |
| 34-4 | ACACACCAA | none | 0 | 0 | 0 |
| 34-5 | ACACAAAAC | yes | none | none | none |
| 34-6 | ACACAACAC | none | 0 | 0 | 0 |
| 34-7 | ACACACAAC | yes | none | none | none |
| 34-8 | ACACACCAC | none | 0 | 0 | 0 |
| 34-9 | ACACAAACA | yes | none | none | none |
| 34-10 | ACACAACCA | none | 0 | 0 | 0 |
| 34-11 | ACACACACA | yes | none | none | none |
| 34-12 | ACACACCCA | none | 0 | 0 | 0 |
| 34-13 | ACACAAACC | yes | none | none | none |
| 34-14 | ACACAACCC | yes | none | none | none |
| 34-15 | ACACACACC | yes | none | none | none |
| 34-16 | ACACACCCC | none | 0 | 0 | 0 |
| 41-1 | CACAAAAAA | yes | yes | none | none |
| 41-2 | CACAAACAA | none | 0 | 0 | 0 |
| 41-3 | CACAACAAA | yes | none | none | none |
| 41-4 | CACAACCAA | none | 0 | 0 | 0 |
| 41-5 | CACAAAAAC | yes | none | none | none |
| 41-6 | CACAAACAC | yes | none | none | none |
| 41-7 | CACAACAAC | yes | none | none | none |
| 41-8 | CACAACCAC | none | 0 | 0 | 0 |
| 41-9 | CACAAAACA | yes | none | none | none |
| 41-10 | CACAAACCA | none | 0 | 0 | 0 |
| 41-11 | CACAACACA | yes | none | none | none |
| 41-12 | CACAACCCA | none | 0 | 0 | 0 |
| 41-13 | CACAAAACC | yes | none | none | none |
| 41-14 | CACAAACCC | yes | none | none | none |
| 41-15 | CACAACACC | yes | none | none | none |
| 41-16 | CACAACCCC | yes | none | none | none |
| 42-1 | CACCCAAAA | yes | none | none | none |
| 42-2 | CACCCACAA | none | 0 | 0 | 0 |
| 42-3 | CACCCCAAA | yes | none | none | none |
| 42-4 | CACCCCCAA | none | 0 | 0 | 0 |
| 42-5 | CACCCAAAC | none | 0 | 0 | 0 |
| 42-6 | CACCCACAC | yes | none | none | none |
| 42-7 | CACCCCAAC | yes | none | none | none |
| 42-8 | CACCCCCAC | yes | none | none | none |
| 42-9 | CACCCAACA | yes | none | none | none |
| 42-10 | CACCCACCA | yes | none | none | none |
| 42-11 | CACCCCACA | yes | none | none | none |
| 42-12 | CACCCCCCA | yes | none | none | none |
| 42-13 | CACCCAACC | yes | none | none | none |
| 42-14 | CACCCACCC | yes | none | none | none |
| 42-15 | CACCCCACC | yes | none | none | none |
| 42-16 | CACCCCCCC | yes | none | none | none |
| 43-1 | CACACAAAA | yes | yes | none | none |
| 43-2 | CACACACAA | none | 0 | 0 | 0 |
| 43-3 | CACACCAAA | yes | none | none | none |
| 43-4 | CACACCCAA | none | 0 | 0 | 0 |
| 43-5 | CACACAAAC | yes | none | none | none |
| 43-6 | CACACACAC | yes | none | none | none |

TABLE 3-continued

Results of hybrid molecule expression and receptor binding analysis

|  |  | EXP | VEGFR-1 | VEGFR-2 | VEGFR-3 |
|---|---|---|---|---|---|
| 43-7 | CACACCAAC | yes | none | none | none |
| 43-8 | CACACCCAC | yes | none | none | none |
| 43-9 | CACACAACA | yes | none | none | none |
| 43-10 | CACACACCA | none | 0 | 0 | 0 |
| 43-11 | CACACCACA | yes | none | none | none |
| 43-12 | CACACCCCA | none | 0 | 0 | 0 |
| 43-13 | CACACAACC | yes | none | none | none |
| 43-14 | CACACACCC | yes | none | none | none |
| 43-15 | CACACCACC | yes | none | none | none |
| 43-16 | CACACCCCC | yes | none | none | none |
| 44-1 | CACCAAAAA | yes | none | none | none |
| 44-2 | CACCAACAA | yes | none | none | none |
| 44-3 | CACCACAAA | yes | none | none | none |
| 44-4 | CACCACCAA | yes | none | none | none |
| 44-5 | CACCAAAAC | yes | none | none | none |
| 44-6 | CACCAACAC | none | 0 | 0 | 0 |
| 44-7 | CACCACAAC | yes | none | none | none |
| 44-8 | CACCACCAC | yes | none | none | none |
| 44-9 | CACCAAACA | yes | none | none | none |
| 44-10 | CACCAACCA | yes | none | none | none |
| 44-11 | CACCACACA | yes | none | none | none |
| 44-12 | CACCACCCA | yes | none | none | none |
| 44-13 | CACCAAACC | yes | none | none | none |
| 44-14 | CACCAACCC | yes | none | none | none |
| 44-15 | CACCACACC | yes | none | none | none |
| 44-16 | CACCACCCC | yes | none | none | none |
| 54-1 | CCACAAAAA | yes | none | none | none |
| 54-2 | CCACAACAA | none | 0 | 0 | 0 |
| 54-3 | CCACACAAA | yes | none | none | none |
| 54-4 | CCACACCAA | none | 0 | 0 | 0 |
| 54-5 | CCACAAAAC | yes | none | none | none |
| 54-6 | CCACAACAC | none | 0 | 0 | 0 |
| 54-7 | CCACACAAC | yes | none | none | none |
| 54-8 | CCACACCAC | none | 0 | 0 | 0 |
| 54-9 | CCACAAACA | yes | none | none | none |
| 54-10 | CCACAACCA | yes | none | none | none |
| 54-11 | CCACACACA | yes | none | none | none |
| 54-12 | CCACACCCA | none | 0 | 0 | 0 |
| 54-13 | CCACAAACC | yes | none | none | none |
| 54-14 | CCACAACCC | none | 0 | 0 | 0 |
| 54-15 | CCACACACC | yes | none | none | none |
| 54-16 | CCACACCCC | none | 0 | 0 | 0 |
| 64-1 | AACCAAAAA | yes | none | none | none |
| 64-2 | AACCAACAA | yes | none | none | none |
| 64-3 | AACCACAAA | yes | none | none | none |
| 64-4 | AACCACCAA | yes | none | none | none |
| 64-5 | AACCAAAAC | yes | none | none | none |
| 64-6 | AACCAACAC | yes | none | none | none |
| 64-7 | AACCACAAC | yes | none | none | none |
| 64-8 | AACCACCAC | yes | none | none | none |
| 64-9 | AACCAAACA | yes | none | none | none |
| 64-10 | AACCAACCA | yes | none | none | none |
| 64-11 | AACCACACA | yes | none | none | none |
| 64-12 | AACCACCCA | yes | none | none | none |
| 64-13 | AACCAAACC | yes | none | none | none |
| 64-14 | AACCAACCC | yes | none | none | none |
| 64-15 | AACCACACC | yes | none | none | none |
| 64-16 | AACCACCCC | yes | none | none | none |
| 83-1 | CAAACAAAA | yes | yes | yes | none |
| 83-2 | CAAACACAA | none | 0 | 0 | 0 |
| 83-3 | CAAACCAAA | yes | yes | yes | none |
| 83-4 | CAAACCCAA | none | 0 | 0 | 0 |
| 83-5 | CAAACAAAC | yes | yes | yes | none |
| 83-6 | CAAACACAC | yes | none | none | none |
| 83-7 | CAAACCAAC | yes | yes | yes | none |
| 83-8 | CAAACCCAC | none | 0 | 0 | 0 |
| 83-9 | CAAACAACA | yes | yes | none | none |
| 83-10 | CAAACACCA | none | 0 | 0 | 0 |
| 83-11 | CAAACCACA | yes | yes | yes | none |
| 83-12 | CAAACCCCA | none | 0 | 0 | 0 |
| 83-13 | CAAACAACC | yes | yes | none | none |
| 83-14 | CAAAGACCC | none | 0 | 0 | 0 |
| 83-15 | CAAACCACC | yes | yes | yes | none |
| 83-16 | CAAACCCCC | none | 0 | 0 | 0 |

TABLE 3-continued

Results of hybrid molecule expression and receptor binding analysis

|  |  | EXP | VEGFR-1 | VEGFR-2 | VEGFR-3 |
|---|---|---|---|---|---|
| 24-1 | CCCCAAAAA | yes | none | none | none |
| 24-2 | CCCCAACAA | yes | none | none | none |
| 24-3 | CCCCACAAA | yes | none | none | none |
| 24-4 | CCCCACCAA | yes | none | none | none |
| 24-5 | CCCCAAAAC | yes | none | none | none |
| 24-6 | CCCCAACAC | yes | none | none | none |
| 24-7 | CCCCACAAC | yes | none | none | none |
| 24-8 | CCCCACCAC | yes | none | none | none |
| 24-9 | CCCCAAACA | yes | none | none | none |
| 24-10 | CCCCAACCA | yes | none | none | none |
| 24-11 | CCCCACACA | yes | none | none | none |
| 24-12 | CCCCACCCA | yes | none | none | none |
| 24-13 | CCCCAAACC | yes | none | none | none |
| 24-14 | CCCCAACCC | yes | none | none | none |
| 24-15 | CCCCACACC | yes | none | none | none |
| 24-16 | CCCCACCCC | yes | none | none | none |
| 32-1 | ACACCAAAA | yes | none | none | none |
| 32-2 | ACACCACAA | none | 0 | 0 | 0 |
| 32-3 | ACACCCAAA | yes | none | none | none |
| 32-4 | ACACCCCAA | none | 0 | 0 | 0 |
| 32-5 | ACACCAAAC | yes | none | none | none |
| 32-6 | ACACCACAC | yes | none | none | none |
| 32-7 | ACACCCAAC | yes | none | none | none |
| 32-8 | ACACCCCAC | yes | none | none | none |
| 32-9 | ACACCAACA | yes | none | none | yes |
| 32-10 | ACACCACCA | none | 0 | 0 | 0 |
| 32-11 | ACACCCACA | yes | none | none | yes |
| 32-12 | ACACCCCCA | none | 0 | 0 | 0 |
| 32-13 | ACACCAACC | yes | none | none | none |
| 32-14 | ACACCACCC | yes | none | none | yes |
| 32-15 | ACACCCACC | yes | none | none | yes |
| 32-16 | ACACCCCCC | yes | none | none | yes |
| 51-1 | CCAAAAAAA | yes | none | none | none |
| 51-2 | CCAAAACAA | yes | none | none | none |
| 51-3 | CCAAACAAA | yes | none | none | none |
| 51-4 | CCAAACCAA | yes | none | none | none |
| 51-5 | CCAAAAAAC | yes | none | none | none |
| 51-6 | CCAAAACAC | yes | none | none | none |
| 51-7 | CCAAACAAC | yes | none | none | none |
| 51-8 | CCAAACCAC | yes | none | none | none |
| 51-9 | CCAAAAACA | yes | none | none | none |
| 51-10 | CCAAAACCA | none | 0 | 0 | 0 |
| 51-11 | CCAAACACA | yes | none | none | none |
| 51-12 | CCAAACCCA | none | 0 | 0 | 0 |
| 51-13 | CCAAAAACC | yes | none | none | none |
| 51-14 | CCAAAACCC | yes | none | none | none |
| 51-15 | CCAAACACC | yes | none | none | none |
| 51-16 | CCAAACCCC | none | 0 | 0 | 0 |
| 52-1 | CCACCAAAA | yes | none | none | none |
| 52-2 | CCACCACAA | none | 0 | 0 | 0 |
| 52-3 | CCACCCAAA | yes | none | none | none |
| 52-4 | CCACCCCAA | none | 0 | 0 | 0 |
| 52-5 | CCACCAAAC | yes | none | none | none |
| 52-6 | CCACCACAC | yes | none | none | none |
| 52-7 | CCACCCAAC | yes | none | none | none |
| 52-8 | CCACCCCAC | yes | none | none | none |
| 52-9 | CCACCAACA | yes | none | none | yes |
| 52-10 | CCACCACCA | none | 0 | 0 | 0 |
| 52-11 | CCACCCACA | yes | none | none | yes |
| 52-12 | CCACCCCCA | none | 0 | 0 | 0 |
| 52-13 | CCACCAACC | none | 0 | 0 | 0 |
| 52-14 | CCACCACCC | yes | none | none | yes |
| 52-15 | CCACCCACC | yes | none | none | yes |
| 52-16 | CCACCCCCC | yes | none | yes | yes |
| 53-1 | CCAACAAAA | yes | none | yes | none |
| 53-2 | CCAACACAA | none | 0 | 0 | 0 |
| 53-3 | CCAACCAAA | yes | yes | yes | yes |
| 53-4 | CCAACCCAA | none | 0 | 0 | 0 |
| 53-5 | CCAACAAAC | yes | none | none | none |
| 53-6 | CCAACACAC | yes | none | none | none |
| 53-7 | CCAACCAAC | yes | none | yes | none |
| 53-8 | CCAACCCAC | yes | none | none | none |
| 53-9 | CCAACAACA | yes | none | none | none |
| 53-10 | CCAACACCA | none | 0 | 0 | 0 |

TABLE 3-continued

| Results of hybrid molecule expression and receptor binding analysis | | | | | |
|---|---|---|---|---|---|
| | | EXP | VEGFR-1 | VEGFR-2 | VEGFR-3 |
| 53-11 | CCAACCACA | yes | none | none | none |
| 53-12 | CCAACCCCA | none | 0 | 0 | 0 |
| 53-13 | CCAACAACC | yes | none | none | none |
| 53-14 | CCAACACCC | yes | none | none | none |
| 53-15 | CCAACCACC | yes | none | none | none |
| 53-16 | CCAACCCCC | yes | none | none | none |
| 61-1 | AACAAAAAA | yes | yes | none | none |
| 61-2 | AACAAACAA | yes | none | none | none |
| 61-3 | AACAACAAA | yes | yes | none | none |
| 61-4 | AACAACCAA | yes | none | none | none |
| 61-5 | AACAAAAAC | yes | none | none | none |
| 61-6 | AACAAACAC | yes | none | none | none |
| 61-7 | AACAACAAC | yes | none | none | none |
| 61-8 | AACAACCAC | yes | none | none | none |
| 61-9 | AACAAAACA | yes | none | none | none |
| 61-10 | AACAAACCA | yes | none | none | none |
| 61-11 | AACAACACA | yes | none | none | none |
| 61-12 | AACAACCCA | yes | none | none | none |
| 61-13 | AACAAAACC | yes | none | none | none |
| 61-14 | AACAAACCC | yes | none | none | none |
| 61-15 | AACAACACC | yes | none | none | none |
| 61-16 | AACAACCCC | yes | none | none | none |
| 62-1 | AACCCAAAA | yes | yes | none | none |
| 62-2 | AACCCACAA | yes | 0 | 0 | 0 |
| 62-3 | AACCCCAAA | yes | none | none | none |
| 62-4 | AACCCCCAA | yes | none | none | none |
| 62-5 | AACCCAAAC | yes | none | none | none |
| 62-6 | AACCCACAC | yes | none | none | none |
| 62-7 | AACCCCAAC | yes | none | none | none |
| 62-8 | AACCCCCAC | yes | none | yes | none |
| 62-9 | AACCCAACA | yes | none | none | none |
| 62-10 | AACCCACCA | yes | none | yes | none |
| 62-11 | AACCCCACA | yes | none | yes | yes |
| 62-12 | AACCCCCCA | yes | none | none | none |
| 62-13 | AACCCAACC | yes | none | yes | none |
| 62-14 | AACCCACCC | yes | none | none | none |
| 62-15 | AACCCCACC | yes | none | none | none |

TABLE 3-continued

| Results of hybrid molecule expression and receptor binding analysis | | | | | |
|---|---|---|---|---|---|
| | | EXP | VEGFR-1 | VEGFR-2 | VEGFR-3 |
| 62-16 | AACCCCCCC | yes | none | none | none |
| 63-1 | AACACAAAA | yes | yes | yes | none |
| 63-2 | AACACACAA | none | 0 | 0 | 0 |
| 63-3 | AACACCAAA | yes | none | yes | none |
| 63-4 | AACACCCAA | none | 0 | 0 | 0 |
| 63-5 | AACACAAAC | yes | none | none | none |
| 63-6 | AACACACAC | yes | none | yes | none |
| 63-7 | AACACCAAC | yes | none | yes | yes |
| 63-8 | AACACCCAC | yes | none | none | none |
| 63-9 | AACACAACA | yes | none | none | none |
| 63-10 | AACACACCA | yes | none | none | none |
| 63-11 | AACACCACA | yes | none | none | none |
| 63-12 | AACACCCCA | yes | 0 | 0 | 0 |
| 63-13 | AACACAACC | yes | none | none | none |
| 63-14 | AACACACCC | yes | none | none | none |
| 63-15 | AACACCACC | yes | none | none | none |
| 63-16 | AACACCCCC | yes | none | none | none |
| 71-1 | ACCAAAAAA | yes | none | none | none |
| 71-2 | ACCAAACAA | yes | none | none | none |
| 71-3 | ACCAACAAA | yes | none | none | none |
| 71-4 | ACCAACCAA | yes | none | none | none |
| 71-5 | ACCAAAAAC | yes | none | none | none |
| 71-6 | ACCAAACAC | yes | none | none | none |
| 71-7 | ACCAACAAC | yes | none | none | none |
| 71-8 | ACCAACCAC | yes | none | none | none |
| 71-9 | ACCAAAACA | yes | none | none | none |
| 71-10 | ACCAAACCA | yes | none | none | none |
| 71-11 | ACCAACACA | yes | none | none | none |
| 71-12 | ACCAACCCA | yes | none | none | none |
| 71-13 | ACCAAAACC | yes | none | none | none |
| 71-14 | ACCAAACCC | yes | none | none | none |
| 71-15 | ACCAACACC | yes | none | none | none |
| 71-16 | ACCAACCCC | yes | none | none | none |
| 73-1 | ACCACAAAA | yes | none | none | none |
| 73-2 | ACCACACAA | yes | none | none | none |
| 73-3 | ACGACCAAA | yes | none | none | none |
| 73-4 | ACCACCCAA | yes | 0 | 0 | 0 |

TABLE 3-continued

Results of hybrid molecule expression and receptor binding analysis

|  |  | EXP | VEGFR-1 | VEGFR-2 | VEGFR-3 |
|---|---|---|---|---|---|
| 73-5 | ACCACAAAC | yes | none | none | none |
| 73-6 | ACCACACAC | yes | none | none | none |
| 73-7 | ACCACCAAC | yes | none | yes | none |
| 73-8 | ACCACCCAC | yes | none | none | none |
| 73-9 | ACCACAACA | yes | none | none | none |
| 73-10 | ACCACACCA | yes | none | none | none |
| 73-11 | ACCACCACA | yes | none | none | none |
| 73-12 | ACCACCCCA | yes | none | none | none |
| 73-13 | ACCACAACC | yes | none | none | none |
| 73-14 | ACCACACCC | yes | none | none | none |
| 73-15 | ACCACCACC | yes | none | yes | none |
| 73-16 | ACCACCCCC | yes | none | none | none |
| 74-1 | ACCCAAAAA | yes | none | none | none |
| 74-2 | ACCCAACAA | yes | none | none | none |
| 74-3 | ACCCACAAA | yes | none | none | none |
| 74-4 | ACCCACCAA | yes | none | none | none |
| 74-5 | ACCCAAAAC | yes | none | none | none |
| 74-6 | ACCCAACAC | yes | none | none | none |
| 74-7 | ACCCACAAC | yes | none | none | none |
| 74-8 | ACCCACCAC | yes | none | yes | none |
| 74-9 | ACCCAAACA | yes | none | none | none |
| 74-10 | ACCCAACCA | yes | none | yes | none |
| 74-11 | ACCCACACA | yes | none | none | none |
| 74-12 | ACCCACCCA | yes | none | yes | none |
| 74-13 | ACCCAAACC | yes | none | none | none |
| 74-14 | ACCCAACCC | yes | none | none | none |
| 74-15 | ACCCACACC | yes | none | none | none |
| 74-16 | ACCCACCCC | yes | none | none | none |
| 82-1 | CAACCAAAA | yes | none | none | none |
| 82-2 | CAACCACAA | none | none | none | none |
| 82-3 | CAACCCAAA | yes | none | none | none |
| 82-4 | CAACCCCAA | none | none | none | none |
| 82-5 | CAACCAAAC | yes | yes | none | none |
| 82-6 | CAACCACAC | none | 0 | 0 | 0 |
| 82-7 | CAACCCAAC | yes | yes | yes | yes |
| 82-8 | CAACCCCAC | none | 0 | 0 | 0 |
| 82-9 | CAACCAACA | yes | yes | yes | yes |
| 82-10 | CAACCACCA | none | 0 | 0 | 0 |
| 82-11 | CAACCCACA | yes | yes | yes | yes |
| 82-12 | CAACCCCCA | none | 0 | 0 | 0 |
| 82-13 | CAACCAACC | yes | yes | none | yes |
| 82-14 | CAACCACCC | yes | none | none | yes |
| 82-15 | CAACCCACC | yes | none | yes | yes |
| 82-16 | CAACCCCCC | yes | none | none | yes |
| 84-1 | CAACAAAAA | yes | yes | none | none |
| 84-2 | CAACAACAA | none | 0 | 0 | 0 |
| 84-3 | CAACACAAA | yes | yes | yes | none |
| 84-4 | CAACACCAA | none | 0 | 0 | 0 |
| 84-5 | CAACAAAAC | yes | yes | none | none |
| 84-6 | CAACAACAC | none | 0 | 0 | 0 |
| 84-7 | CAACACAAC | yes | none | none | none |
| 84-8 | CAACACCAC | none | 0 | 0 | 0 |
| 84-9 | CAACAAACA | yes | yes | yes | yes |
| 84-10 | CAACAACCA | none | 0 | 0 | 0 |
| 84-11 | CAACACACA | yes | yes | yes | yes |
| 84-12 | CAACACCCA | none | 0 | 0 | 0 |
| 84-13 | CAACAAACC | none | 0 | 0 | 0 |
| 84-14 | CAACAACCC | none | 0 | 0 | 0 |
| 84-15 | CAACACACC | none | 0 | 0 | 0 |
| 84-16 | CAACACCCC | none | 0 | 0 | 0 |

Receptor binding properties were analyzed only for constructs that were expressed. If a clone was weakly expressed, its receptor binding properties were analyzed only if its size allowed distinction from endogenous VEGF-A expression, or if its amino acid composition allowed removal of endogenous VEGF-A using monoclonal anti-VEGF-A antibodies (R&D Systems) prior to assaying receptor binding. Although the epitope recognized by this anti-VEGF-A antibody has not been characterized, our preliminary results indicate that the epitope is located within one or more of fragments 2, 3, 4, 7, or 9 of VEGF-A. Thus, antibody precipitation of endogenous VEGF-A was performed for all constructs in which fragments 2, 3, 4, 7, and 9 were derived from VEGF-C. Further mapping of the epitope of this antibody may allow similar examination of additional constructs. For example, if subsequent analysis indicates that the epitope does not reside in fragment 2, constructs in which fragment 2 was derived from VEGF-A can also be analyzed by this method. This procedure was preformed for binding to VEGFR-1 or VEGFR-2, to assess how many low affinity binding hybrid molecules were not detected due to interference with endogenous VEGF. Failure to detect a signal or detection of a weak signal in the receptor binding assays does not conclusively demonstrate lack of or low receptor binding affinity. The intrinsic set-up of the experiment does not allow detection of low affinity binders of VEGFR-1 and VEGFR-2 that are weakly expressed. Thus, the binding assays may have failed to detect low affinity binders of VEGFR-1 and VEGFR-2 for some of the hybrid proteins that were weakly expressed.

In this assay, apparent low receptor binding affinity of a low-level-expressed hybrid molecule could be due to heterodimerization with endogenous VEGF. For example, if a hybrid protein has no receptor-affinity itself, but is able to dimerize with endogenous VEGF-A, such a heterodimer may be capable of binding one of more receptor(s) with low affinity. Purification of chimeric polypeptides of the invention (e.g., using immunoaffinity chromatography with an antibody that recognizes either the myc or HA tag sequences) and using the purified polypeptide in receptor binding assays will resolve any ambiguities caused by endogenous VEGF-A in conditioned media. Alternatively, the hybrid proteins will be expressed in insect cells, e.g., S9 cells, to avoid contamination with endogenous VEGF-A.

Lack of expression or low level expression of a particular construct may be due to properties of the hybrid protein itself, variations in DNA quality, or may reflect mutations in the DNA acquired during construction of the hybrid clone. In the present case, all constructs were sequenced after the first ligation step, and selected clones were sequenced after the second ligation step. Analysis of these sequences indicated that no mutations occurred during the first step, and none of the sequences examined after the second step of construction contained mutations. Thus, any mutations present in the final clone most probably occurred during the final ligation step.

Thirty-six of the 512 clones were sequenced to determine the frequency with which constructs acquired mutations during construction of the clones that resulted in changes at the amino acid level. The constructs that were sequenced were clones 11-1 (SEQ ID NOS: 42-43), 11-16 (SEQ ID NOS: 44-45), 22-1 (SEQ ID NOS: 46-47), 22-16 (SEQ ID NOS: 48-49), 12-1 to 12-16 (SEQ ID NOS: 50-81), and 31-1 to 31-16 (SEQ ID NOS: 82-113). Only 2 of the 36 clones, 12-13 and 12-16, showed a deviation from the expected sequence. Clone 12-16 had undergone a loss of two base pairs at the ligation junction between N45 and C67, resulting in a frameshift mutation after the RCG triplet of fragment C5 and a stop codon only a few codons thereafter. Clone 12-13 had acquired a point mutation which results in the substitution of Asp by Asn at the last C-terminal amino acid of this hybrid protein.

From the 512 hybrid constructs examined, four were chosen for further analysis including sequencing to determine if any mutations occurred during construction of the hybrid protein and repetition of binding assays to confirm initial results. Results from binding assays of these four particular hybrid proteins: constructs 12-13, 12-11, 12-9, and 12-7 indicate that they show novel binding patterns that are not exhibited by known VEGF receptor ligands. 12-9 and 12-13 show binding to VEGFR-1 and VEGFR-3 but not VEGFR-2, whereas 12-7 and 12-11 exhibit binding to all three VEGF receptors.

These results show that it is possible by combinatorial approaches to provide VEGF-related growth factors having modified properties. The novel molecules constructed in some cases have been shown to have modified biological effects compared to their wild-type ancestors, and thus may be used in applications where specificity and fine-tuning of biological effects are necessary. In particular, these experiments demonstrate that it is possible to construct a "super-VEGF", such as clones 12-7 and 12-11, which binds all three known VEGFRs, and therefore should be uniquely potent in inducing vascular growth.

EXAMPLE 4

Examination of VEGF-A and VEGF-C Receptor Binding Epitopes

The VEGF-A/VEGF-C hybrid proteins can be used to examine interactions between VEGF-A or VEGF-C, and their receptors. Analysis of the results from the receptor binding assays, such as those described in Table 3 and Example 3, enable careful investigation of the receptor-binding epitopes of these two VEGF growth factors. The ability of particular hybrid proteins to bind one of the VEGF receptors may be correlated with the presence of one or more particular fragments derived from one of the parent molecules. Such data can help define the amino acid residues important for binding to a specific VEGF receptor. Knowledge of the precise receptor binding epitopes of a particular VEGF protein can facilitate the design of inhibitory molecules useful for therapeutic purposes.

Twenty-one VEGF residues important for interfacing with VEGFR-1 are indicated in large bold text:

GQNHHEVVKFMDVYQRSYCHPI-ETLVDIFQEYPDEIEYIFKPSCVPLMRCGGCC NDE-GLECVPTEESNITMQIMRIKPHQGQHI-GEMSFLQHNKCECRPKKD (SEQ ID NO: 1209)

Data from the chimera experiments indicates that those residues from fragment 2, which corresponds to the N-terminal helix and residues from fragment 7, which corresponds to strand β5 appear particularly important for conferring VEGFR-1 specificity. FIG. 8 is a three-dimensional model of the interaction of a VEGF-A dimer with two VEGFR-1 molecules. The two VEGF-A monomers are colored in green and blue, respectively. Domain 2 of the two VEGFR-1 receptors are depicted in gray. Red represents the location of residues within the VEGF-A monomers important for VEGFR-1 interfacing. These residues are clustered at the two ends of the VEGF dimer and include the N-terminal helix and part of the β5 strand.

The corresponding twenty-one residues in VEGF-C that would analogously be involved in interfacing VEGFR-3 are indicated below in large bold text:

AHYNTEILKSIDNEWRKTQCMPREVCID-VGKEFGVATNTFFK PPCVSVYRCGGCCNSEGLQC-MNTSTSYLSKTLFEITVPLSQGPKPVTISFANHTS CRCMSKLD (SEQ ID NO: 1210)

Interestingly, analysis of the receptor binding patterns from the chimera experiments indicates that a VEGF-C-derived fragment 4 (containing the β2 strand of the molecule) is absolutely required for VEGFR-3 binding specificity. Fragments 5 (which includes the β3 strand) and 8 appear to represent two other important VEGF-C fragments for VEGFR-3 binding. The amino acid sequence of VEGF-C fragments 4 and 5 is EFGVATNTFFKPPCVSVYRCG (SEQ ID NO: 1205). The TNTFxxxP quintet of residues (SEQ ID NO: 1204) is particularly noteworthy because these residues are conserved in human, quail, and bovine VEGF-C and human VEGF-D, all of which bind VEGFR-3. The analogous residues in human VEGF-A, which does not bind VEGFR-3, differ: IEYIxxxS (SEQ ID NO: 1211). FIG. 10 is three-dimensional model of a the interaction between portions of a VEGF-C dimer and a single VEGFR-3 molecule, extrapolated from the VEGF-A/VEGFR-1 model. Blue and green represent the two VEGF-C monomers and grey represents VEGFR-3. Fragment 5 of the green VEGF-C monomer is shown in orange and fragment 4 of the same monomer is shown in white. Residues in red are those located within fragment 4 or 5 that are probably in contact with the receptor.

Figure 9:

FIG. 9 is a three-dimensional model that depicts the groove formed by the fragments that appear to be important for VEGFR-3 specificity. This groove is speculated to accommodate the linker region between domain 2 and 3 of the VEGFR-3 receptor. The entry and the sides of this groove are formed by the fragments that appear to be important for conferring VEGFR-3 specificity. The green and blue indicate the two VEGF-C monomers and the gray indicates the VEGFR-3 receptor molecule. The VEGF-C residues that are believed to participate in binding VEGFR-3 are indicated in yellow.

Although fragments 6 and 9 are involved in interaction with the VEGF receptors, these fragments do not appear to be involved in determining receptor specificity.

EXAMPLE 5

Analysis of Receptor Activation or Inhibition by the Hybrid VEGF Proteins

The VEGF-A/VEGF-C hybrid proteins may be used for therapeutic applications where either activation of inhibition of one or more VEGF receptors is desired. For example, a candidate hybrid protein can be added to stable cell lines expressing a particular VEGF receptor whose activation is necessary for cell survival. Survival of the cell line indicates that the candidate hybrid protein is able to bind and activate that particular VEGF receptor. On the other hand, death of the cell line indicates that the candidate hybrid protein fails to activate the receptor. Exemplary examples of such cell-survival assays have been described in International Patent Publication No. WO 98/07832 and in Achen et al., *Proc Natl Acad Sci USA* 95:548–553 (1998), incorporated herein by reference. This assay employs Ba/F3-NYK-EpoR cells, which are Ba/F3 pre-B cells that have been transfected with a plasmid encoding a chimeric receptor consisting of the extracellular domain of VEGFR-2 and the cytoplasmic domain of the erythropoietin receptor (EpoR). These cells are routinely passaged in interleukin-3 (IL-3) and will die in the absence of IL-3. However, if signaling is induced from the cytoplasmic domain of the chimeric receptor, these cells survive and proliferate in the absence of IL-3. Such signaling is induced by ligands which bind to the VEGFR-2 extracellular domain of the chimeric receptor. For example, binding of VEGF-A or VEGF-D to the VEGFR-2 extracellular domain causes the cells to survive and proliferate in the absence of IL-3. Parental Ba/F3 cells which lack the chimeric receptor are not induced by either VEGF-A or VEGF-D to proliferate in the absence of IL-3, indicating that the responses of the Ba/F3-NYK-EpoR cells to these ligands are totally dependent on the chimeric receptor.

Candidate hybrid proteins can be tested for binding to the VEGFR-2 extracellular domain and subsequent activation of the chimeric receptor by assaying cell survival in the absence of IL-3. On the other hand, hybrid proteins that interfere with the binding of VEGFR-2 ligands, such as VEGF-A or VEGF-D, to the extracellular domain, or with the activation of the cytoplasmic domain, will cause cell death in the absence of IL-3.

Cells are cultured in the presence of IL-3 until required, then washed three times in phosphate buffered saline (PBS), resuspended in IL-3-free cell culture medium (Dulbecco's Modified Eagle's Medium (DMEM) supplemented with fetal calf serum (10%), L-glutamine (1%), geneticin (1 mg/ml), streptomycin (100 μg/ml) and penicillin (60 μg/ml)), and replated in 72-well culture plates (Nunc, Denmark) at a density of approximately 1000 cells/well. To assay for receptor activity, candidate hybrid proteins are added to culture wells at final concentrations of $10^{-10}$ to $10^{-5}$ M and incubated for 1 hour at 37° C. in 10% $CO_2$. For assaying the ability of the candidate hybrid protein to inhibit activation of the VEGFR-2/EpoR receptor, recombinant VEGF-A or VEGF-D is added to the hybrid protein-containing wells at a concentration to produce near-maximal survival of the Ba/F3-NYK-EpoR cells (typically 500 ng/ml). Positive control cultures contain either VEGF-A or VEGF-D supernatant alone and negative control cultures contain neither hybrid protein nor growth factor. Cells are then grown in culture for 48 hours, after which time a solution of 3-(3,4-dimethylthiazol-2-yl)-2,5-diphenyltetrazolium bromide (MTT; 500 μg/ml) is added to the cultures, and incubated for another 30 minutes. MTT is converted to a blue formazan product by mitochondria, thus staining living cells blue. Surviving blue cells in experiments where either activation (hybrid protein alone) or inhibition (hybrid protein+VEGF-A or VEGF-D) was assayed are counted under a microscope with inverted optics (100× magnification) and compared to cell survival in the positive control (VEGF-A or VEGF-D only) wells. Cell survival is normalized such that survival in negative controls is set to 0 (typically no viable cells were seen in negative controls), while survival in positive controls is set to 100% (typically 300–400 cells/well).

Data is analyzed by one way analysis of variance (ANOVA), with a Bonferroni multiple comparisons test carried out post-hoc to test for differences between individual cultures of hybrid protein alone (to assay binding and activation of the receptor), or hybrid protein + VEGF-A or VEGF-D (to assay inhibition of receptor activation), with VEGF-A or VEGF-D alone (positive control).

Repetition of the same assay using cells transfected with different chimeric receptors (e.g., VEGFR-3/EpoR) allows screening for activation of different VEGFRs.

VEGFR-2 (KDR) and VEGFR-3 (Flt4) Autophosphorylation Assays

As an alternative indicator of activity, the ability of a hybrid protein to stimulate autophosphorylation of a particular VEGF receptor can also be examined. A candidate hybrid protein is added to cells expressing a particular VEGF receptor. The cells are then lysed and immunoprecipitated with anti-VEGF receptor antiserum and analyzed by Western blotting using anti-phosphotyrosine antibodies to determine hybrid protein-induced phosphorylation of the VEGF receptor.

An expression vector comprising a polynucleotide encoding a hybrid VEGF molecule of the invention is transfected into an appropriate host cell (e.g., 293-EBNA cells using a calcium phosphate transfection method. About 48 hours after transfection, the growth medium of the transfected cells is changed (e.g., to DMEM medium lacking fetal calf serum) and the cells are incubated (e.g., for 36 more hours) to provide a conditioned medium. The conditioned medium is collected and centrifuged at 5000×g for 20 minutes, and the supernatant is concentrated.

The concentrated conditioned media is used to stimulate cells expressing a VEGF receptor. For example, PAE-KDR cells (Pajusola et al., *Oncogene*, 9:3545–55 (1994); Waltenberger et al., *J. Biol. Chem.*, 269:26988–26995 (1994)) are grown in Ham's F12 medium-10% fetal calf serum (FCS), or confluent NIH 3T3 cells expressing VEGFR-3 are grown in DMEM medium. The cells are starved overnight in DMEM medium or Ham's F12 supplemented with 0.2% bovine serum albumin (BSA), and then incubated for 5 minutes with the unconcentrated, 2-fold, 5-fold, and/or 10-fold concentrated conditioned media. Recombinant human VEGF-A or VEGF-C and conditioned media from mock-transfected cells are exemplary controls. In addition to conditional media, purified hybrid polypeptide can be employed in this or other assays described herein.

After stimulation with conditioned media, the cells are washed twice with ice-cold Tris-Buffered Saline (TBS) containing 100 mM sodium orthovanadate and lysed in RIPA buffer containing 1 mM phenylmethylsulfonyl fluoride (PMSF), 0.1 U/ml aprotinin and 1 mM sodium orthovanadate. The lysates are sonicated, clarified by centrifugation at 16,000×g for 20 minutes and incubated for 3–6 hours on ice with 3–5 µl of antisera specific for VEGFR-3 or VEGFR-2. Immunoprecipitates are bound to protein A-Sepharose, washed three times with RIPA buffer containing 1 mM PMSF, 1 mM sodium orthovanadate, washed twice with 10 mM Tris-HCl (pH 7.4), and subjected to SDS-PAGE using a 7% gel. Polypeptides are transferred to nitrocellulose by Western blotting and analyzed using PY20 phosphotyrosine-specific monoclonal antibodies (Transduction Laboratories) or receptor-specific antiserum and the ECL detection method (Amersham Corp.).

The ability of a hybrid polypeptide to stimulate autophosphorylation (detected using the anti-phosphotyrosine antibodies) is scored as stimulating the receptor. The level of stimulation observed for various concentrations of hybrid polypeptide, relative to known concentrations of VEGF-A or VEGF-C, provide an indication of the potency of receptor stimulation. Polypeptides that have been shown to bind the receptor, but are incapable of stimulating receptor phosphorylation, are scored as inhibitors. Inhibitory activity can be further assayed by mixing a known receptor agonist such as recombinant VEGF-A or VEGF-C with either media alone or with concentrated conditioned media, to determine if the concentrated conditioned media inhibits VEGF-A-mediated or VEGF-C-mediated receptor phosphorylation.

In initial experiments to study tyrosine phosphorylation of VEGFR-2 and VEGFR-3 mediated by selected hybrid molecules which bind VEGFR-2 or VEGFR-3, it was observed that all hybrid proteins tested were able to induce phosphorylation of the receptors, however to a lesser extent than that mediated by VEGF-A or VEGF-C. Further examination of the expression levels of the hybrid proteins in the baculovirus system used to produce the proteins indicate that the proteins are not all expressed in comparable amounts. Differential expression levels of the hybrid proteins may explain some of the lower activities exhibited by these proteins in assaying their ability to stimulate tyrosine phosphorylation of VEGFR-2 and VEGFR-3. In addition, the extent of phosphorylation induced by these hybrid molecules determined using this particular assay may not correlate with biological activity in vivo.

EXAMPLE 6

Analysis of Receptor Binding Affinities of Hybrid Proteins

Preliminary analysis of the 512 hybrid proteins indicate that a number of them are able to bind one or more of the VEGFRs. In addition, results from these experiments suggest that some show differential binding affinities to one of more VEGFRs. For these experiments, the hybrid protein is expressed in an insect cell system, e.g., S9 cells, to eliminate contamination with endogenous VEGF-A found in mammalian cells. To measure the relative binding affinities of selected hybrid proteins, an ELISA-type approach is used. For example, to examine binding affinity for VEGFR-1, serial dilutions of competing VEGFR-1-IgG fusion proteins and a subsaturating concentration of the candidate hybrid protein tagged with the myc epitope is added to microtiter plates coated with VEGFR-1, and incubated until equilibrium is established. The plates are then washed to remove unbound proteins. Hybrid molecules that remain bound to the VEGFR-1 coated plates are detected using an anti-myc antibody conjugated to a readily detectable label e.g., horseradish peroxidase. Binding affinities (EC50) can be calculated as the concentration of competing VEGFR-IgG fusion protein that results in half-maximal binding. These values can be compared with those obtained from analysis of VEGF-A or VEGF-C to determine changes in binding affinity of one or more of the VEGFRs. Similarly, binding to VEGFR-2 is accomplished by using a VEGFR-2-IgG fusion protein, and binding to VEGFR-3 is determined using a VEGFR-3-IgG fusion protein.

EXAMPLE 7

Endothelial Cell Migration in Collagen Gel Mediated by VEGF-A/VEGF-C Hybrid Proteins Both VEGF-A and VEGF-C stimulate endothelial cell migration in collagen gel. The hybrid proteins of the invention are examined to determine if they are also capable of stimulating endothelial cell migration in collagen gel, thus providing another indicia of biological activity. Exemplary examples of such cell migration assays have been described in International Patent Publication No. WO 98/33917, incorporated herein by reference. Briefly, bovine capillary endothelial cells (BCE) are seeded on top of a collagen layer in tissue culture plates. Conditioned media from cells transfected with an expression vector producing the candidate hybrid protein is placed in wells made in collagen gel approximately 4 mm away from the location of the attached BCE cells. The number of BCE cells that have migrated from the original area of attachment in the collagen gel towards the wells containing the hybrid protein is then counted to assess the ability of the hybrid protein to induce cell migration.

BCE cells (Folkman et al., *Proc. Natl. Acad. Sci. (USA)*, 76:5217–5221 (1979)) are cultured as described in Pertovaara et al., *J. Biol. Chem.*, 269:6271–74 (1994). Collagen gels are prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. Tissue culture plates (5 cm diameter) are coated with about 1 mm thick layer of the solution, which is allowed to polymerize at 37° C. BCE cells are seeded atop this layer.

For the migration assays, the cells are allowed to attach inside a plastic ring (1 cm diameter) placed on top of the first collagen layer. After 30 minutes, the ring is removed and unattached cells are rinsed away. A second layer of collagen and a layer of growth medium (5% newborn calf serum (NCS)), solidified by 0.75% low melting point agar (FMC BioProducts, Rockland, Me.), are added. A well (3 mm diameter) is punched through all the layers on both sides of the cell spot at a distance of 4 mm, and media containing a hybrid VEGF polypeptide (or media alone or media containing VEGF-A or VEGF-C to serve as controls) is pipetted daily into the wells. Photomicrographs of the cells migrating out from the spot edge are taken, e.g., after six days, through an Olympus CK 2 inverted microscope equipped with phase-contrast optics. The migrating cells are counted after nuclear staining with the fluorescent dye bisbenzimide (1 mg/ml, Hoechst 33258, Sigma).

The number of cells migrating at different distances from the original area of attachment towards wells containing media conditioned by the non-transfected (control) or transfected (mock; hybrid; VEGF-C; or VEGF-A) cells are determined 6 days after addition of the media. The number of cells migrating out from the original ring of attachment are counted in five adjacent 0.5 mm×0.5 mm squares using a microscope ocular lens grid and 10× magnification with a fluorescence microscope. Cells migrating further than 0.5 mm are counted in a similar way by moving the grid in 0.5 mm steps.

The ability of a hybrid polypeptide to induce migration of BCE cells in indicative of receptor agonist activity. The number of migrating cells in the presence of a hybrid protein versus a similar concentration of VEGF-A or VEGF-C provides an indication of the potency of agonist activity. Polypeptides that have been shown to bind the receptors expressed on BCE cells, but are incapable of stimulating migration, are scored as potential inhibitors. Inhibitory activity can be further assayed by mixing a known receptor agonist such as recombinant VEGF-A or VEGF-C with either media alone or with concentrated conditioned media, to determine if the concentrated conditioned media inhibits VEGF-A-mediated or VEGF-C-mediated BCE migration.

EXAMPLE 8

Analysis of the Ability of Hybrid Proteins to Induce Vascular Permeability

Both VEGF-A and VEGF-C are capable of increasing the permeability of blood vessels. The hybrid proteins of the invention are assayed to determine which of these proteins possess this biological activity and which inhibit it. For example, vascular permeability assays according to Miles and Miles, *J. Physiol* 118:228–257 (1952), incorporated herein in its entirety, are used to analyze the hybrid proteins. Briefly, following intravenous injection of a vital dye, such as pontamine sky blue, animals such as guinea pigs are injected intradermally with a composition containing the candidate hybrid protein being examined. For controls, media alone or media containing VEGF-A or VEGF-C is injected in the same manner. After a period of time, the accumulation of dye at the injection site on the skin is measured. Those hybrid proteins that increase permeability will result in greater accumulation of dye at the injection site as compared to those hybrid proteins that fail to induce vascular permeability.

In a variation of this assay, hybrid polypeptides that are suspected of being inhibitors of VEGF-A or VEGF-C are first mixed with VEGF-A or with VEGF-C at varying ratios (e.g., 50:1, 10:1, 5:1, 2:1, 1:1, 1:2, 1:5, 1:10) and the mixtures are injected intradermally into the animals. In this manner, the ability of the hybrid polypeptide to inhibit VEGF-A-mediated or VEGF-C-mediated vascular permeability is assayed.

EXAMPLE 9

Endothelial Cell Proliferation Assay

The mitogenic activity of hybrid proteins can be examined using endothelial cell proliferation assays such as that described in Breier et al., *Dev* 114:521–532 (1992), incorporated herein in its entirety. The hybrid proteins are expressed in a mammalian cell line e.g., COS cells. Culture supernatants are then collected and assayed for mitogenic activity on bovine aortic endothelial (BAE) cells by adding the supernatants to the BAE cells. After three days, the cells are dissociated with trypsin and counted using a cytometer to determine any effects of the hybrid protein on the proliferative activity of the BAE cells. As negative controls, DMEM supplemented with 10% FCS and the conditioned media from untransfected COS cells or from COS cells transfected with vector alone can be used. Supernatants from cells transfected with constructs expressing proteins that have been shown to induce proliferation of BAE cells (e.g., VEGF-A) can be used as a positive control.

EXAMPLE 10

Examination of the Ability of Hybrid Proteins Expressed Through the Human K14 Keratin Promoter to Induce Growth of Lymphatic Vessels in Skin of Transgenic Mice Experiments are conducted in transgenic mice to analyze the specific effects of overexpression of hybrid proteins in tissues. The physiological effects in vivo provide an indication of receptor activation/inhibition profile and an indication of the potential therapeutic action of a hybrid protein. In one variation, the human K14 keratin promoter which is active in the basal cells of stratified squamous epithelia [Vassar et al., *Proc. Natl. Acad. Sci. (USA)*, 86:1563–1567 (1989)], is used as the expression control element in the recombinant hybrid protein transgene. The vector containing the K14 keratin promoter is described in Vassar et al., *Genes Dev.*, 5:714–727 (1991) and Nelson et al., *J. Cell Biol.* 97:244–251 (1983).

A DNA fragment containing the K14 promoter, hybrid protein cDNA, and K14 polyadenylation signal is synthesized, isolated, and injected into fertilized oocytes of the FVB-NIH mouse strain. The injected zygotes are transplanted to oviducts of pseudopregnant C57BL/6×DBA/2J hybrid mice. The resulting founder mice are then analyzed for the presence of the transgene by polymerase chain reaction of tail DNA using appropriate primers or by Southern analysis.

These transgenic mice are then examined for evidence of angiogenesis or lymphangiogenesis in the skin, such as the lymphangiogenesis seen in transgenic mice that overexpress VEGF-C [see International Publication WO98/33917]. Histological examination of K14-VEGF-C transgenic mice showed that in comparison to the skin of wildtype littermates, the dorsal dermis was atrophic and connective tissue was replaced by large lacunae devoid of red cells, but lined with a thin endothelial layer. These distended vessel-like structures resembled those seen in human lymphangiomas. The number of skin adnexal organs and hair follicles were reduced. In the snout region, an increased number of vessels was also seen.

Examination of the vessels in the skin of the transgenic mice using antibodies that recognize proteins specific for either blood or lymphatic vessels can further verify the identity of these vessels. Collagen types IV, XVIII [Muragaki et al., *Proc. Natl. Acad. Sci. USA*, 92:8763–8776 (1995)] and laminin are expressed in vascular endothelial cells while desmoplakins I and II (Progen) are expressed in lymphatic endothelial cells. See Schmelz et al., *Differentiation*, 57:97–117 (1994).

EXAMPLE 11

Analysis of Hybrid Proteins in Promoting or Inhibiting Myelopoiesis

Overexpression of VEGF-C in the skin of K14-VEGF-C transgenic mice correlates with a distinct alteration in leukocyte populations [see International Publication WO98/33917]. Notably, the measured populations of neutrophils were markedly increased in the transgenic mice. The effects of the hybrid proteins on hematopoiesis can be analyzed using fluorescence-activated cell sorting analysis using antibodies that recognize proteins expressed on specific leukocyte cell populations. Leukocytes populations are analyzed in blood samples taken from the F1 transgenic mice described in Example 13, and from their non-transgenic littermates.

EXAMPLE 12

Effects of Hybrid Proteins on Growth and Differentiation of Human CD34+ Progenitor Cells In Vitro Addition of VEGF-C to cultures of cord blood CD34+ cells induces cell proliferation. Co-culture of GM-CSF, IL-3, GM-CSF+IL-3, or GM-CSF+SCF with VEGF-C leads to an enhancement of proportions of myeloid cells [see International Publication WO98/33917]. Hybrid proteins of the invention can also be examined for their ability to induce growth of CD34+ progenitor cells in vitro. Human CD34+ progenitor cells (HPC, $10 \times 10^3$) are isolated from bone marrow or cord blood mononuclear cells using the MACS CD34 Progenitor cell Isolation Kit (Miltenyi Biotec, Bergish Gladbach, Germany), according to the instructions of the manufacturer and cultured in RPMI 1640 medium supplemented with L-glutamine (2.5 mM), penicillin (125 IE/ml), streptomycin (125 µg/ml) and pooled 10% umbilical cord blood (CB) plasma at 37° C. in a humidified atmosphere in the presence of 5% $CO_2$ for seven days, with or without hybrid protein at concentrations ranging from 10 ng/ml to 1 µg/ml. After seven days, total cell number is evaluated in each culture.

The co-stimulatory effect of hybrid proteins in cultures either supplemented with recombinant human stem cell factor (rhSCF, 20 ng/ml PreproTech, Rocky Hill, N.Y.) alone or a combination of granulocyte macrophage colony stimulating factor (rhGM-CSF, 100 ng/ml, Sandoz, Basel, Switzerland) plus SCF can also be examined. Experiments can also be conducted to analyze the co-stimulatory effects of hybrid protein on total cell yields of serum-free cultures of CB CD34+ HPC cells supplemented with either GM-CSF alone, IL-3 (rhIL-3, 100 U/ml, Behring AG, Marburg, Germany) alone; or a combination of GM-CSF plus IL-3.

Cells from the (7 day) plasma-supplemented cultures described above are also analyzed for the expression of the early granulomonocytic marker molecules lysozyme (LZ) and myeloperoxidase (MPO) as well as the lipopolysaccharide (LPS) receptor CD14 using immunofluorescence.

In another series of experiments, CD34+ cells are cultured in medium supplemented with 50 ng/ml M-CSF, with or without 100 ng/ml hybrid protein, for seven days. After seven days, the cultures were analyzed to determine the percentages of CD14+ cells and mean fluorescence intensity.

EXAMPLE 13

Analysis of Hybrid Proteins Using CAM Assays

The choroallantoic membrane (CAM) assay described in e.g., Oh et al., Dev Biol 188:96–109 (1997), incorporated herein in its entirety, is a commonly used method to examine the in vivo effects of angiogenic factors. Using this assay, VEGF growth factors including both VEGF-A and VEGF-C have been shown to induce the development of blood vessels [Oh et al., Dev Biol 188:96–109 (1997)]. Thus, this method can be used to study the angiogenic properties of the hybrid proteins.

Briefly, on day 4 of development, a window is cut out into the eggshell of chick or quail eggs. The embryos are checked for normal development, the window in the eggshell is sealed with cellotape, and the eggs are incubated until day 13 of development. Approximately 3.3 µg of hybrid protein dissolved in 5 µl of distilled water is added to Thermanox coverslips (Nunc, Naperville, Ill.), which have been cut into disks with diameters of approximately 5 mm, and air dried. Disks without added protein are used as controls. The dried disks are then applied on the chorioallantoic membrane (CAM) of the eggs. After 3 days, the disks are removed and fixed in 3% glutaraldehyde and 2% formaldehyde and rinsed in 0.12 M sodium cacodylate buffer. The fixed specimens are photographed and embedded in Epon resin (Serva, Germany) for semi- (0.75 µm) and ultrathin (70 nm) sectioning. Both semi- and ultrathin sections are cut using an Ultracut S (Leika, Germany). Ultrathins sections are analyzed by an EM 10 (Zeiss, Germany). Specimens are then analyzed for evidence of growth of new capillaries, which would indicate that the hybrid protein being examined is capable of stimulating angiogenesis.

EXAMPLE 14

Analysis of Homo- or Hetero Dimerization of the VEGF-A/VEGF-C Hybrid Proteins Activation of tyrosine receptors is commonly mediated by ligand-induced receptor dimerization. Investigation of interactions between VEGF and VEGFR-2 indicate that receptor dimerization is accomplished via ligand dimerization in which both receptors bind parts of each of the two ligand proteins that constitute the homo- or heterodimer. Mutant VEGF proteins that can bind to VEGFR-2 but are unable to dimerize, cannot activate the receptor [Fuh et al., J Biol Chem 273:11197–11204 (1998)]. All of the VEGF family members are capable of homo- and/or heterodimerization. VEGF-A and VEGF-C fail to heterodimerize with each other. However, some of the VEGF-A/VEGF-C hybrid proteins may dimerize with each other or with one or both of the parent molecules. The hybrid proteins may also be capable of homodimerization. The following protocols are designed to identify dimerization capabilities of the hybrid proteins of the invention. A candidate hybrid protein is co-expressed with a different hybrid protein or one of the parent molecules in a cell line e.g., 293T or S9 cells. Extracts from these cells are prepared and used for immunoprecipitation using an antibody that recognizes only one of the two proteins being examined. The immunoprecipitated proteins are then subjected to SDS-PAGE and analyzed. If both proteins are detected on the gel, heterodimerization occurred between the two proteins being examined. On the other hand, if only the protein recognized by the antibody used during immunoprecipitation is detected, dimerization failed to occur between the two proteins. Since dimerization appears to be critical for receptor activation, hybrid proteins that bind receptor but fail to dimerize with self or with natural VEGF growth factors endogenously expressed by cells are expected to be inhibitors of endogenous vascular endothelial growth factor activity.

Heterodimers comprising a polypeptide of the invention with other polypeptides of the invention or with naturally occurring members of the VEGF family of growth factors may be generated essentially as described in Cao et al., *J. Biol. Chem.*, 271:3154–62 (1996). Briefly, a recombinantly produced hybrid polypeptide is mixed at an equimolar ratio with another recombinantly produced polypeptide of interest, such as a VEGF-A, VEGF-B, VEGF-C, VEGF-D, PlGF, PDGFα, PDGFβ, or c-fos induced growth factor polypeptide. (See, e.g., Collins et al., *Nature*, 316:748–750 (1985) (PDGF-β, GenBank Acc. No. X02811); Claesson-Welsh et al., *Proc. Natl. Acad. Sci. USA*, 86(13):4917–4921 (1989) (PDGF-α, GenBank Acc. No. M22734); Claesson-Welsh et al., *Mol. Cell. Biol.* 8:3476–3486 (1988) (PDGF-β, GenBank Acc. No. M21616); Olofsson et al., *Proc. Natl. Acad. Sci. (USA)*, 93:2576–2581 (1996) (VEGF-B, GenBank Acc. No. U48801); Maglione et al., *Proc. Natl. Acad. Sci. (USA)*, 88(20):9267–9271 (1996) (PlGF, GenBank Acc. No. X54936); Heldin et al., *Growth Factors*, 8:245–252 (1993); Folkman, *Nature Med.*, 1:27–31 (1995); Friesel et al., *FASEB J.*, 9:919–25 (1995); Mustonen et al., *J. Cell. Biol.*, 129:895–98 (1995); Orlandini, S., *Proc. Natl. Acad. Sci. USA*, 93(21):11675–11680 (1996); and others cited elsewhere herein. The mixed polypeptides are incubated in the presence of guanidine-HCl and DTT. The thiol groups are then protected with S-sulfonation, and the protein is dialyzed overnight, initially against urea/glutathione-SH, glutathione-S-S-glutathione, and subsequently against 20 mM Tris-HCl.

The heterodimers are screened to determine their binding affinity with respect to receptors of the VEGF/PDGF family (especially VEGFR-1, VEGFR-2, and VEGFR-3), and their ability to stimulate the receptors (e.g., assaying for dimer-stimulated receptor phosphorylation in cells expressing the receptor of interest on their surface). The binding assays may be competitive binding assays such as those described herein and in the art. In the initial binding assays, recombinantly produced proteins comprising the extracellular domains of receptors are employable, as described in preceding examples for VEGFR-2 and VEGFR-3. Heterodimers that bind and stimulate receptors are useful as recombinant growth factor polypeptides. Heterodimers that bind but do not stimulate receptors are useful as growth factor antagonists. Heterodimers that display agonistic or antagonistic activities in the screening assays are further screened using, e.g., endothelial cell migration assays, vascular permeability assays, and in vivo assays. It will also be apparent from the preceding examples that dimers comprising two VEGF-C polypeptides (i.e., dimers of identical VEGF-C polypeptides as well as dimers of different VEGF-C polypeptides) are advantageously screened for agonistic and antagonistic activities using the same assays.

EXAMPLE 15

Determination of Biological Half-life of the VEGF-A/VEGF-C Hybrid Proteins

Knowledge of the in vivo biological half-life of a compound is valuable for therapeutic applications. Although the biological half-life of the hybrid proteins has not been determined in vivo, preliminary results in vitro indicate that the VEGF-A/VEGF-C hybrid proteins described above exhibit different half-lives. Incubation of cell supernatants containing specific hybrid proteins at 4° C. for approximately two months reveal different protein stabilities for the various hybrid proteins. Examination of the in vivo biological half-life can be determined by injecting iodine-labeled hybrid protein into animals. Briefly, 50 µg of hybrid protein are iodinated using IODO-GEN (Pierce) according to the manufacturer's instructions to a specific radioactivity of approximately 2–10 µCi/µg protein. The iodinated protein is purified using PD-10 Sephadex (Pharmacia) according to the manufacturer's instructions. 12–16 week old mice (weighing 20–25 g) are anesthetized with sodium pentobarbital (1 mg/20 g body weight mouse) during the course of the experiment. 5–10 pmol of the radiolabeled protein diluted in 100 µl sterile saline are is injected into the tail vein over 30 seconds. At specific time points (1 min, 2 min, 4 min, 8 min, 15 min, 30 min, 60 min, and 120 min), 40–50 µl of blood is collected by periorbital bleeding or form the tail artery. 25 µl of the plasma fraction of each blood sample is then spotted onto Whatman filter paper, precipitated with 10% trichloroacetic acid (TCA), and rinsed with ethanol. The amount of radiolabeled protein present in the plasma fraction is determined by quantifying the radioactivity using a gamma counter. Polypeptides that display improved half-life relative to that of naturally occurring VEGFs are a preferred genus of polypeptides of the invention. Polypeptides that show 25%, 50%, 75% or 100% improvement of half-life to that of naturally occurring VEGFs are highly preferred.

EXAMPLE 16

Construction of Hybrid Molecules Using Other VEGF or PDGF Family Proteins

The procedure described in Example 1 can be extended to create hybrid molecules using any of the PDGF/VEGF growth factors. Members of the PDGF/VEGF family, which comprises at least VEGF-A (SEQ ID NOS: 1 and 2), PlGF (SEQ ID NOS: 114 and 115), VEGF-B (SEQ ID NOS: 116 and 117), VEGF-C (SEQ ID NOS: 21 and 22), VEGF-D (SEQ ID NOS: 118 and 119), VEGF-E (SEQ ID NOS: 120 and 121), and NZ2 VEGF (SEQ ID NOS: 122 and 123), D1701 VEGF (SEQ ID NOS: 150 and 151); NZ10 VEGF [described in SEQ ID NO: 11 of International Patent Application PCT/US99/25869, incorporated herein in its entirety]; PDGF-A (SEQ ID NO: 124 and 125), PDGF-B (SEQ ID NO: 126 and 127), and fallotein (SEQ ID NO: 148 & 149) share sufficient homology with each other within the receptor binding domain to permit designing oligonucleotides with unique cohesive ends as taught in Example 1 with respect to VEGF-A and VEFG-C. As shown by the successful results in Examples 1–3, oligonucleotides designed to provide double-stranded fragments having cohesive ends as short as 3–6 bases in length are sufficient to permit successful recombination into novel hybrid molecules (with very few unintended mutations).

While the presence of cohesive ends greatly facilitated ligation of fragments in a desired order and orientation, it will be appreciated that ligation of fragments can also be accomplished without cohesive ends. Blunt-end fragments also can be synthesized and annealed to generate hybrid proteins using the method described above. With a blunt-end strategy, the nucleotide sequences of the parent molecules do not need to be examined for the presence of nucleotide identity to enable the creation of cohesive ends. However, additional post-ligation screening may be required to identify hybrids that contain fragments in the desired order and orientation.

Using such guidelines, oligonucleotide pairs are designed and annealed as described in Example 1 to provide DNA fragments of the receptor for binding domain of two or more VEGF proteins. Combinatorial ligation of the various DNA fragments produces novel hybrid polypeptides that are screened for receptor binding and for biological properties such as ability to stimulate or inhibit endothelial cell growth and migration and modulate vascular permeability.

EXAMPLE 17

Generation of Hybrid Molecules Using PCR-driven DNA Shuffling

The following protocol provides an alternative "DNA shuffling" methodology for generating hybrid vascular endothelial growth factor-encoding polynucleotides and polypeptides. DNA shuffling procedures have been described in the literature for enzymes such as antibiotic-resistance-conferring proteins, and a few other protein families. [See, e.g., Chang et al., *Nature Biotechnology*, 17:793–797 (1999); Kikuchi et al., *Gene*, 236:159–167 (1999); Harayama et al., *TIBTECH*, 16:76–82 (1998); Crameri et al., *Nature*, 391:288–291 (1998); Patten et al., *Curr. Opin. Biotechnology*, 8:724–733 (1997); Zhang et al., *Proc. Natl. Acad. Sci. USA*, 94:4504–09 (1997); Stemmer, *Proc. Natl Acad. Sci. USA*, 91:10747–1074 (1994); and Stemmer, *Nature*, 370:389–391 (1994), all incorporated herein by reference in their entirety.]

Two or more cDNAs encoding vascular endothelial growth factor polypeptides are first cloned and amplified. In a preferred embodiment, only those portions of the cDNAs that encode minimum VEGF receptor-binding domains, and optionally small 5' and 3' additional sequences from the cDNAs, are amplified.

The purified and isolated cDNAs are digested into fragments of about 10–75 base pairs using restriction endonucleases and/or DNaseI, and the fragments of this desired size range are purified and isolated (e.g., by agarose gel electrophoresis, electroelution, and ethanol precipitation).

The purified and isolated fragments from the two or more VEGFs are mixed and subjected to a self-priming polymerase chain reaction to shuffle the fragments in order to form new hybrid molecules. Exemplary PCR protocols are set forth in Kikuchi et al. (1999) and Stemmer (1994). The annealing temperature in the PCR reactions is adjusted based on the level of sequence identity between the original cDNAs, to assure that annealing of heterologous sequences containing imperfect matches is possible. After conducting 25–50 cycles of PCR without primers, an aliquot from the PCR reaction is selected and used as template for a second round of PCR with primers based on 5' and 3' sequences of the original cDNAs. Preferably, the primers also include restriction endonuclease recognition sequences to facilitate cloning the resultant second-round PCR products into an expression vector.

The resultant clones are ligated into an expression vector and transformed or transected into host cells to express the novel hybrid VEGF polypeptides (if any) encoded thereby. The proteins are screened using receptor binding and/or activity assays as set forth in the preceding examples, to select those clones which encode polypeptides having desirable receptor agonist/antagonist profiles.

Index For Sequencing Listing

SEQ ID NOS: 1 & 2 are the nucleotide and amino acid sequences of VEGF-A

SEQ ID NOS: 3–11 are VEGF-A forward primers

SEQ ID NOS: 12–20 are VEGF-A reverse primers

SEQ ID NOS: 21 & 22 are the nucleotide and amino acid sequences of VEGF-C

SEQ ID NOS: 23–31 are VEGF-C forward primers

SEQ ID NOS: 32–40 are VEGF-C reverse primers

SEQ ID NO: 41 is the nucleotide sequence of pSecTagI

SEQ ID NOS: 42 & 43 are the nucleotide and amino acid sequences of clone 11-1. The VEGF receptor binding domain (derived from VEGF-A and VEGF-C) correspond to amino acids 1–102 of SEQ ID NO: 43.

SEQ ID NOS: 44 & 45 are the nucleotide and amino acid sequences of clone 11-16. (VEGF receptor binding domain=amino acids 1–104 of SEQ ID NO: 45).

SEQ ID NOS: 46 & 47 are the nucleotide and amino acid sequences of clone 22-1. (VEGF receptor binding domain=amino acids 1–103 of SEQ ID NO: 47)

SEQ ID NOS: 48 & 49 are the nucleotide and amino acid sequences of clone 22-16. (VEGF receptor binding domain=amino acids 1–105 of SEQ ID NO: 49)

SEQ ID NOS: 50–51 are the nucleotide and amino acid sequences of clone 12-1. (VEGF receptor binding domain=amino acids 1–102 of SEQ ID NO: 51)

SEQ ID NOS: 52–53 are the nucleotide and amino acid sequences of clone 12-2. (VEGF receptor binding domain=amino acids 1–102 of SEQ ID NO: 53)

SEQ ID NOS: 54–55 are the nucleotide and amino acid sequences of clone 12-3. (VEGF receptor binding domain=amino acids 1–102 of SEQ ID NO: 55)

SEQ ID NOS: 56–57 are the nucleotide and amino acid sequences of clone 12-4. (VEGF receptor binding domain=amino acids 1–102 of SEQ ID NO: 57)

SEQ ID NOS: 58–59 are the nucleotide and amino acid sequences of clone 12-5. (VEGF receptor binding domain=amino acids 1–102 of SEQ ID NO: 59)

SEQ ID NOS: 60–61 are the nucleotide and amino acid sequences of clone 12-6. (VEGF receptor binding domain=amino acids 1–102 of SEQ ID NO: 61)

SEQ ID NOS: 62–63 are the nucleotide and amino acid sequences of clone 12-7. (VEGF receptor binding domain=amino acids 1–102 of SEQ ID NO: 63)

SEQ ID NOS: 64–65 are the nucleotide and amino acid sequences of clone 12-8. (VEGF receptor binding domain=amino acids 1–102 of SEQ ID NO: 65)

SEQ ID NOS: 66–67 are the nucleotide and amino acid sequences of clone 12-9. (VEGF receptor binding domain=amino acids 1–104 of SEQ ID NO: 67)

SEQ ID NOS: 68–69 are the nucleotide and amino acid sequences of clone 12-10. (VEGF receptor binding domain=amino acids 1–104 of SEQ ID NO: 69)

SEQ ID NOS: 70–71 are the nucleotide and amino acid sequences of clone 12-11. (VEGF receptor binding domain=amino acids 1–104 of SEQ ID NO: 71)

SEQ ID NOS: 72–73 are the nucleotide and amino acid sequences of clone 12-12. (VEGF receptor binding domain=amino acids 1–104 of SEQ ID NO: 73)

SEQ ID NOS: 74–75 are the nucleotide and amino acid sequences of clone 12-13. (VEGF receptor binding domain=amino acids 1–104 of SEQ ID NO: 75)

SEQ ID NOS: 76–77 are the nucleotide and amino acid sequences of clone 12-14. (VEGF receptor binding domain=amino acids 1–104 of SEQ ID NO: 77)

SEQ ID NOS: 78–79 are the nucleotide and amino acid sequences of clone 12-15. (VEGF receptor binding domain=amino acids 1–104 of SEQ ID NO: 79)

SEQ ID NOS: 80–81 are the nucleotide and amino acid sequences of clone 12-16. (VEGF receptor binding domain=amino acids 1–54 of SEQ ID NO: 81)

SEQ ID NOS: 82–83 are the nucleotide and amino acid sequences of clone 31-1 (VEGF receptor binding domain=amino acids 1–103 of SEQ ID NO: 83)

SEQ ID NOS: 84–85 are the nucleotide and amino acid sequences of clone 31-2 (VEGF receptor binding domain=amino acids 1–103 of SEQ ID NO: 85)

SEQ ID NOS: 86–87 are the nucleotide and amino acid sequences of clone 31-3 (VEGF receptor binding domain=amino acids 1–103 of SEQ ID NO: 87)

SEQ ID NOS: 88–89 are the nucleotide and amino acid sequences of clone 31-4 (VEGF receptor binding domain=amino acids 1–103 of SEQ ID NO: 89)

SEQ ID NOS: 90–91 are the nucleotide and amino acid sequences of clone 31-5 (VEGF receptor binding domain=amino acids 1–103 of SEQ ID NO: 91)

SEQ ID NOS: 92–93 are the nucleotide and amino acid sequences of clone 31-6 (VEGF receptor binding domain=amino acids 1–103 of SEQ ID NO: 93)

SEQ ID NOS: 94–95 are the nucleotide and amino acid sequences of clone 31-7 (VEGF receptor binding domain=amino acids 1–103 of SEQ ID NO: 95)

SEQ ID NOS: 96–97 are the nucleotide and amino acid sequences of clone 31-8 (VEGF receptor binding domain=amino acids 1–103 of SEQ ID NO: 97)

SEQ ID NOS: 98–99 are the nucleotide and amino acid sequences of clone 31-9 (VEGF receptor binding domain=amino acids 1–105 of SEQ ID NO: 99)

SEQ ID NOS: 100–101 are the nucleotide and amino acid sequences of clone 31-10 (VEGF receptor binding domain=amino acids 1–105 of SEQ ID NO: 101)

SEQ ID NOS: 102–103 are the nucleotide and amino acid sequences of clone 31-11 (VEGF receptor binding domain=amino acids 1–105 of SEQ ID NO: 103)

SEQ ID NOS: 104–105 are the nucleotide and amino acid sequences of clone 31-12 (VEGF receptor binding domain=amino acids 1–105 of SEQ ID NO: 105)

SEQ ID NOS: 106–107 are the nucleotide and amino acid sequences of clone 31-13 (VEGF receptor binding domain=amino acids 1–105 of SEQ ID NO: 107)

SEQ ID NOS: 108–109 are the nucleotide and amino acid sequences of clone 31-14 (VEGF receptor binding domain=amino acids 1–105 of SEQ ID NO: 109)

SEQ ID NOS: 110–111 are the nucleotide and amino acid sequences of clone 31-15 (VEGF receptor binding domain=amino acids 1–105 of SEQ ID NO: 111)

SEQ ID NOS: 112–113 are the nucleotide and amino acid sequences of clone 31-16 (VEGF receptor binding domain=amino acids 1–105 of SEQ ID NO: 113)

SEQ ID NOS: 114 & 115 are the nucleotide and amino acid sequences of PlGF

SEQ ID NOS: 116 & 117 are the nucleotide and amino acid sequences of VEGF-B

SEQ ID NOS: 118 & 119 are the nucleotide and amino acid sequences of VEGF-D

SEQ ID NOS: 120 & 121 are the nucleotide and amino acid sequences of VEGF-E

SEQ ID NOS: 122 & 123 are the nucleotide and amino acid sequences of NZ2 VEGF

SEQ ID NOS: 124 & 125 are the nucleotide and amino acid sequences of PDGF-A

SEQ ID NOS: 126 & 127 are the nucleotide and amino acid sequences of PDGF-B

SEQ ID NOS: 128–136 are the amino acid sequences of fragments A1–A9

SEQ ID NOS: 137–145 are the amino acid sequences of fragments C1–C9

SEQ ID NOS: 146 & 147 are the nucleotide and amino acid sequences of the 232 amino acid isoform of VEGF-A SEQ ID NOS: 148 & 149 are the nucleotide and amino acid sequences of fallotein SEQ ID NOS: 150 & 151 are the nucleotide and amino acid sequences D1701 VEGF SEQ ID NOS: 152 & 153 are the nucleotide and amino acid sequences of clone 14-9 (VEGF receptor binding domain=amino acids 1–104 of SEQ ID NO: 153)

SEQ ID NOS: 154 & 155 are the nucleotide and amino acid sequences of clone 23-10 (VEGF receptor binding domain=amino acids 1–105 of SEQ ID NO: 155)

SEQ ID NOS: 156 & 157 are the nucleotide and amino acid sequences of clone 32-14 (VEGF receptor binding domain=amino acids 1–105 of SEQ ID NO: 157)

SEQ ID NOS: 158 & 159 are the nucleotide and amino acid sequences of clone 52-15 (VEGF receptor binding domain=amino acids 1–105 of SEQ ID NO: 159)

SEQ ID NOS: 160 & 161 are the nucleotide and amino acid sequences of clone 53-3 (VEGF receptor binding domain=amino acids 1–103 of SEQ ID NO: 161)

SEQ ID NOS: 162 & 163 are the nucleotide and amino acid sequences of clone 82-7 (VEGF receptor binding domain=amino acids 1–102 of SEQ ID NO: 163)

SEQ ID NOS: 164 & 165 are the nucleotide and amino acid sequences of clone 82-9 (VEGF receptor binding domain=amino acids 1–104 of SEQ ID NO: 165)

SEQ ID NOS: 166 & 167 are the nucleotide and amino acid sequences of clone 82-11 (VEGF receptor binding domain=amino acids 1–104 of SEQ ID NO: 167)

SEQ ID NOS: 168 & 169 are the nucleotide and amino acid sequences of clone 82-13 (VEGF receptor binding domain=amino acids 1–104 of SEQ ID NO: 169)

SEQ ID NOS: 170 & 171 are the nucleotide and amino acid sequences of clone 83-15 (VEGF receptor binding domain=amino acids 1–104 of SEQ ID NO: 171)

SEQ ID NOS: 172 & 173 are the nucleotide and amino acid sequences of clone 84-9 (VEGF receptor binding domain=amino acids 1–104 of SEQ ID NO: 173)

SEQ ID NOS: 174 & 175 are the nucleotide and amino acid sequences of clone 84-11 (VEGF receptor binding domain=amino acids 1–104 of SEQ ID NO: 175)

SEQ ID NOS: 176–1199 are indexed above in Example 1 in Table 2.5.

SEQ ID NO 1200 is the sequence formula P-[PS]-C-V-X(3)-R-C-[GSTA]-G-C-C.

SEQ ID NO 1201 is the sequence formula C-X(22–24)-P-[PSR]-C-V-X(3)-R-C-[GSTA]-G-C-C-X(6)-C-X(32–41)-C.

SEQ ID NO 1202 is the sequence formula C-X(18–28)-P-X-C-X(4)-R-C-N-G-C(1–2)-X(6–12)-C-X(30–46)-C.

SEQ ID NO 1203 is the sequence formula C-X(22–24)-P-[PSR]-C-V-X(3)-R-C-X-G-C-C-X(6)-C-X(32–41)-C.

SEQ ID NO 1204 is the sequence formula TNTFxxxP.

SEQ ID NO 1205 is the sequence formula EFGVATNT-FFKPPCVSVYRCG.

SEQ ID NO: 1206 is the sequence TNTFFKPP.

SEQ ID NO: 1207 is the sequence formula TNTFFKP-PCVxxxR.

SEQ ID NO: 1208 is the sequence formula TNTFFKP-PCVxxxRCGGCC.

SEQ ID NO: 1209 is a sequence of a VEGF region involved in VEGFR-1 binding.

SEQ ID NO: 1210 is a sequence of a VEGF-C region involved in VEGFR-3 binding.

SEQ ID NO: 1211 is the sequence formula IEYIxxxS.

SEQ ID NO: 1212 is the sequence formula $TNTFX_nP$.

All publications and patents cited herein that are relevant to the description of the present invention are hereby incorporated by reference in their entirety.

While the present invention has been described in terms of specific embodiments, it is understood that variations and modifications will occur to those in the art. Accordingly, only such limitations as appear in the appended claims should be placed on the invention.

What is claimed is:

1. A polypeptide comprising an amino acid sequence that is at least 95% identical to a chimeric vascular endothelial growth factor (VEGF) amino acid sequence of the formula:

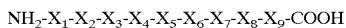

$$NH_2\text{-}X_1\text{-}X_2\text{-}X_3\text{-}X_4\text{-}X_5\text{-}X_6\text{-}X_7\text{-}X_8\text{-}X_9\text{-}COOH$$

wherein $X_1$ is an amino acid sequence selected from the group consisting of amino acids 3–11 of SEQ ID NO: 128 and amino acids 3–11 of SEQ ID NO: 137;

wherein $X_2$ is an amino acid sequence selected from the group consisting of SEQ ID NOs: 129 and 138;

wherein $X_3$ is an amino acid sequence selected from the group consisting of SEQ ID NOs: 130 and 139;

wherein $X_4$ is an amino acid sequence selected from the group consisting of SEQ ID NOs: 131 and 140;

wherein $X_5$ is an amino acid sequence selected from the group consisting of SEQ ID NOs: 132 and 141;

wherein $X_6$ is an amino acid sequence selected from the group consisting of SEQ ID NOs: 133 and 142;

wherein $X_7$ is an amino acid sequence selected from the group consisting of SEQ ID NOs: 134 and 143;

wherein $X_8$ is an amino acid sequence selected from the group consisting of SEQ ID NOs: 135 and 144;

wherein $X_9$ is an amino acid sequence selected from the group consisting of SEQ ID NOs: 136 and 145;

wherein the chimeric VEGF binds to at least one receptor selected from the group consisting of human VEGFR-1, human VEGFR-2, and human VEGFR-3; and wherein the polypeptide binds to at least one receptor selected from the group consisting of human VEGFR-1, human VEGFR-2, and human VEGFR-3.

2. A polypeptide according to claim 1, wherein the polypeptide further includes a signal peptide amino acid sequence connected to the amino acid sequence of the formula $NH_2$-$X_1$-$X_2$-$X_3$-$X_4$-$X_5$-$X_6$-$X_7$-$X_8$-$X_9$-COOH.

3. A polypeptide according to claim 1, wherein the polypeptide further includes an amino-terminal methionine residue.

4. A polypeptide according to claim 1, wherein the polypeptide further includes a tag amino acid sequence connected to the amino acid sequence of the formula $NH_2$-$X_1$-$X_2$-$X_3$-$X_4$-$X_5$-$X_6$-$X_7$-$X_8$-$X_9$-COOH.

5. A polypeptide according to claim 1, wherein the polypeptide further includes one or more amino acid sequences selected from the group consisting of a prepro-VEGF-C signal peptide, a prepro-VEGF-C amino-terminal propeptide, and a prepro-VEGF-C carboxy-terminal propeptide.

6. A polypeptide comprising an amino acid sequence of the formula $X_N$-V/PHD-$X_C$, wherein $X_N$ is selected from the group consisting of amino acids 1–34 of SEQ ID NO: 2, amino acids 1–111 of SEQ ID NO: 22, amino acids 1–34 of SEQ ID NO: 147, or fragments thereof;

wherein V/PHD is a polypeptide according to claim 1;

wherein $X_C$ is selected from the group consisting of amino acids 136–191 of SEQ ID NO: 2, amino acids 217–419 of SEQ ID NO: 22, amino acids 136–232 of SEQ ID NO: 147, and fragments thereof.

7. A composition comprising a polypeptide according to claim 1 in a pharmaceutically acceptable carrier.

8. A polypeptide according to claim 1 that binds to human VEGFR-1 and VEGFR-3.

9. A polypeptide according to claim 1 that binds to human VEGFR-1, VEGFR-2, and VEGFR-3.

10. The polypeptide of claim 1, wherein the amino acid sequence of the polypeptide further comprises a sequence selected from the group consisting of amino acids 136–191 of SEQ ID NO: 2, amino acids 217–419 of SEQ ID NO: 22, amino acids 136–232 of SEQ ID NO: 147, and fragments thereof.

11. The polypeptide of claim 1, further including additional flanking sequence from VEGF-A (SEQ ID NO: 2) or VEGF-C (SEQ ID NO: 22).

12. A polypeptide according to claim 1, wherein $X_4$ is SEQ ID NO: 140, and wherein the polypeptide binds to VEGFR-3.

13. A polypeptide according to claim 12, wherein $X_8$ is SEQ ID NO: 144.

14. A polypeptide according to claim 1, wherein $X_2$ is SEQ ID NO: 129, and wherein the polypeptide binds to VEGFR-1.

15. A polypeptide according to claim 14, wherein $X_7$ is SEQ ID NO: 134.

16. A polypeptide according to claim 14, wherein $X_4$ is SEQ ID NO: 140, and wherein the polypeptide binds to VEGFR-3.

17. A polypeptide comprising an amino acid sequence selected from the group consisting of amino acids 1–102 as set forth in SEQ ID NO: 51; amino acids 1–102 as set forth in SEQ ID NO: 59; amino acids 1–102 as set forth in SEQ ID NO: 63; amino acids 1–104 as set forth in SEQ ID NO: 67; amino acids 1–104 as set forth in SEQ ID NO: 71; amino acids 1–104 as set forth in SEQ ID NO: 75; amino acids 1–104 as set forth in SEQ ID NO: 77; amino acids 1–104 as set forth in SEQ ID NO: 153; amino acids 1–105 as set forth in SEQ ID NO: 155; amino acids 1–105 as set forth in SEQ ID NO: 157; amino acids 1–105 as set forth in SEQ ID NO: 159; amino acids 1–103 as set forth in SEQ ID NO: 161; amino acids 1–102 as set forth in SEQ ID NO: 163; amino acids 1–104 as set forth in SEQ ID NO: 165; amino acids 1–104 as set forth in SEQ ID NO: 167; amino acids 1–104 as set forth in SEQ ID NO: 169; amino acids 1–104 as set forth in SEQ ID NO: 171; amino acids 1–104 as set forth in SEQ ID NO: 173; and amino acids 1–104 as set forth in SEQ ID NO: 175.

18. The polypeptide of claim 17, further including additional flanking sequence from VEGF-A (SEQ ID NO: 2) or VEGF-C (SEQ ID NO: 22).

19. A polypeptide comprising an amino acid sequence at least 95% identical to the amino acid sequence of SEQ ID NO: 175, wherein said polypeptide binds at least one human receptor selected from the group consisting of VEGFR-1, VEGFR-2, and VEGFR-3.

20. The polypeptide of claim 19, herein the amino acid sequence of the polypeptide further comprises a sequence selected from the group consisting of amino acids 136–191 of SEQ ID NO: 2, amino acids 217–419 of SEQ ID NO: 22, amino acids 136–232 of SEQ ID NO: 147, and fragments thereof.

21. A polypeptide comprising an amino acid sequence of the formula $X_N$-V/PHD-$X_C$, wherein $X_N$ is selected from the group consisting of amino acids 1–34 of SEQ ID NO: 2, amino acids 1–111 of SEQ ID NO: 22, amino acids 1–34 of SEQ ID NO: 147, and fragments thereof.

wherein V/PHD is a polypeptide according to claim 19;

wherein $X_C$ is selected from the group consisting of amino acids 136–191 of SEQ ID NO: 2, amino acids 217–419 or SEQ ID NO: 22, amino acids 136–232 of SEQ ID NO: 147, and fragments thereof.

22. The polypeptide of claim 19, further including additional flanking sequence from VEGF-A (SEQ ID NO: 2) or VEGF-C (SEQ ID NO: 22).

23. A polypeptide according to claim 19 that binds to human VEGFR-1, VEGFR-2, and VEGFR-3.

24. The polypeptide of claim 23, wherein the amino acid sequence of the polypeptide further comprises a sequence selected from the group consisting of amino acids 136–191 of SEQ ID NO: 2, amino acids 217–419 of SEQ ID NO: 22, amino acids 136–232 of SEQ ID NO: 147, and fragments thereof.

25. The polypeptide of claim 23, further including additional flanking sequence from VEGF-A (SEQ ID NO: 2) or VEGF-C (SEQ ID NO: 22).

26. A polypeptide that binds human vascular endothelial growth factor receptors VEGFR-1, VEGFR-2, and VEGFR-3, wherein the polypeptide comprises an amino acid sequence selected from the group consisting of:

amino acids 1–102 of SEQ ID NO: 51; amino acids 1–102 of SEQ ID NO: 63; amino acids 1–104 of SEQ ID NO: 71; amino acids 1–104 of SEQ ID NO: 153; amino acids 1–103 of SEQ ID NO: 161; amino acids 1–102 of SEQ ID NO: 163; amino acids 1–104 of SEQ ID NO: 165; amino acids 1–104 of SEQ ID NO: 167; amino acids 1–104 of SEQ ID NO: 173; and amino acids 1–104 of SEQ ID NO: 175.

27. The polypeptide of claim 26, further including additional flanking sequence from VEGF-A (SEQ ID NO: 2) or VEGF-C (SEQ ID NO: 22).

28. A polypeptide that binds human vascular endothelial growth factor receptors VEGFR-1, VEGFR-2, and VEGFR-3, wherein the polypeptide comprises an amino acid sequence selected from the group consisting of amino acids 1–102 of SEQ ID NO: 63; amino acids 1–104 of SEQ ID NO: 71; amino acids 1–104 of SEQ ID NO: 167; and amino acids 1–104 of SEQ ID NO: 175.

29. The polypeptide of claim 28, further including additional flanking sequence from VEGF-A (SEQ ID NO: 2) or VEGF-C (SEQ ID NO: 22).

30. A polypeptide comprising an amino acid sequence that is at least 95% identical to a chimeric vascular endothelial growth factor (VEGF) amino acid sequence encoded by a polynucleotide comprising a nucleotide sequence of the formula:

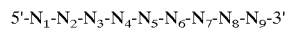

$$5'\text{-}N_1\text{-}N_2\text{-}N_3\text{-}N_4\text{-}N_5\text{-}N_6\text{-}N_7\text{-}N_8\text{-}N_9\text{-}3'$$

where-in $N_1$ is a nucleotide sequence selected from the group consisting of nucleotides 7–34 of SEQ ID NO: 3 and nucleotides 7–34 of SEQ ID NO: 23;

wherein $N_2$ is a nucleotide sequence selected from the group consisting of nucleotides 1–32 of SEQ ID NO: 4 and nucleotides 1–35 of SEQ ID NO: 24;

wherein $N_3$ is a nucleotide sequence selected from the group consisting of nucleotides 1–31 of SEQ ID NO: 5 and nucleotides 1–31 of SEQ ID NO: 25;

wherein $N_4$ is a nucleotide sequence selected from the group consisting of nucleotides 10–33 of SEQ ID NO: band nucleotides 10–33 of SEQ ID NO: 26;

wherein $N_5$ is a nucleotide sequence selected from the group consisting of nucleotides 1–37 of SEQ ID NO: 7 and nucleotides 1–37 of SEQ ID NO: 27;

wherein $N_6$ is a nucleotide sequence selected from the group consisting of nucleotides 3–28 of SEQ ID NO: 8 and nucleotides 3–28 of SEQ ID NO: 28;

wherein $N_7$ is a nucleotide sequence selected from the group consisting of nucleotides 1–46 of SEQ ID NO: 9 and nucleotides 1–46 of SEQ ID NO: 29;

wherein $N_8$ is a nucleotide sequence selected from the group consisting of nucleotides 1–43 of SEQ ID NO: 10 and nucleotides 1–49 of SEQ ID NO: 30;

wherein $N_9$ is a nucleotide sequence selected from the group consisting of nucleotides 1–39 of SEQ ID NO: 11 and nucleotides 1–39 of SEQ ID NO: 31;

wherein $5'\text{-}N_1\text{-}N_2\text{-}N_3\text{-}N_4\text{-}N_5\text{-}N_6\text{-}N_7\text{-}N_8\text{-}N_9\text{-}3'$ is nut identical to nucleotides 156 to 461 of SEQ ID NO: 1 or nucleotides 685 to 999 of SEQ ID NO: 21;

wherein the chimeric VEGF binds to at least one receptor selected from the group consisting of human VEGFR-1, human VEGFR-2, and human VEGFR-3; and wherein the polypeptide binds to at least one receptor selected from the group consisting of human VEGFR-1, human VEGFR-2, and human VEGFR-3.

31. A polypeptide according to 30, wherein the polypeptide further includes a signal peptide amino acid sequence.

32. A polypeptide according to claim 30, wherein the polypeptide further includes an amino-terminal methionine residue.

33. A polypeptide according to claim 30, wherein the polypeptide further includes a tag amino acid sequence.

34. A polypeptide according to claim 30, wherein the polypeptide further includes one or more amino acid sequences selected from the group consisting of a prepro-VEGF-C signal peptide, a prepro-VEGF-C amino-terminal propeptide, and a prepro-VEGF-C carboxy-terminal propeptide.

35. A composition comprising a polypeptide according to claim 30 in a pharmaceutically acceptable carrier.

36. The polypeptide of claim 30, further including additional flanking sequence from VEGF-A (SEQ ID NO: 2) or VEGF-C (SEQ ID NO: 22).

37. A polypeptide according to claim 30, wherein $N_4$ is nucleotides 10–33 of SEQ ID NO: 26, and wherein the polypeptide binds to VEGFR-3.

38. A polypeptide according to claim 37, wherein $N_8$ is nucleotides 1–49 of SEQ ID NO: 30.

39. A polypeptide according to claim 30, wherein $N_2$ is nucleotides 1–32 of SEQ ID NO: 4, and wherein the polypeptide binds to VEGFR-1.

40. A polypeptide according to claim 39, wherein $N_7$ is nucleotides 1–46 of SEQ ID NO: 9.

41. A polypeptide according to claim 39, wherein $N_4$ is nucleotides 10–33 of SEQ ID NO: 26, and wherein the polypeptide binds to VEGFR-3.

42. A polypeptide comprising an amino acid sequence of the formula $X_N$-V/PHD-$X_C$, wherein $X_N$ is selected from the group consisting of amino acids 1–34 of SEQ ID NO: 2, amino acids 1–111 of SEQ ID NO: 22, amino acids 1–34 of SEQ ID NO: 147, and fragments thereof;

wherein V/PHD is a polypeptide according to claim 30;

wherein $X_C$ is selected from the group consisting of amino acids 136–191 of SEQ ID NO: 2, amino acids 217–419 of SEQ ID NO: 22, amino acids 136–232 of SEQ ID NO: 147, and fragments thereof.

43. A polypeptide comprising an amino acid sequence encoded by a polynucleotide comprising a nucleotide sequence that is at least 95% identical to nucleotides 8–322 of SEQ ID NO: 174, wherein the polypeptide binds to at least one receptor selected from the group consisting of human VEGFR-1, human VEGFR-2, and human VEGFR-3.

44. The polypeptide of claim 43, further including additional flanking sequence from VEGF-A (SEQ ID NO: 2) or VEGF-C (SEQ ID NO: 22).

45. A polypeptide comprising an amino acid sequence that is encoded by a polynucleotide comprising a nucleotide sequence at least 95% identical to a nucleotide sequence of the formula:

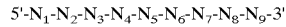

wherein $N_1$ is a nucleotide sequence selected from the group consisting of nucleotides 7–34 of SEQ ID NO: 3 and nucleotides 7–34 of SEQ ID NO: 23;

wherein $N_2$ is a nucleotide sequence selected from the group consisting of nucleotides 1–32 of SEQ ID NO: 4 and nucleotides 1–35 of SEQ ID NO: 24;

wherein $N_3$ is a nucleotide sequence selected from the group consisting of nucleotides 1–31 of SEQ ID NO: 5 and nucleotides 1–31 of SEQ ID NO: 25;

wherein $N_4$ is a nucleotide sequence selected from the group consisting of nucleotides 10–33 of SEQ ID NO: 6 and nucleotides 10–33 of SEQ ID NO: 26;

wherein $N_5$ is a nucleotide sequence selected from the group consisting of nucleotides 1–37 of SEQ ID NO: 7 and nucleotides 1–37 of SEQ ID NO: 27;

wherein $N_6$ is a nucleotide sequence selected from the group consisting of nucleotides 3–28 of SEQ ID NO: 8 and nucleotides 3–28 of SEQ ID NO: 28;

wherein $N_7$ is a nucleotide sequence selected from the group consisting of nucleotides 1–46 of SEQ ID NO: 9 and nucleotides 1–46 of SEQ ID NO: 29;

wherein $N_8$ is a nucleotide sequence selected from the group consisting of nucleotides 1–43 of SEQ ID NO: 10 and nucleotides 1–49 of SEQ ID NO: 30;

wherein $N_3$ is a nucleotide sequence selected from the group consisting of nucleotides 1–39 of SEQ ID NO: 11 and nucleotides 1–39 of SEQ ID NO: 31;

wherein 5'-$N_1$-$N_2$-$N_3$-$N_4$-$N_5$-$N_6$-$N_7$-$N_8$-$N_9$-3' is not identical to nucleotides 156 to 461 of SEQ ID NO: 1 or nucleotides 685 to 999 of SEQ ID NO: 21; and wherein the polypeptide binds to at least one receptor selected from the group consisting of human VEGFR-1, human VEGFR-2, and human VEGFR-3.

46. The polypeptide of claim 45, further including additional flanking sequence from VEGF-A (SEQ ID NO: 22).

47. A polypeptide comprising an amino acid sequence at least 95% identical to an amino acid sequence selected from the group consisting of: amino acids 1–102 as set forth in SEQ ID NO: 51; amino acids 1–102 as set forth in SEQ ID NO: 59; amino acids 1–102 as set forth in SEQ ID NO: 63; amino acids 1–104 as set forth in SEQ ID NO: 67; amino acids 1–104 as set forth in SEQ ID NO: 71; amino acids 1–104 as set forth in SEQ ID NO: 75; amino acids 1–104 as set forth in SEQ ID NO: 77; amino acids 1–104 as set forth in SEQ ID NO: 153; amino acids 1–105 as set forth in SEQ ID NO: 155; amino acids 1–105 as set forth in SEQ ID NO: 157; amino acids 1–105 as set forth in SEQ ID NO: 159; amino acids 1–103 as set forth in SEQ ID NO: 161; amino acids 1–102 as set forth in SEQ ID NO: 163; amino acids 1–104 as set forth in SEQ ID NO: 165; amino acids 1–104 as set forth in SEQ ID NO: 167; amino acids 1–104 as set forth in SEQ ID NO: 169; amino acids 1–104 as set forth in SEQ ID NO: 171; amino acids 1–104 as set forth in SEQ ID NO: 173; and amino acids 1–104 as set forth in SEQ ID NO: 175, wherein the polypeptide binds to at least one human vascular endothelial growth factor receptor selected from VEGFR-1, VEGFR-2, and VEGFR-3.

48. The polypeptide of claim 47, further including additional flanking sequence from VEGF-A (SEQ ID NO: 2) or VEGF-C (SEQ ID NO: 22).

49. A polypeptide comprising an amino acid sequence at least 95% identical to an amino acid sequence selected from tho group consisting of:

amino acids 1–102 of SEQ ID NO: 51; amino acids 1–102 of SEQ ID NO: 63; amino acids 1–104 of SEQ ID NO: 71; amino acids 1–104 of SEQ ID NO: 153; amino acids 1–103 of SEQ ID NO: 161; amino acids 1–102 of SEQ ID NO: 163; amino acids 1–104 of SEQ ID NO: 165; amino acids 1–104 of SEQ ID NO: 167; amino acids 1–104 of SEQ ID NO: 173; and amino acids 1–104 of SEQ ID NO: 175, wherein the polypeptide binds human vascular endothelial growth factor receptors VEGFR-1, VEGFR-2, and VEGFR-3.

50. The polypeptide of claim 49, further including additional flanking sequence from VEGF-A (SEQ ID NO: 2) or VEGF-C (SEQ ID NO: 22).

* * * * *

UNITED STATES PATENT AND TRADEMARK OFFICE
CERTIFICATE OF CORRECTION

PATENT NO. : 6,965,010 B2  Page 1 of 1
APPLICATION NO. : 09/795006
DATED : November 15, 2005
INVENTOR(S) : Kari Alitalo et al.

It is certified that error appears in the above-identified patent and that said Letters Patent is hereby corrected as shown below:

In Claim 20, column 269, line 36, please delete "herein" and insert --wherein--
In Claim 21, column 269, line 46, please delete "thereof." and insert --thereof;--
In Claim 30, column 270, line 31, please delete "where-in" and insert --wherein--
In Claim 30, column 270, line 41-42, please delete "SEQ ID NO: band" and insert --SEQ ID NO: 6 and--
In Claim 30, column 270, line 59, please delete "nut" and insert --not--
In Claim 46, column 272, line 23, please delete "VEGF-A (SEQ ID NO: 22)" and insert --VEGF-A (SEQ ID NO: 2 or VEGF-C (SEQ ID NO: 22)--
In Claim 49, column 272, line 51, please delete "tho" and insert --the--

Signed and Sealed this

Twentieth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 6,965,010 B2                                               Page 1 of 1
APPLICATION NO. : 09/795006
DATED : November 15, 2005
INVENTOR(S) : Kari Alitalo et al.

It is certified that error appears in the above-identified patent and that said Letters Patent is hereby corrected as shown below:

In the Sequence Listing:

At Column 103-268, please delete the sequence listing (SEQ ID NOs: 1-175) and insert the following paragraph:

--The patent contains a lengthy 'Sequence Listing' section. A copy of the 'Sequence Listing' is available in electronic form from the USPTO web site (http://seqdata.uspto.gov/?pageRequest=docDetail&DocID=US0695010B2). An electronic copy of the 'Sequence Listing' will also be available from the USPTO upon request and payment of the fee set forth in 37 CFR 1.19(b)(3).--

Signed and Sealed this

Eleventh Day of January, 2011

David J. Kappos
*Director of the United States Patent and Trademark Office*

SEQUENCE LISTING

<160> NUMBER OF SEQ ID NOS: 175

<210> SEQ ID NO 1
<211> LENGTH: 990
<212> TYPE: DNA
<213> ORGANISM: Homo sapiens
<220> FEATURE:
<221> NAME/KEY: CDS
<222> LOCATION: (57)..(629)

<400> SEQUENCE: 1

```
cagtgtgctg gcggcccggc gcgagccggc ccggccccgg tcgggcctcc gaaacc atg      59
                                                                Met
                                                                  1 aac ttt ctg ctg tct tgg gtg cat tgg agc ctc gcc ttg ctg ctc tac       107
Asn Phe Leu Leu Ser Trp Val His Trp Ser Leu Ala Leu Leu Leu Tyr
              5                  10                  15 ctc cac cat gcc aag tgg tcc cag gct gca ccc atg gca gaa gga gga       155
Leu His His Ala Lys Trp Ser Gln Ala Ala Pro Met Ala Glu Gly Gly
         20                  25                  30 ggg cag aat cat cac gaa gtg gtg aag ttc atg gat gtc tat cag cgc       203
Gly Gln Asn His His Glu Val Val Lys Phe Met Asp Val Tyr Gln Arg
 35                  40                  45 agc tac tgc cat cca atc gag acc ctg gtg gac atc ttc cag gag tac       251
Ser Tyr Cys His Pro Ile Glu Thr Leu Val Asp Ile Phe Gln Glu Tyr
 50                  55                  60                  65 cct gat gag atc gag tac atc ttc aag cca tcc tgt gtg ccc ctg atg       299
Pro Asp Glu Ile Glu Tyr Ile Phe Lys Pro Ser Cys Val Pro Leu Met
                 70                  75                  80 cga tgc ggg ggc tgc tgc aat gac gag ggc ctg gag tgt gtg ccc act       347
Arg Cys Gly Gly Cys Cys Asn Asp Glu Gly Leu Glu Cys Val Pro Thr
             85                  90                  95 gag gag tcc aac atc acc atg cag att atg cgg atc aaa cct cac caa       395
Glu Glu Ser Asn Ile Thr Met Gln Ile Met Arg Ile Lys Pro His Gln
        100                 105                 110 ggc cag cac ata gga gag atg agc ttc cta cag cac aac aaa tgt gaa       443
Gly Gln His Ile Gly Glu Met Ser Phe Leu Gln His Asn Lys Cys Glu
    115                 120                 125 tgc aga cca aag aaa gat aga gca aga caa gaa aat ccc tgt ggg cct       491
Cys Arg Pro Lys Lys Asp Arg Ala Arg Gln Glu Asn Pro Cys Gly Pro
130                 135                 140                 145 tgc tca gag cgg aga aag cat ttg ttt gta caa gat ccg cag acg tgt       539
Cys Ser Glu Arg Arg Lys His Leu Phe Val Gln Asp Pro Gln Thr Cys
                150                 155                 160 aaa tgt tcc tgc aaa aac aca gac tcg cgt tgc aag gcg agg cag ctt       587
Lys Cys Ser Cys Lys Asn Thr Asp Ser Arg Cys Lys Ala Arg Gln Leu
            165                 170                 175 gag tta aac gaa cgt act tgc aga tgt gac aag ccg agg cgg                629
Glu Leu Asn Glu Arg Thr Cys Arg Cys Asp Lys Pro Arg Arg
        180                 185                 190 tgagccgggc aggaggaagg agcctccctc agggtttcgg gaaccagatc tctcaccagg      689
aaagactgat acagaacgat cgatacagaa accacgctgc cgccaccaca ccatcaccat      749
cgacagaaca gtccttaatc cagaaacctg aaatgaagga agaggagact ctgcgcagag      809
cactttgggt ccggagggcg agactccggc ggaagcattc ccggcgggt gacccagcac       869 ggtccctctt ggaattggat tcgccatttt attttcttg ctgctaaatc accgagcccg       929
gaagattaga gagttttatt tctgggattc ctgtagacac accgcggccg ccagcacact      989
```

-continued g                                                                                                              990

<210> SEQ ID NO 2
<211> LENGTH: 191
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
     50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 3
gatcctgggc agaatcatca cgaagtggtg aaat                                              34

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 4
tcatggatgt ctatcagcgc agctactgcc at                                                32

<210> SEQ ID NO 5
<211> LENGTH: 42
<212> TYPE: DNA
<213> ORGANISM: Artificial Sequence

```
-continued

<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 5
ccgatcgaga cactggtgga catcttccag gaatagaaga gc                          42

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 6
cgctcttcga ataccctgat gagatcgagt aca                                    33

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 7
tcttcaagcc atcctgcgtg ccctgatga gatgtggc                                38

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 8
ccgggttgct gcaatgacga agggctgg                                          28

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 9
agtgcgttcc caccgaggag tccaacatca ccatgcagat tatgag                      46

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 10
aattaaacct caccaagggc agcacatcgg agagatgagc ttt                         43
```

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 11
ctccagcata acaaatgtga atgtagacca aagaaagatt gagtcttcgc          50

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 12
ccacttcgtg atgattctgc ccag                                      24

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 13
tcggatggca gtagctgcgc tgatagacat ccatgaattt ca                  42

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 14
tcgagctctt ctattcctgg aagatgtcca ccagtgtctc ga                  42

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 15
tggcttgaag atgtactcga tctcatcagg gtattcgaag agcggtac            48

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

```
<400> SEQUENCE: 16
catggccaca tctcatcagg ggcacgcagg a                              31

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 17
gcactccagc ccttcgtcat tgcagcaacc cgggtac                        37

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 18
aattctcata atctgcatgg tgatgttgga ctcctcggtg ggaac               45

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 19
catctctccg atgtgctgcc cttggtgagg ttt                            33

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 20
ggccgcgaag actcaatctt tctttggtct acattcacat ttgttatgct ggagaaagct    60

<210> SEQ ID NO 21
<211> LENGTH: 1997
<212> TYPE: DNA
<213> ORGANISM: Homo sapiens
<220> FEATURE:
<221> NAME/KEY: CDS
<222> LOCATION: (352)..(1608)

<400> SEQUENCE: 21
cccgccccgc ctctccaaaa agctacaccg acgcggaccg cggcggcgtc ctccctcgcc    60
ctcgcttcac ctcgcgggct ccgaatgcgg ggagctcgga tgtccggttt cctgtgaggc   120
ttttacctga cacccgccgc ctttcccgg cactggctgg gagggcgccc tgcaaagttg    180
ggaacgcgga gccccggacc cgctcccgcc gcctccggct cgcccagggg gggtcgccgg   240
```

-continued

```
gaggagcccg ggggagaggg accaggaggg gcccgcggcc tcgcaggggc gcccgcgccc    300
ccacccctgc ccccgccagc ggaccggtcc cccaccccg gtccttccac c atg cac      357
                                                      Met His
                                                        1 ttg ctg ggc ttc ttc tct gtg gcg tgt tct ctg ctc gcc gct gcg ctg      405
Leu Leu Gly Phe Phe Ser Val Ala Cys Ser Leu Leu Ala Ala Ala Leu
         5                  10                  15 ctc ccg ggt cct cgc gag gcg ccc gcc gcc gcc gcc gcc ttc gag tcc      453
Leu Pro Gly Pro Arg Glu Ala Pro Ala Ala Ala Ala Ala Phe Glu Ser
    20                  25                  30 gga ctc gac ctc tcg gac gcg gag ccc gac gcg ggc gag gcc acg gct      501
Gly Leu Asp Leu Ser Asp Ala Glu Pro Asp Ala Gly Glu Ala Thr Ala
 35                  40                  45                  50 tat gca agc aaa gat ctg gag gag cag tta cgg tct gtg tcc agt gta      549
Tyr Ala Ser Lys Asp Leu Glu Glu Gln Leu Arg Ser Val Ser Ser Val
                 55                  60                  65 gat gaa ctc atg act gta ctc tac cca gaa tat tgg aaa atg tac aag      597
Asp Glu Leu Met Thr Val Leu Tyr Pro Glu Tyr Trp Lys Met Tyr Lys
             70                  75                  80 tgt cag cta agg aaa gga ggc tgg caa cat aac aga gaa cag gcc aac      645
Cys Gln Leu Arg Lys Gly Gly Trp Gln His Asn Arg Glu Gln Ala Asn
         85                  90                  95 ctc aac tca agg aca gaa gag act ata aaa ttt gct gca gca cat tat      693
Leu Asn Ser Arg Thr Glu Glu Thr Ile Lys Phe Ala Ala Ala His Tyr
    100                 105                 110 aat aca gag atc ttg aaa agt att gat aat gag tgg aga aag act caa      741
Asn Thr Glu Ile Leu Lys Ser Ile Asp Asn Glu Trp Arg Lys Thr Gln
115                 120                 125                 130 tgc atg cca cgg gag gtg tgt ata gat gtg ggg aag gag ttt gga gtc      789
Cys Met Pro Arg Glu Val Cys Ile Asp Val Gly Lys Glu Phe Gly Val
                135                 140                 145 gcg aca aac acc ttc ttt aaa cct cca tgt gtg tcc gtc tac aga tgt      837
Ala Thr Asn Thr Phe Phe Lys Pro Pro Cys Val Ser Val Tyr Arg Cys
            150                 155                 160 ggg ggt tgc tgc aat agt gag ggg ctg cag tgc atg aac acc agc acg      885
Gly Gly Cys Cys Asn Ser Glu Gly Leu Gln Cys Met Asn Thr Ser Thr
        165                 170                 175 agc tac ctc agc aag acg tta ttt gaa att aca gtg cct ctc tct caa      933
Ser Tyr Leu Ser Lys Thr Leu Phe Glu Ile Thr Val Pro Leu Ser Gln
    180                 185                 190 ggc ccc aaa cca gta aca atc agt ttt gcc aat cac act tcc tgc cga      981
Gly Pro Lys Pro Val Thr Ile Ser Phe Ala Asn His Thr Ser Cys Arg
195                 200                 205                 210 tgc atg tct aaa ctg gat gtt tac aga caa gtt cat tcc att att aga     1029
Cys Met Ser Lys Leu Asp Val Tyr Arg Gln Val His Ser Ile Ile Arg
                215                 220                 225 cgt tcc ctg cca gca aca cta cca cag tgt cag gca gcg aac aag acc     1077
Arg Ser Leu Pro Ala Thr Leu Pro Gln Cys Gln Ala Ala Asn Lys Thr
            230                 235                 240 tgc ccc acc aat tac atg tgg aat aat cac atc tgc aga tgc ctg gct     1125
Cys Pro Thr Asn Tyr Met Trp Asn Asn His Ile Cys Arg Cys Leu Ala
        245                 250                 255 cag gaa gat ttt atg ttt tcc tcg gat gct gga gat gac tca aca gat     1173
Gln Glu Asp Phe Met Phe Ser Ser Asp Ala Gly Asp Asp Ser Thr Asp
    260                 265                 270 gga ttc cat gac atc tgt gga cca aac aag gag ctg gat gaa gag acc     1221
Gly Phe His Asp Ile Cys Gly Pro Asn Lys Glu Leu Asp Glu Glu Thr
275                 280                 285                 290
```

-continued

```
tgt cag tgt gtc tgc aga gcg ggg ctt cgg cct gcc agc tgt gga ccc      1269
Cys Gln Cys Val Cys Arg Ala Gly Leu Arg Pro Ala Ser Cys Gly Pro
            295                 300                 305 cac aaa gaa cta gac aga aac tca tgc cag tgt gtc tgt aaa aac aaa      1317
His Lys Glu Leu Asp Arg Asn Ser Cys Gln Cys Val Cys Lys Asn Lys
        310                 315                 320 ctc ttc ccc agc caa tgt ggg gcc aac cga gaa ttt gat gaa aac aca      1365
Leu Phe Pro Ser Gln Cys Gly Ala Asn Arg Glu Phe Asp Glu Asn Thr
    325                 330                 335 tgc cag tgt gta tgt aaa aga acc tgc ccc aga aat caa ccc cta aat      1413
Cys Gln Cys Val Cys Lys Arg Thr Cys Pro Arg Asn Gln Pro Leu Asn
340                 345                 350 cct gga aaa tgt gcc tgt gaa tgt aca gaa agt cca cag aaa tgc ttg      1461
Pro Gly Lys Cys Ala Cys Glu Cys Thr Glu Ser Pro Gln Lys Cys Leu
355                 360                 365                 370 tta aaa gga aag aag ttc cac cac caa aca tgc agc tgt tac aga cgg      1509
Leu Lys Gly Lys Lys Phe His His Gln Thr Cys Ser Cys Tyr Arg Arg
                375                 380                 385 cca tgt acg aac cgc cag aag gct tgt gag cca gga ttt tca tat agt      1557
Pro Cys Thr Asn Arg Gln Lys Ala Cys Glu Pro Gly Phe Ser Tyr Ser
            390                 395                 400 gaa gaa gtg tgt cgt tgt gtc cct tca tat tgg aaa aga cca caa atg      1605
Glu Glu Val Cys Arg Cys Val Pro Ser Tyr Trp Lys Arg Pro Gln Met
        405                 410                 415 agc taagattgta ctgttttcca gttcatcgat tttctattat ggaaaactgt          1658
Ser gttgccacag tagaactgtc tgtgaacaga gagacccttg tgggtccatg ctaacaaaga   1718
caaaagtctg tctttcctga accatgtgga taactttaca gaaatggact ggagctcatc   1778
tgcaaaaggc ctcttgtaaa gactggtttt ctgccaatga ccaaacagcc aagattttcc   1838
tcttgtgatt tctttaaaag aatgactata taatttattt ccactaaaaa tattgtttct   1898
gcattcattt ttatagcaac aacaattggt aaaactcact gtgatcaata tttttatatc   1958
atgcaaaata tgtttaaaat aaaatgaaaa ttgtattat                          1997
```

<210> SEQ ID NO 22
<211> LENGTH: 419
<212> TYPE: PRT
<213> ORGANISM: Homo sapiens

<400> SEQUENCE: 22

```
Met His Leu Leu Gly Phe Phe Ser Val Ala Cys Ser Leu Leu Ala Ala
 1               5                  10                  15

Ala Leu Leu Pro Gly Pro Arg Glu Ala Pro Ala Ala Ala Ala Ala Phe
             20                  25                  30

Glu Ser Gly Leu Asp Leu Ser Asp Ala Glu Pro Asp Ala Gly Glu Ala
         35                  40                  45

Thr Ala Tyr Ala Ser Lys Asp Leu Glu Glu Gln Leu Arg Ser Val Ser
     50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                 85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125
```

```
Thr Gln Cys Met Pro Arg Glu Val Cys Ile Asp Val Gly Lys Glu Phe
        130                 135                 140
Gly Val Ala Thr Asn Thr Phe Phe Lys Pro Pro Cys Val Ser Val Tyr
145                 150                 155                 160
Arg Cys Gly Gly Cys Cys Asn Ser Glu Gly Leu Gln Cys Met Asn Thr
                165                 170                 175
Ser Thr Ser Tyr Leu Ser Lys Thr Leu Phe Glu Ile Thr Val Pro Leu
            180                 185                 190
Ser Gln Gly Pro Lys Pro Val Thr Ile Ser Phe Ala Asn His Thr Ser
        195                 200                 205
Cys Arg Cys Met Ser Lys Leu Asp Val Tyr Arg Gln Val His Ser Ile
    210                 215                 220
Ile Arg Arg Ser Leu Pro Ala Thr Leu Pro Gln Cys Gln Ala Ala Asn
225                 230                 235                 240
Lys Thr Cys Pro Thr Asn Tyr Met Trp Asn Asn His Ile Cys Arg Cys
                245                 250                 255
Leu Ala Gln Glu Asp Phe Met Phe Ser Ser Asp Ala Gly Asp Asp Ser
            260                 265                 270
Thr Asp Gly Phe His Asp Ile Cys Gly Pro Asn Lys Glu Leu Asp Glu
        275                 280                 285
Glu Thr Cys Gln Cys Val Cys Arg Ala Gly Leu Arg Pro Ala Ser Cys
290                 295                 300
Gly Pro His Lys Glu Leu Asp Arg Asn Ser Cys Gln Cys Val Cys Lys
305                 310                 315                 320
Asn Lys Leu Phe Pro Ser Gln Cys Gly Ala Asn Arg Glu Phe Asp Glu
                325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
        355                 360                 365
Cys Leu Leu Lys Gly Lys Lys Phe His His Gln Thr Cys Ser Cys Tyr
    370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Lys Arg Pro
                405                 410                 415
Gln Met Ser

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 23
gatcctgcac attataatac cgagatcctg aaat                              34

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor
```

```
<400> SEQUENCE: 24
ctattgataa tgagtggaga aagactcagt gcatg                              35

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 25
ccgagagagg tgtgtatcga cgtggggaag gaatagaaga gc                      42

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 26
cgctcttcga atttggagtc gcgacaaaca cct                                33

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 27
tcttcaagcc accatgtgtg tccgtgtaca gatgtggc                           38

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 28
ccgggttgct gcaatagtga ggggctgc                                      28

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 29
agtgcatgaa cacgtccacg agctacctca gcaagacgct gtttga                  46

<210> SEQ ID NO 30
<211> LENGTH: 49
<212> TYPE: DNA
```

<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 30
aattacagtg cctctctctc aagggcccaa accagtgaca atcagcttt                49

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 31
gccaatcaca cttcctgccg atgcatgtct aagctggatt gagtcttcgc               50

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 32
ggatctcggt attataatgt gcag                                           24

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 33
tcggcatgca ctgagtcttt ctccactcat tatcaataga tttca                    45

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 34
tcgagctctt ctattccttc cccacgtcga tacacacctc tc                       42

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Artificial
      chimeric oligonucleotide sequence derived from multiple vertebrate
      vascular endothelial growth factor

<400> SEQUENCE: 35
tggcttgaag aaggtgtttg tcgcgactcc aaattcgaag agcggtac                 48

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Artificial
chimeric oligonucleotide sequence derived from multiple vertebrate
vascular endothelial growth factor

<400> SEQUENCE: 36
catggccaca tctgtacacg gacacacatg g                              31

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Artificial
chimeric oligonucleotide sequence derived from multiple vertebrate
vascular endothelial growth factor

<400> SEQUENCE: 37
gcactgcagc ccctcactat tgcagcaacc cgggtac                        37

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Artificial
chimeric oligonucleotide sequence derived from multiple vertebrate
vascular endothelial growth factor

<400> SEQUENCE: 38
aatttcaaac agcgtcttgc tgaggtagct cgtggacgtg ttcat               45

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Artificial
chimeric oligonucleotide sequence derived from multiple vertebrate
vascular endothelial growth factor

<400> SEQUENCE: 39
gattgtcact ggtttgggcc cttgagagag aggcactgt                      39

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Artificial
chimeric oligonucleotide sequence derived from multiple vertebrate
vascular endothelial growth factor

<400> SEQUENCE: 40
ggccgcgaag actcaatcca gcttagacat gcatcggcag gaagtgtgat tggcaaagct    60

<210> SEQ ID NO 41
<211> LENGTH: 5070
<212> TYPE: DNA
<213> ORGANISM: Artificial Sequence
<220> FEATURE:
<223> OTHER INFORMATION: Description of Artificial Sequence: pSecTagI
Vector <400> SEQUENCE: 41

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata     300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctcg cgcgtgttga caattaatca    840
tcggcatagt atatcggcat agtataatac gacaaggtga ggaactaaac catggagaca    900
gacacactcc tgctatgggt actgctgctc tgggttccag gttccactgg tgacgcggcc    960
caggatccgt ctcccatgcc gatttggtct tcgaacaaaa actcatctca gaagaggatc   1020
tgaatagcgc cgtcgaccat catcatcatc atcattgagt ttaaacccgc tgatcagcct   1080
cgactgtgcc ttctagttgc cagccatctg ttgtttgccc ctccccgtg ccttccttga    1140
ccctggaagg tgccactccc actgtccttt cctaataaaa tgaggaaatt gcatcgcatt   1200
gtctgagtag gtgtcattct attctggggg gtggggtggg gcaggacagc aaggggagg    1260
attgggaaga taatagcagg catgctgggg atgcggtggg ctctatggct tctgaggcgg   1320
aaagaaccag ctggggctct aggggtatc cccacgcgcc ctgtagcggc cattaagcg     1380
cggcgggtgt ggtggttacg cgcagcgtga ccgctacact tgccagcgcc ctagcgcccg   1440
ctcctttcgc tttcttccct cctttctcg ccacgttcgc cggctttccc cgtcaagctc    1500
taaatcgggg catccctta gggttccgat ttagtgcttt acggcacctc gaccccaaaa    1560
aacttgatta gggtgatggt tcacgtagtg ggccatcgcc ctgatagacg ttttcgcc     1620
ctttgacgtt ggagtccacg ttctttaata gtggactctt gttccaaact ggaacaacac   1680
tcaaccctat ctcggtctat tcttttgatt tataagggat tttggggatt tcggcctatt   1740
ggttaaaaaa tgagctgatt taacaaaaat ttaacgcgaa ttaattctgt ggaatgtgtg   1800
tcagttaggg tgtggaaagt ccccaggctc cccagcaggc agaagtatgc aaagcatgca   1860
tctcaattag tcagcaacca ggtgtggaaa gtccccaggc tccccagcag gcagaagtat   1920
gcaaagcatg catctcaatt agtcagcaac catagtcccg cccctaactc cgcccatccc   1980
gcccctaact ccgcccagtt ccgcccattc tccgccccat ggctgactaa ttttttttat   2040
ttatgcagag gccgaggccg cctctgcctc tgagctattc cagaagtagt gaggaggctt   2100
ttttggaggc ctaggctttt gcaaaaagct cccgggagct gtgtatatcca ttttcggatc   2160
tgatcagcac gtgttgacaa ttaatcatcg gcatagtata tcggcatagt ataatacgac   2220
aaggtgagga actaaaccat ggctaagttg accagtgccg ttccggtgct caccgcgcgc   2280
```

```
gacgtcgccg gagcggtcga gttctggacc gaccggctcg ggttctcccg ggacttcgtg     2340
gaggacgact tcgccggtgt ggtccgggac gacgtgaccc tgttcatcag cgcggtccag     2400
gaccaggtgg tgccggacaa caccctggcc tgggtgtggg tgcgcggcct ggacgagctg     2460
tacgccgagt ggtcggaggt cgtgtccacg aacttccggg acgcctccgg gccggccatg     2520
accgagatcg gcgagcagcc gtgggggcgg gagttcgccc tgcgcgaccc ggccggcaac     2580
tgcgtgcact tcgtggccga ggagcaggac tgacacgtgc tacgagattt cgattccacc     2640
gccgccttct atgaaaggtt gggcttcgga atcgttttcc gggacgccgg ctggatgatc     2700
ctccagcgcg gggatctcat gctggagttc ttcgcccacc ccaacttgtt tattgcagct     2760
tataatggtt acaaataaag caatagcatc acaaatttca caaataaagc attttttca     2820 ctgcattcta gttgtggttt gtccaaactc atcaatgtat cttatcatgt ctgtataccg     2880
tcgacctcta gctagagctt ggcgtaatca tggtcatagc tgtttcctgt gtgaaattgt     2940
tatccgctca caattccaca acacatacga gccggaagca taaagtgtaa agcctggggt     3000
gcctaatgag tgagctaact cacattaatt gcgttgcgct cactgcccgc tttccagtcg     3060
ggaaacctgt cgtgccagct gcattaatga atcggccaac gcgcggggag aggcggtttg     3120
cgtattgggc gctcttccgc ttcctcgctc actgactcgc tgcgctcggt cgttcggctg     3180
cggcgagcgg tatcagctca ctcaaaggcg gtaatacggt tatccacaga atcaggggat     3240
aacgcaggaa agaacatgtg agcaaaaggc cagcaaaagg ccaggaaccg taaaaaggcc     3300
gcgttgctgg cgttttttcca taggctccgc cccctgacg agcatcacaa aaatcgacgc     3360
tcaagtcaga ggtggcgaaa cccgacagga ctataaagat accaggcgtt tccccctgga     3420
agctccctcg tgcgctctcc tgttccgacc ctgccgctta ccggatacct gtccgccttt     3480
ctcccttcgg gaagcgtggc gctttctcaa tgctcacgct gtaggtatct cagttcggtg     3540
taggtcgttc gctccaagct gggctgtgtg cacgaacccc ccgttcagcc cgaccgctgc     3600
gccttatccg gtaactatcg tcttgagtcc aacccggtaa gacacgactt atcgccactg     3660
gcagcagcca ctggtaacag gattagcaga gcgaggtatg taggcggtgc tacagagttc     3720
ttgaagtggt ggcctaacta cggctacact agaaggacag tatttggtat ctgcgctctg     3780
ctgaagccag ttaccttcgg aaaaagagtt ggtagctctt gatccggcaa acaaaccacc     3840
gctggtagcg gtggtttttt tgtttgcaag cagcagatta cgcgcagaaa aaaggatct     3900 caagaagatc ctttgatctt ttctacgggg tctgacgctc agtggaacga aaactcacgt     3960
taagggattt tggtcatgag attatcaaaa aggatcttca cctagatcct tttaaattaa     4020
aaatgaagtt ttaaatcaat ctaaagtata tatgagtaaa cttggtctga cagttaccaa     4080
tgcttaatca gtgaggcacc tatctcagcg atctgtctat ttcgttcatc catagttgcc     4140 tgactcccg tcgtgtagat aactacgata cgggagggct taccatctgg ccccagtgct     4200
gcaatgatac cgcgagaccc acgctcaccg gctccagatt tatcagcaat aaaccagcca     4260
gccggaaggg ccgagcgcag aagtggtcct gcaactttat ccgcctccat ccagtctatt     4320
aattgttgcc gggaagctag agtaagtagt tcgccagtta atagtttgcg caacgttgtt     4380
gccattgcta caggcatcgt ggtgtcacgc tcgtcgtttg gtatggcttc attcagctcc     4440
ggttcccaac gatcaaggcg agttacatga tcccccatgt tgtgcaaaaa agcggttagc     4500
tccttcggtc ctccgatcgt tgtcagaagt aagttggccg cagtgttatc actcatggtt     4560
atggcagcac tgcataattc tcttactgtc atgccatccg taagatgctt ttctgtgact     4620
ggtgagtact caaccaagtc attctgagaa tagtgtatgc ggcgaccgag ttgctcttgc     4680
```

```
ccggcgtcaa tacgggataa taccgcgcca catagcagaa ctttaaaagt gctcatcatt      4740
ggaaaacgtt cttcggggcg aaaactctca aggatcttac cgctgttgag atccagttcg      4800
atgtaaccca ctcgtgcacc caactgatct tcagcatctt ttactttcac cagcgtttct      4860
gggtgagcaa aaacaggaag gcaaaatgcc gcaaaaaagg gaataagggc gacacggaaa      4920
tgttgaatac tcatactctt cctttttcaa tattattgaa gcatttatca gggttattgt      4980
ctcatgagcg gatacatatt tgaatgtatt tagaaaaata aacaaatagg ggttccgcgc      5040
acatttcccc gaaaagtgcc acctgacgtc                                      5070
```

<210> SEQ ID NO 42
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 42

```
ggatcct ggg cag aat cat cac gaa gtg gtg aaa ttc atg gat gtc tat        49
        Gly Gln Asn His His Glu Val Val Lys Phe Met Asp Val Tyr
        1               5                   10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
15                  20                  25                  30 gaa tac cct gat gag atc gag tac atc ttc aag cca tcc tgc gtg ccc       145
Glu Tyr Pro Asp Glu Ile Glu Tyr Ile Phe Lys Pro Ser Cys Val Pro
                35                  40                  45 ctg atg aga tgt ggg ggt tgc tgc aat gac gaa ggg ctg gag tgc gtt       193
Leu Met Arg Cys Gly Gly Cys Cys Asn Asp Glu Gly Leu Glu Cys Val
            50                  55                  60 ccc acc gag gag tcc aac atc acc atg cag att atg aga att aaa cct       241
Pro Thr Glu Glu Ser Asn Ile Thr Met Gln Ile Met Arg Ile Lys Pro
65                  70                  75 cac caa ggg cag cac atc gga gag atg agc ttt ctc cag cat aac aaa       289
His Gln Gly Gln His Ile Gly Glu Met Ser Phe Leu Gln His Asn Lys
    80                  85                  90 tgt gaa tgt aga cca aag aaa gat ttg gtc ttc gaa caa aaa ctc atc       337
Cys Glu Cys Arg Pro Lys Lys Asp Leu Val Phe Glu Gln Lys Leu Ile
95                  100                 105                 110 tca gaa gag gat ctg aat agc gcc gtc gac cat cat cat cat cat cat       385
Ser Glu Glu Asp Leu Asn Ser Ala Val Asp His His His His His His
                115                 120                 125 tga                                                                   388
```

<210> SEQ ID NO 43
<211> LENGTH: 126
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 43

```
Gly Gln Asn His His Glu Val Val Lys Phe Met Asp Val Tyr Gln Arg
1               5                   10                  15

Ser Tyr Cys His Pro Ile Glu Thr Leu Val Asp Ile Phe Gln Glu Tyr
            20                  25                  30

Pro Asp Glu Ile Glu Tyr Ile Phe Lys Pro Ser Cys Val Pro Leu Met
```

-continued

```
                35                  40                  45
Arg Cys Gly Gly Cys Cys Asn Asp Glu Gly Leu Glu Cys Val Pro Thr
 50                  55                  60

Glu Glu Ser Asn Ile Thr Met Gln Ile Met Arg Ile Lys Pro His Gln
 65                  70                  75                  80

Gly Gln His Ile Gly Glu Met Ser Phe Leu Gln His Asn Lys Cys Glu
                 85                  90                  95

Cys Arg Pro Lys Lys Asp Leu Val Phe Gln Lys Leu Ile Ser Glu
            100                 105                 110

Glu Asp Leu Asn Ser Ala Val Asp His His His His His
            115                 120                 125
```

<210> SEQ ID NO 44
<211> LENGTH: 394
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(391)

<400> SEQUENCE: 44

```
ggatcct ggg cag aat cat cac gaa gtg gtg aaa ttc atg gat gtc tat        49
        Gly Gln Asn His His Glu Val Val Lys Phe Met Asp Val Tyr
         1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa tac cct gat gag atc gag tac atc ttc aag cca tcc tgc gtg ccc       145
Glu Tyr Pro Asp Glu Ile Glu Tyr Ile Phe Lys Pro Ser Cys Val Pro
                 35                  40                  45 ctg atg aga tgt ggg ggt tgc tgc aat agt gag ggg ctg cag tgc atg       193
Leu Met Arg Cys Gly Gly Cys Cys Asn Ser Glu Gly Leu Gln Cys Met
             50                  55                  60 aac acg tcc acg agc tac ctc agc aag acg ctg ttt gaa att aca gtg       241
Asn Thr Ser Thr Ser Tyr Leu Ser Lys Thr Leu Phe Glu Ile Thr Val
 65                  70                  75 cct ctc tct caa ggg ccc aaa cca gtg aca atc agc ttt gcc aat cac       289
Pro Leu Ser Gln Gly Pro Lys Pro Val Thr Ile Ser Phe Ala Asn His
 80                  85                  90 act tcc tgc cga tgc atg tct aag ctg gat ttg gtc ttc gaa caa aaa       337
Thr Ser Cys Arg Cys Met Ser Lys Leu Asp Leu Val Phe Glu Gln Lys
 95                 100                 105                 110 ctc atc tca gaa gag gat ctg aat agc gcc gtc gac cat cat cat cat       385
Leu Ile Ser Glu Glu Asp Leu Asn Ser Ala Val Asp His His His His
                115                 120                 125 cat cat tga                                                           394
His His
```

<210> SEQ ID NO 45
<211> LENGTH: 128
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 45

```
Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Tyr
```

```
                    20                  25                  30

Pro Asp Glu Ile Glu Tyr Ile Phe Lys Pro Ser Cys Val Pro Leu Met
        35                  40                  45

Arg Cys Gly Gly Cys Cys Asn Ser Glu Gly Leu Gln Cys Met Asn Thr
 50                  55                  60

Ser Thr Ser Tyr Leu Ser Lys Thr Leu Phe Glu Ile Thr Val Pro Leu
 65                  70                  75                  80

Ser Gln Gly Pro Lys Pro Val Thr Ile Ser Phe Ala Asn His Thr Ser
                85                  90                  95

Cys Arg Cys Met Ser Lys Leu Asp Leu Val Phe Glu Gln Lys Leu Ile
            100                 105                 110

Ser Glu Glu Asp Leu Asn Ser Ala Val Asp His His His His His His
            115                 120                 125
```

```
<210> SEQ ID NO 46
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 46 ggatcct gca cat tat aat acc gag atc ctg aaa tct att gat aat gag      49
        Ala His Tyr Asn Thr Glu Ile Leu Lys Ser Ile Asp Asn Glu
         1               5                  10 tgg aga aag act cag tgc atg ccg aga gag gtg tgt atc gac gtg ggg      97
Trp Arg Lys Thr Gln Cys Met Pro Arg Glu Val Cys Ile Asp Val Gly
 15                  20                  25                  30 aag gaa ttt gga gtc gcg aca aac acc ttc ttc aag cca cca tgt gtg     145
Lys Glu Phe Gly Val Ala Thr Asn Thr Phe Phe Lys Pro Pro Cys Val
                35                  40                  45 tcc gtg tac aga tgt ggg ggt tgc tgc aat gac gaa ggg ctg gag tgc     193
Ser Val Tyr Arg Cys Gly Gly Cys Cys Asn Asp Glu Gly Leu Glu Cys
             50                  55                  60 gtt ccc acc gag gag tcc aac atc acc atg cag att atg aga att aaa     241
Val Pro Thr Glu Glu Ser Asn Ile Thr Met Gln Ile Met Arg Ile Lys
         65                  70                  75 cct cac caa ggg cag cac atc gga gag atg agc ttt ctc cag cat aac     289
Pro His Gln Gly Gln His Ile Gly Glu Met Ser Phe Leu Gln His Asn
     80                  85                  90 aaa tgt gaa tgt aga cca aag aaa gat ttg gtc ttc gaa caa aaa ctc     337
Lys Cys Glu Cys Arg Pro Lys Lys Asp Leu Val Phe Glu Gln Lys Leu
 95                 100                 105                 110 atc tca gaa gag gat ctg aat agc gcc gtc gac cat cat cat cat         385
Ile Ser Glu Glu Asp Leu Asn Ser Ala Val Asp His His His His
                115                 120                 125 cat tga                                                              391
His
```

```
<210> SEQ ID NO 47
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 47

Ala His Tyr Asn Thr Glu Ile Leu Lys Ser Ile Asp Asn Glu Trp Arg
```

```
                1               5              10              15
Lys Thr Gln Cys Met Pro Arg Glu Val Cys Ile Asp Val Gly Lys Glu
                    20                  25                  30

Phe Gly Val Ala Thr Asn Thr Phe Phe Lys Pro Pro Cys Val Ser Val
            35                  40                  45

Tyr Arg Cys Gly Gly Cys Cys Asn Asp Glu Gly Leu Glu Cys Val Pro
        50                  55                  60

Thr Glu Glu Ser Asn Ile Thr Met Gln Ile Met Arg Ile Lys Pro His
 65                  70                  75                  80

Gln Gly Gln His Ile Gly Glu Met Ser Phe Leu Gln His Asn Lys Cys
                85                  90                  95

Glu Cys Arg Pro Lys Lys Asp Leu Val Phe Glu Gln Lys Leu Ile Ser
            100                 105                 110

Glu Glu Asp Leu Asn Ser Ala Val Asp His His His His His
        115                 120                 125
```

```
<210> SEQ ID NO 48
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 48 ggatcct gca cat tat aat acc gag atc ctg aaa tct att gat aat gag      49
        Ala His Tyr Asn Thr Glu Ile Leu Lys Ser Ile Asp Asn Glu
         1               5                  10 tgg aga aag act cag tgc atg ccg aga gag gtg tgt atc gac gtg ggg      97
Trp Arg Lys Thr Gln Cys Met Pro Arg Glu Val Cys Ile Asp Val Gly
 15                  20                  25                  30 aag gaa ttt gga gtc gcg aca aac acc ttc ttc aag cca cca tgt gtg    145
Lys Glu Phe Gly Val Ala Thr Asn Thr Phe Phe Lys Pro Pro Cys Val
                 35                  40                  45 tcc gtg tac aga tgt ggg ggt tgc tgc aat agt gag ggg ctg cag tgc    193
Ser Val Tyr Arg Cys Gly Gly Cys Cys Asn Ser Glu Gly Leu Gln Cys
             50                  55                  60 atg aac acg tcc acg agc tac ctc agc aag acg ctg ttt gaa att aca    241
Met Asn Thr Ser Thr Ser Tyr Leu Ser Lys Thr Leu Phe Glu Ile Thr
         65                  70                  75 gtg cct ctc tct caa ggg ccc aaa cca gtg aca atc agc ttt gcc aat    289
Val Pro Leu Ser Gln Gly Pro Lys Pro Val Thr Ile Ser Phe Ala Asn
 80                  85                  90 cac act tcc tgc cga tgc atg tct aag ctg gat ttg gtc ttc gaa caa    337
His Thr Ser Cys Arg Cys Met Ser Lys Leu Asp Leu Val Phe Glu Gln
 95                 100                 105                 110 aaa ctc atc tca gaa gag gat ctg aat agc gcc gtc gac cat cat cat    385
Lys Leu Ile Ser Glu Glu Asp Leu Asn Ser Ala Val Asp His His His
             115                 120                 125 cat cat cat tga                                                     397
His His His <210> SEQ ID NO 49
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA
```

<400> SEQUENCE: 49

```
Ala His Tyr Asn Thr Glu Ile Leu Lys Ser Ile Asp Asn Glu Trp Arg
 1               5                  10                  15

Lys Thr Gln Cys Met Pro Arg Glu Val Cys Ile Asp Val Gly Lys Glu
             20                  25                  30

Phe Gly Val Ala Thr Asn Thr Phe Phe Lys Pro Pro Cys Val Ser Val
         35                  40                  45

Tyr Arg Cys Gly Gly Cys Cys Asn Ser Glu Gly Leu Gln Cys Met Asn
     50                  55                  60

Thr Ser Thr Ser Tyr Leu Ser Lys Thr Leu Phe Glu Ile Thr Val Pro
 65                  70                  75                  80

Leu Ser Gln Gly Pro Lys Pro Val Thr Ile Ser Phe Ala Asn His Thr
                 85                  90                  95

Ser Cys Arg Cys Met Ser Lys Leu Asp Leu Val Phe Glu Gln Lys Leu
            100                 105                 110

Ile Ser Glu Glu Asp Leu Asn Ser Ala Val Asp His His His His
        115                 120                 125

His
```

<210> SEQ ID NO 50
<211> LENGTH: 322
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 50

```
ggatcct ggg cag aat cat cac gaa gtg gtg aaa ttc atg gat gtc tat        49
        Gly Gln Asn His His Glu Val Val Lys Phe Met Asp Val Tyr
          1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc gtt       193
Val Tyr Arg Cys Gly Gly Cys Cys Asn Asp Glu Gly Leu Glu Cys Val
             50                  55                  60 ccc acc gag gag tcc aac atc acc atg cag att atg aga att aaa cct       241
Pro Thr Glu Glu Ser Asn Ile Thr Met Gln Ile Met Arg Ile Lys Pro
 65                  70                  75 cac caa ggg cag cac atc gga gag atg agc ttt ctc cag cat aac aaa       289
His Gln Gly Gln His Ile Gly Glu Met Ser Phe Leu Gln His Asn Lys
         80                  85                  90 tgt gaa tgt aga cca aag aaa gat ttg gtc ttc                           322
Cys Glu Cys Arg Pro Lys Lys Asp Leu Val Phe
 95                 100                 105
```

<210> SEQ ID NO 51
<211> LENGTH: 105
<212> TYPE: PRT
<213> ORGANISM: Artificial Sequence
<220> FEATURE:
<223> OTHER INFORMATION: Description of Artificial Sequence: amino acid sequence of hybrid DNA

<400> SEQUENCE: 51

```
Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
            20                  25                  30

Gly Val Ala Thr Asn Thr Phe Phe Lys Pro Pro Cys Val Ser Val Tyr
        35                  40                  45

Arg Cys Gly Cys Cys Asn Asp Glu Gly Leu Glu Cys Val Pro Thr
 50                  55                  60

Glu Glu Ser Asn Ile Thr Met Gln Ile Met Arg Ile Lys Pro His Gln
65                  70                  75                  80

Gly Gln His Ile Gly Glu Met Ser Phe Leu Gln His Asn Lys Cys Glu
                85                  90                  95

Cys Arg Pro Lys Lys Asp Leu Val Phe
            100                 105

<210> SEQ ID NO 52
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 52 ggatcct ggg cag aat cat cac gaa gtg gtg aaa ttc atg gat gtc tat        49
        Gly Gln Asn His His Glu Val Val Lys Phe Met Asp Val Tyr
         1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc atg       193
Val Tyr Arg Cys Gly Gly Cys Cys Asn Asp Glu Gly Leu Glu Cys Met
             50                  55                  60 aac acg tcc acg agc tac ctc agc aag acg ctg ttt gaa att aaa cct       241
Asn Thr Ser Thr Ser Tyr Leu Ser Lys Thr Leu Phe Glu Ile Lys Pro
 65                  70                  75 cac caa ggg cag cac atc gga gag atg agc ttt ctc cag cat aac aaa       289
His Gln Gly Gln His Ile Gly Glu Met Ser Phe Leu Gln His Asn Lys
         80                  85                  90 tgt gaa tgt aga cca aag aaa gat ttg gtc ttc gaa caa aaa ctc atc       337
Cys Glu Cys Arg Pro Lys Lys Asp Leu Val Phe Glu Gln Lys Leu Ile
 95                 100                 105                 110 tca gaa gag gat ctg aat agc gcc gtc gac cat cat cat cat cat cat       385
Ser Glu Glu Asp Leu Asn Ser Ala Val Asp His His His His His His
                115                 120                 125 tga                                                                    388

<210> SEQ ID NO 53
<211> LENGTH: 126
<212> TYPE: PRT
<213> ORGANISM: Artificial Sequence
<220> FEATURE:
<223> OTHER INFORMATION: Description of Artificial Sequence:   amino
      acid sequence of hybrid DNA

<400> SEQUENCE: 53

Gly Gln Asn His His Glu Val Val Lys Phe Met Asp Val Tyr Gln Arg
```

```
                 1               5              10              15
Ser Tyr Cys His Pro Ile Glu Thr Leu Val Asp Ile Phe Gln Glu Phe
                20                  25                  30

Gly Val Ala Thr Asn Thr Phe Phe Lys Pro Pro Cys Val Ser Val Tyr
                35                  40                  45

Arg Cys Gly Cys Cys Asn Asp Glu Gly Leu Glu Cys Met Asn Thr
                50                  55                  60

Ser Thr Ser Tyr Leu Ser Lys Thr Leu Phe Glu Ile Lys Pro His Gln
 65                 70                  75                  80

Gly Gln His Ile Gly Glu Met Ser Phe Leu Gln His Asn Lys Cys Glu
                85                  90                  95

Cys Arg Pro Lys Lys Asp Leu Val Phe Glu Gln Lys Leu Ile Ser Glu
                100                 105                 110

Glu Asp Leu Asn Ser Ala Val Asp His His His His His His
                115                 120                 125
```

<210> SEQ ID NO 54
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 54

```
ggatcct ggg cag aat cat cac gaa gtg gtg aaa ttc atg gat gtc tat         49
        Gly Gln Asn His His Glu Val Val Lys Phe Met Asp Val Tyr
         1               5                  10
cag cgc agc tac tgc cat ccg atc gag aca ctg gtg gac atc ttc cag         97
Gln Arg Ser Tyr Cys His Pro Ile Glu Thr Leu Val Asp Ile Phe Gln
 15                  20                  25                  30
gaa ttt gga gtc gcg aca aac acc ttc ttc aag cca cca tgt gtg tcc        145
Glu Phe Gly Val Ala Thr Asn Thr Phe Phe Lys Pro Pro Cys Val Ser
                 35                  40                  45
gtg tac aga tgt ggg ggt tgc tgc aat agt gag ggg ctg cag tgc gtt        193
Val Tyr Arg Cys Gly Gly Cys Cys Asn Ser Glu Gly Leu Gln Cys Val
             50                  55                  60
ccc acc gag gag tcc aac atc acc atg cag att atg aga att aaa cct        241
Pro Thr Glu Glu Ser Asn Ile Thr Met Gln Ile Met Arg Ile Lys Pro
 65                  70                  75
cac caa ggg cag cac atc gga gag atg agc ttt ctc cag cat aac aaa        289
His Gln Gly Gln His Ile Gly Glu Met Ser Phe Leu Gln His Asn Lys
                 80                  85                  90
tgt gaa tgt aga cca aag aaa gat ttg gtc ttc gaa caa aaa ctc atc        337
Cys Glu Cys Arg Pro Lys Lys Asp Leu Val Phe Glu Gln Lys Leu Ile
  95                 100                 105                 110
tca gaa gag gat ctg aat agc gcc gtc gac cat cat cat cat cat cat        385
Ser Glu Glu Asp Leu Asn Ser Ala Val Asp His His His His His His
                 115                 120                 125
tga                                                                    388
```

<210> SEQ ID NO 55
<211> LENGTH: 126
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 55

```
Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
                20                  25                  30

Gly Val Ala Thr Asn Thr Phe Phe Lys Pro Pro Cys Val Ser Val Tyr
```

```
                  35                  40                  45
Arg Cys Gly Gly Cys Cys Asn Ser Glu Gly Leu Gln Cys Val Pro Thr
     50                  55                  60

Glu Glu Ser Asn Ile Thr Met Gln Ile Met Arg Ile Lys Pro His Gln
 65                  70                  75                  80

Gly Gln His Ile Gly Glu Met Ser Phe Leu Gln His Asn Lys Cys Glu
                 85                  90                  95

Cys Arg Pro Lys Lys Asp Leu Val Phe Gln Lys Leu Ile Ser Glu
             100                 105                 110

Glu Asp Leu Asn Ser Ala Val Asp His His His His His
             115                 120                 125

<210> SEQ ID NO 56
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 56 ggatcct ggg cag aat cat cac gaa gtg gtg aaa ttc atg gat gtc tat      49
        Gly Gln Asn His His Glu Val Val Lys Phe Met Asp Val Tyr
         1               5                  10 cag cgc agc tac tgc cat ccg atc gag aca ctg gtg gac atc ttc cag      97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc     145
Glu Phe Gly Val Ala Thr Asn Thr Phe Phe Lys Pro Pro Cys Val Ser
                 35                  40                  45 gtg tac aga tgt ggg ggt tgc tgc aat agt gag ggg ctg cag tgc atg     193
Val Tyr Arg Cys Gly Gly Cys Cys Asn Ser Glu Gly Leu Gln Cys Met
             50                  55                  60 aac acg tcc acg agc tac ctc agc aag acg ctg ttt gaa att aaa cct     241
Asn Thr Ser Thr Ser Tyr Leu Ser Lys Thr Leu Phe Glu Ile Lys Pro
 65                  70                  75 cac caa ggg cag cac atc gga gag atg agc ttt ctc cag cat aac aaa     289
His Gln Gly Gln His Ile Gly Glu Met Ser Phe Leu Gln His Asn Lys
             80                  85                  90 tgt gaa tgt aga cca aag aaa gat ttg gtc ttc gaa caa aaa ctc atc     337
Cys Glu Cys Arg Pro Lys Lys Asp Leu Val Phe Glu Gln Lys Leu Ile
 95                 100                 105                 110 tca gaa gag gat ctg aat agc gcc gtc gac cat cat cat cat cat         385
Ser Glu Glu Asp Leu Asn Ser Ala Val Asp His His His His His
                115                 120                 125 tga                                                                  388

<210> SEQ ID NO 57
<211> LENGTH: 126
<212> TYPE: PRT
<213> ORGANISM: Artificial Sequence
<220> FEATURE:
<223> OTHER INFORMATION: Description of Artificial Sequence:  Artificial
      chimeric amino acid sequence derived from multiple vertebrate
      vascular endothelial growth factors

<400> SEQUENCE: 57

Gly Gln Asn His His Glu Val Val Lys Phe Met Asp Val Tyr Gln Arg
 1               5                  10                  15

```
                    20                  25                  30
Gly Val Ala Thr Asn Thr Phe Phe Lys Pro Pro Cys Val Ser Val Tyr
            35                  40                  45

Arg Cys Gly Gly Cys Cys Asn Ser Glu Gly Leu Gln Cys Met Asn Thr
        50                  55                  60

Ser Thr Ser Tyr Leu Ser Lys Thr Leu Phe Glu Ile Lys Pro His Gln
65                  70                  75                  80

Gly Gln His Ile Gly Glu Met Ser Phe Leu Gln His Asn Lys Cys Glu
                85                  90                  95

Cys Arg Pro Lys Lys Asp Leu Val Phe Glu Gln Lys Leu Ile Ser Glu
            100                 105                 110

Glu Asp Leu Asn Ser Ala Val Asp His His His His His
        115                 120                 125

<210> SEQ ID NO 58
<211> LENGTH: 322
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 58 ggatcct ggg cag aat cat cac gaa gtg gtg aaa ttc atg gat gtc tat        49
        Gly Gln Asn His His Glu Val Val Lys Phe Met Asp Val Tyr
          1               5                  10 cag cgc agc tac tgc cat ccg atc gag aca ctg gtg gac atc ttc cag       97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc      145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc gtt      193
Val Tyr Arg Cys Gly Gly Cys Cys Asn Asp Glu Gly Leu Glu Cys Val
             50                  55                  60 ccc acc gag gag tcc aac atc acc atg cag att atg aga att aaa cct      241
Pro Thr Glu Glu Ser Asn Ile Thr Met Gln Ile Met Arg Ile Lys Pro
 65                  70                  75 cac caa ggg cag cac atc gga gag atg agc ttt gcc aat cac act tcc      289
His Gln Gly Gln His Ile Gly Glu Met Ser Phe Ala Asn His Thr Ser
 80                  85                  90 tgc cga tgc atg tct aag ctg gat ttg gtc ttc                          322
Cys Arg Cys Met Ser Lys Leu Asp Leu Val Phe
 95                 100                 105

<210> SEQ ID NO 59
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 59

Gly Gln Asn His His Glu Val Val Lys Phe Met Asp Val Tyr Gln Arg
  1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45
```

```
Arg Cys Gly Gly Cys Cys Asn Asp Glu Gly Leu Glu Cys Val Pro Thr
     50                  55                  60

Glu Glu Ser Asn Ile Thr Met Gln Ile Met Arg Ile Lys Pro His Gln
 65                  70                  75                  80

Gly Gln His Ile Gly Glu Met Ser Phe Ala Asn His Thr Ser Cys Arg
                 85                  90                  95

Cys Met Ser Lys Leu Asp Leu Val Phe
             100                 105

<210> SEQ ID NO 60
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 60 ggatcct ggg cag aat cat cac gaa gtg gtg aaa ttc atg gat gtc tat       49
        Gly Gln Asn His His Glu Val Val Lys Phe Met Asp Val Tyr
         1               5                  10 cag cgc agc tac tgc cat ccg atc gag aca ctg gtg gac atc ttc cag       97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc      145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc atg      193
Val Tyr Arg Cys Gly Gly Cys Cys Asn Asp Glu Gly Leu Glu Cys Met
             50                  55                  60 aac acg tcc acg agc tac ctc agc aag acg ctg ttt gaa att aaa cct      241
Asn Thr Ser Thr Ser Tyr Leu Ser Lys Thr Leu Phe Glu Ile Lys Pro
         65                  70                  75 cac caa ggg cag cac atc gga gag atg agc ttt gcc aat cac act tcc      289
His Gln Gly Gln His Ile Gly Glu Met Ser Phe Ala Asn His Thr Ser
 80                  85                  90 tgc cga tgc atg tct aag ctg gat ttg gtc ttc gaa caa aaa ctc atc      337
Cys Arg Cys Met Ser Lys Leu Asp Leu Val Phe Glu Gln Lys Leu Ile
 95                 100                 105                 110 tca gaa gag gat ctg aat agc gcc gtc gac cat cat cat cat cat cat      385
Ser Glu Glu Asp Leu Asn Ser Ala Val Asp His His His His His His
             115                 120                 125 tga                                                                    388

<210> SEQ ID NO 61
<211> LENGTH: 126
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 61

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45
```

```
Arg Cys Gly Gly Cys Cys Asn Asp Glu Gly Leu Glu Cys Met Asn Thr
    50                  55                  60

Ser Thr Ser Tyr Leu Ser Lys Thr Leu Phe Glu Ile Lys Pro His Gln
 65                  70                  75                  80

Gly Gln His Ile Gly Glu Met Ser Phe Ala Asn His Thr Ser Cys Arg
                 85                  90                  95

Cys Met Ser Lys Leu Asp Leu Val Phe Glu Gln Lys Leu Ile Ser Glu
                100                 105                 110

Glu Asp Leu Asn Ser Ala Val Asp His His His His His His
                115                 120                 125
```

<210> SEQ ID NO 62
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 62

```
ggatcct ggg cag aat cat cac gaa gtg gtg aaa ttc atg gat gtc tat        49
        Gly Gln Asn His His Glu Val Val Lys Phe Met Asp Val Tyr
         1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                 35                  40                  45 gtg tac aga tgt ggg ggt tgc tgc aat agt gag ggg ctg cag tgc gtt       193
Val Tyr Arg Cys Gly Gly Cys Cys Asn Ser Glu Gly Leu Gln Cys Val
                50                  55                  60 ccc acc gag gag tcc aac atc acc atg cag att atg aga att aaa cct       241
Pro Thr Glu Glu Ser Asn Ile Thr Met Gln Ile Met Arg Ile Lys Pro
             65                  70                  75 cac caa ggg cag cac atc gga gag atg agc ttt gcc aat cac act tcc       289
His Gln Gly Gln His Ile Gly Glu Met Ser Phe Ala Asn His Thr Ser
 80                  85                  90 tgc cga tgc atg tct aag ctg gat ttg gtc ttc gaa caa aaa ctc atc       337
Cys Arg Cys Met Ser Lys Leu Asp Leu Val Phe Glu Gln Lys Leu Ile
 95                 100                 105                 110 tca gaa gag gat ctg aat agc gcc gtc gac cat cat cat cat cat           385
Ser Glu Glu Asp Leu Asn Ser Ala Val Asp His His His His His
                115                 120                 125 tga                                                                    388
```

<210> SEQ ID NO 63
<211> LENGTH: 126
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 63

```
Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
                20                  25                  30

Gly Val Ala Thr Asn Thr Phe Phe Lys Pro Pro Cys Val Ser Val Tyr
```

```
                    35                  40                  45
Arg Cys Gly Gly Cys Cys Asn Ser Glu Gly Leu Gln Cys Val Pro Thr
        50                  55                  60

Glu Glu Ser Asn Ile Thr Met Gln Ile Met Arg Ile Lys Pro His Gln
 65                  70                  75                  80

Gly Gln His Ile Gly Glu Met Ser Phe Ala Asn His Thr Ser Cys Arg
                85                  90                  95

Cys Met Ser Lys Leu Asp Leu Val Phe Glu Gln Lys Leu Ile Ser Glu
            100                 105                 110

Glu Asp Leu Asn Ser Ala Val Asp His His His His His
        115                 120                 125

<210> SEQ ID NO 64
<211> LENGTH: 388
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(385)

<400> SEQUENCE: 64 ggatcct ggg cag aat cat cac gaa gtg gtg aaa ttc atg gat gtc tat         49
        Gly Gln Asn His His Glu Val Val Lys Phe Met Asp Val Tyr
         1               5                  10 cag cgc agc tac tgc cat ccg atc gag aca ctg gtg gac atc ttc cag         97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc        145
Glu Phe Gly Val Ala Thr Asn Thr Phe Phe Lys Pro Pro Cys Val Ser
                35                  40                  45 gtg tac aga tgt ggg ggt tgc tgc aat agt gag ggg ctg cag tgc atg        193
Val Tyr Arg Cys Gly Gly Cys Cys Asn Ser Glu Gly Leu Gln Cys Met
             50                  55                  60 aac acg tcc acg agc tac ctc agc aag acg ctg ttt gaa att aaa cct        241
Asn Thr Ser Thr Ser Tyr Leu Ser Lys Thr Leu Phe Glu Ile Lys Pro
 65                  70                  75 cac caa ggg cag cac atc gga gag atg agc ttt gcc aat cac act tcc        289
His Gln Gly Gln His Ile Gly Glu Met Ser Phe Ala Asn His Thr Ser
         80                  85                  90 tgc cga tgc atg tct aag ctg gat ttg gtc ttc gaa caa aaa ctc atc        337
Cys Arg Cys Met Ser Lys Leu Asp Leu Val Phe Glu Gln Lys Leu Ile
 95                 100                 105                 110 tca gaa gag gat ctg aat agc gcc gtc gac cat cat cat cat cat            385
Ser Glu Glu Asp Leu Asn Ser Ala Val Asp His His His His His
                115                 120                 125 tga                                                                    388

<210> SEQ ID NO 65
<211> LENGTH: 126
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 65

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
            20                  25                  30
```

```
Gly Val Ala Thr Asn Thr Phe Phe Lys Pro Pro Cys Val Ser Val Tyr
         35                  40                  45

Arg Cys Gly Cys Cys Asn Ser Glu Gly Leu Gln Cys Met Asn Thr
 50                  55                  60

Ser Thr Ser Tyr Leu Ser Lys Thr Leu Phe Glu Ile Lys Pro His Gln
 65                  70                  75                  80

Gly Gln His Ile Gly Glu Met Ser Phe Ala Asn His Thr Ser Cys Arg
                 85                  90                  95

Cys Met Ser Lys Leu Asp Leu Val Phe Glu Gln Lys Leu Ile Ser Glu
             100                 105                 110

Glu Asp Leu Asn Ser Ala Val Asp His His His His His
             115                 120                 125
```

<210> SEQ ID NO 66
<211> LENGTH: 394
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(391)

<400> SEQUENCE: 66

```
ggatcct ggg cag aat cat cac gaa gtg gtg aaa ttc atg gat gtc tat     49
        Gly Gln Asn His His Glu Val Val Lys Phe Met Asp Val Tyr
         1               5                  10 cag cgc agc tac tgc cat ccg atc gag aca ctg gtg gac atc ttc cag    97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc   145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc gtt   193
Val Tyr Arg Cys Gly Gly Cys Cys Asn Asp Glu Gly Leu Glu Cys Val
             50                  55                  60 ccc acc gag gag tcc aac atc acc atg cag att atg aga att aca gtg   241
Pro Thr Glu Glu Ser Asn Ile Thr Met Gln Ile Met Arg Ile Thr Val
 65                  70                  75 cct ctc tct caa ggg ccc aaa cca gtg aca atc agc ttt ctc cag cat   289
Pro Leu Ser Gln Gly Pro Lys Pro Val Thr Ile Ser Phe Leu Gln His
         80                  85                  90 aac aaa tgt gaa tgt aga cca aag aaa gat ttg gtc ttc gaa caa aaa   337
Asn Lys Cys Glu Cys Arg Pro Lys Lys Asp Leu Val Phe Glu Gln Lys
 95                 100                 105                 110 ctc atc tca gaa gag gat ctg aat agc gcc gtc gac cat cat cat cat   385
Leu Ile Ser Glu Glu Asp Leu Asn Ser Ala Val Asp His His His His
                115                 120                 125 cat cat tga                                                       394
His His
```

<210> SEQ ID NO 67
<211> LENGTH: 128
<212> TYPE: PRT
<213> ORGANISM: Artificial Sequence
<220> FEATURE:
<223> OTHER INFORMATION: Description of Artificial Sequence:   amino
      acid sequence of hybrid DNA

<400> SEQUENCE: 67

```
Gly Gln Asn His His Glu Val Val Lys Phe Met Asp Val Tyr Gln Arg
 1               5                  10                  15
```

```
Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Asp Glu Gly Leu Glu Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Leu Gln His Asn Lys
             85                  90                  95

Cys Glu Cys Arg Pro Lys Lys Asp Leu Val Phe Glu Gln Lys Leu Ile
            100                 105                 110

Ser Glu Glu Asp Leu Asn Ser Ala Val Asp His His His His His
            115                 120                 125
```

```
<210> SEQ ID NO 68
<211> LENGTH: 394
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(391)

<400> SEQUENCE: 68
```

```
ggatcct ggg cag aat cat cac gaa gtg gtg aaa ttc atg gat gtc tat       49
        Gly Gln Asn His His Glu Val Val Lys Phe Met Asp Val Tyr
         1               5                  10 cag cgc agc tac tgc cat ccg atc gag aca ctg gtg gac atc ttc cag       97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc      145
Glu Phe Gly Val Ala Thr Asn Thr Phe Phe Lys Pro Pro Cys Val Ser
             35                  40                  45 gtg tac aga tgt ggg ggt tgc tgc aat gac gaa ggg ctg gag tgc atg      193
Val Tyr Arg Cys Gly Gly Cys Cys Asn Asp Glu Gly Leu Glu Cys Met
         50                  55                  60 aac acg tcc acg agc tac ctc agc aag acg ctg ttt gaa att aca gtg      241
Asn Thr Ser Thr Ser Tyr Leu Ser Lys Thr Leu Phe Glu Ile Thr Val
 65                  70                  75 cct ctc tct caa ggg ccc aaa cca gtg aca atc agc ttt ctc cag cat      289
Pro Leu Ser Gln Gly Pro Lys Pro Val Thr Ile Ser Phe Leu Gln His
             80                  85                  90 aac aaa tgt gaa tgt aga cca aag aaa gat ttg gtc ttc gaa caa aaa      337
Asn Lys Cys Glu Cys Arg Pro Lys Lys Asp Leu Val Phe Glu Gln Lys
 95                 100                 105                 110 ctc atc tca gaa gag gat ctg aat agc gcc gtc gac cat cat cat cat      385
Leu Ile Ser Glu Glu Asp Leu Asn Ser Ala Val Asp His His His His
            115                 120                 125 cat cat tga                                                          394
His His
```

```
<210> SEQ ID NO 69
<211> LENGTH: 128
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 69
```

```
Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
            20                  25                  30

Gly Val Ala Thr Asn Thr Phe Phe Lys Pro Pro Cys Val Ser Val Tyr
        35                  40                  45

Arg Cys Gly Gly Cys Cys Asn Asp Glu Gly Leu Glu Cys Met Asn Thr
    50                  55                  60

Ser Thr Ser Tyr Leu Ser Lys Thr Leu Phe Glu Ile Thr Val Pro Leu
65                  70                  75                  80

Ser Gln Gly Pro Lys Pro Val Thr Ile Ser Phe Leu Gln His Asn Lys
                85                  90                  95

Cys Glu Cys Arg Pro Lys Lys Asp Leu Val Phe Glu Gln Lys Leu Ile
                100                 105                 110

Ser Glu Glu Asp Leu Asn Ser Ala Val Asp His His His His His
            115                 120                 125

<210> SEQ ID NO 70
<211> LENGTH: 394
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(391)

<400> SEQUENCE: 70 ggatcct ggg cag aat cat cac gaa gtg gtg aaa ttc atg gat gtc tat       49
        Gly Gln Asn His His Glu Val Val Lys Phe Met Asp Val Tyr
         1               5                  10 cag cgc agc tac tgc cat ccg atc gag aca ctg gtg gac atc ttc cag      97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc      145
Glu Phe Gly Val Ala Thr Asn Thr Phe Phe Lys Pro Pro Cys Val Ser
                35                  40                  45 gtg tac aga tgt ggg ggt tgc tgc aat agt gag ggg ctg cag tgc gtt      193
Val Tyr Arg Cys Gly Gly Cys Cys Asn Ser Glu Gly Leu Gln Cys Val
            50                  55                  60 ccc acc gag gag tcc aac atc acc atg cag att atg aga att aca gtg      241
Pro Thr Glu Glu Ser Asn Ile Thr Met Gln Ile Met Arg Ile Thr Val
65                  70                  75 cct ctc tct caa ggg ccc aaa cca gtg aca atc agc ttt ctc cag cat      289
Pro Leu Ser Gln Gly Pro Lys Pro Val Thr Ile Ser Phe Leu Gln His
80                  85                  90 aac aaa tgt gaa tgt aga cca aag aaa gat ttg gtc ttc gaa caa aaa      337
Asn Lys Cys Glu Cys Arg Pro Lys Lys Asp Leu Val Phe Glu Gln Lys
 95                 100                 105                 110 ctc atc tca gaa gag gat ctg aat agc gcc gtc gac cat cat cat cat      385
Leu Ile Ser Glu Glu Asp Leu Asn Ser Ala Val Asp His His His His
                115                 120                 125 cat cat tga                                                          394
His His <210> SEQ ID NO 71
<211> LENGTH: 128
<212> TYPE: PRT
<213> ORGANISM: Artificial Sequence
<220> FEATURE:
<223> OTHER INFORMATION: Description of Artificial Sequence: amino acid
``` sequence of hybrid DNA

<400> SEQUENCE: 71

| Gly | Gln | Asn | His | His | Glu | Val | Val | Lys | Phe | Met | Asp | Val | Tyr | Gln | Arg |
|---|---|---|---|---|---|---|---|---|---|---|---|---|---|---|---|
| 1 | | | | 5 | | | | | 10 | | | | | 15 | |

| Ser | Tyr | Cys | His | Pro | Ile | Glu | Thr | Leu | Val | Asp | Ile | Phe | Gln | Glu | Phe |
|---|---|---|---|---|---|---|---|---|---|---|---|---|---|---|---|
| | | | 20 | | | | 25 | | | | | 30 | | | |

| Gly | Val | Ala | Thr | Asn | Thr | Phe | Phe | Lys | Pro | Pro | Cys | Val | Ser | Val | Tyr |
|---|---|---|---|---|---|---|---|---|---|---|---|---|---|---|---|
| | | 35 | | | | | 40 | | | | | 45 | | | |

| Arg | Cys | Gly | Gly | Cys | Cys | Asn | Ser | Glu | Gly | Leu | Gln | Cys | Val | Pro | Thr |
|---|---|---|---|---|---|---|---|---|---|---|---|---|---|---|---|
| | 50 | | | | | 55 | | | | | 60 | | | | |

| Glu | Glu | Ser | Asn | Ile | Thr | Met | Gln | Ile | Met | Arg | Ile | Thr | Val | Pro | Leu |
|---|---|---|---|---|---|---|---|---|---|---|---|---|---|---|---|
| 65 | | | | | 70 | | | | | 75 | | | | | 80 |

| Ser | Gln | Gly | Pro | Lys | Pro | Val | Thr | Ile | Ser | Phe | Leu | Gln | His | Asn | Lys |
|---|---|---|---|---|---|---|---|---|---|---|---|---|---|---|---|
| | | | | 85 | | | | | 90 | | | | | 95 | |

| Cys | Glu | Cys | Arg | Pro | Lys | Lys | Asp | Leu | Val | Phe | Glu | Gln | Lys | Leu | Ile |
|---|---|---|---|---|---|---|---|---|---|---|---|---|---|---|---|
| | | | | 100 | | | | | 105 | | | | | 110 | |

| Ser | Glu | Glu | Asp | Leu | Asn | Ser | Ala | Val | Asp | His | His | His | His | His | His |
|---|---|---|---|---|---|---|---|---|---|---|---|---|---|---|---|
| | 115 | | | | | 120 | | | | | 125 | | | | |

<210> SEQ ID NO 72
<211> LENGTH: 394
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(391)

<400> SEQUENCE: 72

| ggatcct | ggg | cag | aat | cat | cac | gaa | gtg | gtg | aaa | ttc | atg | gat | gtc | tat | 49 |
|---|---|---|---|---|---|---|---|---|---|---|---|---|---|---|---|
| | Gly | Gln | Asn | His | His | Glu | Val | Val | Lys | Phe | Met | Asp | Val | Tyr | |
| | 1 | | | | 5 | | | | | 10 | | | | | |

| cag | cgc | agc | tac | tgc | cat | ccg | atc | gag | aca | ctg | gtg | gac | atc | ttc | cag | 97 |
|---|---|---|---|---|---|---|---|---|---|---|---|---|---|---|---|---|
| Gln | Arg | Ser | Tyr | Cys | His | Pro | Ile | Glu | Thr | Leu | Val | Asp | Ile | Phe | Gln | |
| 15 | | | | | 20 | | | | | 25 | | | | | 30 | |

| gaa | ttt | gga | gtc | gcg | aca | aac | acc | ttc | ttc | aag | cca | cca | tgt | gtg | tcc | 145 |
|---|---|---|---|---|---|---|---|---|---|---|---|---|---|---|---|---|
| Glu | Phe | Gly | Val | Ala | Thr | Asn | Thr | Phe | Phe | Lys | Pro | Pro | Cys | Val | Ser | |
| | | | | 35 | | | | | 40 | | | | | 45 | | |

| gtg | tac | aga | tgt | ggg | ggt | tgc | tgc | aat | agt | gag | ggg | ctg | cag | tgc | atg | 193 |
|---|---|---|---|---|---|---|---|---|---|---|---|---|---|---|---|---|
| Val | Tyr | Arg | Cys | Gly | Gly | Cys | Cys | Asn | Ser | Glu | Gly | Leu | Gln | Cys | Met | |
| | | 50 | | | | | 55 | | | | | 60 | | | | |

| aac | acg | tcc | acg | agc | tac | ctc | agc | aag | acg | ctg | ttt | gaa | att | aca | gtg | 241 |
|---|---|---|---|---|---|---|---|---|---|---|---|---|---|---|---|---|
| Asn | Thr | Ser | Thr | Ser | Tyr | Leu | Ser | Lys | Thr | Leu | Phe | Glu | Ile | Thr | Val | |
| | 65 | | | | | 70 | | | | | 75 | | | | | |

| cct | ctc | tct | caa | ggg | ccc | aaa | cca | gtg | aca | atc | agc | ttt | ctc | cag | cat | 289 |
|---|---|---|---|---|---|---|---|---|---|---|---|---|---|---|---|---|
| Pro | Leu | Ser | Gln | Gly | Pro | Lys | Pro | Val | Thr | Ile | Ser | Phe | Leu | Gln | His | |
| 80 | | | | | 85 | | | | | 90 | | | | | | |

| aac | aaa | tgt | gaa | tgt | aga | cca | aag | aaa | gat | ttg | gtc | ttc | gaa | caa | aaa | 337 |
|---|---|---|---|---|---|---|---|---|---|---|---|---|---|---|---|---|
| Asn | Lys | Cys | Glu | Cys | Arg | Pro | Lys | Lys | Asp | Leu | Val | Phe | Glu | Gln | Lys | |
| 95 | | | | | 100 | | | | | 105 | | | | | 110 | |

| ctc | atc | tca | gaa | gag | gat | ctg | aat | agc | gcc | gtc | gac | cat | cat | cat | 385 |
|---|---|---|---|---|---|---|---|---|---|---|---|---|---|---|---|
| Leu | Ile | Ser | Glu | Glu | Asp | Leu | Asn | Ser | Ala | Val | Asp | His | His | His | |
| | | | | 115 | | | | | 120 | | | | | 125 | |

| cat | cat | tga | | | | | | | | | | | | | 394 |
|---|---|---|---|---|---|---|---|---|---|---|---|---|---|---|---|
| His | His | | | | | | | | | | | | | | |

<210> SEQ ID NO 73
<211> LENGTH: 128
<212> TYPE: PRT

```
<213> ORGANISM: Artificial Sequence
<220> FEATURE:
<223> OTHER INFORMATION: Description of Artificial Sequence: amino acid
      sequence of hybrid DNA

<400> SEQUENCE: 73

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Ser Glu Gly Leu Gln Cys Met Asn Thr
     50                  55                  60

Ser Thr Ser Tyr Leu Ser Lys Thr Leu Phe Glu Ile Thr Val Pro Leu
 65                  70                  75                  80

Ser Gln Gly Pro Lys Pro Val Thr Ile Ser Phe Leu Gln His Asn Lys
                 85                  90                  95

Cys Glu Cys Arg Pro Lys Lys Asp Leu Val Phe Glu Gln Lys Leu Ile
             100                 105                 110

Ser Glu Glu Asp Leu Asn Ser Ala Val Asp His His His His His
         115                 120                 125

<210> SEQ ID NO 74
<211> LENGTH: 394
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(391)

<400> SEQUENCE: 74 ggatcct ggg cag aat cat cac gaa gtg gtg aaa ttc atg gat gtc tat        49
        Gly Gln Asn His His Glu Val Val Lys Phe Met Asp Val Tyr
         1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc gtt       193
Val Tyr Arg Cys Gly Gly Cys Cys Asn Asp Glu Gly Leu Glu Cys Val
             50                  55                  60 ccc acc gag gag tcc aac atc acc atg cag att atg aga att aca gtg       241
Pro Thr Glu Glu Ser Asn Ile Thr Met Gln Ile Met Arg Ile Thr Val
 65                  70                  75 cct ctc tct caa ggg ccc aaa cca gtg aca atc agc ttt gcc aat cac       289
Pro Leu Ser Gln Gly Pro Lys Pro Val Thr Ile Ser Phe Ala Asn His
         80                  85                  90 act tcc tgc cga tgc atg tct aag ctg aat ttg gtc ttc gaa caa aaa       337
Thr Ser Cys Arg Cys Met Ser Lys Leu Asn Leu Val Phe Glu Gln Lys
 95                 100                 105                 110 ctc atc tca gaa gag gat ctg aat agc gcc gtc gac cat cat cat cat       385
Leu Ile Ser Glu Glu Asp Leu Asn Ser Ala Val Asp His His His His
                 115                 120                 125 cat cat tga                                                            394
His His
```

```
<210> SEQ ID NO 75
<211> LENGTH: 128
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 75

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Asp Glu Gly Leu Glu Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Ala Asn His Thr Ser
                 85                  90                  95

Cys Arg Cys Met Ser Lys Leu Asn Leu Val Phe Glu Gln Lys Leu Ile
            100                 105                 110

Ser Glu Glu Asp Leu Asn Ser Ala Val Asp His His His His
            115                 120                 125

<210> SEQ ID NO 76
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 76 ggatcct ggg cag aat cat cac gaa gtg gtg aaa ttc atg gat gtc tat        49
        Gly Gln Asn His His Glu Val Val Lys Phe Met Asp Val Tyr
         1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc atg       193
Val Tyr Arg Cys Gly Gly Cys Cys Asn Asp Glu Gly Leu Glu Cys Met
             50                  55                  60 aac acg tcc acg agc tac ctc agc aag acg ctg ttt gaa att aca gtg       241
Asn Thr Ser Thr Ser Tyr Leu Ser Lys Thr Leu Phe Glu Ile Thr Val
 65                  70                  75 cct ctc tct caa ggg ccc aaa cca gtg aca atc agc ttt gcc aat cac       289
Pro Leu Ser Gln Gly Pro Lys Pro Val Thr Ile Ser Phe Ala Asn His
             80                  85                  90 act tcc tgc cga tgc atg tct aag ctg gat ttg gtcttc                    328
Thr Ser Cys Arg Cys Met Ser Lys Leu Asp Leu
 95                 100                 105

<210> SEQ ID NO 77
<211> LENGTH: 105
<212> TYPE: PRT
<213> ORGANISM: Artificial Sequence
```

```
<220> FEATURE:
<223> OTHER INFORMATION: Description of Artificial Sequence:  amino acid
      sequence of hybrid DNA

<400> SEQUENCE: 77

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
            20                  25                  30

Gly Val Ala Thr Asn Thr Phe Phe Lys Pro Pro Cys Val Ser Val Tyr
        35                  40                  45

Arg Cys Gly Gly Cys Cys Asn Asp Glu Gly Leu Glu Cys Met Asn Thr
    50                  55                  60

Ser Thr Ser Tyr Leu Ser Lys Thr Leu Phe Glu Ile Thr Val Pro Leu
 65                  70                  75                  80

Ser Gln Gly Pro Lys Pro Val Thr Ile Ser Phe Ala Asn His Thr Ser
                85                  90                  95

Cys Arg Cys Met Ser Lys Leu Asp Leu
            100                 105

<210> SEQ ID NO 78
<211> LENGTH: 394
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(391)

<400> SEQUENCE: 78 ggatcct ggg cag aat cat cac gaa gtg gtg aaa ttc atg gat gtc tat        49
        Gly Gln Asn His His Glu Val Val Lys Phe Met Asp Val Tyr
         1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                 35                  40                  45 gtg tac aga tgt ggg ggt tgc tgc aat agt gag ggg ctg cag tgc gtt       193
Val Tyr Arg Cys Gly Gly Cys Cys Asn Ser Glu Gly Leu Gln Cys Val
             50                  55                  60 ccc acc gag gag tcc aac atc acc atg cag att atg aga att aca gtg       241
Pro Thr Glu Glu Ser Asn Ile Thr Met Gln Ile Met Arg Ile Thr Val
         65                  70                  75 cct ctc tct caa ggg ccc aaa cca gtg aca atc agc ttt gcc aat cac       289
Pro Leu Ser Gln Gly Pro Lys Pro Val Thr Ile Ser Phe Ala Asn His
     80                  85                  90 act tcc tgc cga tgc atg tct aag ctg gat ttg gtc ttc gaa caa aaa       337
Thr Ser Cys Arg Cys Met Ser Lys Leu Asp Leu Val Phe Glu Gln Lys
 95                 100                 105                 110 ctc atc tca gaa gag gat ctg aat agc gcc gtc gac cat cat cat cat       385
Leu Ile Ser Glu Glu Asp Leu Asn Ser Ala Val Asp His His His His
                115                 120                 125 cat cat tga                                                           394
His His <210> SEQ ID NO 79
<211> LENGTH: 128
<212> TYPE: PRT
<213> ORGANISM: Artificial Sequence
```

```
<220> FEATURE:
<223> OTHER INFORMATION: Description of Artificial Sequence: amino acid
      sequence of hybrid DNA

<400> SEQUENCE: 79

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
            20                  25                  30

Gly Val Ala Thr Asn Thr Phe Phe Lys Pro Pro Cys Val Ser Val Tyr
        35                  40                  45

Arg Cys Gly Gly Cys Cys Asn Ser Glu Gly Leu Gln Cys Val Pro Thr
 50                  55                  60

Glu Glu Ser Asn Ile Thr Met Gln Ile Met Arg Ile Thr Val Pro Leu
65                  70                  75                  80

Ser Gln Gly Pro Lys Pro Val Thr Ile Ser Phe Ala Asn His Thr Ser
                85                  90                  95

Cys Arg Cys Met Ser Lys Leu Asp Leu Val Phe Glu Gln Lys Leu Ile
            100                 105                 110

Ser Glu Glu Asp Leu Asn Ser Ala Val Asp His His His His
        115                 120                 125

<210> SEQ ID NO 80
<211> LENGTH: 392
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(169)

<400> SEQUENCE: 80 ggatcct ggg cag aat cat cac gaa gtg gtg aaa ttc atg gat gtc tat         49
        Gly Gln Asn His His Glu Val Val Lys Phe Met Asp Val Tyr
         1               5                  10 cag cgc agc tac tgc cat ccg atc gag aca ctg gtg gac atc ttc cag         97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc         145
Glu Phe Gly Val Ala Thr Asn Thr Phe Phe Lys Pro Pro Cys Val Ser
                35                  40                  45 gtg tac aga tgt ggg ttg ctg caa tagtgagggg ctgcagtgca tgaacacgtc        199
Val Tyr Arg Cys Gly Leu Leu Gln
            50 cacgagctac ctcagcaaga cgctgtttga aattacagtg cctctctctc aagggcccaa       259 accagtgaca atcagctttg ccaatcacac ttcctgccga tgcatgtcta agctggattt       319 ggtcttcgaa caaaaactca tctcagaaga ggatctgaat agcgccgtcg accatcatca       379 tcatcatcat tga                                                          392

<210> SEQ ID NO 81
<211> LENGTH: 54
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 81

Gly Gln Asn His His Glu Val Val Lys Phe Met Asp Val Tyr Gln Arg
 1               5                  10                  15
```

Ser Tyr Cys His Pro Ile Glu Thr Leu Val Asp Ile Phe Gln Glu Phe
            20                  25                  30

Gly Val Ala Thr Asn Thr Phe Phe Lys Pro Pro Cys Val Ser Val Tyr
        35                  40                  45

Arg Cys Gly Leu Leu Gln
    50

<210> SEQ ID NO 82
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 82

```
ggatcct ggg cag aat cat cac gaa gtg gtg aaa tct att gat aat gag        49
        Gly Gln Asn His His Glu Val Val Lys Ser Ile Asp Asn Glu
          1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
                 35                  40                  45 ccc ctg atg aga tgt ggg ggt tgc tgc aat gac gaa ggg ctg gag tgc       193
Pro Leu Met Arg Cys Gly Gly Cys Cys Asn Asp Glu Gly Leu Glu Cys
         50                  55                  60 gtt ccc acc gag gag tcc aac atc acc atg cag att atg aga att aaa       241
Val Pro Thr Glu Glu Ser Asn Ile Thr Met Gln Ile Met Arg Ile Lys
 65                  70                  75 cct cac caa ggg cag cac atc gga gag atg agc ttt ctc cag cat aac       289
Pro His Gln Gly Gln His Ile Gly Glu Met Ser Phe Leu Gln His Asn
         80                  85                  90 aaa tgt gaa tgt aga cca aag aaa gat ttg gtc ttc gaa caa aaa ctc       337
Lys Cys Glu Cys Arg Pro Lys Lys Asp Leu Val Phe Glu Gln Lys Leu
 95                 100                 105                 110 atc tca gaa gag gat ctg aat agc gcc gtc gac cat cat cat cat           385
Ile Ser Glu Glu Asp Leu Asn Ser Ala Val Asp His His His His
                115                 120                 125 cat tga                                                                391
His
```

<210> SEQ ID NO 83
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 83

Gly Gln Asn His His Glu Val Val Lys Ser Ile Asp Asn Glu Trp Arg
  1               5                  10                  15

Lys Thr Gln Cys Met Pro Ile Glu Thr Leu Val Asp Ile Phe Gln Glu
                 20                  25                  30

Tyr Pro Asp Glu Ile Glu Tyr Ile Phe Lys Pro Ser Cys Val Pro Leu
             35                  40                  45

Met Arg Cys Gly Gly Cys Cys Asn Asp Glu Gly Leu Glu Cys Val Pro
         50                  55                  60

```
Thr Glu Glu Ser Asn Ile Thr Met Gln Ile Met Arg Ile Lys Pro His
 65                  70                  75                  80

Gln Gly Gln His Ile Gly Glu Met Ser Phe Leu Gln His Asn Lys Cys
             85                  90                  95

Glu Cys Arg Pro Lys Lys Asp Leu Val Phe Glu Gln Lys Leu Ile Ser
            100                 105                 110

Glu Glu Asp Leu Asn Ser Ala Val Asp His His His His His
            115                 120                 125
```

```
<210> SEQ ID NO 84
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 84
```

```
ggatcct ggg cag aat cat cac gaa gtg gtg aaa tct att gat aat gag        49
        Gly Gln Asn His His Glu Val Val Lys Ser Ile Asp Asn Glu
         1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
             35                  40                  45 ccc ctg atg aga tgt ggg ggt tgc tgc aat gac gaa ggg ctg gag tgc       193
Pro Leu Met Arg Cys Gly Gly Cys Cys Asn Asp Glu Gly Leu Glu Cys
         50                  55                  60 atg aac acg tcc acg agc tac ctc agc aag acg ctg ttt gaa att aaa       241
Met Asn Thr Ser Thr Ser Tyr Leu Ser Lys Thr Leu Phe Glu Ile Lys
 65                  70                  75 cct cac caa ggg cag cac atc gga gag atg agc ttt ctc cag cat aac       289
Pro His Gln Gly Gln His Ile Gly Glu Met Ser Phe Leu Gln His Asn
         80                  85                  90 aaa tgt gaa tgt aga cca aag aaa gat ttg gtc ttc gaa caa aaa ctc       337
Lys Cys Glu Cys Arg Pro Lys Lys Asp Leu Val Phe Glu Gln Lys Leu
 95                 100                 105                 110 atc tca gaa gag gat ctg aat agc gcc gtc gac cat cat cat cat          385
Ile Ser Glu Glu Asp Leu Asn Ser Ala Val Asp His His His His
                115                 120                 125 cat tga                                                               391
His
```

```
<210> SEQ ID NO 85
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 85
```

```
Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Ser Cys Val Pro Leu
         35                  40                  45
```

```
Met Arg Cys Gly Gly Cys Cys Asn Asp Glu Gly Leu Glu Cys Met Asn
        50                  55                  60

Thr Ser Thr Ser Tyr Leu Ser Lys Thr Leu Phe Glu Ile Lys Pro His
65              70                  75                      80

Gln Gly Gln His Ile Gly Glu Met Ser Phe Leu Gln His Asn Lys Cys
                85                  90                  95

Glu Cys Arg Pro Lys Lys Asp Leu Val Phe Gln Lys Leu Ile Ser
            100                 105                 110

Glu Glu Asp Leu Asn Ser Ala Val Asp His His His His His
            115                 120                 125

<210> SEQ ID NO 86
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 86 ggatcct ggg cag aat cat cac gaa gtg gtg aaa tct att gat aat gag      49
        Gly Gln Asn His His Glu Val Val Lys Ser Ile Asp Asn Glu
        1               5                   10 tgg aga aag act cag tgc atg ccg atc gag aca ctg gtg gac atc ttc      97
Trp Arg Lys Thr Gln Cys Met Pro Ile Glu Thr Leu Val Asp Ile Phe
15                  20                  25                  30 cag gaa tac cct gat gag atc gag tac atc ttc aag cca tcc tgc gtg    145
Gln Glu Tyr Pro Asp Glu Ile Glu Tyr Ile Phe Lys Pro Ser Cys Val
                35                  40                  45 ccc ctg atg aga tgt ggg ggt tgc tgc aat agt gag ggg ctg cag tgc    193
Pro Leu Met Arg Cys Gly Gly Cys Cys Asn Ser Glu Gly Leu Gln Cys
            50                  55                  60 gtt ccc acc gag gag tcc aac atc acc atg cag att atg aga att aaa    241
Val Pro Thr Glu Glu Ser Asn Ile Thr Met Gln Ile Met Arg Ile Lys
65                  70                  75 cct cac caa ggg cag cac atc gga gag atg agc ttt ctc cag cat aac    289
Pro His Gln Gly Gln His Ile Gly Glu Met Ser Phe Leu Gln His Asn
    80                  85                  90 aaa tgt gaa tgt aga cca aag aaa gat ttg gtc ttc gaa caa aaa ctc    337
Lys Cys Glu Cys Arg Pro Lys Lys Asp Leu Val Phe Glu Gln Lys Leu
95                  100                 105                 110 atc tca gaa gag gat ctg aat agc gcc gtc gac cat cat cat cat        385
Ile Ser Glu Glu Asp Leu Asn Ser Ala Val Asp His His His His
                115                 120                 125 cat tga                                                              391
His

<210> SEQ ID NO 87
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 87

Gly Gln Asn His His Glu Val Val Lys Ser Ile Asp Asn Glu Trp Arg
1               5                   10                  15

Lys Thr Gln Cys Met Pro Ile Glu Thr Leu Val Asp Ile Phe Gln Glu
            20                  25                  30
```

```
Tyr Pro Asp Glu Ile Glu Tyr Ile Phe Lys Pro Ser Cys Val Pro Leu
        35                  40                  45

Met Arg Cys Gly Gly Cys Cys Asn Ser Glu Gly Leu Gln Cys Val Pro
    50                  55                  60

Thr Glu Glu Ser Asn Ile Thr Met Gln Ile Met Arg Ile Lys Pro His
65                  70                  75                  80

Gln Gly Gln His Ile Gly Glu Met Ser Phe Leu Gln His Asn Lys Cys
                85                  90                  95

Glu Cys Arg Pro Lys Lys Asp Leu Val Phe Glu Gln Lys Leu Ile Ser
            100                 105                 110

Glu Glu Asp Leu Asn Ser Ala Val Asp His His His His His
            115                 120                 125

<210> SEQ ID NO 88
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 88 ggatcct ggg cag aat cat cac gaa gtg gtg aaa tct att gat aat gag        49
        Gly Gln Asn His His Glu Val Val Lys Ser Ile Asp Asn Glu
        1               5                   10 tgg aga aag act cag tgc atg ccg atc gag aca ctg gtg gac atc ttc        97
Trp Arg Lys Thr Gln Cys Met Pro Ile Glu Thr Leu Val Asp Ile Phe
15                  20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
                35                  40                  45 ccc ctg atg aga tgt ggg ggt tgc tgc aat agt gag ggg ctg cag tgc       193
Pro Leu Met Arg Cys Gly Gly Cys Cys Asn Ser Glu Gly Leu Gln Cys
            50                  55                  60 atg aac acg tcc acg agc tac ctc agc aag acg ctg ttt gaa att aaa       241
Met Asn Thr Ser Thr Ser Tyr Leu Ser Lys Thr Leu Phe Glu Ile Lys
        65                  70                  75 cct cac caa ggg cag cac atc gga gag atg agc ttt ctc cag cat aac       289
Pro His Gln Gly Gln His Ile Gly Glu Met Ser Phe Leu Gln His Asn
    80                  85                  90 aaa tgt gaa tgt aga cca aag aaa gat ttg gtc ttc gaa caa aaa ctc       337
Lys Cys Glu Cys Arg Pro Lys Lys Asp Leu Val Phe Glu Gln Lys Leu
95                  100                 105                 110 atc tca gaa gag gat ctg aat agc gcc gtc gac cat cat cat cat           385
Ile Ser Glu Glu Asp Leu Asn Ser Ala Val Asp His His His His
                115                 120                 125 cat tga                                                               391
His

<210> SEQ ID NO 89
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 89

Gly Gln Asn His His Glu Val Val Lys Ser Ile Asp Asn Glu Trp Arg
1               5                   10                  15
```

```
Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Ser Cys Val Pro Leu
         35                  40                  45

Met Arg Cys Gly Gly Cys Cys Asn Ser Glu Gly Leu Gln Cys Met Asn
     50                  55                  60

Thr Ser Thr Ser Tyr Leu Ser Lys Thr Leu Phe Glu Ile Lys Pro His
 65                  70                  75                  80

Gln Gly Gln His Ile Gly Glu Met Ser Phe Leu Gln His Asn Lys Cys
                 85                  90                  95

Glu Cys Arg Pro Lys Lys Asp Leu Val Phe Glu Gln Lys Leu Ile Ser
            100                 105                 110

Glu Glu Asp Leu Asn Ser Ala Val Asp His His His His His
            115                 120                 125
```

```
<210> SEQ ID NO 90
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 90
```

```
ggatcct ggg cag aat cat cac gaa gtg gtg aaa tct att gat aat gag        49
        Gly Gln Asn His His Glu Val Val Lys Ser Ile Asp Asn Glu
         1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
                 35                  40                  45 ccc ctg atg aga tgt ggg ggt tgc tgc aat gac gaa ggg ctg gag tgc       193
Pro Leu Met Arg Cys Gly Gly Cys Cys Asn Asp Glu Gly Leu Glu Cys
         50                  55                  60 gtt ccc acc gag gag tcc aac atc acc atg cag att atg aga att aaa       241
Val Pro Thr Glu Glu Ser Asn Ile Thr Met Gln Ile Met Arg Ile Lys
 65                  70                  75 cct cac caa ggg cag cac atc gga gag atg agc ttt gcc aat cac act       289
Pro His Gln Gly Gln His Ile Gly Glu Met Ser Phe Ala Asn His Thr
 80                  85                  90 tcc tgc cga tgc atg tct aag ctg gat ttg gtc ttc gaa caa aaa ctc       337
Ser Cys Arg Cys Met Ser Lys Leu Asp Leu Val Phe Glu Gln Lys Leu
 95                 100                 105                 110 atc tca gaa gag gat ctg aat agc gcc gtc gac cat cat cat cat            385
Ile Ser Glu Glu Asp Leu Asn Ser Ala Val Asp His His His His
                115                 120                 125 cat tga                                                                 391
His
```

```
<210> SEQ ID NO 91
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 91
```

```
Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
            20                  25                  30

Tyr Pro Asp Glu Ile Glu Tyr Ile Phe Lys Pro Ser Cys Val Pro Leu
        35                  40                  45

Met Arg Cys Gly Cys Cys Asn Asp Glu Gly Leu Glu Cys Val Pro
    50                  55                  60

Thr Glu Glu Ser Asn Ile Thr Met Gln Ile Met Arg Ile Lys Pro His
65                  70                  75                  80

Gln Gly Gln His Ile Gly Glu Met Ser Phe Ala Asn His Thr Ser Cys
                85                  90                  95

Arg Cys Met Ser Lys Leu Asp Leu Val Phe Glu Gln Lys Leu Ile Ser
            100                 105                 110

Glu Glu Asp Leu Asn Ser Ala Val Asp His His His His His
            115                 120                 125
```

<210> SEQ ID NO 92
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 92

```
ggatcct ggg cag aat cat cac gaa gtg gtg aaa tct att gat aat gag        49
        Gly Gln Asn His His Glu Val Val Lys Ser Ile Asp Asn Glu
         1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
                 35                  40                  45 ccc ctg atg aga tgt ggg ggt tgc tgc aat gac gaa ggg ctg gag tgc       193
Pro Leu Met Arg Cys Gly Gly Cys Cys Asn Asp Glu Gly Leu Glu Cys
             50                  55                  60 atg aac acg tcc acg agc tac ctc agc aag acg ctg ttt gaa att aaa       241
Met Asn Thr Ser Thr Ser Tyr Leu Ser Lys Thr Leu Phe Glu Ile Lys
 65                  70                  75 cct cac caa ggg cag cac atc gga gag atg agc ttt gcc aat cac act       289
Pro His Gln Gly Gln His Ile Gly Glu Met Ser Phe Ala Asn His Thr
     80                  85                  90 tcc tgc cga tgc atg tct aag ctg gat ttg gtc ttc gaa caa aaa ctc       337
Ser Cys Arg Cys Met Ser Lys Leu Asp Leu Val Phe Glu Gln Lys Leu
 95                 100                 105                 110 atc tca gaa gag gat ctg aat agc gcc gtc gac cat cat cat cat           385
Ile Ser Glu Glu Asp Leu Asn Ser Ala Val Asp His His His His
                115                 120                 125 cat tga                                                                391
His
```

<210> SEQ ID NO 93
<211> LENGTH: 127
<212> TYPE: PRT
<213> ORGANISM: Artificial Sequence
<220> FEATURE:
<223> OTHER INFORMATION: Description of Artificial Sequence: amino acid -continued sequence of hybrid DNA

<400> SEQUENCE: 93

Gly Gln Asn His His Glu Val Val Lys Ser Ile Asp Asn Glu Trp Arg
 1               5                   10                  15

Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Ser Cys Val Pro Leu
         35                  40                  45

Met Arg Cys Gly Gly Cys Cys Asn Asp Glu Gly Leu Glu Cys Met Asn
     50                  55                  60

Thr Ser Thr Ser Tyr Leu Ser Lys Thr Leu Phe Glu Ile Lys Pro His
 65                  70                  75                  80

Gln Gly Gln His Ile Gly Glu Met Ser Phe Ala Asn His Thr Ser Cys
                 85                  90                  95

Arg Cys Met Ser Lys Leu Asp Leu Val Phe Glu Gln Lys Leu Ile Ser
            100                 105                 110

Glu Glu Asp Leu Asn Ser Ala Val Asp His His His His His His
            115                 120                 125

<210> SEQ ID NO 94
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 94 ggatcct ggg cag aat cat cac gaa gtg gtg aaa tct att gat aat gag        49
        Gly Gln Asn His His Glu Val Val Lys Ser Ile Asp Asn Glu
         1               5                   10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15              20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
             35                  40                  45 ccc ctg atg aga tgt ggg ggt tgc tgc aat agt gag ggg ctg cag tgc       193
Pro Leu Met Arg Cys Gly Gly Cys Cys Asn Ser Glu Gly Leu Gln Cys
         50                  55                  60 gtt ccc acc gag gag tcc aac atc acc atg cag att atg aga att aaa       241
Val Pro Thr Glu Glu Ser Asn Ile Thr Met Gln Ile Met Arg Ile Lys
 65                  70                  75 cct cac caa ggg cag cac atc gga gag atg agc ttt gcc aat cac act       289
Pro His Gln Gly Gln His Ile Gly Glu Met Ser Phe Ala Asn His Thr
 80                  85                  90 tcc tgc cga tgc atg tct aag ctg gat ttg gtc ttc gaa caa aaa ctc       337
Ser Cys Arg Cys Met Ser Lys Leu Asp Leu Val Phe Glu Gln Lys Leu
 95                 100                 105                 110 atc tca gaa gag gat ctg aat agc gcc gtc gac cat cat cat cat           385
Ile Ser Glu Glu Asp Leu Asn Ser Ala Val Asp His His His His
                115                 120                 125 cat tga                                                               391
His

<210> SEQ ID NO 95
<211> LENGTH: 127
<212> TYPE: PRT

```
<213> ORGANISM: Artificial Sequence
<220> FEATURE:
<223> OTHER INFORMATION: Description of Artificial Sequence: amino acid
      sequence of hybrid DNA

<400> SEQUENCE: 95

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
            20                  25                  30

Tyr Pro Asp Glu Ile Glu Tyr Ile Phe Lys Pro Ser Cys Val Pro Leu
        35                  40                  45

Met Arg Cys Gly Gly Cys Cys Asn Ser Glu Gly Leu Gln Cys Val Pro
    50                  55                  60

Thr Glu Glu Ser Asn Ile Thr Met Gln Ile Met Arg Ile Lys Pro His
65                  70                  75                  80

Gln Gly Gln His Ile Gly Glu Met Ser Phe Ala Asn His Thr Ser Cys
                85                  90                  95

Arg Cys Met Ser Lys Leu Asp Leu Val Phe Glu Gln Lys Leu Ile Ser
            100                 105                 110

Glu Glu Asp Leu Asn Ser Ala Val Asp His His His His His
            115                 120                 125

<210> SEQ ID NO 96
<211> LENGTH: 391
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(388)

<400> SEQUENCE: 96 ggatcct ggg cag aat cat cac gaa gtg gtg aaa tct att gat aat gag        49
        Gly Gln Asn His His Glu Val Val Lys Ser Ile Asp Asn Glu
         1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15              20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
                35                  40                  45 ccc ctg atg aga tgt ggg ggt tgc tgc aat agt gag ggg ctg cag tgc       193
Pro Leu Met Arg Cys Gly Gly Cys Cys Asn Ser Glu Gly Leu Gln Cys
            50                  55                  60 atg aac acg tcc acg agc tac ctc agc aag acg ctg ttt gaa att aaa       241
Met Asn Thr Ser Thr Ser Tyr Leu Ser Lys Thr Leu Phe Glu Ile Lys
 65                 70                  75 cct cac caa ggg cag cac atc gga gag atg agc ttt gcc aat cac act       289
Pro His Gln Gly Gln His Ile Gly Glu Met Ser Phe Ala Asn His Thr
         80                  85                  90 tcc tgc cga tgc atg tct aag ctg gat ttg gtc ttc gaa caa aaa ctc       337
Ser Cys Arg Cys Met Ser Lys Leu Asp Leu Val Phe Glu Gln Lys Leu
 95                 100                 105                 110 atc tca gaa gag gat ctg aat agc gcc gtc gac cat cat cat cat cat       385
Ile Ser Glu Glu Asp Leu Asn Ser Ala Val Asp His His His His His
                115                 120                 125 cat tga                                                                391
His
```

```
<210> SEQ ID NO 97
<211> LENGTH: 127
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 97

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
                20                  25                  30

Tyr Pro Asp Glu Ile Glu Tyr Ile Phe Lys Pro Ser Cys Val Pro Leu
            35                  40                  45

Met Arg Cys Gly Gly Cys Cys Asn Ser Glu Gly Leu Gln Cys Met Asn
        50                  55                  60

Thr Ser Thr Ser Tyr Leu Ser Lys Thr Leu Phe Glu Ile Lys Pro His
65                  70                  75                  80

Gln Gly Gln His Ile Gly Glu Met Ser Phe Ala Asn His Thr Ser Cys
                85                  90                  95

Arg Cys Met Ser Lys Leu Asp Leu Val Phe Glu Gln Lys Leu Ile Ser
                100                 105                 110

Glu Glu Asp Leu Asn Ser Ala Val Asp His His His His His
            115                 120                 125

<210> SEQ ID NO 98
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 98 ggatcct ggg cag aat cat cac gaa gtg gtg aaa tct att gat aat gag        49
        Gly Gln Asn His His Glu Val Val Lys Ser Ile Asp Asn Glu
         1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg       145
Gln Glu Tyr Pro Asp Glu Ile Glu Tyr Ile Phe Lys Pro Ser Cys Val
                 35                  40                  45 ccc ctg atg aga tgt ggg ggt tgc tgc aat gac gaa ggg ctg gag tgc       193
Pro Leu Met Arg Cys Gly Gly Cys Cys Asn Asp Glu Gly Leu Glu Cys
             50                  55                  60 gtt ccc acc gag gag tcc aac atc acc atg cag att atg aga att aca       241
Val Pro Thr Glu Glu Ser Asn Ile Thr Met Gln Ile Met Arg Ile Thr
         65                  70                  75 gtg cct ctc tct caa ggg ccc aaa cca gtg aca atc agc ttt ctc cag       289
Val Pro Leu Ser Gln Gly Pro Lys Pro Val Thr Ile Ser Phe Leu Gln
     80                  85                  90 cat aac aaa tgt gaa tgt aga cca aag aaa gat ttg gtc ttc gaa caa       337
His Asn Lys Cys Glu Cys Arg Pro Lys Lys Asp Leu Val Phe Glu Gln
 95                 100                 105                 110 aaa ctc atc tca gaa gag gat ctg aat agc gcc gtc gac cat cat cat       385
Lys Leu Ile Ser Glu Glu Asp Leu Asn Ser Ala Val Asp His His His
                115                 120                 125 cat cat cat tga                                                       397
```

-continued

His His His

<210> SEQ ID NO 99
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 99

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
            20                  25                  30

Tyr Pro Asp Glu Ile Glu Tyr Ile Phe Lys Pro Ser Cys Val Pro Leu
        35                  40                  45

Met Arg Cys Gly Gly Cys Cys Asn Asp Glu Gly Leu Glu Cys Val Pro
    50                  55                  60

Thr Glu Glu Ser Asn Ile Thr Met Gln Ile Met Arg Ile Thr Val Pro
65                  70                  75                  80

Leu Ser Gln Gly Pro Lys Pro Val Thr Ile Ser Phe Leu Gln His Asn
                85                  90                  95

Lys Cys Glu Cys Arg Pro Lys Lys Asp Leu Val Phe Glu Gln Lys Leu
            100                 105                 110

Ile Ser Glu Glu Asp Leu Asn Ser Ala Val Asp His His His His
        115                 120                 125

His

<210> SEQ ID NO 100
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 100 ggatcct ggg cag aat cat cac gaa gtg gtg aaa tct att gat aat gag      49
        Gly Gln Asn His His Glu Val Val Lys Ser Ile Asp Asn Glu
         1               5                  10 tgg aga aag act cag tgc atg ccg atc gag aca ctg gtg gac atc ttc      97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg     145
Gln Glu Tyr Pro Asp Glu Ile Glu Tyr Ile Phe Lys Pro Ser Cys Val
                35                  40                  45 ccc ctg atg aga tgt ggg ggt tgc tgc aat gac gaa ggg ctg gag tgc     193
Pro Leu Met Arg Cys Gly Gly Cys Cys Asn Asp Glu Gly Leu Glu Cys
            50                  55                  60 atg aac acg tcc acg agc tac ctc agc aag acg ctg ttt gaa att aca     241
Met Asn Thr Ser Thr Ser Tyr Leu Ser Lys Thr Leu Phe Glu Ile Thr
        65                  70                  75 gtg cct ctc tct caa ggg ccc aaa cca gtg aca atc agc ttt ctc cag     289
Val Pro Leu Ser Gln Gly Pro Lys Pro Val Thr Ile Ser Phe Leu Gln
    80                  85                  90 cat aac aaa tgt gaa tgt aga cca aag aaa gat ttg gtc ttc gaa caa     337
His Asn Lys Cys Glu Cys Arg Pro Lys Lys Asp Leu Val Phe Glu Gln
95                  100                 105                 110

```
aaa ctc atc tca gaa gag gat ctg aat agc gcc gtc gac cat cat cat      385
Lys Leu Ile Ser Glu Glu Asp Leu Asn Ser Ala Val Asp His His His
                115                 120                 125 cat cat cat tga                                                       397
His His His
```

<210> SEQ ID NO 101
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 101

```
Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
            20                  25                  30

Tyr Pro Asp Glu Ile Glu Tyr Ile Phe Lys Pro Ser Cys Val Pro Leu
        35                  40                  45

Met Arg Cys Gly Gly Cys Cys Asn Asp Glu Gly Leu Glu Cys Met Asn
    50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Leu Gln His Asn
            85                  90                  95

Lys Cys Glu Cys Arg Pro Lys Lys Asp Leu Val Phe Glu Gln Lys Leu
            100                 105                 110

Ile Ser Glu Glu Asp Leu Asn Ser Ala Val Asp His His His His
            115                 120                 125

His
```

<210> SEQ ID NO 102
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 102

```
ggatcct ggg cag aat cat cac gaa gtg gtg aaa tct att gat aat gag        49
        Gly Gln Asn His His Glu Val Val Lys Ser Ile Asp Asn Glu
         1               5                  10 tgg aga aag act cag tgc atg ccg atc gag aca ctg gtg gac atc ttc       97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg      145
Gln Glu Tyr Pro Asp Glu Ile Glu Tyr Ile Phe Lys Pro Ser Cys Val
                35                  40                  45 ccc ctg atg aga tgt ggg ggt tgc tgc aat agt gag ggg ctg cag tgc      193
Pro Leu Met Arg Cys Gly Gly Cys Cys Asn Ser Glu Gly Leu Gln Cys
            50                  55                  60 gtt ccc acc gag gag tcc aac atc acc atg cag att atg aga att aca      241
Val Pro Thr Glu Glu Ser Asn Ile Thr Met Gln Ile Met Arg Ile Thr
65                  70                  75 gtg cct ctc tct caa ggg ccc aaa cca gtg aca atc agc ttt ctc cag      289
Val Pro Leu Ser Gln Gly Pro Lys Pro Val Thr Ile Ser Phe Leu Gln
            80                  85                  90
```

```
cat aac aaa tgt gaa tgt aga cca aag aaa gat ttg gtc ttc gaa caa         337
His Asn Lys Cys Glu Cys Arg Pro Lys Lys Asp Leu Val Phe Glu Gln
 95             100                 105                 110 aaa ctc atc tca gaa gag gat ctg aat agc gcc gtc gac cat cat cat         385
Lys Leu Ile Ser Glu Glu Asp Leu Asn Ser Ala Val Asp His His His
            115                 120                 125 cat cat cat tga                                                         397
His His His
```

<210> SEQ ID NO 103
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 103

```
Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
            20                  25                  30

Tyr Pro Asp Glu Ile Glu Tyr Ile Phe Lys Pro Ser Cys Val Pro Leu
        35                  40                  45

Met Arg Cys Gly Gly Cys Cys Asn Ser Glu Gly Leu Gln Cys Val Pro
    50                  55                  60

Thr Glu Glu Ser Asn Ile Thr Met Gln Ile Met Arg Ile Thr Val Pro
65                  70                  75                  80

Leu Ser Gln Gly Pro Lys Pro Val Thr Ile Ser Phe Leu Gln His Asn
                85                  90                  95

Lys Cys Glu Cys Arg Pro Lys Lys Asp Leu Val Phe Glu Gln Lys Leu
            100                 105                 110

Ile Ser Glu Glu Asp Leu Asn Ser Ala Val Asp His His His His
        115                 120                 125

His
```

<210> SEQ ID NO 104
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 104

```
ggatcct ggg cag aat cat cac gaa gtg gtg aaa tct att gat aat gag         49
        Gly Gln Asn His His Glu Val Val Lys Ser Ile Asp Asn Glu
         1               5                  10 tgg aga aag act cag tgc atg ccg atc gag aca ctg gtg gac atc ttc         97
Trp Arg Lys Thr Gln Cys Met Pro Ile Glu Thr Leu Val Asp Ile Phe
 15                  20                  25                  30 cag gaa tac cct gat gag atc gag tac atc ttc aag cca tcc tgc gtg        145
Gln Glu Tyr Pro Asp Glu Ile Glu Tyr Ile Phe Lys Pro Ser Cys Val
                35                  40                  45 ccc ctg atg aga tgt ggg ggt tgc tgc aat agt gag ggg ctg cag tgc        193
Pro Leu Met Arg Cys Gly Gly Cys Cys Asn Ser Glu Gly Leu Gln Cys
            50                  55                  60 atg aac acg tcc acg agc tac ctc agc aag acg ctg ttt gaa att aca        241
Met Asn Thr Ser Thr Ser Tyr Leu Ser Lys Thr Leu Phe Glu Ile Thr
```

```
                   65                  70                  75
gtg cct ctc tct caa ggg ccc aaa cca gtg aca atc agc ttt ctc cag      289
Val Pro Leu Ser Gln Gly Pro Lys Pro Val Thr Ile Ser Phe Leu Gln
        80                  85                  90 cat aac aaa tgt gaa tgt aga cca aag aaa gat ttg gtc ttc gaa caa      337
His Asn Lys Cys Glu Cys Arg Pro Lys Lys Asp Leu Val Phe Glu Gln
 95                 100                 105                 110 aaa ctc atc tca gaa gag gat ctg aat agc gcc gtc gac cat cat cat      385
Lys Leu Ile Ser Glu Glu Asp Leu Asn Ser Ala Val Asp His His His
                115                 120                 125 cat cat cat tga                                                      397
His His His <210> SEQ ID NO 105
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 105

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
            20                  25                  30

Tyr Pro Asp Glu Ile Glu Tyr Ile Phe Lys Pro Ser Cys Val Pro Leu
        35                  40                  45

Met Arg Cys Gly Gly Cys Cys Asn Ser Glu Gly Leu Gln Cys Met Asn
    50                  55                  60

Thr Ser Thr Ser Tyr Leu Ser Lys Thr Leu Phe Glu Ile Thr Val Pro
 65                 70                  75                  80

Leu Ser Gln Gly Pro Lys Pro Val Thr Ile Ser Phe Leu Gln His Asn
                85                  90                  95

Lys Cys Glu Cys Arg Pro Lys Lys Asp Leu Val Phe Glu Gln Lys Leu
            100                 105                 110

Ile Ser Glu Glu Asp Leu Asn Ser Ala Val Asp His His His His His
        115                 120                 125

His

<210> SEQ ID NO 106
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 106 ggatcct ggg cag aat cat cac gaa gtg gtg aaa tct att gat aat gag      49
        Gly Gln Asn His His Glu Val Val Lys Ser Ile Asp Asn Glu
         1               5                  10 tgg aga aag act cag tgc atg ccg atc gag aca ctg gtg gac atc ttc      97
Trp Arg Lys Thr Gln Cys Met Pro Ile Glu Thr Leu Val Asp Ile Phe
 15                 20                  25                  30 cag gaa tac cct gat gag atc gag tac atc ttc aag cca tcc tgc gtg     145
Gln Glu Tyr Pro Asp Glu Ile Glu Tyr Ile Phe Lys Pro Ser Cys Val
                35                  40                  45 ccc ctg atg aga tgt ggg ggt tgc tgc aat gac gaa ggg ctg gag tgc     193
```

```
                Pro Leu Met Arg Cys Gly Gly Cys Cys Asn Asp Glu Gly Leu Glu Cys
                                 50                  55                  60 gtt ccc acc gag gag tcc aac atc acc atg cag att atg aga att aca                 241
Val Pro Thr Glu Glu Ser Asn Ile Thr Met Gln Ile Met Arg Ile Thr
             65                  70                  75 gtg cct ctc tct caa ggg ccc aaa cca gtg aca atc agc ttt gcc aat                 289
Val Pro Leu Ser Gln Gly Pro Lys Pro Val Thr Ile Ser Phe Ala Asn
 80                  85                  90 cac act tcc tgc cga tgc atg tct aag ctg gat ttg gtc ttc gaa caa                 337
His Thr Ser Cys Arg Cys Met Ser Lys Leu Asp Leu Val Phe Glu Gln
 95                 100                 105                 110 aaa ctc atc tca gaa gag gat ctg aat agc gcc gtc gac cat cat cat                 385
Lys Leu Ile Ser Glu Glu Asp Leu Asn Ser Ala Val Asp His His His
                115                 120                 125 cat cat cat tga                                                                 397
His His His
```

```
<210> SEQ ID NO 107
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 107

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Ser Cys Val Pro Leu
         35                  40                  45

Met Arg Cys Gly Gly Cys Cys Asn Asp Glu Gly Leu Glu Cys Val Pro
     50                  55                  60

Thr Glu Glu Ser Asn Ile Thr Met Gln Ile Met Arg Ile Thr Val Pro
 65                  70                  75                  80

Leu Ser Gln Gly Pro Lys Pro Val Thr Ile Ser Phe Ala Asn His Thr
                 85                  90                  95

Ser Cys Arg Cys Met Ser Lys Leu Asp Leu Val Phe Glu Gln Lys Leu
            100                 105                 110

Ile Ser Glu Glu Asp Leu Asn Ser Ala Val Asp His His His His His
        115                 120                 125

His
```

```
<210> SEQ ID NO 108
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 108 ggatcct ggg cag aat cat cac gaa gtg gtg aaa tct att gat aat gag           49
        Gly Gln Asn His His Glu Val Val Lys Ser Ile Asp Asn Glu
         1               5                  10 tgg aga aag act cag tgc atg ccg atc gag aca ctg gtg gac atc ttc           97
Trp Arg Lys Thr Gln Cys Met Pro Ile Glu Thr Leu Val Asp Ile Phe
 15                  20                  25                  30
```

```
cag gaa tac cct gat gag atc gag tac atc ttc aag cca tcc tgc gtg      145
Gln Glu Tyr Pro Asp Glu Ile Glu Tyr Ile Phe Lys Pro Ser Cys Val
             35                  40                  45 ccc ctg atg aga tgt ggg ggt tgc tgc aat gac gaa ggg ctg gag tgc      193
Pro Leu Met Arg Cys Gly Gly Cys Cys Asn Asp Glu Gly Leu Glu Cys
         50                  55                  60 atg aac acg tcc acg agc tac ctc agc aag acg ctg ttt gaa att aca      241
Met Asn Thr Ser Thr Ser Tyr Leu Ser Lys Thr Leu Phe Glu Ile Thr
     65                  70                  75 gtg cct ctc tct caa ggg ccc aaa cca gtg aca atc agc ttt gcc aat      289
Val Pro Leu Ser Gln Gly Pro Lys Pro Val Thr Ile Ser Phe Ala Asn
 80                  85                  90 cac act tcc tgc cga tgc atg tct aag ctg gat ttg gtc ttc gaa caa      337
His Thr Ser Cys Arg Cys Met Ser Lys Leu Asp Leu Val Phe Glu Gln
 95                 100                 105                 110 aaa ctc atc tca gaa gag gat ctg aat agc gcc gtc gac cat cat cat      385
Lys Leu Ile Ser Glu Glu Asp Leu Asn Ser Ala Val Asp His His His
                115                 120                 125 cat cat cat tga                                                       397
His His His
```

```
<210> SEQ ID NO 109
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 109

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Ser Cys Val Pro Leu
         35                  40                  45

Met Arg Cys Gly Gly Cys Cys Asn Asp Glu Gly Leu Glu Cys Met Asn
     50                  55                  60

Thr Ser Thr Ser Tyr Leu Ser Lys Thr Leu Phe Glu Ile Thr Val Pro
 65                  70                  75                  80

Leu Ser Gln Gly Pro Lys Pro Val Thr Ile Ser Phe Ala Asn His Thr
                 85                  90                  95

Ser Cys Arg Cys Met Ser Lys Leu Asp Leu Val Phe Glu Gln Lys Leu
            100                 105                 110

Ile Ser Glu Glu Asp Leu Asn Ser Ala Val Asp His His His His His
        115                 120                 125

His
```

```
<210> SEQ ID NO 110
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

<400> SEQUENCE: 110 ggatcct ggg cag aat cat cac gaa gtg gtg aaa tct att gat aat gag       49
        Gly Gln Asn His His Glu Val Val Lys Ser Ile Asp Asn Glu
         1               5                  10
```

-continued

```
tgg aga aag act cag tgc atg ccg atc gag aca ctg gtg gac atc ttc    97
Trp Arg Lys Thr Gln Cys Met Pro Ile Glu Thr Leu Val Asp Ile Phe
 15              20                  25                  30 cag gaa tac cct gat gag atc gag tac atc ttc aag cca tcc tgc gtg   145
Gln Glu Tyr Pro Asp Glu Ile Glu Tyr Ile Phe Lys Pro Ser Cys Val
                 35                  40                  45 ccc ctg atg aga tgt ggg ggt tgc tgc aat agt gag ggg ctg cag tgc   193
Pro Leu Met Arg Cys Gly Gly Cys Cys Asn Ser Glu Gly Leu Gln Cys
             50                  55                  60 gtt ccc acc gag gag tcc aac atc acc atg cag att atg aga att aca   241
Val Pro Thr Glu Glu Ser Asn Ile Thr Met Gln Ile Met Arg Ile Thr
         65                  70                  75 gtg cct ctc tct caa ggg ccc aaa cca gtg aca atc agc ttt gcc aat   289
Val Pro Leu Ser Gln Gly Pro Lys Pro Val Thr Ile Ser Phe Ala Asn
     80                  85                  90 cac act tcc tgc cga tgc atg tct aag ctg gat ttg gtc ttc gaa caa   337
His Thr Ser Cys Arg Cys Met Ser Lys Leu Asp Leu Val Phe Glu Gln
 95                 100                 105                 110 aaa ctc atc tca gaa gag gat ctg aat agc gcc gtc gac cat cat cat   385
Lys Leu Ile Ser Glu Glu Asp Leu Asn Ser Ala Val Asp His His His
                115                 120                 125 cat cat cat tga                                                    397
His His His
```

<210> SEQ ID NO 111
<211> LENGTH: 129
<212> TYPE: PRT
<213> ORGANISM: Artificial Sequence
<220> FEATURE:
<223> OTHER INFORMATION: Description of Artificial Sequence: amino acid
       sequence of hybrid DNA

<400> SEQUENCE: 111

```
Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Ser Cys Val Pro Leu
         35                  40                  45

Met Arg Cys Gly Gly Cys Cys Asn Ser Glu Gly Leu Gln Cys Val Pro
     50                  55                  60

Thr Glu Glu Ser Asn Ile Thr Met Gln Ile Met Arg Ile Thr Val Pro
 65                  70                  75                  80

Leu Ser Gln Gly Pro Lys Pro Val Thr Ile Ser Phe Ala Asn His Thr
                 85                  90                  95

Ser Cys Arg Cys Met Ser Lys Leu Asp Leu Val Phe Glu Gln Lys Leu
            100                 105                 110

Ile Ser Glu Glu Asp Leu Asn Ser Ala Val Asp His His His His
        115                 120                 125

His
```

<210> SEQ ID NO 112
<211> LENGTH: 397
<212> TYPE: DNA
<213> ORGANISM: Artificial Sequence
<220> FEATURE:
<223> OTHER INFORMATION: Description of Artificial Sequence: Hybrid DNA
<221> NAME/KEY: CDS
<222> LOCATION: (8)..(394)

```
<400> SEQUENCE: 112 ggatcct ggg cag aat cat cac gaa gtg gtg aaa tct att gat aat gag      49
        Gly Gln Asn His His Glu Val Val Lys Ser Ile Asp Asn Glu
         1               5                  10 tgg aga aag act cag tgc atg ccg atc gag aca ctg gtg gac atc ttc      97
Trp Arg Lys Thr Gln Cys Met Pro Ile Glu Thr Leu Val Asp Ile Phe
 15              20                  25                  30 cag gaa tac cct gat gag atc gag tac atc ttc aag cca tcc tgc gtg     145
Gln Glu Tyr Pro Asp Glu Ile Glu Tyr Ile Phe Lys Pro Ser Cys Val
                 35                  40                  45 ccc ctg atg aga tgt ggg ggt tgc tgc aat agt gag ggg ctg cag tgc     193
Pro Leu Met Arg Cys Gly Gly Cys Cys Asn Ser Glu Gly Leu Gln Cys
             50                  55                  60 atg aac acg tcc acg agc tac ctc agc aag acg ctg ttt gaa att aca     241
Met Asn Thr Ser Thr Ser Tyr Leu Ser Lys Thr Leu Phe Glu Ile Thr
                 65                  70                  75 gtg cct ctc tct caa ggg ccc aaa cca gtg aca atc agc ttt gcc aat     289
Val Pro Leu Ser Gln Gly Pro Lys Pro Val Thr Ile Ser Phe Ala Asn
 80                  85                  90 cac act tcc tgc cga tgc atg tct aag ctg gat ttg gtc ttc gaa caa     337
His Thr Ser Cys Arg Cys Met Ser Lys Leu Asp Leu Val Phe Glu Gln
 95                 100                 105                 110 aaa ctc atc tca gaa gag gat ctg aat agc gcc gtc gac cat cat cat     385
Lys Leu Ile Ser Glu Glu Asp Leu Asn Ser Ala Val Asp His His His
                115                 120                 125 cat cat cat tga                                                     397
His His His <210> SEQ ID NO 113
<211> LENGTH: 129
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 113

Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
                 20                  25                  30

Tyr Pro Asp Glu Ile Glu Tyr Ile Phe Lys Pro Ser Cys Val Pro Leu
             35                  40                  45

Met Arg Cys Gly Gly Cys Cys Asn Ser Glu Gly Leu Gln Cys Met Asn
         50                  55                  60

Thr Ser Thr Ser Tyr Leu Ser Lys Thr Leu Phe Glu Ile Thr Val Pro
 65                  70                  75                  80

Leu Ser Gln Gly Pro Lys Pro Val Thr Ile Ser Phe Ala Asn His Thr
                 85                  90                  95

Ser Cys Arg Cys Met Ser Lys Leu Asp Leu Val Phe Glu Gln Lys Leu
            100                 105                 110

Ile Ser Glu Glu Asp Leu Asn Ser Ala Val Asp His His His His His
        115                 120                 125

His

<210> SEQ ID NO 114
<211> LENGTH: 1645
<212> TYPE: DNA
<213> ORGANISM: Homo sapiens
```

<220> FEATURE:
<221> NAME/KEY: CDS
<222> LOCATION: (322)..(768)

<400> SEQUENCE: 114

```
gggattcggg ccgcccagct acgggaggac ctggagtggc actgggcgcc cgacggacca      60
tccccgggac ccgcctgccc ctcggcgccc cgcccgccg gccgctccc cgtcgggttc       120 cccagccaca gccttaccta cgggctcctg actccgcaag gcttccagaa gatgctcgaa     180
ccaccggccg gggcctcggg gcagcagtga gggaggcgtc cagcccccca ctcagctctt     240
ctcctcctgt gccaggggct ccccggggga tgagcatggt ggttttccct cggagccccc    300
tggctcggga cgtctgagaa g atg ccg gtc atg agg ctg ttc cct tgc ttc       351
                       Met Pro Val Met Arg Leu Phe Pro Cys Phe
                        1               5                  10 ctg cag ctc ctg gcc ggg ctg gcg ctg cct gct gtg ccc ccc cag cag       399
Leu Gln Leu Leu Ala Gly Leu Ala Leu Pro Ala Val Pro Pro Gln Gln
            15                  20                  25 tgg gcc ttg tct gct ggg aac ggc tcg tca gag gtg gaa gtg gta ccc       447
Trp Ala Leu Ser Ala Gly Asn Gly Ser Ser Glu Val Glu Val Val Pro
30                  35                  40 ttc cag gaa gtg tgg ggc cgc agc tac tgc cgg gcg ctg gag agg ctg       495
Phe Gln Glu Val Trp Gly Arg Ser Tyr Cys Arg Ala Leu Glu Arg Leu
        45                  50                  55 gtg gac gtc gtg tcc gag tac ccc agc gag gtg gag cac atg ttc agc       543
Val Asp Val Val Ser Glu Tyr Pro Ser Glu Val Glu His Met Phe Ser
    60                  65                  70 cca tcc tgt gtc tcc ctg ctg cgc tgc acc ggc tgc tgc ggc gat gag       591
Pro Ser Cys Val Ser Leu Leu Arg Cys Thr Gly Cys Cys Gly Asp Glu
75                  80                  85                  90 aat ctg cac tgt gtg ccg gtg gag acg gcc aat gtc acc atg cag ctc       639
Asn Leu His Cys Val Pro Val Glu Thr Ala Asn Val Thr Met Gln Leu
                95                  100                 105 cta aag atc cgt tct ggg gac cgg ccc tcc tac gtg gag ctg acg ttc       687
Leu Lys Ile Arg Ser Gly Asp Arg Pro Ser Tyr Val Glu Leu Thr Phe
            110                 115                 120 tct cag cac gtt cgc tgc gaa tgc cgg cct ctg cgg gag aag atg aag       735
Ser Gln His Val Arg Cys Glu Cys Arg Pro Leu Arg Glu Lys Met Lys
        125                 130                 135 ccg gaa agg tgc ggc gat gct gtt ccc cgg agg taacccaccc cttggaggag     788
Pro Glu Arg Cys Gly Asp Ala Val Pro Arg Arg
    140                 145 agagaccccg cacccggctc gtgtatttat taccgtcaca ctcttcagtg actcctgctg    848
gtacctgccc tctatttatt agccaactgt ttccctgctg aatgcctcgc tcccttcaag   908 acgagggca gggaaggaca ggaccctcag gaattcagtg ccttcaacaa cgtgagagaa    968
agagagaagc cagccacaga cccctgggag cttccgcttt gaaagaagca agacacgtgg   1028
cctcgtgagg ggcaagctag gccccagagg ccctggaggt ctccagggc ctgcagaagg    1088 aaagaagggg gccctgctac ctgttcttgg gcctcaggct ctgcacagac aagcagccct   1148
tgctttcgga gctcctgtcc aaagtaggga tgcggattct gctggggccg ccacggcctg   1208
gtggtgggaa ggccggcagc gggcggaggg gattcagcca cttccccctc ttcttctgaa   1268
gatcagaaca ttcagctctg gagaacagtg gttgcctggg gcttttgcc actccttgtc    1328 ccccgtgatc tcccctcaca ctttgccatt tgcttgtact gggacattgt tctttccggc   1388
cgaggtgcca ccaccctgcc cccactaaga gacacataca gagtgggccc cgggctggag   1448
aaagagctgc ctggatgaga aacagctcag ccagtgggga tgaggtcacc aggggaggag   1508
```

```
cctgtgcgtc ccagctgaag gcagtggcag gggagcaggt tccccaaggg ccctggcacc    1568
cccacaagct gtccctgcag ggccatctga ctgccaagcc agattctctt gaataaagta    1628
ttctagtgtg gaaacgc                                                    1645

<210> SEQ ID NO 115
<211> LENGTH: 149
<212> TYPE: PRT
<213> ORGANISM: Homo sapiens

<400> SEQUENCE: 115

Met Pro Val Met Arg Leu Phe Pro Cys Phe Leu Gln Leu Leu Ala Gly
 1               5                  10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140

Ala Val Pro Arg Arg
145

<210> SEQ ID NO 116
<211> LENGTH: 570
<212> TYPE: DNA
<213> ORGANISM: Homo sapiens
<220> FEATURE:
<221> NAME/KEY: CDS
<222> LOCATION: (4)..(570)

<400> SEQUENCE: 116 acc atg agc cct ctg ctc cgc cgc ctg ctg ctc gcc gca ctc ctg cag       48
    Met Ser Pro Leu Leu Arg Arg Leu Leu Leu Ala Ala Leu Leu Gln
     1               5                  10                  15 ctg gcc ccc gcc cag gcc cct gtc tcc cag cct gat gcc cct ggc cac       96
Leu Ala Pro Ala Gln Ala Pro Val Ser Gln Pro Asp Ala Pro Gly His
            20                  25                  30 cag agg aaa gtg gtg tca tgg ata gat gtg tat act cgc gct acc tgc      144
Gln Arg Lys Val Val Ser Trp Ile Asp Val Tyr Thr Arg Ala Thr Cys
        35                  40                  45 cag ccc cgg gag gtg gtg gtg ccc ttg act gtg gag ctc atg ggc acc      192
Gln Pro Arg Glu Val Val Val Pro Leu Thr Val Glu Leu Met Gly Thr
    50                  55                  60 gtg gcc aaa cag ctg gtg ccc agc tgc gtg act gtg cag cgc tgt ggt      240
Val Ala Lys Gln Leu Val Pro Ser Cys Val Thr Val Gln Arg Cys Gly
65                  70                  75 ggc tgc tgc cct gac gat ggc ctg gag tgt gtg ccc act ggg cag cac      288
Gly Cys Cys Pro Asp Asp Gly Leu Glu Cys Val Pro Thr Gly Gln His
                85                  90                  95
```

```
caa gtc cgg atg cag atc ctc atg atc cgg tac ccg agc agt cag ctg      336
Gln Val Arg Met Gln Ile Leu Met Ile Arg Tyr Pro Ser Ser Gln Leu
            100                 105                 110 ggg gag atg tcc ctg gaa gaa cac agc cag tgt gaa tgc aga cct aaa      384
Gly Glu Met Ser Leu Glu Glu His Ser Gln Cys Glu Cys Arg Pro Lys
    115                 120                 125 aaa aag gac agt gct gtg aag cca gac agc ccc agg ccc ctc tgc cca      432
Lys Lys Asp Ser Ala Val Lys Pro Asp Ser Pro Arg Pro Leu Cys Pro
130                 135                 140 cgc tgc acc cag cac cac cag cgc cct gac ccc cgg acc tgc cgc tgc      480
Arg Cys Thr Gln His His Gln Arg Pro Asp Pro Arg Thr Cys Arg Cys
145                 150                 155 cgc tgc cga cgc cgc agc ttc ctc cgt tgc caa ggg cgg ggc tta gag      528
Arg Cys Arg Arg Arg Ser Phe Leu Arg Cys Gln Gly Arg Gly Leu Glu
160                 165                 170                 175 ctc aac cca gac acc tgc agg tgc cgg aag ctg cga agg tga              570
Leu Asn Pro Asp Thr Cys Arg Cys Arg Lys Leu Arg Arg
                180                 185

<210> SEQ ID NO 117
<211> LENGTH: 188
<212> TYPE: PRT
<213> ORGANISM: Homo sapiens

<400> SEQUENCE: 117

Met Ser Pro Leu Leu Arg Arg Leu Leu Leu Ala Ala Leu Leu Gln Leu
 1               5                  10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
    130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185

<210> SEQ ID NO 118
<211> LENGTH: 2029
<212> TYPE: DNA
<213> ORGANISM: Homo sapiens
<220> FEATURE:
<221> NAME/KEY: CDS
<222> LOCATION: (411)..(1472)

<400> SEQUENCE: 118
```

-continued

```
gttgggttcc agctttctgt agctgtaagc attggtggcc acaccacctc cttacaaagc      60
aactagaacc tgcggcatac attggagaga ttttttaat tttctggaca tgaagtaaat      120
ttagagtgct ttctaatttc aggtagaaga catgtccacc ttctgattat ttttggagaa     180
cattttgatt tttttcatct ctctctcccc acccctaaga ttgtgcaaaa aaagcgtacc     240
ttgcctaatt gaaataattt cattggattt tgatcagaac tgattatttg gttttctgtg     300
tgaagttttg aggtttcaaa ctttccttct ggagaatgcc ttttgaaaca attttctcta     360
gctgcctgat gtcaactgct tagtaatcag tggatattga aatattcaaa atg tac       416
                                                       Met Tyr
                                                         1 aga gag tgg gta gtg gtg aat gtt ttc atg atg ttg tac gtc cag ctg       464
Arg Glu Trp Val Val Val Asn Val Phe Met Met Leu Tyr Val Gln Leu
        5                  10                  15 gtg cag ggc tcc agt aat gaa cat gga cca gtg aag cga tca tct cag       512
Val Gln Gly Ser Ser Asn Glu His Gly Pro Val Lys Arg Ser Ser Gln
 20                  25                  30 tcc aca ttg gaa cga tct gaa cag cag atc agg gct gct tct agt ttg       560
Ser Thr Leu Glu Arg Ser Glu Gln Gln Ile Arg Ala Ala Ser Ser Leu
 35                  40                  45                  50 gag gaa cta ctt cga att act cac tct gag gac tgg aag ctg tgg aga       608
Glu Glu Leu Leu Arg Ile Thr His Ser Glu Asp Trp Lys Leu Trp Arg
                 55                  60                  65 tgc agg ctg agg ctc aaa agt ttt acc agt atg gac tct cgc tca gca       656
Cys Arg Leu Arg Leu Lys Ser Phe Thr Ser Met Asp Ser Arg Ser Ala
             70                  75                  80 tcc cat cgg tcc act agg ttt gcg gca act ttc tat gac att gaa aca       704
Ser His Arg Ser Thr Arg Phe Ala Ala Thr Phe Tyr Asp Ile Glu Thr
         85                  90                  95 cta aaa gtt ata gat gaa gaa tgg caa aga act cag tgc agc cct aga       752
Leu Lys Val Ile Asp Glu Glu Trp Gln Arg Thr Gln Cys Ser Pro Arg
100                 105                 110 gaa acg tgc gtg gag gtg gcc agt gag ctg ggg aag agt acc aac aca       800
Glu Thr Cys Val Glu Val Ala Ser Glu Leu Gly Lys Ser Thr Asn Thr
115                 120                 125                 130 ttc ttc aag ccc cct tgt gtg aac gtg ttc cga tgt ggt ggc tgt tgc       848
Phe Phe Lys Pro Pro Cys Val Asn Val Phe Arg Cys Gly Gly Cys Cys
                135                 140                 145 aat gaa gag agc ctt atc tgt atg aac acc agc acc tcg tac att tcc       896
Asn Glu Glu Ser Leu Ile Cys Met Asn Thr Ser Thr Ser Tyr Ile Ser
            150                 155                 160 aaa cag ctc ttt gag ata tca gtg cct ttg aca tca gta cct gaa tta       944
Lys Gln Leu Phe Glu Ile Ser Val Pro Leu Thr Ser Val Pro Glu Leu
        165                 170                 175 gtg cct gtt aaa gtt gcc aat cat aca ggt tgt aag tgc ttg cca aca       992
Val Pro Val Lys Val Ala Asn His Thr Gly Cys Lys Cys Leu Pro Thr
    180                 185                 190 gcc ccc cgc cat cca tac tca att atc aga aga tcc atc cag atc cct       1040
Ala Pro Arg His Pro Tyr Ser Ile Ile Arg Arg Ser Ile Gln Ile Pro
195                 200                 205                 210 gaa gaa gat cgc tgt tcc cat tcc aag aaa ctc tgt cct att gac atg       1088
Glu Glu Asp Arg Cys Ser His Ser Lys Lys Leu Cys Pro Ile Asp Met
                215                 220                 225 cta tgg gat agc aac aaa tgt aaa tgt gtt ttg cag gag gaa aat cca       1136
Leu Trp Asp Ser Asn Lys Cys Lys Cys Val Leu Gln Glu Glu Asn Pro
            230                 235                 240 ctt gct gga aca gaa gac cac tct cat ctc cag gaa cca gct ctc tgt       1184
Leu Ala Gly Thr Glu Asp His Ser His Leu Gln Glu Pro Ala Leu Cys
```

-continued

```
                   245                 250                 255
ggg cca cac atg atg ttt gac gaa gat cgt tgc gag tgt gtc tgt aaa    1232
Gly Pro His Met Met Phe Asp Glu Asp Arg Cys Glu Cys Val Cys Lys
        260                 265                 270 aca cca tgt ccc aaa gat cta atc cag cac ccc aaa aac tgc agt tgc    1280
Thr Pro Cys Pro Lys Asp Leu Ile Gln His Pro Lys Asn Cys Ser Cys
275                 280                 285                 290 ttt gag tgc aaa gaa agt ctg gag acc tgc tgc cag aag cac aag cta    1328
Phe Glu Cys Lys Glu Ser Leu Glu Thr Cys Cys Gln Lys His Lys Leu
                295                 300                 305 ttt cac cca gac acc tgc agc tgt gag gac aga tgc ccc ttt cat acc    1376
Phe His Pro Asp Thr Cys Ser Cys Glu Asp Arg Cys Pro Phe His Thr
            310                 315                 320 aga cca tgt gca agt ggc aaa aca gca tgt gca aag cat tgc cgc ttt    1424
Arg Pro Cys Ala Ser Gly Lys Thr Ala Cys Ala Lys His Cys Arg Phe
        325                 330                 335 cca aag gag aaa agg gct gcc cag ggg ccc cac agc cga aag aat cct    1472
Pro Lys Glu Lys Arg Ala Ala Gln Gly Pro His Ser Arg Lys Asn Pro
    340                 345                 350 tgattcagcg ttccaagttc cccatccctg tcattttaa cagcatgctg ctttgccaag   1532
ttgctgtcac tgttttttc ccaggtgtta aaaaaaaaat ccattttaca cagcaccaca   1592
gtgaatccag accaaccttc cattcacacc agctaaggag tccctggttc attgatggat   1652
gtcttctagc tgcagatgcc tctgcgcacc aaggaatgga gaggagggga cccatgtaat   1712
ccttttgttt agttttgttt ttgttttttg gtgaatgaga aagtgtgct ggtcatggaa    1772
tggcaggtgt catatgactg attactcaga gcagatgagg aaaactgtag tctctgagtc   1832
ctttgctaat cgcaactctt gtgaattatt ctgattcttt tttatgcaga atttgattcg   1892
tatgatcagt actgactttc tgattactgt ccagcttata gtcttccagt ttaatgaact   1952
accatctgat gtttcatatt taagtgtatt taaagaaaat aaacaccatt attcaagcca   2012
aaaaaaaaaa aaaaaa                                                   2029
```

<210> SEQ ID NO 119
<211> LENGTH: 354
<212> TYPE: PRT
<213> ORGANISM: Homo sapiens

<400> SEQUENCE: 119

```
Met Tyr Arg Glu Trp Val Val Asn Val Phe Met Met Leu Tyr Val
  1               5                  10                  15

Gln Leu Val Gln Gly Ser Ser Asn Glu His Gly Pro Val Lys Arg Ser
             20                  25                  30

Ser Gln Ser Thr Leu Glu Arg Ser Glu Gln Ile Arg Ala Ala Ser
         35                  40                  45

Ser Leu Glu Glu Leu Leu Arg Ile Thr His Ser Glu Asp Trp Lys Leu
     50                  55                  60

Trp Arg Cys Arg Leu Arg Leu Lys Ser Phe Thr Ser Met Asp Ser Arg
 65                  70                  75                  80

Ser Ala Ser His Arg Ser Thr Arg Phe Ala Ala Thr Phe Tyr Asp Ile
                 85                  90                  95

Glu Thr Leu Lys Val Ile Asp Glu Glu Trp Gln Arg Thr Gln Cys Ser
                100                 105                 110

Pro Arg Glu Thr Cys Val Glu Val Ala Ser Glu Leu Gly Lys Ser Thr
            115                 120                 125

Asn Thr Phe Phe Lys Pro Pro Cys Val Asn Val Phe Arg Cys Gly Gly
```

```
            130                 135                 140
Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Ser Ile Gln
        195                 200                 205

Ile Pro Glu Glu Asp Arg Cys Ser His Ser Lys Lys Leu Cys Pro Ile
210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 120
<211> LENGTH: 1830
<212> TYPE: DNA
<213> ORGANISM: Orf virus
<220> FEATURE:
<221> NAME/KEY: CDS
<222> LOCATION: (312)..(755)

<400> SEQUENCE: 120
cggccacgcg gccgcgaact gcgcgctcgc gcgcgtggcg accgcgctga cgcgccgcgt      60
gcccgcgagc cggcacggcc tcgcggaggg cggcacgccg ccgtggacgc tgctgctggc     120
ggtggccgcg gtggcggtgc tcggcgtggt ggcaatttcg ctgctgcgcc gcgcgctaag     180
aatacggttt agatactcaa agtctatcca gacacttaga gtgtaacttt gagtaaaaaa     240
tgtaaatact aacgccaaaa tttcgatagt tgttaagcaa tatataacat ttttaaaacg     300
tcatcaccag c atg aag tta aca gct acg tta caa gtt gtt gtt gca ttg     350
            Met Lys Leu Thr Ala Thr Leu Gln Val Val Val Ala Leu
              1               5                  10 tta ata tgt atg tat aat ttg cca gaa tgc gtg tct cag agt aat gat     398
Leu Ile Cys Met Tyr Asn Leu Pro Glu Cys Val Ser Gln Ser Asn Asp
        15                  20                  25 tca cct cct tca acc aat gac tgg atg cgt aca cta gac aaa agt ggt     446
Ser Pro Pro Ser Thr Asn Asp Trp Met Arg Thr Leu Asp Lys Ser Gly
 30                  35                  40                  45 tgt aaa cct aga gat act gtt gtt tat ttg gga gaa gaa tat cca gaa     494
Cys Lys Pro Arg Asp Thr Val Val Tyr Leu Gly Glu Glu Tyr Pro Glu
                50                  55                  60
```

-continued

| | | |
|---|---|---|
| agc act aac cta caa tat aat ccc cgg tgc gta act gtt aaa cga tgc<br>Ser Thr Asn Leu Gln Tyr Asn Pro Arg Cys Val Thr Val Lys Arg Cys<br>                  65                          70                          75 | 542 |
| agt ggt tgc tgt aac ggt gac ggt caa ata tgt aca gcg gtt gaa aca<br>Ser Gly Cys Cys Asn Gly Asp Gly Gln Ile Cys Thr Ala Val Glu Thr<br>        80                          85                          90 | 590 |
| aga aat aca act gta aca gtt tca gta acc ggc gtg tct agt tcg tct<br>Arg Asn Thr Thr Val Thr Val Ser Val Thr Gly Val Ser Ser Ser Ser<br>        95                        100                     105 | 638 |
| ggt act aat agt ggt gta tct act aac ctt caa aga ata agt gtt aca<br>Gly Thr Asn Ser Gly Val Ser Thr Asn Leu Gln Arg Ile Ser Val Thr<br>110                        115                     120                  125 | 686 |
| gaa cac aca aag tgc gat tgt att ggt aga aca acg aca aca cct acg<br>Glu His Thr Lys Cys Asp Cys Ile Gly Arg Thr Thr Thr Thr Pro Thr<br>                130                     135                     140 | 734 |
| acc act agg gaa cct aga cga taactaataa caaaaaatgt ttattttgt<br>Thr Thr Arg Glu Pro Arg Arg<br>                145 | 785 |
| aaatacttaa ttattacaca ctttacaata atctcaaaaa taaattgcgt gcccggacgg | 845 |
| ctgcagctgg tgacgctgct gtgtcacaca ctgcgtattc gattcaagtt cactaacgcc | 905 |
| actaaactag ttgtgcgtgt ccgagtgtta accgtacgtc aaactaacat cttacctgtc | 965 |
| cgtgacaaga actaaaactt gaaccacata ttttttaaagt atatttaaca aaatcactca | 1025 |
| cactcacaca atcataaaca ccacaaccac aaccaaacac gcatgagaat taatattctt | 1085 |
| acttatccgt aacactctat gctgtacatc aacgcatcag agcagtctga gtctgactaa | 1145 |
| tgcggcaaa cgggaacgca ggcgcgacat aatcactgag aatctccgca gcaaccgctc | 1205 |
| aaggacatct ctagcgctaa cggctgtttg tcattccccc gtgtgttcat ctcacacgac | 1265 |
| attgtgaccg tcgcaaagca cacattcaaa gtgccgcatg tggaagaatt caccgtcgag | 1325 |
| acacacacca taattaaaca agatcagtgc ataagagaga ttagcattct acagcacacc | 1385 |
| acgtgcgaat acggacctcg taattgttta gactagaaca cctctggtct aaacaacatg | 1445 |
| tccgatctta gaacagagtt tatgacgcat atgtaactgt gttctttatg tagaagttat | 1505 |
| cttttatgtc actcccttgt cttagatgag ttatacatga catgatgtat gtgtcgcccg | 1565 |
| cggcggcgcg gggcgctcgg cggcggggct gctgcgcgcg gcgggcccgc ggtggcggcg | 1625 |
| gctggcgcgg cgctgcggcc gcgggcgcgc ggcggggtag cggcccgccc gcccgggcgc | 1685 |
| ccgccgcagc ccttgccccg gaccaggcgc cacggagcaa agtgaaaaag gaccgcctag | 1745 |
| cagtcgagac cctcccgccg cagccgcgac accccacacc cgccttccac ccgccagacg | 1805 |
| ccaacaccac agccaacaag catgc | 1830 |

<210> SEQ ID NO 121
<211> LENGTH: 148
<212> TYPE: PRT
<213> ORGANISM: Orf virus

<400> SEQUENCE: 121

Met Lys Leu Thr Ala Thr Leu Gln Val Val Val Ala Leu Leu Ile Cys
1               5                   10                  15

Met Tyr Asn Leu Pro Glu Cys Val Ser Gln Ser Asn Asp Ser Pro
            20                  25                  30

Ser Thr Asn Asp Trp Met Arg Thr Leu Asp Lys Ser Gly Cys Lys Pro
        35                  40                  45

Arg Asp Thr Val Val Tyr Leu Gly Glu Glu Tyr Pro Glu Ser Thr Asn

```
                50                  55                  60
Leu Gln Tyr Asn Pro Arg Cys Val Thr Val Lys Arg Cys Ser Gly Cys
 65                  70                  75                  80

Cys Asn Gly Asp Gly Gln Ile Cys Thr Ala Val Glu Thr Arg Asn Thr
                 85                  90                  95

Thr Val Thr Val Ser Val Thr Gly Val Ser Ser Ser Gly Thr Asn
            100                 105                 110

Ser Gly Val Ser Thr Asn Leu Gln Arg Ile Ser Val Thr Glu His Thr
            115                 120                 125

Lys Cys Asp Cys Ile Gly Arg Thr Thr Thr Pro Thr Thr Thr Arg
130                 135                 140

Glu Pro Arg Arg
145

<210> SEQ ID NO 122
<211> LENGTH: 851
<212> TYPE: DNA
<213> ORGANISM: Orf virus
<220> FEATURE:
<221> NAME/KEY: CDS
<222> LOCATION: (2)..(223)

<400> SEQUENCE: 122 c ggc cac gcg gcc gcg aac tgc gcg ctc gcg cgc gtg gcg acc gcg ctg        49
  Gly His Ala Ala Ala Asn Cys Ala Leu Ala Arg Val Ala Thr Ala Leu
   1               5                  10                  15 acg cgc cgc gtg ccc gcg agc cgg cac ggc ctc gcg gag ggc ggc acg           97
Thr Arg Arg Val Pro Ala Ser Arg His Gly Leu Ala Glu Gly Gly Thr
             20                  25                  30 ccg ccg tgg acg ctg ctg ctg gcg gtg gcc gcg gtg acg gtg ctc ggc          145
Pro Pro Trp Thr Leu Leu Leu Ala Val Ala Ala Val Thr Val Leu Gly
         35                  40                  45 gtg gtg gcg gtt tca ctg ctg cgg cgc gcg ctg cgg gta cgc tac cgc          193
Val Val Ala Val Ser Leu Leu Arg Arg Ala Leu Arg Val Arg Tyr Arg
     50                  55                  60 ttc gcg cgg ccg gcc gcg ctg cgc gcg tag ccgcgcaaaa tgtaaattat            243
Phe Ala Arg Pro Ala Ala Leu Arg Ala
 65                  70 aacgcccaac ttttaagggt gaggcgccat gaagttgctc gtcggcatac tagtagccgt        303
gtgcttgcac cagtatctgc tgaacgcgga cagcaacacg aaaggatggt ccgaagtgct       363
gaaaggcagc gagtgcaagc ctaggccgat tgttgttcct gtaagcgaga cgcacccaga       423
gctgacttct cagcggttca acccgccgtg tgtcacgttg atgcgatgcg gcgggtgctg       483
caacgacgag agcttggaat gcgtccccac ggaagaagta acgtgagca tggaactcct       543 gggggcgtcg ggctccggta gtaacgggat gcaacgtctg agcttcgtag agcataagaa       603
atgcgattgt agaccacgat tcacaaccac gccaccgacg accacaaggc cgcccagaag       663
acgccgctag aactttttat ggaccgcaga tccaaacgat ggatgcgatc aggtacatgc       723
ggaagaaggc gccacggagc aaagtgaaaa aggaccgcct agcagtcgag accctcccgc       783
cgcagccgcg gacaccccac acccgccttc cacccgccag acgccaacac cgcagccaac       843
aagcatgc                                                                 851

<210> SEQ ID NO 123
<211> LENGTH: 73
<212> TYPE: PRT
<213> ORGANISM: Orf virus
```

-continued

```
<400> SEQUENCE: 123

Gly His Ala Ala Ala Asn Cys Ala Leu Ala Arg Val Ala Thr Ala Leu
 1               5                  10                  15

Thr Arg Arg Val Pro Ala Ser Arg His Gly Leu Ala Glu Gly Gly Thr
                20                  25                  30

Pro Pro Trp Thr Leu Leu Ala Val Ala Val Thr Val Leu Gly
            35                  40                  45

Val Val Ala Val Ser Leu Leu Arg Arg Ala Leu Arg Val Arg Tyr Arg
    50                  55                  60

Phe Ala Arg Pro Ala Ala Leu Arg Ala
 65                 70

<210> SEQ ID NO 124
<211> LENGTH: 2305
<212> TYPE: DNA
<213> ORGANISM: Homo sapiens
<220> FEATURE:
<221> NAME/KEY: CDS
<222> LOCATION: (404)..(991)

<400> SEQUENCE: 124
ttcttggggc tgatgtccgc aaatatgcag aattaccggc cgggtcgctc ctgaagccag      60
cgcggggagc gagcgcggcg gcggccagca ccgggaacgc accgaggaag aagcccagcc     120
cccgccctcc gccccttccg tccccacccc ctaccggcg gcccaggagg ctccccggct      180
gcggcgcgca ctccctgttt ctcctcctcc tggctggcgc tgcctgcctc tccgcactca     240
ctgctcgccg ggcgccgtcc gccagctccg tgctccccgc gccaccctcc tccgggccgc     300
gctccctaag ggatggtact gaatttcgcc gccacaggag accggctgga gcgcccgccc     360
cgcgcctcgc ctctcctccg agcagccagc gcctcgggac gcg atg agg acc ttg       415
                                            Met Arg Thr Leu
                                             1 gct tgc ctg ctg ctc ctc ggc tgc gga tac ctc gcc cat gtt ctg gcc       463
Ala Cys Leu Leu Leu Leu Gly Cys Gly Tyr Leu Ala His Val Leu Ala
 5              10                  15                  20 gag gaa gcc gag atc ccc cgc gag gtg atc gag agg ctg gcc cgc agt       511
Glu Glu Ala Glu Ile Pro Arg Glu Val Ile Glu Arg Leu Ala Arg Ser
            25                  30                  35 cag atc cac agc atc cgg gac ctc cag cga ctc ctg gag ata gac tcc       559
Gln Ile His Ser Ile Arg Asp Leu Gln Arg Leu Leu Glu Ile Asp Ser
        40                  45                  50 gta ggg agt gag gat tct ttg gac acc agc ctg aga gct cac ggg gtc       607
Val Gly Ser Glu Asp Ser Leu Asp Thr Ser Leu Arg Ala His Gly Val
    55                  60                  65 cac gcc act aag cat gtg ccc gag aag cgg ccc ctg ccc att cgg agg       655
His Ala Thr Lys His Val Pro Glu Lys Arg Pro Leu Pro Ile Arg Arg
 70                 75                  80 aag aga agc atc gag gaa gct gtc ccc gct gtc tgc aag acc agg acg       703
Lys Arg Ser Ile Glu Glu Ala Val Pro Ala Val Cys Lys Thr Arg Thr
 85                 90                  95                 100 gtc att tac gag att cct cgg agt cag gtc gac ccc acg tcc gcc aac       751
Val Ile Tyr Glu Ile Pro Arg Ser Gln Val Asp Pro Thr Ser Ala Asn
                105                 110                 115 ttc ctg atc tgg ccc ccg tgc gtg gag gtg aaa cgc tgc acc ggc tgc       799
Phe Leu Ile Trp Pro Pro Cys Val Glu Val Lys Arg Cys Thr Gly Cys
                120                 125                 130 tgc aac acg agc agt gtc aag tgc cag ccc tcc cgc gtc cac cac cgc       847
Cys Asn Thr Ser Ser Val Lys Cys Gln Pro Ser Arg Val His His Arg
                135                 140                 145
```

```
agc gtc aag gtg gcc aag gtg gaa tac gtc agg aag aag cca aaa tta      895
Ser Val Lys Val Ala Lys Val Glu Tyr Val Arg Lys Lys Pro Lys Leu
    150                 155                 160 aaa gaa gtc cag gtg agg tta gag gag cat ttg gag tgc gcc tgc gcg      943
Lys Glu Val Gln Val Arg Leu Glu Glu His Leu Glu Cys Ala Cys Ala
165                 170                 175                 180 acc aca agc ctg aat ccg gat tat cgg gaa gag gac acg gat gtg agg      991
Thr Thr Ser Leu Asn Pro Asp Tyr Arg Glu Glu Asp Thr Asp Val Arg
                185                 190                 195 tgaggatgag ccgcagccct ttcctgggac atggatgtac atggcgtgtt acattcctga   1051
acctactatg tacggtgctt tattgccagt gtgcggtctt tgttctcctc cgtgaaaaac   1111
tgtgtccgag aacactcggg agaacaaaga gacagtgcac atttgtttaa tgtgacatca   1171
aagcaagtat tgtagcactc ggtgaagcag taagaagctt ccttgtcaaa agagagaga   1231 gagagagaga gagagaaaac aaaaccacaa atgacaaaaa caaaacggac tcacaaaaat   1291
atctaaactc gatgagatgg agggtcgccc cgtgggatgg aagtgcagag gtctcagcag   1351
actggatttc tgtccgggtg gtcacaggtg ctttttttgcc gaggatgcag agcctgcttt   1411
gggaacgact ccagaggggt gctggtgggc tctgcagggc ccgcaggaag caggaatgtc   1471
ttggaaaccg ccacgcgaac tttagaaacc acacctcctc gctgtagtat ttaagcccat   1531
acagaaacct tcctgagagc cttaagtggt tttttttttt gtttttgttt tgttttttt    1591 ttttttgttt tttttttttt tttttttttt tacaccataa agtgattatt aagcttcctt   1651
ttactctttg gctagctttt tttttttttt tttttttttt tttttttaat tatctcttgg   1711
atgacattta caccgataac acacaggctg ctgtaactgt caggacagtg cgacggtatt   1771
tttcctagca agatgcaaac taatgagatg tattaaaata aacatggtat acctacctat   1831
gcatcatttc ctaaatgttt ctggcttttgt gtttctccct taccctgctt tatttgttaa   1891
tttaagccat tttgaaagaa ctatgcgtca accaatcgta cgccgtccct gcggcacctg   1951
ccccagagcc cgtttgtggc tgagtgacaa cttgttcccc gcagtgcaca cctagaatgc   2011
tgtgttccca cgcggcacgt gagatgcatt gccgcttctg tctgtgttgt tggtgtgccc   2071
tggtgccgtg gtggcggtca ctccctctgc tgccagtgtt tggacagaac ccaaattctt   2131 tattttttggt aagatattgt gctttacctg tattaacaga aatgtgtgtg tgtggtttgt   2191
ttttttgtaa aggtgaagtt tgtatgttta cctaatatta cctgttttgt atacctgaga   2251
gcctgctatg ttcttctttt gttgatccaa aattaaaaaa aaaataccac caac          2305

<210> SEQ ID NO 125
<211> LENGTH: 196
<212> TYPE: PRT
<213> ORGANISM: Homo sapiens

<400> SEQUENCE: 125

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80
```

```
Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 126
<211> LENGTH: 2137
<212> TYPE: DNA
<213> ORGANISM: Homo sapiens
<220> FEATURE:
<221> NAME/KEY: CDS
<222> LOCATION: (983)..(1705)

<400> SEQUENCE: 126
ccctgcctgc tccctgcgc acccgcagcc tccccgctg cctccctagg gctcccctcc      60
ggccgccagc gcccatttt cattccctag atagagatac tttgcgcgca cacacataca    120
tacgcgcgca aaaggaaaa aaaaaaaaa aagcccaccc tccagcctcg ctgcaaagag     180
aaaaccggag cagccgcagc tcgcagctcg cagcccgcag cccgcagagg acgcccagag   240
cggcgagcgg gcgggcagac ggaccgacgg actcgcgccg cgtccacctg tcggccgggc   300
ccagccgagc gcgcagcggg cacgccgcgc gcgcggagca gccgtgcccg ccgcccgggc   360
ccgccgccag ggcgcacacg ctcccgcccc cctacccggc ccgggcggga gtttgcacct   420
ctccctgccc gggtgctcga gctgccgttg caaagccaac tttggaaaaa gttttttggg   480
ggagacttgg gccttgaggt gcccagctcc gcgctttccg attttggggg cctttccaga   540
aaatgttgca aaaagctaa gccggcgggc agaggaaaac gcctgtagcc ggcgagtgaa    600
gacgaaccat cgactgccgt gttccttttc ctcttggagg ttggagtccc ctgggcgccc   660
ccacacggct agacgcctcg gctggttcgc gacgcagccc cccggccgtg gatgctgcac   720
tcgggctcgg gatccgccca ggtagcggcc tcggacccag gtcctgcgcc caggtcctcc   780 cctgccccc agcgacggag ccggggccgg gggcggcggc gccggggca tgcgggtgag    840 ccgcggctgc agaggcctga gcgcctgatc gccgcggacc cgagccgagc ccaccccct   900 ccccagcccc ccaccctggc cgcggggcg gcgcgctcga tctacgcgtt cggggccccg   960
cggggccggg cccggagtcg gc atg aat cgc tgc tgg gcg ctc ttc ctg tct  1012
                         Met Asn Arg Cys Trp Ala Leu Phe Leu Ser
                          1               5                  10 ctc tgc tgc tac ctg cgt ctg gtc agc gcc gag ggg gac ccc att ccc   1060
Leu Cys Cys Tyr Leu Arg Leu Val Ser Ala Glu Gly Asp Pro Ile Pro
            15                  20                  25 gag gag ctt tat gag atg ctg agt gac cac tcg atc cgc tcc ttt gat   1108
Glu Glu Leu Tyr Glu Met Leu Ser Asp His Ser Ile Arg Ser Phe Asp
        30                  35                  40
```

```
gat ctc caa cgc ctg ctg cac gga gac ccc gga gag gaa gat ggg gcc      1156
Asp Leu Gln Arg Leu Leu His Gly Asp Pro Gly Glu Glu Asp Gly Ala
            45                  50                  55 gag ttg gac ctg aac atg acc cgc tcc cac tct gga ggc gag ctg gag      1204
Glu Leu Asp Leu Asn Met Thr Arg Ser His Ser Gly Gly Glu Leu Glu
60                  65                  70 agc ttg gct cgt gga aga agg agc ctg ggt tcc ctg acc att gct gag      1252
Ser Leu Ala Arg Gly Arg Arg Ser Leu Gly Ser Leu Thr Ile Ala Glu
 75                  80                  85                  90 ccg gcc atg atc gcc gag tgc aag acg cgc acc gag gtg ttc gag atc      1300
Pro Ala Met Ile Ala Glu Cys Lys Thr Arg Thr Glu Val Phe Glu Ile
                 95                 100                 105 tcc cgg cgc ctc ata gac cgc acc aac gcc aac ttc ctg gtg tgg ccg      1348
Ser Arg Arg Leu Ile Asp Arg Thr Asn Ala Asn Phe Leu Val Trp Pro
            110                 115                 120 ccc tgt gtg gag gtg cag cgc tgc tcc ggc tgc tgc aac aac cgc aac      1396
Pro Cys Val Glu Val Gln Arg Cys Ser Gly Cys Cys Asn Asn Arg Asn
        125                 130                 135 gtg cag tgc cgc ccc acc cag gtg cag ctg cga cct gtc cag gtg aga      1444
Val Gln Cys Arg Pro Thr Gln Val Gln Leu Arg Pro Val Gln Val Arg
140                 145                 150 aag atc gag att gtg cgg aag aag cca atc ttt aag aag gcc acg gtg      1492
Lys Ile Glu Ile Val Arg Lys Lys Pro Ile Phe Lys Lys Ala Thr Val
155                 160                 165                 170 acg ctg gaa gac cac ctg gca tgc aag tgt gag aca gtg gca gct gca      1540
Thr Leu Glu Asp His Leu Ala Cys Lys Cys Glu Thr Val Ala Ala Ala
                175                 180                 185 cgg cct gtg acc cga agc ccg ggg ggt tcc cag gag cag cga gcc aaa      1588
Arg Pro Val Thr Arg Ser Pro Gly Gly Ser Gln Glu Gln Arg Ala Lys
            190                 195                 200 acg ccc caa act cgg gtg acc att cgg acg gtg cga gtc cgc cgg ccc      1636
Thr Pro Gln Thr Arg Val Thr Ile Arg Thr Val Arg Val Arg Arg Pro
        205                 210                 215 ccc aag ggc aag cac cgg aaa ttc aag cac acg cat gac aag acg gca      1684
Pro Lys Gly Lys His Arg Lys Phe Lys His Thr His Asp Lys Thr Ala
220                 225                 230 ctg aag gag acc ctt gga gcc taggggcatc ggcaggagag tgtgtgggca         1735
Leu Lys Glu Thr Leu Gly Ala
235                 240 gggttattta atatggtatt tgctgtattg ccccatgggg gccttggagt agataatatt    1795
gtttccctcg tccgtctgtc tcgatgcctg attcggacgg ccaatggtgc ctcccccacc    1855
cctccacgtg tccgtccacc cttccatcag cgggtctcct cccagcggcc tccggctctt    1915
gcccagcagc tcaagaagaa aaagaaggac tgaactccat cgccatcttc ttcccttaac    1975
tccaagaact tgggataaga gtgtgagaga gactgatggg gtcgctcttt ggggggaaacg   2035 ggttccttcc cctgcacctg gcctgggcca cacctgagcg ctgtggactg tcctgaggag    2095
ccctgaggac ctctcagcat agcctgcctg atccctgaac cc                      2137

<210> SEQ ID NO 127
<211> LENGTH: 241
<212> TYPE: PRT
<213> ORGANISM: Homo sapiens

<400> SEQUENCE: 127

Met Asn Arg Cys Trp Ala Leu Phe Leu Ser Leu Cys Cys Tyr Leu Arg
  1               5                  10                  15

Leu Val Ser Ala Glu Gly Asp Pro Ile Pro Glu Glu Leu Tyr Glu Met
```

-continued

```
                    20                  25                  30
Leu Ser Asp His Ser Ile Arg Ser Phe Asp Asp Leu Gln Arg Leu Leu
            35                  40                  45
His Gly Asp Pro Gly Glu Glu Asp Gly Ala Glu Leu Asp Leu Asn Met
        50                  55                  60
Thr Arg Ser His Ser Gly Gly Glu Leu Glu Ser Leu Ala Arg Gly Arg
    65                  70                  75                  80
Arg Ser Leu Gly Ser Leu Thr Ile Ala Glu Pro Ala Met Ile Ala Glu
                85                  90                  95
Cys Lys Thr Arg Thr Glu Val Phe Glu Ile Ser Arg Arg Leu Ile Asp
            100                 105                 110
Arg Thr Asn Ala Asn Phe Leu Val Trp Pro Pro Cys Val Glu Val Gln
        115                 120                 125
Arg Cys Ser Gly Cys Cys Asn Asn Arg Asn Val Gln Cys Arg Pro Thr
    130                 135                 140
Gln Val Gln Leu Arg Pro Val Gln Val Arg Lys Ile Glu Ile Val Arg
145                 150                 155                 160
Lys Lys Pro Ile Phe Lys Lys Ala Thr Val Thr Leu Glu Asp His Leu
                165                 170                 175
Ala Cys Lys Cys Glu Thr Val Ala Ala Ala Arg Pro Val Thr Arg Ser
            180                 185                 190
Pro Gly Gly Ser Gln Glu Gln Arg Ala Lys Thr Pro Gln Thr Arg Val
        195                 200                 205
Thr Ile Arg Thr Val Arg Val Arg Arg Pro Pro Lys Gly Lys His Arg
    210                 215                 220
Lys Phe Lys His Thr His Asp Lys Thr Ala Leu Lys Glu Thr Leu Gly
225                 230                 235                 240
Ala
```

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 128

```
Asp Pro Gly Gln Asn His His Glu Val Val Lys
 1               5                  10
```

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 129

```
Phe Met Asp Val Tyr Gln Arg Ser Tyr Cys His
 1               5                  10
```

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: synthetic
    peptide -continued

```
<400> SEQUENCE: 130

Pro Ile Glu Thr Leu Val Asp Ile Phe Gln
 1               5                  10

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 131

Glu Tyr Pro Asp Glu Ile Glu Tyr
 1               5

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 132

Ile Phe Lys Pro Ser Cys Val Pro Leu Met Arg Cys Gly
 1               5                  10

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 133

Gly Cys Cys Asn Asp Glu Gly Leu
 1               5

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 134

Glu Cys Val Pro Thr Glu Glu Ser Asn Ile Thr Met Gln Ile Met Arg
 1               5                  10                  15

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 135

Ile Lys Pro His Gln Gly Gln His Ile Gly Glu Met Ser Phe
 1               5                  10

<210> SEQ ID NO 136
<211> LENGTH: 13
```

<212> TYPE: PRT
<213> ORGANISM: Artificial Sequence
<220> FEATURE:
<223> OTHER INFORMATION: Description of Artificial Sequence: synthetic
      peptide

<400> SEQUENCE: 136

Leu Gln His Asn Lys Cys Glu Cys Arg Pro Lys Lys Asp
 1               5                  10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 137

Asp Pro Ala His Tyr Asn Thr Glu Ile Leu Lys
 1               5                  10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 138

Ser Ile Asp Asn Glu Trp Arg Lys Thr Gln Cys Met
 1               5                  10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 139

Pro Arg Glu Val Cys Ile Asp Val Gly Lys
 1               5                  10

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 140

Glu Phe Gly Val Ala Thr Asn Thr
 1               5

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 141

Phe Phe Lys Pro Pro Cys Val Ser Val Tyr Arg Cys Gly

-continued

```
<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 142

Gly Cys Cys Asn Ser Glu Gly Leu
 1               5

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 143

Gln Cys Met Asn Thr Ser Thr Ser Tyr Leu Ser Lys Thr Leu Phe Glu
 1               5                  10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 144

Ile Thr Val Pro Leu Ser Gln Gly Pro Lys Pro Val Thr Ile Ser Phe
 1               5                  10                  15

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 145

Ala Asn His Thr Ser Cys Arg Cys Met Ser Lys Leu Asp
 1               5                  10

<210> SEQ ID NO 146
<211> LENGTH: 815
<212> TYPE: DNA
<213> ORGANISM: Homo sapiens
<220> FEATURE:
<221> NAME/KEY: CDS
<222> LOCATION: (69)..(767)

<400> SEQUENCE: 146
gaattcgaat tccagtgtgc tggcggccgc gcgcgagccg cgccggcccc ggtcgggcct      60 ccgaaacc atg aac ttt ctg ctg tct tgg gtg cat tgg agc ctc gcc ttg     110
         Met Asn Phe Leu Leu Ser Trp Val His Trp Ser Leu Ala Leu
          1               5                  10 ctg ctc tac ctc cac cat gcc aag tgg tcc cag gct gca ccc atg gca     158
Leu Leu Tyr Leu His His Ala Lys Trp Ser Gln Ala Ala Pro Met Ala
15                  20                  25                  30
```

-continued

| | |
|---|---|
| gaa gga gga ggg cag aat cat cac gaa gtg gtg aag ttc atg gat gtc<br>Glu Gly Gly Gly Gln Asn His His Glu Val Val Lys Phe Met Asp Val<br>35 40 45 | 206 |
| tat cag cgc agc tac tgc cat cca atc gag acc ctg gtg gac atc ttc<br>Tyr Gln Arg Ser Tyr Cys His Pro Ile Glu Thr Leu Val Asp Ile Phe<br>50 55 60 | 254 |
| cag gag tac cct gat gag atc gag tac atc ttc aag cca tcc tgt gtg<br>Gln Glu Tyr Pro Asp Glu Ile Glu Tyr Ile Phe Lys Pro Ser Cys Val<br>65 70 75 | 302 |
| ccc ctg atg cga tgc ggg ggc tgc tgc aat gac gag ggc ctg gag tgt<br>Pro Leu Met Arg Cys Gly Gly Cys Cys Asn Asp Glu Gly Leu Glu Cys<br>80 85 90 | 350 |
| gtg ccc act gag gag tcc aac atc acc atg cag att atg cgg atc aaa<br>Val Pro Thr Glu Glu Ser Asn Ile Thr Met Gln Ile Met Arg Ile Lys<br>95 100 105 110 | 398 |
| cct cac caa ggc cag cac ata gga gag atg agc ttc cta cag cac aac<br>Pro His Gln Gly Gln His Ile Gly Glu Met Ser Phe Leu Gln His Asn<br>115 120 125 | 446 |
| aaa tgt gaa tgc aga cca aag aaa gat aga gca aga caa gaa aaa aaa<br>Lys Cys Glu Cys Arg Pro Lys Lys Asp Arg Ala Arg Gln Glu Lys Lys<br>130 135 140 | 494 |
| tca gtt cga gga aag gga aag ggg caa aaa cga aag cgc aag aaa tcc<br>Ser Val Arg Gly Lys Gly Lys Gly Gln Lys Arg Lys Arg Lys Lys Ser<br>145 150 155 | 542 |
| cgg tat aag tcc tgg agc gtg tac gtt ggt gcc cgc tgc tgt cta atg<br>Arg Tyr Lys Ser Trp Ser Val Tyr Val Gly Ala Arg Cys Cys Leu Met<br>160 165 170 | 590 |
| ccc tgg agc ctc cct ggc ccc cat ccc tgt ggg cct tgc tca gag cgg<br>Pro Trp Ser Leu Pro Gly Pro His Pro Cys Gly Pro Cys Ser Glu Arg<br>175 180 185 190 | 638 |
| aga aag cat ttg ttt gta caa gat ccg cag acg tgt aaa tgt tcc tgc<br>Arg Lys His Leu Phe Val Gln Asp Pro Gln Thr Cys Lys Cys Ser Cys<br>195 200 205 | 686 |
| aaa aac aca gac tcg cgt tgc aag gcg agg cag ctt gag tta aac gaa<br>Lys Asn Thr Asp Ser Arg Cys Lys Ala Arg Gln Leu Glu Leu Asn Glu<br>210 215 220 | 734 |
| cgt act tgc aga tgt gac aag ccg agg cgg tga gccgggctgg aggaaggagc<br>Arg Thr Cys Arg Cys Asp Lys Pro Arg Arg<br>225 230 | 787 |
| ctcccctcagg gtttcgggaa ccagatcc | 815 |

<210> SEQ ID NO 147
<211> LENGTH: 232
<212> TYPE: PRT
<213> ORGANISM: Homo sapiens

<400> SEQUENCE: 147

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

-continued

```
Thr Glu Glu Ser Asn Ile Thr Met Gln Ile Met Arg Ile Lys Pro His
            100                 105                 110
Gln Gly Gln His Ile Gly Glu Met Ser Phe Leu Gln His Asn Lys Cys
        115                 120                 125
Glu Cys Arg Pro Lys Lys Asp Arg Ala Arg Gln Glu Lys Lys Ser Val
    130                 135                 140
Arg Gly Lys Gly Lys Gly Gln Lys Arg Lys Lys Ser Arg Tyr
145                 150                 155                 160
Lys Ser Trp Ser Val Tyr Val Gly Ala Arg Cys Cys Leu Met Pro Trp
                165                 170                 175
Ser Leu Pro Gly Pro His Pro Cys Gly Pro Cys Ser Glu Arg Arg Lys
            180                 185                 190
His Leu Phe Val Gln Asp Pro Gln Thr Cys Lys Cys Ser Cys Lys Asn
        195                 200                 205
Thr Asp Ser Arg Cys Lys Ala Arg Gln Leu Glu Leu Asn Glu Arg Thr
    210                 215                 220
Cys Arg Cys Asp Lys Pro Arg Arg
225                 230
```

<210> SEQ ID NO 148
<211> LENGTH: 3007
<212> TYPE: DNA
<213> ORGANISM: Homo sapiens
<220> FEATURE:
<221> NAME/KEY: CDS
<222> LOCATION: (492)..(1529)

<400> SEQUENCE: 148

```
gcccggagag ccgcatctat tggcagcttt gttattgatc agaaactgct cgccgccgac      60
ttggcttcca gtctggctgc gggcaaccct tgagttttcg cctctgtcct gtccccgaa      120 ctgacaggtg ctcccagcaa cttgctgggg acttctcgcc gctcccccgc gtccccaccc     180
cctcattcct ccctcgcctt caccccacc cccaccactt cgccacagct caggatttgt      240
ttaaaccttg ggaaactggt tcaggtccag gttttgcttt gatccttttc aaaaactgga     300
gacacagaag agggctctag gaaaaagttt tggatgggat tatgtggaaa ctaccctgcg     360
attctctgct gccagagcag gctcggcgct tccaccccag tgcagccttc ccctggcggt     420
ggtgaaagag actcgggagt cgctgcttcc aaagtgcccg ccgtgagtga gctctcaccc     480
cagtcagcca a atg agc ctc ttc ggg ctt ctc ctg ctg aca tct gcc ctg    530
            Met Ser Leu Phe Gly Leu Leu Leu Leu Thr Ser Ala Leu
              1               5                  10 gcc ggc cag aga cag ggg act cag gcg gaa tcc aac ctg agt agt aaa     578
Ala Gly Gln Arg Gln Gly Thr Gln Ala Glu Ser Asn Leu Ser Ser Lys
         15                  20                  25 ttc cag ttt tcc agc aac aag gaa cag aac gga gta caa gat cct cag     626
Phe Gln Phe Ser Ser Asn Lys Glu Gln Asn Gly Val Gln Asp Pro Gln
 30                  35                  40                  45 cat gag aga att att act gtg tct act aat gga agt att cac agc cca     674
His Glu Arg Ile Ile Thr Val Ser Thr Asn Gly Ser Ile His Ser Pro
                 50                  55                  60 agg ttt cct cat act tat cca aga aat acg gtc ttg gta tgg aga tta     722
Arg Phe Pro His Thr Tyr Pro Arg Asn Thr Val Leu Val Trp Arg Leu
             65                  70                  75 gta gca gta gag gaa aat gta tgg ata caa ctt acg ttt gat gaa aga     770
Val Ala Val Glu Glu Asn Val Trp Ile Gln Leu Thr Phe Asp Glu Arg
         80                  85                  90
```

-continued

| | | |
|---|---|---|
| ttt ggg ctt gaa gac cca gaa gat gac ata tgc aag tat gat ttt gta<br>Phe Gly Leu Glu Asp Pro Glu Asp Asp Ile Cys Lys Tyr Asp Phe Val<br> 95                          100                      105 | | 818 |
| gaa gtt gag gaa ccc agt gat gga act ata tta ggg cgc tgg tgt ggt<br>Glu Val Glu Glu Pro Ser Asp Gly Thr Ile Leu Gly Arg Trp Cys Gly<br>110                        115                      120                      125 | | 866 |
| tct ggt act gta cca gga aaa cag att tct aaa gga aat caa att agg<br>Ser Gly Thr Val Pro Gly Lys Gln Ile Ser Lys Gly Asn Gln Ile Arg<br>               130                      135                      140 | | 914 |
| ata aga ttt gta tct gat gaa tat ttt cct tct gaa cca ggg ttc tgc<br>Ile Arg Phe Val Ser Asp Glu Tyr Phe Pro Ser Glu Pro Gly Phe Cys<br>             145                      150                      155 | | 962 |
| atc cac tac aac att gtc atg cca caa ttc aca gaa gct gtg agt cct<br>Ile His Tyr Asn Ile Val Met Pro Gln Phe Thr Glu Ala Val Ser Pro<br>        160                      165                      170 | | 1010 |
| tca gtg cta ccc cct tca gct ttg cca ctg gac ctg ctt aat aat gct<br>Ser Val Leu Pro Pro Ser Ala Leu Pro Leu Asp Leu Leu Asn Asn Ala<br>175                        180                      185 | | 1058 |
| ata act gcc ttt agt acc ttg gaa gac ctt att cga tat ctt gaa cca<br>Ile Thr Ala Phe Ser Thr Leu Glu Asp Leu Ile Arg Tyr Leu Glu Pro<br>190                        195                      200                      205 | | 1106 |
| gag aga tgg cag ttg gac tta gaa gat cta tat agg cca act tgg caa<br>Glu Arg Trp Gln Leu Asp Leu Glu Asp Leu Tyr Arg Pro Thr Trp Gln<br>             210                      215                      220 | | 1154 |
| ctt ctt ggc aag gct ttt gtt ttt gga aga aaa tcc aga gtg gtg gat<br>Leu Leu Gly Lys Ala Phe Val Phe Gly Arg Lys Ser Arg Val Val Asp<br>               225                      230                      235 | | 1202 |
| ctg aac ctt cta aca gag gag gta aga tta tac agc tgc aca cct cgt<br>Leu Asn Leu Leu Thr Glu Glu Val Arg Leu Tyr Ser Cys Thr Pro Arg<br>        240                      245                      250 | | 1250 |
| aac ttc tca gtg tcc ata agg gaa gaa cta aag aga acc gat acc att<br>Asn Phe Ser Val Ser Ile Arg Glu Glu Leu Lys Arg Thr Asp Thr Ile<br>255                        260                      265 | | 1298 |
| ttc tgg cca ggt tgt ctc ctg gtt aaa cgc tgt ggt ggg aac tgt gcc<br>Phe Trp Pro Gly Cys Leu Leu Val Lys Arg Cys Gly Gly Asn Cys Ala<br>270                        275                      280                      285 | | 1346 |
| tgt tgt ctc cac aat tgc aat gaa tgt caa tgt gtc cca agc aaa gtt<br>Cys Cys Leu His Asn Cys Asn Glu Cys Gln Cys Val Pro Ser Lys Val<br>               290                      295                      300 | | 1394 |
| act aaa aaa tac cac gag gtc ctt cag ttg aga cca aag acc ggt gtc<br>Thr Lys Lys Tyr His Glu Val Leu Gln Leu Arg Pro Lys Thr Gly Val<br>             305                      310                      315 | | 1442 |
| agg gga ttg cac aaa tca ctc acc gac gtg gcc ctg gag cac cat gag<br>Arg Gly Leu His Lys Ser Leu Thr Asp Val Ala Leu Glu His His Glu<br>        320                      325                      330 | | 1490 |
| gag tgt gac tgt gtg tgc aga ggg agc aca gga gga tag ccgcatcacc<br>Glu Cys Asp Cys Val Cys Arg Gly Ser Thr Gly Gly<br>335                        340                      345 | | 1539 |
| accagcagct cttgcccaga gctgtgcagt gcagtggctg attctattag agaacgtatg | | 1599 |
| cgttatctcc atccttaatc tcagttgttt gcttcaagga cctttcatct tcaggattta | | 1659 |
| cagtgcattc tgaaagagga gacatcaaac agaattagga gttgtgcaac agctcttttg | | 1719 |
| agaggaggcc taaggacag gagaaaaggt cttcaatcgt ggaaagaaaa ttaaatgttg | | 1779 |
| tattaaatag atcaccagct agtttcagag ttaccatgta cgtattccac tagctgggtt | | 1839 |
| ctgtatttca gttctttcga tacggcttag ggtaatgtca gtacaggaaa aaaactgtgc | | 1899 |
| aagtgagcac ctgattccgt tgccttgctt aactctaaag ctccatgtcc tgggcctaaa | | 1959 |
| atcgtataaa atctggatt tttttttttt ttttgctcat attcacatat gtaaaccaga | | 2019 |

-continued

```
acattctatg tactacaaac ctggttttta aaaggaact atgttgctat gaattaaact    2079
tgtgtcgtgc tgataggaca gactggattt ttcatatttc ttattaaaat ttctgccatt    2139
tagaagaaga gaactacatt catggtttgg aagagataaa cctgaaaaga agagtggcct    2199
tatcttcact ttatcgataa gtcagtttat ttgtttcatt gtgtacattt ttatattctc    2259
cttttgacat tataactgtt ggcttttcta atcttgttaa atatatctat ttttaccaaa    2319
ggtatttaat attctttttt atgacaactt agatcaacta ttttagctt ggtaaatttt     2379 tctaaacaca attgttatag ccagaggaac aaagatgata taaatattg ttgctctgac     2439 aaaaatacat gtatttcatt ctcgtatggt gctagagtta gattaatctg cattttaaaa    2499
aactgaattg aatagaatt ggtaagttgc aaagactttt tgaaaataat taaattatca     2559
tatcttccat tcctgttatt ggagatgaaa ataaaaagca acttatgaaa gtagacattc    2619
agatccagcc attactaacc tattccttt ttggggaaat ctgagcctag ctcagaaaaa     2679
cataaagcac cttgaaaaag acttggcagc ttcctgataa agcgtgctgt gctgtgcagt    2739
aggaacacat cctatttatt gtgatgttgt ggttttatta tcttaaactc tgttccatac    2799
acttgtataa atacatggat attttatgt acagaagtat gtctcttaac cagttcactt     2859
attgtactct ggcaatttaa aagaaaatca gtaaaatatt ttgcttgtaa aatgcttaat    2919
atcgtgccta ggttatgtgg tgactatttg aatcaaaaat gtattgaatc atcaaataaa    2979
agaatgtggc tattttgggg agaaaatt                                      3007
```

<210> SEQ ID NO 149
<211> LENGTH: 345
<212> TYPE: PRT
<213> ORGANISM: Homo sapiens

<400> SEQUENCE: 149

```
Met Ser Leu Phe Gly Leu Leu Leu Thr Ser Ala Leu Ala Gly Gln
 1               5                  10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190
```

-continued

```
Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
        210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Val Lys Arg Cys Gly Asn Cys Ala Cys Cys Leu
        275                 280                 285

His Asn Cys Asn Glu Cys Gln Cys Val Pro Ser Lys Val Thr Lys Lys
        290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 150
<211> LENGTH: 399
<212> TYPE: DNA
<213> ORGANISM: Orf virus
<220> FEATURE:
<221> NAME/KEY: CDS
<222> LOCATION: (1)..(399)

<400> SEQUENCE: 150 atg aag ttt ctc gtc ggc ata ctg gta gct gtg tgc ttg cac cag tat      48
Met Lys Phe Leu Val Gly Ile Leu Val Ala Val Cys Leu His Gln Tyr
1               5                   10                  15 ctg ctg aac gcg gac agc acg aaa aca tgg tcc gaa gtg ttt gaa aac      96
Leu Leu Asn Ala Asp Ser Thr Lys Thr Trp Ser Glu Val Phe Glu Asn
            20                  25                  30 agc ggg tgc aag cca agg ccg atg gtc ttt cga gta cac gac gag cac     144
Ser Gly Cys Lys Pro Arg Pro Met Val Phe Arg Val His Asp Glu His
        35                  40                  45 ccg gag cta act tct cag cgg ttc aac ccg ccg tgt gtc acg ttg atg     192
Pro Glu Leu Thr Ser Gln Arg Phe Asn Pro Pro Cys Val Thr Leu Met
    50                  55                  60 cga tgc ggc ggg tgc tgc aac gac gag agc tta gaa tgc gtc ccc acg     240
Arg Cys Gly Gly Cys Cys Asn Asp Glu Ser Leu Glu Cys Val Pro Thr
65                  70                  75                  80 gaa gag gca aac gta acg atg caa ctc atg gga gcg tcg gtc tcc ggt     288
Glu Glu Ala Asn Val Thr Met Gln Leu Met Gly Ala Ser Val Ser Gly
                85                  90                  95 ggt aac ggg atg caa cat ctg agc ttc gta gag cat aag aaa tgc gat     336
Gly Asn Gly Met Gln His Leu Ser Phe Val Glu His Lys Lys Cys Asp
            100                 105                 110 tgt aaa cca cca ctc acg acc acg cca ccg acg acc aca agg ccg ccc     384
Cys Lys Pro Pro Leu Thr Thr Thr Pro Pro Thr Thr Thr Arg Pro Pro
        115                 120                 125 aga aga cgc cgc tag                                                 399
Arg Arg Arg Arg
    130

<210> SEQ ID NO 151
```

<211> LENGTH: 132
<212> TYPE: PRT
<213> ORGANISM: Orf virus

<400> SEQUENCE: 151

|

```
<223> OTHER INFORMATION: Description of Artificial Sequence: amino acid
      sequence of hybrid DNA

<400> SEQUENCE: 153

Gly Gln Asn His His Glu Val Val Lys Phe Met Asp Val Tyr Gln Arg
 1               5                  10                  15

Ser Tyr Cys His Pro Ile Glu Thr Leu Val Asp Ile Phe Gln Glu Phe
                20                  25                  30

Gly Val Ala Thr Asn Thr Phe Phe Lys Pro Ser Cys Val Pro Leu Met
            35                  40                  45

Arg Cys Gly Gly Cys Cys Asn Asp Glu Gly Leu Glu Cys Val Pro Thr
        50                  55                  60

Glu Glu Ser Asn Ile Thr Met Gln Ile Met Arg Ile Thr Val Pro Leu
65                  70                  75                  80

Ser Gln Gly Pro Lys Pro Val Thr Ile Ser Phe Leu Gln His Asn Lys
                85                  90                  95

Cys Glu Cys Arg Pro Lys Lys Asp Leu
                100                 105

<210> SEQ ID NO 154
<211> LENGTH: 331
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 154 ggatcct gca cat tat aat acc gag atc ctg aaa tct att gat aat gag        49
        Ala His Tyr Asn Thr Glu Ile Leu Lys Ser Ile Asp Asn Glu
         1               5                  10 tgg aga aag act cag tgc atg ccg aga gag gtg tgt atc gac gtg ggg        97
Trp Arg Lys Thr Gln Cys Met Pro Arg Glu Val Cys Ile Asp Val Gly
 15                  20                  25                  30 aag gaa tac cct gat gag atc gag tac atc ttc aag cca cca tgt gtg       145
Lys Glu Tyr Pro Asp Glu Ile Glu Tyr Ile Phe Lys Pro Pro Cys Val
                 35                  40                  45 tcc gtg tac aga tgt ggg ggt tgc tgc aat gac gaa ggg ctg gag tgc       193
Ser Val Tyr Arg Cys Gly Gly Cys Cys Asn Asp Glu Gly Leu Glu Cys
             50                  55                  60 atg aac acg tcc acg agc tac ctc agc aag acg ctg ttt gaa att aca       241
Met Asn Thr Ser Thr Ser Tyr Leu Ser Lys Thr Leu Phe Glu Ile Thr
 65                  70                  75 gtg cct ctc tct caa ggg ccc aaa cca gtg aca atc agc ttt ctc cag       289
Val Pro Leu Ser Gln Gly Pro Lys Pro Val Thr Ile Ser Phe Leu Gln
     80                  85                  90 cat aac aaa tgt gaa tgt aga cca aag aaa gat ttggtcttc                 331
His Asn Lys Cys Glu Cys Arg Pro Lys Lys Asp
 95                 100                 105

<210> SEQ ID NO 155
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 155

Ala His Tyr Asn Thr Glu Ile Leu Lys Ser Ile Asp Asn Glu Trp Arg
 1               5                  10                  15
```

-continued

```
Lys Thr Gln Cys Met Pro Arg Glu Val Cys Ile Asp Val Gly Lys Glu
             20                  25                  30

Tyr Pro Asp Glu Ile Glu Tyr Ile Phe Lys Pro Pro Cys Val Ser Val
         35                  40                  45

Tyr Arg Cys Gly Gly Cys Cys Asn Asp Glu Gly Leu Glu Cys Met Asn
     50                  55                  60

Thr Ser Thr Ser Tyr Leu Ser Lys Thr Leu Phe Glu Ile Thr Val Pro
 65                  70                  75                  80

Leu Ser Gln Gly Pro Lys Pro Val Thr Ile Ser Phe Leu Gln His Asn
                 85                  90                  95

Lys Cys Glu Cys Arg Pro Lys Lys Asp
            100                 105
```

<210> SEQ ID NO 156
<211> LENGTH: 331
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 156

```
ggatcct ggg cag aat cat cac gaa gtg gtg aaa tct att gat aat gag      49
        Gly Gln Asn His His Glu Val Val Lys Ser Ile Asp Asn Glu
         1               5                  10 tgg aga aag act cag tgc atg ccg atc gag aca ctg gtg gac atc ttc      97
Trp Arg Lys Thr Gln Cys Met Pro Ile Glu Thr Leu Val Asp Ile Phe
 15                  20                  25                  30 cag gaa ttt gga gtc gcg aca aac acc ttc ttc aag cca cca tgt gtg     145
Gln Glu Phe Gly Val Ala Thr Asn Thr Phe Phe Lys Pro Pro Cys Val
                 35                  40                  45 tcc gtg tac aga tgt ggg ggt tgc tgc aat gac gaa ggg ctg gag tgc     193
Ser Val Tyr Arg Cys Gly Gly Cys Cys Asn Asp Glu Gly Leu Glu Cys
             50                  55                  60 atg aac acg tcc acg agc tac ctc agc aag acg ctg ttt gaa att aca     241
Met Asn Thr Ser Thr Ser Tyr Leu Ser Lys Thr Leu Phe Glu Ile Thr
 65                  70                  75 gtg cct ctc tct caa ggg ccc aaa cca gtg aca atc agc ttt gcc aat     289
Val Pro Leu Ser Gln Gly Pro Lys Pro Val Thr Ile Ser Phe Ala Asn
 80                  85                  90 cac act tcc tgc cga tgc atg tct aag ctg gat ttggtcttc               331
His Thr Ser Cys Arg Cys Met Ser Lys Leu Asp
 95                 100                 105
```

<210> SEQ ID NO 157
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 157

```
Gly Gln Asn His His Glu Val Val Lys Ser Ile Asp Asn Glu Trp Arg
 1               5                  10                  15

Lys Thr Gln Cys Met Pro Ile Glu Thr Leu Val Asp Ile Phe Gln Glu
             20                  25                  30

Phe Gly Val Ala Thr Asn Thr Phe Phe Lys Pro Pro Cys Val Ser Val
         35                  40                  45
```

-continued

```
Tyr Arg Cys Gly Gly Cys Cys Asn Asp Glu Gly Leu Glu Cys Met Asn
 50                  55                  60
Thr Ser Thr Ser Tyr Leu Ser Lys Thr Leu Phe Glu Ile Thr Val Pro
 65                  70                  75                  80
Leu Ser Gln Gly Pro Lys Pro Val Thr Ile Ser Phe Ala Asn His Thr
                 85                  90                  95
Ser Cys Arg Cys Met Ser Lys Leu Asp
            100                 105
```

<210> SEQ ID NO 158
<211> LENGTH: 331
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 158

```
ggatcct gca cat tat aat acc gag atc ctg aaa tct att gat aat gag      49
        Ala His Tyr Asn Thr Glu Ile Leu Lys Ser Ile Asp Asn Glu
          1               5                  10 tgg aga aag act cag tgc atg ccg atc gag aca ctg gtg gac atc ttc      97
Trp Arg Lys Thr Gln Cys Met Pro Ile Glu Thr Leu Val Asp Ile Phe
 15                  20                  25                  30 cag gaa ttt gga gtc gcg aca aac acc ttc ttc aag cca cca tgt gtg     145
Gln Glu Phe Gly Val Ala Thr Asn Thr Phe Phe Lys Pro Pro Cys Val
                 35                  40                  45 tcc gtg tac aga tgt ggg ggt tgc tgc aat agt gag ggg ctg cag tgc     193
Ser Val Tyr Arg Cys Gly Gly Cys Cys Asn Ser Glu Gly Leu Gln Cys
             50                  55                  60 gtt ccc acc gag gag tcc aac atc acc atg cag att atg aga att aca     241
Val Pro Thr Glu Glu Ser Asn Ile Thr Met Gln Ile Met Arg Ile Thr
 65                  70                  75 gtg cct ctc tct caa ggg ccc aaa cca gtg aca atc agc ttt gcc aat     289
Val Pro Leu Ser Gln Gly Pro Lys Pro Val Thr Ile Ser Phe Ala Asn
 80                  85                  90 cac act tcc tgc cga tgc atg tct aag ctg gat ttggtcttc               331
His Thr Ser Cys Arg Cys Met Ser Lys Leu Asp
 95                 100                 105
```

<210> SEQ ID NO 159
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 159

```
Ala His Tyr Asn Thr Glu Ile Leu Lys Ser Ile Asp Asn Glu Trp Arg
  1               5                  10                  15

Lys Thr Gln Cys Met Pro Ile Glu Thr Leu Val Asp Ile Phe Gln Glu
             20                  25                  30

Phe Gly Val Ala Thr Asn Thr Phe Phe Lys Pro Pro Cys Val Ser Val
         35                  40                  45

Tyr Arg Cys Gly Gly Cys Cys Asn Ser Glu Gly Leu Gln Cys Val Pro
     50                  55                  60

Thr Glu Glu Ser Asn Ile Thr Met Gln Ile Met Arg Ile Thr Val Pro
 65                  70                  75                  80

Leu Ser Gln Gly Pro Lys Pro Val Thr Ile Ser Phe Ala Asn His Thr
```

-continued

```
                        85                  90                  95
Ser Cys Arg Cys Met Ser Lys Leu Asp
            100                 105

<210> SEQ ID NO 160
<211> LENGTH: 325
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 160 ggatcct gca cat tat aat acc gag atc ctg aaa tct att gat aat gag        49
        Ala His Tyr Asn Thr Glu Ile Leu Lys Ser Ile Asp Asn Glu
          1               5                  10 tgg aga aag act cag tgc atg ccg atc gag aca ctg gtg gac atc ttc        97
Trp Arg Lys Thr Gln Cys Met Pro Ile Glu Thr Leu Val Asp Ile Phe
 15                  20                  25                  30 cag gaa tac cct gat gag atc gag tac atc ttc aag cca cca tgt gtg       145
Gln Glu Tyr Pro Asp Glu Ile Glu Tyr Ile Phe Lys Pro Pro Cys Val
                 35                  40                  45 tcc gtg tac aga tgt ggg ggt tgc tgc aat agt gag ggg ctg cag tgc       193
Ser Val Tyr Arg Cys Gly Gly Cys Cys Asn Ser Glu Gly Leu Gln Cys
             50                  55                  60 gtt ccc acc gag gag tcc aac atc acc atg cag att atg aga att aaa       241
Val Pro Thr Glu Glu Ser Asn Ile Thr Met Gln Ile Met Arg Ile Lys
         65                  70                  75 cct cac caa ggg cag cac atc gga gag atg agc ttt ctc cag cat aac       289
Pro His Gln Gly Gln His Ile Gly Glu Met Ser Phe Leu Gln His Asn
     80                  85                  90 aaa tgt gaa tgt aga cca aag aaa gat ttg gtc ttc                       325
Lys Cys Glu Cys Arg Pro Lys Lys Asp Leu Val
 95                 100                 105

<210> SEQ ID NO 161
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 161

Ala His Tyr Asn Thr Glu Ile Leu Lys Ser Ile Asp Asn Glu Trp Arg
  1               5                  10                  15

Lys Thr Gln Cys Met Pro Ile Glu Thr Leu Val Asp Ile Phe Gln Glu
             20                  25                  30

Tyr Pro Asp Glu Ile Glu Tyr Ile Phe Lys Pro Pro Cys Val Ser Val
         35                  40                  45

Tyr Arg Cys Gly Gly Cys Cys Asn Ser Glu Gly Leu Gln Cys Val Pro
     50                  55                  60

Thr Glu Glu Ser Asn Ile Thr Met Gln Ile Met Arg Ile Lys Pro His
 65                  70                  75                  80

Gln Gly Gln His Ile Gly Glu Met Ser Phe Leu Gln His Asn Lys Cys
                 85                  90                  95

Glu Cys Arg Pro Lys Lys Asp Leu Val
            100                 105

<210> SEQ ID NO 162
```

```
<211> LENGTH: 322
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 162 ggatcct gca cat tat aat acc gag atc ctg aaa ttc atg gat gtc tat        49
        Ala His Tyr Asn Thr Glu Ile Leu Lys Phe Met Asp Val Tyr
          1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca cca tgt gtg tcc       145
Glu Phe Gly Val Ala Thr Asn Thr Phe Phe Lys Pro Pro Cys Val Ser
                     35                  40                  45 gtg tac aga tgt ggg ggt tgc tgc aat agt gag ggg ctg cag tgc gtt       193
Val Tyr Arg Cys Gly Gly Cys Cys Asn Ser Glu Gly Leu Gln Cys Val
                 50                  55                  60 ccc acc gag gag tcc aac atc acc atg cag att atg aga att aaa cct       241
Pro Thr Glu Glu Ser Asn Ile Thr Met Gln Ile Met Arg Ile Lys Pro
             65                  70                  75 cac caa ggg cag cac atc gga gag atg agc ttt gcc aat cac act tcc       289
His Gln Gly Gln His Ile Gly Glu Met Ser Phe Ala Asn His Thr Ser
         80                  85                  90 tgc cga tgc atg tct aag ctg gat ttg gtc ttc                           322
Cys Arg Cys Met Ser Lys Leu Asp Leu Val Phe
 95                 100                 105

<210> SEQ ID NO 163
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 163

Ala His Tyr Asn Thr Glu Ile Leu Lys Phe Met Asp Val Tyr Gln Arg
  1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Ser Glu Gly Leu Gln Cys Val Pro Thr
     50                  55                  60

Glu Glu Ser Asn Ile Thr Met Gln Ile Met Arg Ile Lys Pro His Gln
 65                  70                  75                  80

Gly Gln His Ile Gly Glu Met Ser Phe Ala Asn His Thr Ser Cys Arg
                 85                  90                  95

Cys Met Ser Lys Leu Asp Leu Val Phe
            100                 105

<210> SEQ ID NO 164
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)
```

<400> SEQUENCE: 164

```
ggatcct gca cat tat aat acc gag atc ctg aaa ttc atg gat gtc tat         49
        Ala His Tyr Asn Thr Glu Ile Leu Lys Phe Met Asp Val Tyr
        1               5                   10 cag cgc agc tac tgc cat ccg atc gag aca ctg gtg gac atc ttc cag         97
Gln Arg Ser Tyr Cys His Pro Ile Glu Thr Leu Val Asp Ile Phe Gln
 15              20                  25                  30 gaa ttt gga gtc gcg aca aac acc ttc ttc aag cca cca tgt gtg tcc        145
Glu Phe Gly Val Ala Thr Asn Thr Phe Phe Lys Pro Pro Cys Val Ser
                 35                  40                  45 gtg tac aga tgt ggg ggt tgc tgc aat gac gaa ggg ctg gag tgc gtt        193
Val Tyr Arg Cys Gly Gly Cys Cys Asn Asp Glu Gly Leu Glu Cys Val
             50                  55                  60 ccc acc gag gag tcc aac atc acc atg cag att atg aga att aca gtg        241
Pro Thr Glu Glu Ser Asn Ile Thr Met Gln Ile Met Arg Ile Thr Val
         65                  70                  75 cct ctc tct caa ggg ccc aaa cca gtg aca atc agc ttt ctc cag cat        289
Pro Leu Ser Gln Gly Pro Lys Pro Val Thr Ile Ser Phe Leu Gln His
     80                  85                  90 aac aaa tgt gaa tgt aga cca aag aaa gat ttg gtcttc                     328
Asn Lys Cys Glu Cys Arg Pro Lys Lys Asp Leu
 95                 100                 105
```

<210> SEQ ID NO 165
<211> LENGTH: 105
<212> TYPE: PRT
<213> ORGANISM: Artificial Sequence
<220> FEATURE:
<223> OTHER INFORMATION: Description of Artificial Sequence: amino acid sequence of hybrid DNA

<400> SEQUENCE: 165

```
Ala His Tyr Asn Thr Glu Ile Leu Lys Phe Met Asp Val Tyr Gln Arg
 1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Asp Glu Gly Leu Glu Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Leu Gln His Asn Lys
                 85                  90                  95

Cys Glu Cys Arg Pro Lys Lys Asp Leu
            100                 105
```

<210> SEQ ID NO 166
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 166

```
ggatcct gca cat tat aat acc gag atc ctg aaa ttc atg gat gtc tat         49
        Ala His Tyr Asn Thr Glu Ile Leu Lys Phe Met Asp Val Tyr
        1               5                   10
```

```
cag cgc agc tac tgc cat ccg atc gag aca ctg gtg gac atc ttc cag      97
Gln Arg Ser Tyr Cys His Pro Ile Glu Thr Leu Val Asp Ile Phe Gln
 15              20                  25                  30 gaa ttt gga gtc gcg aca aac acc ttc ttc aag cca cca tgt gtg tcc     145
Glu Phe Gly Val Ala Thr Asn Thr Phe Phe Lys Pro Pro Cys Val Ser
             35                  40                  45 gtg tac aga tgt ggg ggt tgc tgc aat agt gag ggg ctg cag tgc gtt     193
Val Tyr Arg Cys Gly Gly Cys Cys Asn Ser Glu Gly Leu Gln Cys Val
                 50                  55                  60 ccc acc gag gag tcc aac atc acc atg cag att atg aga att aca gtg     241
Pro Thr Glu Glu Ser Asn Ile Thr Met Gln Ile Met Arg Ile Thr Val
             65                  70                  75 cct ctc tct caa ggg ccc aaa cca gtg aca atc agc ttt ctc cag cat     289
Pro Leu Ser Gln Gly Pro Lys Pro Val Thr Ile Ser Phe Leu Gln His
 80                  85                  90 aac aaa tgt gaa tgt aga cca aag aaa gat ttg gtcttc                  328
Asn Lys Cys Glu Cys Arg Pro Lys Lys Asp Leu
 95                 100                 105

<210> SEQ ID NO 167
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 167

Ala His Tyr Asn Thr Glu Ile Leu Lys Phe Met Asp Val Tyr Gln Arg
 1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Ser Glu Gly Leu Gln Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Leu Gln His Asn Lys
                 85                  90                  95

Cys Glu Cys Arg Pro Lys Lys Asp Leu
            100                 105

<210> SEQ ID NO 168
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 168 ggatcct gca cat tat aat acc gag atc ctg aaa ttc atg gat gtc tat     49
        Ala His Tyr Asn Thr Glu Ile Leu Lys Phe Met Asp Val Tyr
         1               5                  10 cag cgc agc tac tgc cat ccg atc gag aca ctg gtg gac atc ttc cag     97
Gln Arg Ser Tyr Cys His Pro Ile Glu Thr Leu Val Asp Ile Phe Gln
 15              20                  25                  30 gaa ttt gga gtc gcg aca aac acc ttc ttc aag cca cca tgt gtg tcc    145
Glu Phe Gly Val Ala Thr Asn Thr Phe Phe Lys Pro Pro Cys Val Ser
             35                  40                  45
```

```
gtg tac aga tgt ggg ggt tgc tgc aat gac gaa ggg ctg gag tgc gtt      193
Val Tyr Arg Cys Gly Gly Cys Cys Asn Asp Glu Gly Leu Glu Cys Val
            50                  55                  60 ccc acc gag gag tcc aac atc acc atg cag att atg aga att aca gtg      241
Pro Thr Glu Glu Ser Asn Ile Thr Met Gln Ile Met Arg Ile Thr Val
        65                  70                  75 cct ctc tct caa ggg ccc aaa cca gtg aca atc agc ttt gcc aat cac      289
Pro Leu Ser Gln Gly Pro Lys Pro Val Thr Ile Ser Phe Ala Asn His
    80                  85                  90 act tcc tgc cga tgc atg tct aag ctg gat ttg gtcttc                   328
Thr Ser Cys Arg Cys Met Ser Lys Leu Asp Leu
95                 100                 105

<210> SEQ ID NO 169
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 169

Ala His Tyr Asn Thr Glu Ile Leu Lys Phe Met Asp Val Tyr Gln Arg
  1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Pro Cys Val Ser Val Tyr
         35                  40                  45

Arg Cys Gly Gly Cys Cys Asn Asp Glu Gly Leu Glu Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Ala Asn His Thr Ser
                 85                  90                  95

Cys Arg Cys Met Ser Lys Leu Asp Leu
            100                 105

<210> SEQ ID NO 170
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 170 ggatcct gca cat tat aat acc gag atc ctg aaa ttc atg gat gtc tat      49
        Ala His Tyr Asn Thr Glu Ile Leu Lys Phe Met Asp Val Tyr
          1               5                  10 cag cgc agc tac tgc cat ccg atc gag aca ctg gtg gac atc ttc cag      97
Gln Arg Ser Tyr Cys His Pro Ile Glu Thr Leu Val Asp Ile Phe Gln
 15                  20                  25                  30 gaa tac cct gat gag atc gag tac atc ttc aag cca cca tgt gtg tcc     145
Glu Tyr Pro Asp Glu Ile Glu Tyr Ile Phe Lys Pro Pro Cys Val Ser
                 35                  40                  45 gtg tac aga tgt ggg ggt tgc tgc aat agt gag ggg ctg cag tgc gtt     193
Val Tyr Arg Cys Gly Gly Cys Cys Asn Ser Glu Gly Leu Gln Cys Val
             50                  55                  60 ccc acc gag gag tcc aac atc acc atg cag att atg aga att aca gtg     241
Pro Thr Glu Glu Ser Asn Ile Thr Met Gln Ile Met Arg Ile Thr Val
         65                  70                  75
```

```
                   65                  70                  75
cct ctc tct caa ggg ccc aaa cca gtg aca atc agc ttt gcc aat cac         289
Pro Leu Ser Gln Gly Pro Lys Pro Val Thr Ile Ser Phe Ala Asn His
        80                  85                  90 act tcc tgc cga tgc atg tct aag ctg gat ttg gtcttc                      328
Thr Ser Cys Arg Cys Met Ser Lys Leu Asp Leu
 95                 100                 105

<210> SEQ ID NO 171
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 171

Ala His Tyr Asn Thr Glu Ile Leu Lys Phe Met Asp Val Tyr Gln Arg
 1               5                  10                  15

Ser Tyr Cys His Pro Ile Glu Thr Leu Val Asp Ile Phe Gln Glu Tyr
                20                  25                  30

Pro Asp Glu Ile Glu Tyr Ile Phe Lys Pro Pro Cys Val Ser Val Tyr
            35                  40                  45

Arg Cys Gly Gly Cys Cys Asn Ser Glu Gly Leu Gln Cys Val Pro Thr
        50                  55                  60

Glu Glu Ser Asn Ile Thr Met Gln Ile Met Arg Ile Thr Val Pro Leu
 65                 70                  75                  80

Ser Gln Gly Pro Lys Pro Val Thr Ile Ser Phe Ala Asn His Thr Ser
                85                  90                  95

Cys Arg Cys Met Ser Lys Leu Asp Leu
                100                 105

<210> SEQ ID NO 172
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)

<400> SEQUENCE: 172 ggatcct gca cat tat aat acc gag atc ctg aaa ttc atg gat gtc tat         49
        Ala His Tyr Asn Thr Glu Ile Leu Lys Phe Met Asp Val Tyr
         1               5                  10 cag cgc agc tac tgc cat ccg atc gag aca ctg gtg gac atc ttc cag         97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca tcc tgc gtg ccc         145
Glu Phe Gly Val Ala Thr Asn Thr Phe Phe Lys Pro Ser Cys Val Pro
                35                  40                  45 ctg atg aga tgt ggg ggt tgc tgc aat gac gaa ggg ctg gag tgc gtt         193
Leu Met Arg Cys Gly Gly Cys Cys Asn Asp Glu Gly Leu Glu Cys Val
            50                  55                  60 ccc acc gag gag tcc aac atc acc atg cag att atg aga att aca gtg         241
Pro Thr Glu Glu Ser Asn Ile Thr Met Gln Ile Met Arg Ile Thr Val
 65                 70                  75 cct ctc tct caa ggg ccc aaa cca gtg aca atc agc ttt ctc cag cat         289
Pro Leu Ser Gln Gly Pro Lys Pro Val Thr Ile Ser Phe Leu Gln His
        80                  85                  90 aac aaa tgt gaa tgt aga cca aag aaa gat ttg gtcttc                      328
```

```
Asn Lys Cys Glu Cys Arg Pro Lys Lys Asp Leu
 95             100             105
```

<210> SEQ ID NO 173
<211> LENGTH: 105
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 173

```
Ala His Tyr Asn Thr Glu Ile Leu Lys Phe Met Asp Val Tyr Gln Arg
  1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Ser Cys Val Pro Leu Met
         35                  40                  45

Arg Cys Gly Gly Cys Cys Asn Asp Glu Gly Leu Glu Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Leu Gln His Asn Lys
                 85                  90                  95

Cys Glu Cys Arg Pro Lys Lys Asp Leu
            100                 105
```

<210> SEQ ID NO 174
<211> LENGTH: 328
<212> TYPE: DNA
<213> ORGANISM: Artificial Sequence
<220> FEATURE:
<223> OTHER INFORMATION: Description of Artificial Sequence: hybrid DNA
<221> NAME/KEY: CDS
<222> LOCATION: (8)..(322)
<223> OTHER INFORMATION:

<400> SEQUENCE: 174

```
ggatcct gca cat tat aat acc gag atc ctg aaa ttc atg gat gtc tat        49
        Ala His Tyr Asn Thr Glu Ile Leu Lys Phe Met Asp Val Tyr
          1               5                  10 cag cgc agc tac tgc cat ccg atc gag aca ctg gtg gac atc ttc cag        97
Gln Arg Ser Tyr Cys His Pro Ile Glu Thr Leu Val Asp Ile Phe Gln
 15                  20                  25                  30 gaa ttt gga gtc gcg aca aac acc ttc ttc aag cca tcc tgc gtg ccc       145
Glu Phe Gly Val Ala Thr Asn Thr Phe Phe Lys Pro Ser Cys Val Pro
                 35                  40                  45 ctg atg aga tgt ggg ggt tgc tgc aat agt gag ggg ctg cag tgc gtt       193
Leu Met Arg Cys Gly Gly Cys Cys Asn Ser Glu Gly Leu Gln Cys Val
             50                  55                  60 ccc acc gag gag tcc aac atc acc atg cag att atg aga att aca gtg       241
Pro Thr Glu Glu Ser Asn Ile Thr Met Gln Ile Met Arg Ile Thr Val
 65                  70                  75 cct ctc tct caa ggg ccc aaa cca gtg aca atc agc ttt ctc cag cat       289
Pro Leu Ser Gln Gly Pro Lys Pro Val Thr Ile Ser Phe Leu Gln His
             80                  85                  90 aac aaa tgt gaa tgt aga cca aag aaa gat ttg gtcttc                    328
Asn Lys Cys Glu Cys Arg Pro Lys Lys Asp Leu
 95                 100             105
```

<210> SEQ ID NO 175
<211> LENGTH: 105

-continued

```
<212> TYPE: PRT
<213> ORGANISM: Artificial Sequence
<220> FEATURE:
<223> OTHER INFORMATION: Description of Artificial Sequence: amino acid
      sequence of hybrid DNA

<400> SEQUENCE: 175

Ala His Tyr Asn Thr Glu Ile Leu Lys Phe Met Asp Val Tyr Gln Arg
  1               5                  10                  15

Ser Tyr Cys His Pro Ile Glu Thr Leu Val Asp Ile Phe Gln Glu Phe
             20                  25                  30

Gly Val Ala Thr Asn Thr Phe Phe Lys Pro Ser Cys Val Pro Leu Met
         35                  40                  45

Arg Cys Gly Gly Cys Cys Asn Ser Glu Gly Leu Gln Cys Val Pro Thr
     50                  55                  60

Glu Glu Ser Asn Ile Thr Met Gln Ile Met Arg Ile Thr Val Pro Leu
 65                  70                  75                  80

Ser Gln Gly Pro Lys Pro Val Thr Ile Ser Phe Leu Gln His Asn Lys
                 85                  90                  95

Cys Glu Cys Arg Pro Lys Lys Asp Leu
            100                 105
```